US011773129B2

(12) United States Patent
Cairo et al.

(10) Patent No.: US 11,773,129 B2
(45) Date of Patent: Oct. 3, 2023

(54) METHODS OF PREVENTING OR TREATING ATHEROSCLEROSIS WITH INHIBITORS OF SPECIFIC ISOENZYMES OF HUMAN NEURAMINIDASE

(71) Applicants: THE GOVERNORS OF THE UNIVERSITY OF ALBERTA, Edmonton (CA); VALORISATION HSJ, LIMITED PARTNERSHIP, Quebec (CA)

(72) Inventors: Christopher Cairo, Edmonton (CA); Alexey Pchejetski, Mont-Royal (CA); Tianlin Guo, Montreal (CA)

(73) Assignees: The Governors of the University of Alberta, Alberta (CA); Valorisation HSJ, Limited Partnership, Quebec (CA)

( * ) Notice: Subject to any disclaimer, the term of this patent is extended or adjusted under 35 U.S.C. 154(b) by 0 days.

(21) Appl. No.: 16/616,426

(22) PCT Filed: May 25, 2018

(86) PCT No.: PCT/CA2018/050613

§ 371 (c)(1),
(2) Date: Nov. 22, 2019

(87) PCT Pub. No.: WO2018/213933

PCT Pub. Date: Nov. 29, 2018

(65) Prior Publication Data

US 2020/0239512 A1 Jul. 30, 2020

Related U.S. Application Data

(60) Provisional application No. 62/510,968, filed on May 25, 2017.

(51) Int. Cl.

| | |
|---|---|
| *C07H 15/02* | (2006.01) |
| *C07H 15/18* | (2006.01) |
| *C07H 15/26* | (2006.01) |
| *A61P 9/10* | (2006.01) |

(52) U.S. Cl.
CPC ................ *C07H 15/26* (2013.01); *A61P 9/10* (2018.01); *C07H 15/02* (2013.01); *C07H 15/18* (2013.01)

(58) Field of Classification Search
CPC ........ C07H 15/02; C07H 15/18; C07H 15/26; A61K 31/351; A61K 31/4192; C07D 405/06; C07D 405/12; C07D 309/28; A61P 29/00; A61P 9/10
USPC ........................................................... 514/43
See application file for complete search history.

(56) References Cited

U.S. PATENT DOCUMENTS

| | | | | |
|---|---|---|---|---|
| 5,360,817 A * | 11/1994 | von Izstein | A61P 31/14 514/459 |
| 5,639,786 A * | 6/1997 | Von Itzstein | C07D 309/28 514/459 |
| 6,548,476 B1 * | 4/2003 | Wu | A61P 43/00 514/3.7 |
| 2007/0074300 A1 | 3/2007 | Igdoura et al. | |
| 2022/0110919 A1 | 4/2022 | Pchejetski et al. | |

FOREIGN PATENT DOCUMENTS

| | | | | |
|---|---|---|---|---|
| WO | WO 95/20583 * | 8/1995 | C07D 309/28 |
| WO | WO 96/04265 * | 2/1996 | C07D 225/02 |
| WO | WO 96/04265 A1 | 2/1996 | |
| WO | WO-2005056047 A1 | 6/2005 | |
| WO | WO 2007/036041 A1 | 4/2007 | |
| WO | WO 2011/006208 A1 | 1/2011 | |
| WO | WO 2016/033660 A1 | 3/2016 | |
| WO | WO 2019/075009 A2 | 4/2019 | |
| WO | WO-2020107124 A1 | 6/2020 | |

OTHER PUBLICATIONS

Ye et al, European Journal of Medicinal Chemistry, 2012, 54, 764-770.*
PCT International Search Report and Written Opinion dated Jul. 18, 2018 issued in PCT/CA2018/050613 [WO/2018/213933].
PCT International Preliminary Report on Patentability dated Nov. 26, 2019 issued in PCT/CA2018/050613 [WO/2018/213933].
Guo et al., (Feb. 2018) "Selective Inhibitors of Human Neuraminidase 3," *J. Med. Chem.*, 61(5): 1990-2008 (19 pages).

(Continued)

*Primary Examiner* — Ganapathy Krishnan

(74) *Attorney, Agent, or Firm* — Elaine Ramesh; Emily M. Haliday; Weaver Austin Villeneuve & Sampson LLP

(57) ABSTRACT

The present invention provides a method of preventing or treating atherosclerosis or a symptom thereof comprising administering to a subject in need thereof a specific inhibitor of neuraminidase 1 (neu1); neuraminidase 3 (neu3); or a bispecific inhibitor of neu1 or neu3 of formula I; (I) and a compound of formula I.

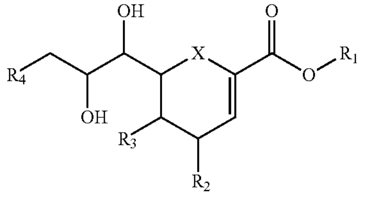

24 Claims, 34 Drawing Sheets

Specification includes a Sequence Listing.

(56) References Cited

OTHER PUBLICATIONS

Mack et al., (Apr. 1998) "Synthese von 6-thiosialinsäuren," *Tetrahedron*, 54(18): 4521-4538 (18 pages).
Vorwerk et al., (Jul. 1998) "Carbocyclic Analogues of N-Acetyl-2,3-didehydro-2-deoxy-D-neuraminic Acid (Neu5Ac2en, DANA): Synthesis and Inhibition of Viral and Bacterial Neuraminidases," *Angew. Chem. Int. Ed.,* 37(12): 1732-1734 (3 pages).
European Extended Search Report dated Feb. 25, 2021 issued in EP 18805828.3.
White Elizabeth J. et al: (Sep. 2018) "Sialidase down-regulation reduces non-HDL cholesterol, inhibits leukocyte transmisgration, and attenuates atherosclerosis in ApoE knockout mice", *Journal of Biological Chemistry*, 293(38): 14689-14706.
Yang Abraham Ernest (Apr. 2012) "The Effects of Hypomorphic Sialidase Expression On Atherosclerosis" *A Thesis for the Degree of Doctor of Philosophy, McMaster University, Hamilton, Ontario* (357pages).
Albohy, A. et al. (2013) "Identification of Selective Nanomolar Inhibitors of the Human Neuraminidase, NEU4" Med Chem Let., 4: 532-537.
Alioglu, B. et al. (2010) "An Experience of Oseltamivir Phosphate (Tamiflu) in a Pediatric Patient with Chronic Idiopathic Thrombocytopenia Purpura: A Case Report" Pathophysiol Haemost Thromb, 37: 55-58.
Guo, T. et al. (Nov. 2018) "Selective Inhibitors of Human Neuraminidase 1 (NEU1)" J. Med. Chem., 61: 11261-11279.
Hama, R. (2016) "The mechanisms of delayed onset type adverse reactions to oseltamivir" Infectious Diseases, 48(9): 651-660.
Hata, K. et al., "Limited Inhibitory Effects of Oseltamivir and Zanamivir on Human Sialidases", Antimicrobial Agents And Chemotherapy, Oct. 2008, vol. 52, No. 10, pp. 3484-3491.
Jansen, A. J. G. et al. (2015) "Sialidase inhibition to increase platelet counts: A new treatment option for thrombocytopenia" American Journal of Hematologt., 90(5): E94-E95.
Jia, F. et al. (2016) "Integrin-mediated cell migration is blocked by inhibitors of human neuraminidase" Biochimica et Biophysica Acta, 1861: 1170-1179.
PCT International Preliminary Report on Patentability dated May 25, 2021 issued in PCT/CA2019/051715 [WO/2020/107124].
PCT International Search Report and Written Opinion dated Feb. 24, 2020 issued in PCT/CA2019/051715 [WO/2020/107124].
Richards, M.R. et al., "Molecular Dynamics Simulations of Viral Neuraminidase Inhibitors with the Human Neuraminidase Enzymes: Insights into Isoenzyme Selectivity", Bioorganic & Medicinal Chemistry, 2018, pp. 1-33.
Wong, Z. X. et al. (2011) "Oseltamivir treatment of mice before or after mild influenza infection reduced cellular and cytokine inflammation in the lung" Influenza and Other Respiratory Viruses, 5: 343-350.
Zhang, Y. et al. (2013) "Identification of Selective Inhibitors for Human Neuraminidase Isoenzymes Using C4,C7-Modified 2-Deoxy-2,3-didehydro-N-acetylneuraminic Acid (DANA) Analogues" J Med Chem, 56: 2948-2958.
Zou, Y. et al. (2010) "Inhibition of human neuraminidase 3 (NEU3) by C9-triazole derivatives of 2,3-didehydro-N-acetyl-neuraminic acid" Bioorganic & Medicinal Chemistry Letters, 20: 7529-7533.
Holzer, C.T. et al., "Inhibition of Sialidases From Viral, Bacterial and Mammalian Sources by Analogues of 2-deoxy-2,3-didehydro-N-acetylneuraminic Acid Modified at the C-4 Position", Glycoconjugate Journal, 1993, vol. 10, No. 1, pp. 40-44.
Ikeda, K. et al., "Synthesis of 2-deoxy-2,3-didehydro-N-acetylneuraminic Acid Analogues Modified at the C-4 and C-9 Positions And Their Behaviour Towards Sialidase From Influenza Virus and Pig Liver Membrane", Carbohydrate Research, 2001, vol. 330, No. 1, pp. 31-41.
Islam, T. et al., "Anti-influenza Drug Discovery: Are We Ready for the Next Pandemic?", Advances in Carbohydrate Chemistry and Biochemistry, Academic Press, 2007, vol. 61, pp. 293-352.
Kiefel, M.J. et al., "Recent Advances in the Synthesis of Sialic Acid Derivatives and Sialylmimetics as Biological Probes", Chemical Reviews, 2002, vol. 102, No. 2, pp. 471-490.
Laborda, P. et al., "Influenza Neuraminidase Inhibitors: Synthetic Approaches, Derivatives and Biological Activity", Molecules, 2016, vol. 21, No. 11, 1513, 40 pages.
Smith, B. et al., "Analysis of Inhibitor Binding in Influenza Virus Neuraminidase", Protein Science, 2001, vol. 10, No. 4, pp. 689-696.
Suzuki, T. et al., "Inhibition of Human Parainfluenza Virus Type 1 Sialidase by Analogs of 2-deoxy-2,3-didehydro-N-acetylneuraminic Acid", Glycoconjugate Journal, 2001, vol. 18, No. 4, pp. 331-337.
Von Itzstein, M. et al., "Rational Design of Potent Sialidase-based Inhibitors of Influenza Virus Replication", Nature, 1993, vol. 363, No. 6428, pp. 418-423.
Ye, D. et al., "Synthesis of C-4-modified Zanamivir Analogs as Neuraminidase Inhibitors and Their Anti-AIV Activities", European Journal of Medicinal Chemistry, 2012, vol. 54, pp. 764-770.

* cited by examiner

Compound 31

Control

>NP_000425.1 neuraminidase -1 precursor [Homo sapiens]

MTGERPSTALPDRRWGPRILGFWGGCRVWVFAAIFLLLSLAASWSKAENDFGLVQPLVTMEQLLWVSGRQIGSVDTFRIP
LITATPRGTLLAFAEARKMSSSDEGAKFIALRRSMDQGSTWSPTAFIVNDGDVPDGLNLGAVVSDVETGVVFLFYSLCAH
KAGCQVASTMLVWSKDDGVSWSTPRNLSLDIGTEVFAPGPGSGIQKQREPRKGRLIVCGHGTLERDGVFCLLSDDHGASW
RYGSGVSGIPYGQPKQENDFNPDECQPYELPDGSVVINARNQNNYHCHCRIVLRSYDACDTLRPRDVTFDPELVDPVVAA
GAVVTSSGIVFFSNPAHPEFRVNLTLRWSFSNGTSWRKETVQLWPGPSGYSSLATLEGSMDGEEQAPQLYVLYEKGRNHY
TESISVAKISVYGTL

>NP_005374.2 neuraminidase-2 [Homo sapiens]
MASLPVLQKESVFQSGAHAYRIPALLYLPGQQSLLAFAEQRASKKDEHAELIVLRRGDYDAPTHQVQWQAQEVVAQARLD
GHRSMNPCPLYDAQTGTLFLFFIAIPGQVTEQQQLQTRANVTRLCQVTSTDHGRTWSSPRDLTDAAIGPAYREWSTFAVG
PGHCLQLHDRARSLVVPAYAYRKLHPIQRPIPSAFCFLSHDHGRTWARGHFVAQDTLECQVAEVETGEQRVVTLNARSHL
RARVQAQSTNDGLDFQESQLVKKLVEPPPQGCQGSVISFPSPRSGPGSPAQWLLYTHPTHSWQRADLGAYLNPRPPAPEA
WSEPVLLAKGSCAYSDLQSMGTGPDGSPLFGCLYEANDYEEIVFLMFTLKQAFPAEYLPQ >sp|Q9UQ49| neuraminidase-3_HUMAN isoform 1 of Sialidase-3
MEEVTTCSFNSPLFRQEDDRGITYRIPALLYIPPTHTFLAFAEKRSTRRDEDALHLVLRRGLRIGQLVQWGPLKPLMEAT
LPGHRTMNPCPVWEQKSGCVFLFFICVRGHVTERQQIVSGRNAARLCFIYSQDAGCSWSEVRDLTEEVIGSELKHWATFA
VGPGHGIQLQSGRLVIPAYTYYIPSWFFCFQLPCKTRPHSLMIYSDDLGVTWHHGRLIRPMVTVECEVAEVTGRAGHPVL
YCSARTPNRCRAEALSTDHGEGFQRLALSRQLCEPPHGCQGSVVSFRPLEIPHRCQDSSSKDAPTIQQSSPGSSLRLEEE
AGTPSESWLLYSHPTSRKQRVDLGIYLNQTPLEAACWSRPWILHCGPCGYSDLAALEEEGLFGCLFECGTKQECEQIAFR
LFTHREILSHLQGDCTSPGRNPSQFKSN >sp|Q9UQ49-2| neuraminidase-3_HUMAN Isoform 2 of Sialidase-3
MRPADLPPRPMEESPASSSAPTETEEPGSSAEVMEEVTTCSFNSPLFRQEDDRGITYRIPALLYIPPTHTFLAFAEKRST
RRDEDALHLVLRRGLRIGQLVQWGPLKPLMEATLPGHRTMNPCPVWEQKSGCVFLFFICVRGHVTERQQIVSGRNAARLC
FIYSQDAGCSWSEVRDLTEEVIGSELKHWATFAVGPGHGIQLQSGRLVIPAYTYYIPSWFFCFQLPCKTRPHSLMIYSDD
LGVTWHHGRLIRPMVTVECEVAEVTGRAGHPVLYCSARTPNRCRAEALSTDHGEGFQRLALSRQLCEPPHGCQGSVVSFR
PLEIPHRCQDSSSKDAPTIQQSSPGSSLRLEEEAGTPSESWLLYSHPTSRKQRVDLGIYLNQTPLEAACWSRPWILHCGP
CGYSDLAALEEEGLFGCLFECGTKQECEQIAFRLFTHREILSHLQGDCTSPGRNPSQFKSN >NP_542779.2 neuraminidase-4 isoform 1 [Homo sapiens]
MMSSAAFPRWLSMGVPRTPSRTVLFERERTGLTYRVPSLLPVPPGPTLLAFVEQRLSPDDSHAHRLVLRRGTLAGGSVRW
GALHVLGTAALAEHRSMNPCPVHDAGTGTVFLFFIAVLGHTPEAVQIATGRNAARLCCVASRDAGLSWGSARDLTEEAIG
GAVQDWATFAVGPGHGVQLPSGRLLVPAYTYRVDRRECFGKICRTSPHSFAFYSDDHGRTWRCGGLVPNLRSGECQLAAV
DGGQAGSFLYCNARSPLGSRVQALSTDEGTSFLPAERVASLPETAWGCQGSIVGFPAPAPNRPRDDSWSVGPGSPLQPPL
LGPGVHEPPEEAAVDPRGGQVPGGPFSRLQPRGDGPRQPGPRPGVSGDVGSWTLALPMPFAAPPQSPTWLLYSHPVGRRA
RLHMGIRLSQSPLDPRSWTEPWVIYEGPSGYSDLASIGPAPEGGLVFACLYESGARTSYDEISFCTFSLREVLENVPASP
KPPNLGDKPRGCCWPS >NP_001161071.1 neuraminidase-4 isoform 2 [Homo sapiens]
MMSSAAFPRWLQSMGVPRTPSRTVLFERERTGLTYRVPSLLPVPPGPTLLAFVEQRLSPDDSHAHRLVLRRGTLAGGSVR
WGALHVLGTAALAEHRSMNPCPVHDAGTGTVFLFFIAVLGHTPEAVQIATGRNAARLCCVASRDAGLSWGSARDLTEEAI
GGAVQDWATFAVGPGHGVQLPSGRLLVPAYTYRVDRRECFGKICRTSPHSFAFYSDDHGRTWRCGGLVPNLRSGECQLAA
VDGGQAGSFLYCNARSPLGSRVQALSTDEGTSFLPAERVASLPETAWGCQGSIVGFPAPAPNRPRDDSWSVGPGSPLQPP
LLGPGVHEPPEEAAVDPRGGQVPGGPFSRLQPRGDGPRQPGPRPGVSGDVGSWTLALPMPFAAPPQSPTWLLYSHPVGRR
ARLHMGIRLSQSPLDPRSWTEPWVIYEGPSGYSDLASIGPAPEGGLVFACLYESGARTSYDEISFCTFSLREVLENVPAS
PKPPNLGDKPRGCCWPS >NP_001161072.1 sialidase-4 isoform 3 [Homo sapiens]
MGVPRTPSRTVLFERERTGLTYRVPSLLPVPPGPTLLAFVEQRLSPDDSHAHRLVLRRGTLAGGSVRWGALHVLGTAALA
EHRSMNPCPVHDAGTGTVFLFFIAVLGHTPEAVQIATGRNAARLCCVASRDAGLSWGSARDLTEEAIGGAVQDWATFAVG
PGHGVQLPSGRLLVPAYTYRVDRRECFGKICRTSPHSFAFYSDDHGRTWRCGGLVPNLRSGECQLAAVDGGQAGSFLYCN
ARSPLGSRVQALSTDEGTSFLPAERVASLPETAWGCQGSIVGFPAPAPNRPRDDSWSVGPGSPLQPPLLGPGVHEPPEEA
AVDPRGGQVPGGPFSRLQPRGDGPRQPGPRPGVSGDVGSWTLALPMPFAAPPQSPTWLLYSHPVGRRARLHMGIRLSQSP
LDPRSWTEPWVIYEGPSGYSDLASIGPAPEGGLVFACLYESGARTSYDEISFCTFSLREVLENVPASPKPPNLGDKPRGC
CWPS

FIG. 16

```
NP_000425.1       MTGERPSTALPDRRWGPRILGFWGGCRVWVFAAIFLLLSLAASWSKAENDFGLV---QPL
NP_005374.2       ------------------------------------------------------MASLPV
sp|Q9UQ49|        ------------------------------------------------------MEEVTT
sp|Q9UQ49-2|      ----MRPADLPPRPMEES-----------------PASSSAPTETEEPGSSAEVMEEVTT
NP_001161071.1    ---MMSSAAFP------------------------------RWLQSMG---------VP-
NP_542779.2       ---MMSSAAFP------------------------------RWL-SMG---------VP-
NP_001161072.1    ----------------------------------------------MG---------VP-
Consensus         XXXXXXXXXXXXXXXXXXXXXXXXXXXXXXXXXXXXXXXXXXXXXXXXXXXXXXXXXXXX

NP_000425.1       VTMEQLLWVSGRQIGSVDTFRIPLITA-TPRGTLLAFAEARKMSSSDEGAKFIALRRSMD
NP_005374.2       L--QKESVF----QSGAHAYRIPALLYLPGQQSLLAFAEQRA-SKKDEHAELIVLRRGDY
sp|Q9UQ49|        CSFNSPLFR--QEDDRGITYRIPALLYIPPTHTFLAFAEKRS-TRRDEDALHLVLRRGLR
sp|Q9UQ49-2|      CSFNSPLFR--QEDDRGITYRIPALLYIPPTHTFLAFAEKRS-TRRDEDALHLVLRRGLR
NP_001161071.1    RTPSRTVLF--ERERTGLTYRVPSLLPVPPGPTLLAFVEQRL-SPDDSHAHRLVLRRGTL
NP_542779.2       RTPSRTVLF--ERERTGLTYRVPSLLPVPPGPTLLAFVEQRL-SPDDSHAHRLVLRRGTL
NP_001161072.1    RTPSRTVLF--ERERTGLTYRVPSLLPVPPGPTLLAFVEQRL-SPDDSHAHRLVLRRGTL
                     .              ::*:* :       ::***.* *  :  *. *  :.***.
Consensus         XXXXXXXXXXXXXXXXXXXXRXPXXXXXXXXXXXLAFXEXRXXXXXDXXAXXXXLRRXXX

NP_000425.1       Q----GSTWSPTAFIVNDGDVPDGLNLGAVVSDVETGVVFLFYSLCAH--------KAGC
NP_005374.2       DAPTHQVQWQAQEVVAQARLDGHRSMNPCPLYDAQTGTLFLFFIAIPGQVTEQQQLQTRA
sp|Q9UQ49|        I--GQLVQWGPLKPLMEATLPGHRTMNPCPVWEQKSGCVFLFFICVRGHVTERQQIVSGR
sp|Q9UQ49-2|      I--GQLVQWGPLKPLMEATLPGHRTMNPCPVWEQKSGCVFLFFICVRGHVTERQQIVSGR
NP_001161071.1    A--GGSVRWGALHVLGTAALAEHRSMNPCPVHDAGTGTVFLFFIAVLGHTPEAVQIATGR
NP_542779.2       A--GGSVRWGALHVLGTAALAEHRSMNPCPVHDAGTGTVFLFFIAVLGHTPEAVQIATGR
NP_001161072.1    A--GGSVRWGALHVLGTAALAEHRSMNPCPVHDAGTGTVFLFFIAVLGHTPEAVQIATGR
                          *     :       .     . : :  :* :***:             :
Consensus         XXXXXXXXWXXXXXXXXXXXXXXXXXXXXXXXXXXXGXXFLFXXXXXXXXXXXXXXXXXX

NP_000425.1       QVASTMLVWSKDDGVSWSTPRNLSLDI-G-----TEVFAPGPGSGIQKQREPRKGRLIVC
NP_005374.2       NVTRLCQVTSTDHGRTWSSPRDLTDAAIGPAYREWSTFAVGPGHCLQLHDR--ARSLVVP
sp|Q9UQ49|        NAARLCFIYSQDAGCSWSEVRDLTEEVIGSELKHWATFAVGPGHGIQLQS----GRLVIP
sp|Q9UQ49-2|      NAARLCFIYSQDAGCSWSEVRDLTEEVIGSELKHWATFAVGPGHGIQLQS----GRLVIP
NP_001161071.1    NAARLCCVASRDAGLSWGSARDLTEEAIGGAVQDWATFAVGPGHGVQLPS----GRLLVP
NP_542779.2       NAARLCCVASRDAGLSWGSARDLTEEAIGGAVQDWATFAVGPGHGVQLPS----GRLLVP
NP_001161072.1    NAARLCCVASRDAGLSWGSARDLTEEAIGGAVQDWATFAVGPGHGVQLPS----GRLLVP
                  :.:    : * * * :*.  *:*:    *       .** ***  :*         *::
Consensus         XXXXXXXXXSXDXGXXWXXXRXLXXXXXGXXXXXXXXXFAXGPGXXXQXXXXXXXXXLXXX

NP_000425.1       -------------GHGTLERDGVFCLLSDDHGASWRYGSGVSGIPYGQPKQENDFNPDEC
NP_005374.2       AYAYRKL------HPIQRPIPSAFCFLSHDHGRTWARGHFVAQ-DT-----------LEC
sp|Q9UQ49|        AYTYYIPSWFFCFQLPCKTRPHSLMIYSDDLGVTWHHGRLIRPMVT-----------VEC
sp|Q9UQ49-2|      AYTYYIPSWFFCFQLPCKTRPHSLMIYSDDLGVTWHHGRLIRPMVT-----------VEC
NP_001161071.1    AYTYRVDR-RECFGKICRTSPHSFAFYSDDHGRTWRCGGLVPNLRS-----------GEC
NP_542779.2       AYTYRVDR-RECFGKICRTSPHSFAFYSDDHGRTWRCGGLVPNLRS-----------GEC
NP_001161072.1    AYTYRVDR-RECFGKICRTSPHSFAFYSDDHGRTWRCGGLVPNLRS-----------GEC
                                         : : *.* * :*  *  :                 **
Consensus         XXXXXXXXXXXXXXXXXXXXXXXXXXXSXDXGXXWXXGXXXXXXXXXXXXXXXXXXXXEC
```

FIG. 17A

```
NP_000425.1       QPYELPDGSV----VINARNQN----------------------------NYHCHCRIVL
NP_005374.2       QVAEVETGEQ-RVVTLNARSHLRARVQAQSTNDGLDFQESQLVKKLVEPPPQGCQGSVI-
sp|Q9UQ49|        EVAEVTGRAGHPVLYCSARTPNRCRAEALSTDHGEGFQRLALSRQLCE-PPHGCQGSVV-
sp|Q9UQ49-2|      EVAEVTGRAGHPVLYCSARTPNRCRAEALSTDHGEGFQRLALSRQLCE-PPHGCQGSVV-
NP_001161071.1    QLAAVDGGQAGSFLYCNARSPLGSRVQALSTDEGTSFLPAERVASLPE-TAWGCQGSIV-
NP_542779.2       QLAAVDGGQAGSFLYCNARSPLGSRVQALSTDEGTSFLPAERVASLPE-TAWGCQGSIV-
NP_001161072.1    QLAAVDGGQAGSFLYCNARSPLGSRVQALSTDEGTSFLPAERVASLPE-TAWGCQGSIV-
                  :   :          .**.                                  *:  ::
Consensus         XXXXXXXXXXXXXXXXARXXXXXXXXXXXXXXXXXXXXXXXXXXXXXXXXXXXCXXXXXX

NP_000425.1       RSYDACDT-LRPRDVTF--------DPELVDPVV--------------------------
NP_005374.2       -SFPSPRS------------GP--------------------------------------
sp|Q9UQ49|        -SFRPLEIPHRCQDSSSKDAP---------------------------------------
sp|Q9UQ49-2|      -SFRPLEIPHRCQDSSSKDAP---------------------------------------
NP_001161071.1    -GFPAPAP-NRPRDDSWSVGPGSPLQPPLLGPGVHEPPEEAAVDPRGGQVPGGPFSRLQP
NP_542779.2       -GFPAPAP-NRPRDDSWSVGPGSPLQPPLLGPGVHEPPEEAAVDPRGGQVPGGPFSRLQP
NP_001161072.1    -GFPAPAP-NRPRDDSWSVGPGSPLQPPLLGPGVHEPPEEAAVDPRGGQVPGGPFSRLQP
                   .:
Consensus         XXXXXXXXXXXXXXXXXXXXXXXXXXXXXXXXXXXXXXXXXXXXXXXXXXXXXXXXXXXX

NP_000425.1       ---------------------------AAGAVVTSSGIVFFSNPAHPEFRVNLTLRWSFS
NP_005374.2       --------------------------------GSPAQWLLYTHPTHSWQRADLGAYLNPR
sp|Q9UQ49|        -----TIQQSSPGS---------SLRLEEEAGTPSESWLLYSHPTSRKQRVDLGIYLNQT
sp|Q9UQ49-2|      -----TIQQSSPGS---------SLRLEEEAGTPSESWLLYSHPTSRKQRVDLGIYLNQT
NP_001161071.1    RGDGPRQPGPRPGVSGDVGSWTLALPMPFAAPPQSPTWLLYSHPVGRRARLHMGIRLSQS
NP_542779.2       RGDGPRQPGPRPGVSGDVGSWTLALPMPFAAPPQSPTWLLYSHPVGRRARLHMGIRLSQS
NP_001161072.1    RGDGPRQPGPRPGVSGDVGSWTLALPMPFAAPPQSPTWLLYSHPVGRRARLHMGIRLSQS
                                                        ::::*.    * .:     .
Consensus         XXXXXXXXXXXXXXXXXXXXXXXXXXXXXXXXXXXXXXXXXXXPXXXXXRXXXXXXXXXX

NP_000425.1       --NGTSWRKETVQLWPGPSGYSSLATLEGSMDGEEQAPQLYVLYEKGRNHYTESISVAKI
NP_005374.2       PPAPEAWS-EPVLLAKGSCAYSDLQSMGTGPDGS---PLFGCLYEAN---DYEEIVFLMF
sp|Q9UQ49|        PLEAACWS-RPWILHCGPCGYSDLAALE----EE---GLFGCLFECGTKQECEQIAFRLF
sp|Q9UQ49-2|      PLEAACWS-RPWILHCGPCGYSDLAALE----EE---GLFGCLFECGTKQECEQIAFRLF
NP_001161071.1    PLDPRSWT-EPWVIYEGPSGYSDLASIGPAPEGG---LVFACLYESGARTSYDEISFCTF
NP_542779.2       PLDPRSWT-EPWVIYEGPSGYSDLASIGPAPEGG---LVFACLYESGARTSYDEISFCTF
NP_001161072.1    PLDPRSWT-EPWVIYEGPSGYSDLASIGPAPEGG---LVFACLYESGARTSYDEISFCTF
                       .*  .   :  *  ..**.* ::          :  *:* .    :.* .  :
Consensus         XXXXXXWXXXXXXXXXXGXXXYSXLXXXXXXXXXXXXXXXXXXLXEXXXXXXXXXIXXXXX

NP_000425.1       SVYGTL-----------------------
NP_005374.2       TLKQAFPAEY---LPQ-------------
sp|Q9UQ49|        THREILSHLQGDCTSPGRNPSQFKSN---
sp|Q9UQ49-2|      THREILSHLQGDCTSPGRNPSQFKSN---
NP_001161071.1    SLREVLENVPASPKPPNLGDKPRGCCWPS
NP_542779.2       SLREVLENVPASPKPPNLGDKPRGCCWPS
NP_001161072.1    SLREVLENVPASPKPPNLGDKPRGCCWPS
                  :   :
Consensus         XXXXXXXXXXXXXXXXXXXXXXXXXXXXX
```

FIG. 17B

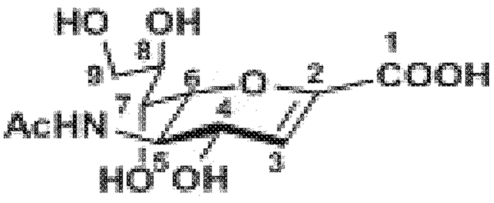
1
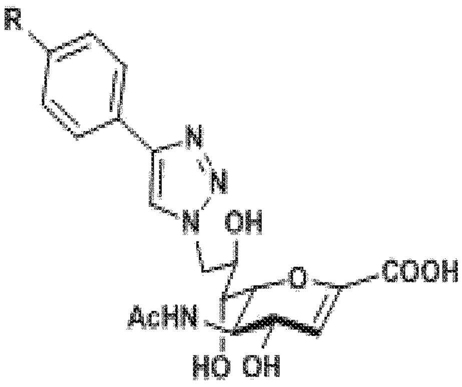
7
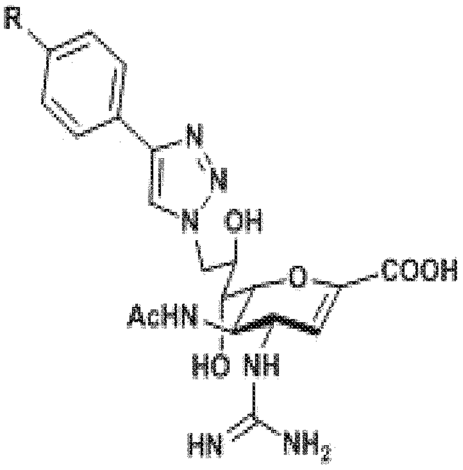
8
FIG. 18

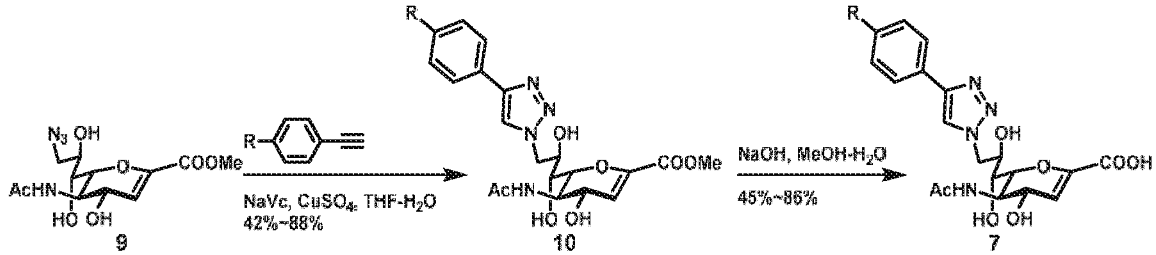
9 10 7
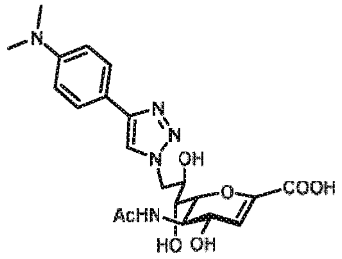
7a
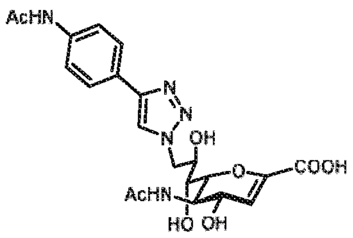
7b
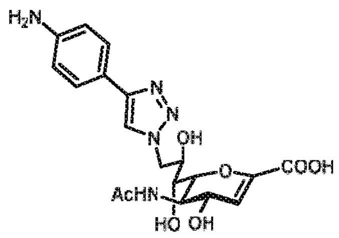
7c
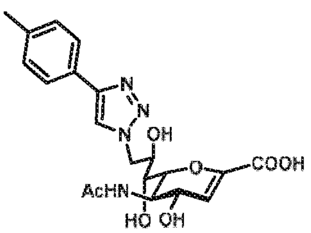
7d
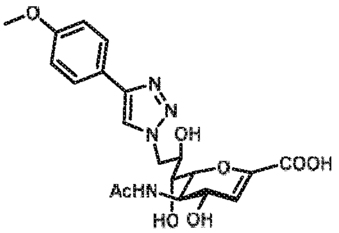
7e
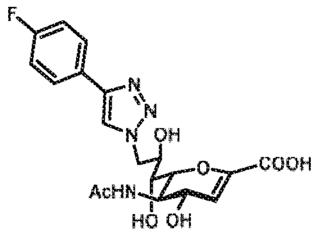
7f
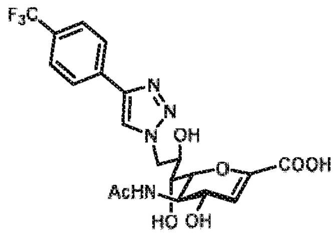
7g
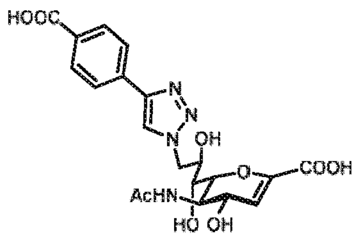
7h
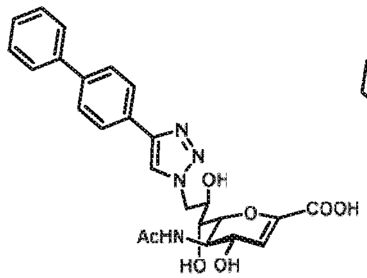
7i
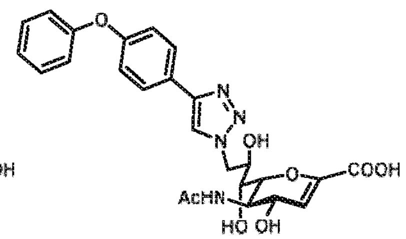
7j
FIG. 19

19 20 21 22 23 24 8b 19, 25, 25a, 25b, 25c, 25d

I-25

II-82ftzlpro

II-34

METHODS OF PREVENTING OR TREATING ATHEROSCLEROSIS WITH INHIBITORS OF SPECIFIC ISOENZYMES OF HUMAN NEURAMINIDASE

CROSS REFERENCE TO RELATED APPLICATIONS

This application is a national phase of PCT Application Serial No CA2018/050613 filed on May 25, 2018 and published in English under PCT Article 21(2), which itself claims benefit of U.S. provisional application Ser. No. 62/510,968, filed on May 25, 2017. All documents above are incorporated herein in their entirety by reference.

STATEMENT REGARDING FEDERALLY SPONSORED RESEARCH OR DEVELOPMENT

N.A.

FIELD OF THE INVENTION

The present invention relates to methods of preventing or treating atherosclerosis with inhibitors of specific isoenzymes of human neuraminidase. More specifically, the present invention is concerned with specific and bispecific inhibitors of neu1, or neu3.

REFERENCE TO SEQUENCE LISTING

Pursuant to 37 C.F.R. 1.821(c), a sequence listing is submitted herewith as an ASCII compliant text file named 765-PCT-SEQUENCE LISTING-12810-665_ST25, that was created on May 24, 2018 and having a size of 34 kilobytes.

The content of the aforementioned file named 765-PCT-SEQUENCE LISTING-12810-665_ST25 is hereby incorporated by reference in its entirety.

BACKGROUND OF THE INVENTION

Atherosclerosis, a chronic inflammatory disease of the medium and large arteries, is currently the most common cause of heart attacks, strokes and vascular disease (Lozano, 2010). It is characterized by lipid retention and inflammation of the vessel wall. The disease starts from the uptake by resident macrophages of atherogenic modified low-density lipoproteins (LDL) resulting in formation of arterial fatty streaks and eventually atheromatous plaques. The disease manifests with the endothelial disruption, inflammatory cascade, proliferation of smooth muscle cells, migration of monocytes into the tunica media and formation of atheromatous plaques (Spitz, 2016) occurring initially at the sites of reduced blood flow. Previous studies have identified a vast number of risk factors contributing to atherosclerosis in human population including hyperlipidemia, smoking, hypertension, genetic predisposition, age, sex, and obesity (Kalanuria, 2012); however, the cellular, biochemical, and molecular mechanisms underlying plaque development are still not fully understood. A critical role in the initiation and progression of atherosclerosis belongs to activation of the endothelial cells (Meager, 1999). It leads to secretion of proinflammatory cytokines, chemokines and increased expression of the adhesion surface molecules, which results in leukocyte adhesion and migration into the subendothelial space, where they differentiate into macrophages (Weber, 2008). Another crucial step in atherogenesis is infiltration of low-density lipoproteins (LDL) from the circulation into the subendothelial space of the artery wall, where they become modified and recognized by residential macrophages (Lusis, 2000). Uptake of modified LDL by macrophages leads to uncontrolled accumulation of cholesterol converting them to foam cells and triggering a cascade of immune responses that collectively lead to atheroma (Yu, 2013).

High levels of circulating cholesterol associated with LDL particles is a well-known risk factor for development and progression of atherosclerosis (Bentzon, 2014; Keys, 1997; and Martin, 1986). However at least 46% of first cardiovascular events occur in people with LDL levels at the normal range (Packard, 2008), suggesting that atherosclerosis is triggered not only by the increase of LDL level but also by changes in their composition including chemical modification of LDL molecules (Ahotupa, 2010).

Neuraminidases (encoded in mammals by the Neu1-Neu4 genes) catalyze the removal of sialic acids from glycoproteins, oligosaccharides, and sialylated glycolipids (Pilatte, 1993). Neuraminidases 1-4 have different, yet overlapping tissue expression, intracellular localization and substrate specificity. They play important physiological roles, regulating immune response, cell proliferation, metabolism, normal development and carcinogenesis by desialylation a wide spectrum of physiological substrates (Pshezhetsky, 2013).

The present description refers to a number of documents, the content of which is herein incorporated by reference in their entirety.

SUMMARY OF THE INVENTION

The present invention shows that specific neuraminidase enzymes present on the surface of hematopoietic cells and/or arterial endothelium contribute to development of atherosclerosis by removing sialic acid residues from glycan chains of LDL glycoproteins and glycolipids. More particularly, it demonstrates that in vitro desialylation of a major LDL glycoprotein—Apolipoprotein B 100 (ApoB) by human neuraminidases 1 and 3 increases the uptake of human LDL by cultured human macrophages, but not by hepatocytes. It also leads to increased accumulation of LDL in the aortic wall of mice. The present invention also demonstrates that LDL sialylation is increased in neu1 deficient models of atherosclerosis. It further shows that in the murine model of atherosclerosis, Apolipoprotein E (ApoE) knockout mice, genetic deficiency of neuraminidases 1 and 3 or treatment of mice with specific inhibitors of these enzymes significantly delays formation of fatty streaks in the aortic root without affecting the plasma cholesterol and LDL levels. It also shows that LDL levels are increased in the plasma of Neu1 KO mice. This is the first evidence identifying specific enzymes responsible for this important early step in atherosclerosis. The data support that neuraminidases 1 and 3 trigger the initial phase of atherosclerosis, leading to formation of aortic fatty streaks by reducing sialylation of LDL and increasing their uptake rate.

More specifically, in accordance with the present invention, there are provided the following items and items':

Item 1. A method of preventing or treating atherosclerosis or a symptom thereof comprising administering to a subject in need thereof a specific inhibitor of neuraminidase 1 (neu1); neuraminidase 3 (neu3); or a bispecific inhibitor of neu1 or neu3.

Item 2. The method of item 1, wherein the specific inhibitor is a compound of formula I (I)

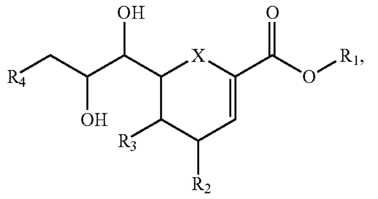

wherein $R_1$ is H; a C1-C10 alkyl; C1-C10 heteroalkyl; C3-C7 cycloalkyl; C3-C7 heterocycloalkyl; or C3-C8 aryl; or C3-C8 heteroaryl; wherein the alkyl, heteroalkyl, cycloalkyl, heterocycloalkyl, aryl and heteroaryl are optionally substituted by at least one substituent, each substituent being independently a C1-C10 alkyl, a C3-C8 cycloalkyl, a C3-C7 aryl, an halogen, an amide or an hydroxyl;

$R_2$ is H; —OH, —NHC(=NH)$NH_2$; or azide;

$R_3$ is —NHC(O)$(CH_2)$n$R_5$, wherein $R_5$ is H; —OH; C1-C10 alkyl; C1-C10 heteroalkyl; C3-C7 cycloalkyl; C3-C7 heterocycloalkyl; or C3-C8 aryl; wherein the alkyl, heteroalkyl, cycloalkyl, heterocycloalkyl, and aryl are optionally substituted by at least one substituent, each substituent being independently a C1-C10 alkyl, a C3-C8 cycloalkyl, a C3-C7 aryl, an halogen, an amide or an hydroxyl; and n is 0 or 1;

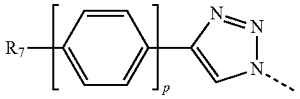

$R_4$ is H; —OH; —O-alkyl; —NHC(O)$R_6$; or wherein $R_6$ is H, C1-C10 alkyl; or C3-C7 aryl;

$R_7$ is H; halogen; —O-alkyl; —C(O)OH; amine; acetamide; —C1-C10 alkyl; —O-C3-C7 aryl; or —$(CH_2)$qNH(CO)aryl;

p is 0, 1, 2 or 3; and q is 0 or 1; and

X is O, $CH_2$ or S, with the proviso that when $R_2$ and $R_4$ are OH, $R_3$ is not —NHC(O)$CH_3$, or is an ester, solvate, hydrate or pharmaceutical salt thereof.

Item 3. The method of item 2, wherein $R_3$ is —NHC(O)$(CH_2)$n$R_5$.

Item 4. The method of item 2, wherein n is 0.

Item 5. The method of item 4, wherein $R_5$ is cycloalkyl.

Item 6. The method of item 4, wherein $R_5$ is aryl.

Item 7. The method of item 2, wherein n is 1.

Item 8. The method of item 7, wherein $R_5$ is H.

Item 9. The method of item 7, wherein $R_5$ is C1-C5 alkyl.

Item 10. The method of item 9, wherein the C1-C5 alkyl is branched.

Item 11. The method of any one of items 2-10, wherein $R_2$ is OH.

Item 12. The method of any one of items 2-9, wherein $R_2$ is —NHC(=NH)$NH_2$.

Item 13. The method of any one of items 2-9, wherein $R_2$ is azido.

Item 14. The method of any one of items 2-13, wherein $R_4$ is —OH.

Item 15. The method of any one of items 2-13, wherein $R_4$ is —NHC(O) $R_6$.

Item 16. The method of item 15, wherein $R_6$ is C3-C6 or C1-C10 alkyl.

Item 17. The method of item 16, wherein $R_6$ is C3-C6 of C1-C10 alkyl is branched.

Item 18. The method of item 15, wherein $R_6$ is C3-C7 aryl.

Item 19. The method of any one of items 2-13, wherein $R_4$ is

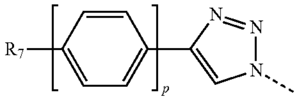

wherein $R_7$ and p are as defined in item 2.

Item 20. The method of item 19, wherein p is 0.

Item 21. The method of item 20, wherein $R_7$ is —$(CH_2)$qNH(CO)aryl.

Item 22. The method of item 20, wherein $R_7$ is -hydroxy C1-C10 alkyl.

Item 23. The method of item 19, wherein p is 1.

Item 24. The method of item 23, wherein $R_7$ is halogen.

Item 25. The method of item 23, wherein $R_7$ is O-alkyl.

Item 26. The method of item 23, wherein $R_7$ is —C(O)OH.

Item 27. The method of item 23, wherein $R_7$ is amine.

Item 28. The method of item 23, wherein $R_7$ is acetamide.

Item 29. The method of item 23, wherein $R_7$ is —C1-C10 alkyl.

Item 30. The method of item 23, wherein $R_7$ is —$CH_2$NH(CO)aryl.

Item 31. The method of item 23, wherein $R_7$ is —O—C3-C7 aryl.

Item 32. The method of item 19, wherein p is 2.

Item 33. The method of item 32, wherein $R_7$ is H.

Item 34. The method of item 2, wherein:

(i) $R_3$ is —NHC(O)$(CH_2)$n$CH_3$, wherein n is 0 to 7;

(ii) $R_2$ is —OH or —NHC(=NH)$NH_2$; and (iii) $R_4$ is —OH or

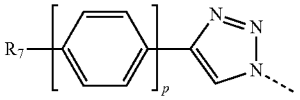, wherein p is 1, 2 or 3, and $R_7$ is H, —C(=O)OH, phenyl, or phenyloxy.

Item 35. The method of any one of items 2-34, wherein X is O.

Item 36. The method of any one of items 2-35, wherein $R_1$ is H or alkyl.

Item 37. The method of item 2, wherein the compound is of formula I, wherein X is O, $R_1$ is H, and $R_3$, $R_2$ and $R_4$ are as set forth below:

| R$_3$ (at position C5) is $CH_3C(O)NH$— | | |
|---|---|---|
| compound | R$_2$ (at position C4) | R$_4$ (at position C9) |
| 6 | 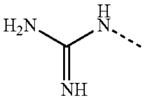 | HO—; |
| 7a | HO— | 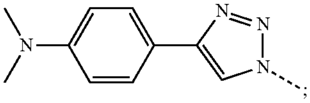 |
| 7b | HO— | 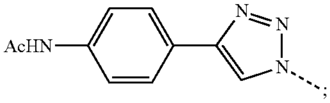 |
| 7c | HO— | 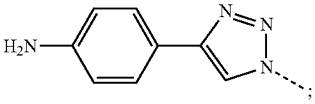 |
| 7d | HO— | 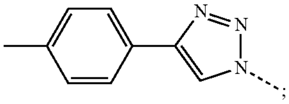 |
| 7e | HO— | 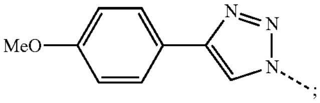 |
| 7f | HO— | 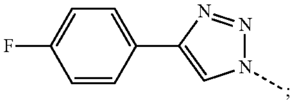 |
| 7g | HO— | 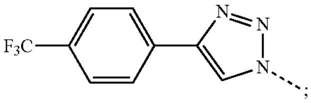 |
| 7h | HO— | 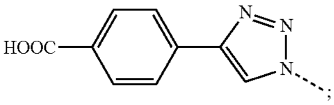 |
| 7i | HO— | 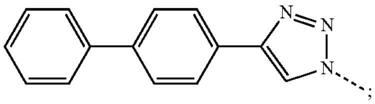 |
| 7j | HO— | 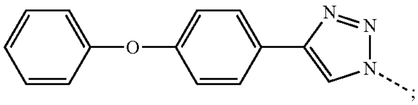 |
| 8a | 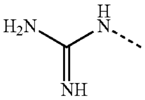 | 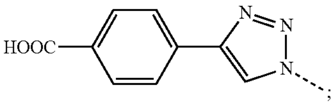 |
| 8b | 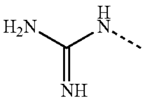 | 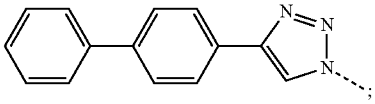 |

-continued
| | | |
|---|---|---|
| 13 | $N_3$— | 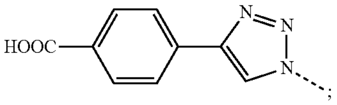 |
| 26 | HO— | 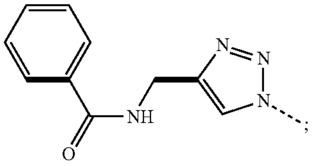 |
| 27 | HO— | 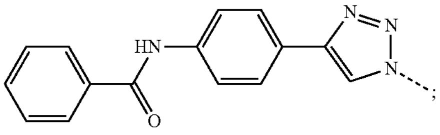 |
| C9-4HMT-DANA (28) | HO— | 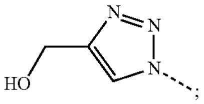 |
$R_2$ (at position C4) is HO—
| | $R_3$ (at position C5) | $R_4$ (at position C9) |
|---|---|---|
| 29 | 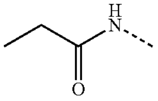 | HO—; |
| 30 | 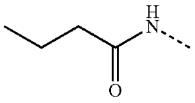 | HO—; |
| 31 | 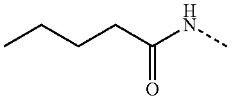 | HO—; |
| 32 | 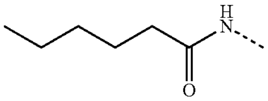 | HO—; |
| 33 | 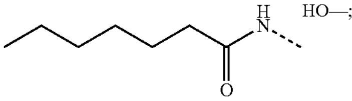 | HO—; |
| 34 | 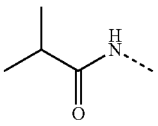 | HO—; |
| 35 | 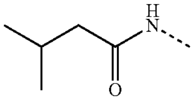 | HO—; |
| 36 | 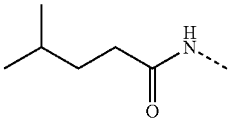 | HO—; |

-continued
| | | |
|---|---|---|
| 37 | 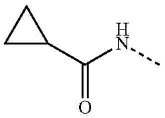 | HO—; |
| 38 | 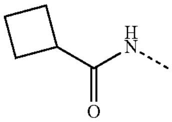 | HO—; |
| 39 | 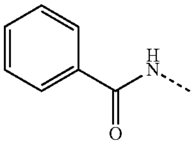 | HO—; |
| 40 | 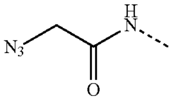 | HO—; |
| 49 | 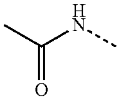 | 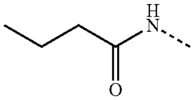; |
| 50 | 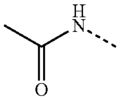 | 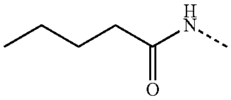; |
| 51 | 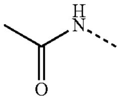 | 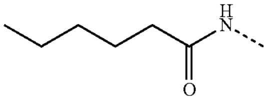; |
| 52 | 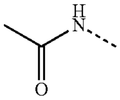 | 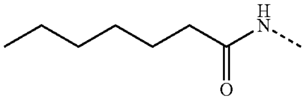; |
| 53 | 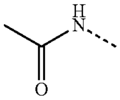 | 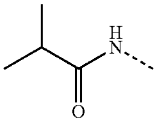; |
| 54 | 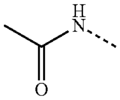 | 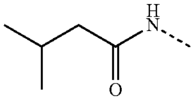; |
| 55 | 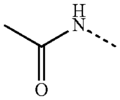 | 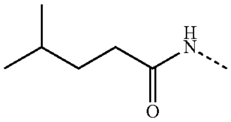; |
| 56 | 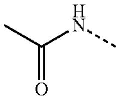 | 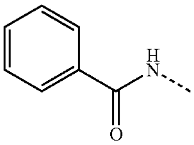; or |

-continued
| | | |
|---|---|---|
| 57 | 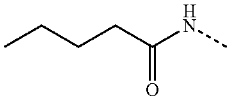 | 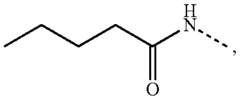 |
or an ester, solvate, hydrate or pharmaceutical salt thereof.
Item 38. The method of item 2, wherein the compound is of formula I, wherein X is O, $R_1$ is H, and $R_3$, $R_2$ and $R_4$ are as set forth below:
| $R_3$ (at position C5) is $CH_3C(O)NH$— | | |
|---|---|---|
| compound | $R_2$ (at position C4) | $R_4$ (at position C9) |
| 7h | HO— | 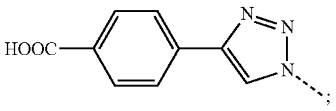 |
| 7i | HO— | 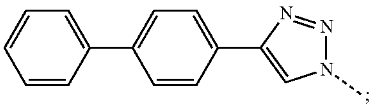 |
| 7j | HO— | 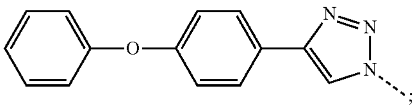 |
| 8a | 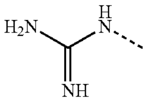 | 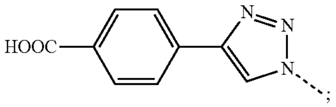 |
| 8b | 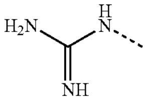 | 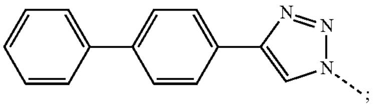 |
| $R_2$ (at position C4) is HO— | | |
|---|---|---|
| | $R_3$ (at position C5) | $R_4$ (at position C9) |
| 31 | 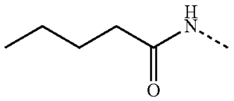 | HO—; |
| 32 | 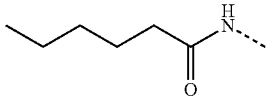 | HO—; |
| 33 | 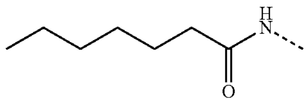 | HO—; |
| 36 | 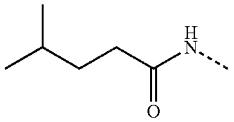 | HO—; |

-continued

| | | |
|---|---|---|
| 51 | 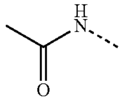 | 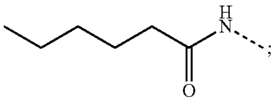; |
| 54 | 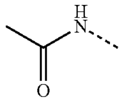 | 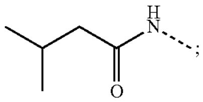; |
| 56 | 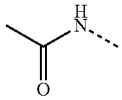 | 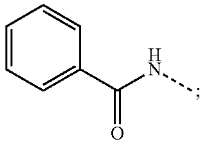; or |
| 57 | 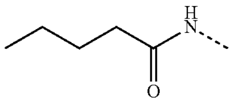 | 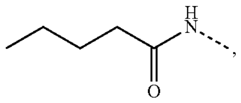, |

or an ester, solvate, hydrate or pharmaceutical salt thereof.

Item 39. The method of any one of items 2-38, wherein the compound of formula I is of formula Ia:

(Ia)

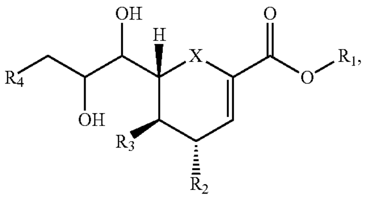

wherein $R_1$, $R_2$, $R_3$, $R_4$ and X are as defined in any one of items 2-38.

Item 40. The method of any one of items 2-38, wherein the compound of formula I is of formula Ib:

(Ib)

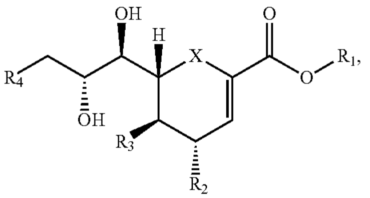

wherein $R_1$, $R_2$, $R_3$, $R_4$ and X are as defined in any one of any one of items 2-38.

Item 41. The method of any one of items 1 to 40, wherein the inhibitor is a specific or bispecific inhibitor of neu1.

Item 42. The method of any one of items 1 to 40, wherein the inhibitor is a specific or bispecific inhibitor of neu3.

Item 43. The method of item 42, wherein the inhibitor reduces the total plasma cholesterol and/or plasma LDL.

Item 44. A method of reducing inflammation comprising administering to a subject in need thereof a specific or bispecific inhibitor of neuraminidase 1 or neuraminidase 3.

Item 45. The method of items 44, wherein the specific inhibitor is as defined in any one of items 2 to 36.

Item 46. A compound of formula I (I)

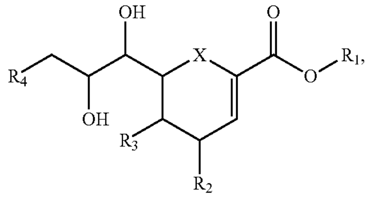

wherein $R_1$ is H, a C1-C10 alkyl, C1-C10 heteroalkyl; C3-C7 cycloalkyl; C3-C7 heterocycloalkyl, C3-C8 aryl; or C3-C8 heteroaryl; wherein the alkyl, heteroalkyl, cycloalkyl, heterocycloalkyl, aryl and heteroaryl are optionally substituted by at least one substituent, each substituent being independently a C1-C10 alkyl, a C3-C8 cycloalkyl, a C3-C7 aryl, an halogen, an amide or an hydroxyl;

$R_2$ is H; —OH; —NHC(=NH)$NH_2$; azide; amine; or NHC(=O)R;

wherein R is —$NH(CH_2)_m$COOH, wherein m is 1, 2 or 3;

$R_3$ is —NHC(O)$(CH_2)$n$R_5$, wherein $R_5$ is H; —OH; C1-C10 alkyl; C1-C10 heteroalkyl; C3-C7 cycloalkyl; C3-C7 heterocycloalkyl; C3-C8 aryl; or C3-C8 heteroaryl, wherein the alkyl, heteroalkyl, cycloalkyl, heterocycloalkyl, aryl and heteroaryl are optionally substituted by at least one substituent, each substituent being independently a C1-C10 alkyl, a C3-C8 cycloalkyl, a C3-C7 aryl; an halogen; an amide; or an hydroxyl; and n is 0 or 1;

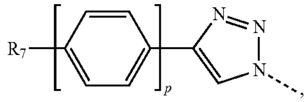, $R_4$ is H; —OH; —O-alkyl; —NHC(O)$R_6$; and wherein $R_6$ is H, C1-C10 alkyl; C3-C7 aryl;

$R_7$ is H; halogen; —O-alkyl; —C(O)OH; amine; amide; —C1-C10 alkyl; —O—C3-C7 aryl; —$(CH_2)$qNH(CO) aryl;

p is 0, 1, 2 or 3; and q is 0 or 1; and

X is O, $CH_2$ or S, or an ester, solvate, hydrate or pharmaceutical salt thereof, with the proviso that:

when $R_2$ and $R_4$ is —OH, $R_3$ is not —NHC(═O)$CH_3$, —NHC(═O)$CH_2CH_3$, —NHC(═O)$(CH_2)_2CH_3$, —NHC(═O)$CH(CH_3)_2$, —NHC(═O)$CH_2CH(CH_3)_2$, —NHC(═O)cyclopropyl, —NHC(═O)cyclobutyl, or —NHC(═O)phenyl;

when $R_2$ is —OH and $R_3$ is —NHC(═O)$CH_3$, $R_4$ is not -1,2,3-triazolyl-$CH_2$OH, —NHC(═O)$(CH_2)_2CH_3$, —NHC(═O)$(CH_2)_3CH_3$, —NHC(═O)$CH(CH_3)_2$, —NHC(═O)$CH_2CH(CH_3)_2$, or —NHC(═O)phenyl; and when $R_3$ is —NHC(═O)$CH_3$ and $R_4$ is OH, $R_2$ is not —NHC(═NH)$NH_2$.

Item 47. The compound of item 46, with the further proviso that:

when $R_3$ is —NHC(═O)$CH_3$, $R_2$ is —OH, and $R_4$ is

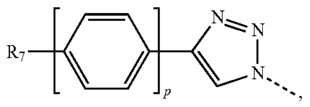

$R_7$ is not —$N(CH_3)_2$, —NHC(═O)$CH_3$, —$NH_2$, —$CH_3$, —$OCH_3$, F, —$CF_3$, or —C(═O)OH.

Item 48. The compound of item 46, wherein $R_3$ is —NHC(O)$(CH_2)$n$R_5$.

Item 49. The compound of item 46, wherein n is 1.

Item 50. The compound of item 49, wherein $R_5$ is H.

Item 51. The compound of item 49, wherein $R_5$ is C1-C5 alkyl.

Item 52. The compound of item 51, wherein the C1-C5 alkyl is branched.

Item 53. The compound of item 49, wherein $R_5$ is heteroaryl.

Item 54. The compound of item 53, wherein $R_5$ is

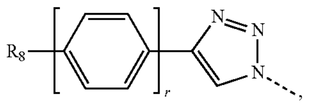

wherein $R_8$ is —$CF_3$, —$CH_3$, —C(═O)OH, —$OCH_3$, F, —$NH_2$, —$N(CH_3)_2$, or —NHC(═O)$CH_3$.

Item 55. The compound of item 53, wherein r is 1.

Item 56. The compound of any one of items 46-55, wherein $R_2$ is OH.

Item 57. The compound of any one of items 46-55, wherein $R_2$ is —NHC(═NH)$NH_2$.

Item 58. The compound of any one of items 46-55, wherein $R_2$ is azido.

Item 59. The compound of any one of items 46-55, wherein $R_2$ is —$NH_2$.

Item 60. The compound of any one of items 46-55, wherein $R_2$ is —NHC(═O)NH$(CH_2)_o$C(═O)OH, wherein o is 1, 2 or 3.

Item 61. The compound of any one of items 46-60, wherein $R_4$ is —OH.

Item 62. The compound of any one of items 46-60, wherein $R_4$ is —NHC(O)C3-C6 alkyl.

Item 63. The compound of any one of items 46-60, wherein $R_4$ is

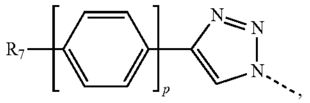

wherein $R_7$ and p are as defined in item 46.

Item 64. The compound of item 63, wherein p is 0.

Item 65. The compound of item 64, wherein $R_7$ is —$(CH_2)$qNH(CO)aryl.

Item 66. The compound of item 63, wherein p is 1.

Item 67. The compound of item 66, wherein $R_7$ is halogen.

Item 68. The compound of item 66, wherein $R_7$ is O-alkyl.

Item 69. The compound of item 66, wherein $R_7$ is —C(O)OH.

Item 70. The compound of item 66, wherein $R_7$ is amine.

Item 71. The compound of item 66, wherein $R_7$ is acetamide.

Item 72. The compound of item 66, wherein $R_7$ is —C1-C10 alkyl.

Item 73. The compound of item 66, wherein $R_7$ is —$CH_2$NH(CO)aryl.

Item 74. The compound of item 66, wherein $R_7$ is —O—C3-C7 aryl.

Item 75. The compound of item 63, wherein p is 2.

Item 76. The compound of item 75, wherein $R_7$ is H.

Item 77. The compound of any one of items 46 to 76, wherein X is O.

Item 78. The method of any one of items 46 to 77, wherein $R_1$ is H or alkyl.

Item 79. The compound of item 46, wherein:

(i) $R_3$ is —NHC(O)$(CH_2)$n$CH_3$, wherein n is 0 to 7;

(ii) $R_2$ is —OH or —NHC(═NH)$NH_2$; and (iii) $R_4$ is —OH or

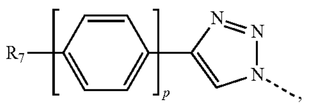

wherein p is 1, 2 or 3, and $R_7$ is H, —C(═O)OH, phenyl, or phenyloxy.

Item 80. The compound of item 46, wherein the compound is of formula I, wherein X is O, $R_1$ is H, and $R_3$, $R_2$ and $R_4$ are as set forth below:

| $R_3$ (at position C5) is $CH_3C(O)NH$— | | |
|---|---|---|
| compound | $R_2$ (at position C4) | $R_4$ (at position C9) |
| 7a | HO— | 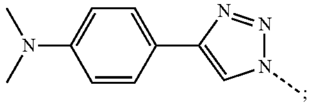 |
| 7b | HO— | 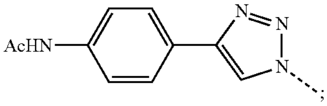 |
| 7c | HO— | 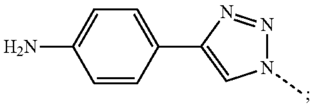 |
| 7d | HO— | 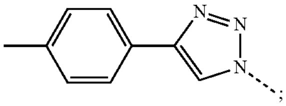 |
| 7e | HO— | 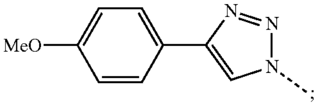 |
| 7f | HO— | 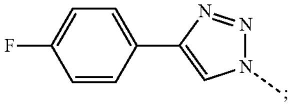 |
| 7g | HO— | 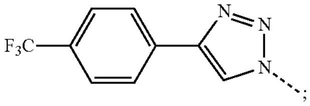 |
| 7h | HO— | 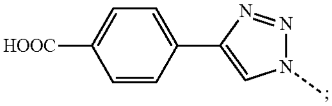 |
| 7i | HO— | 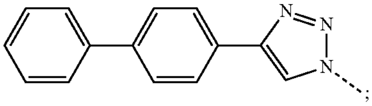 |
| 7j | HO— | 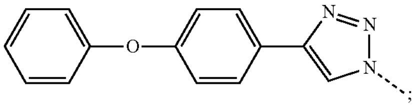 |
| 8a | 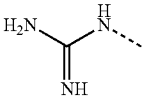 | 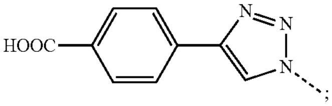 |
| 8b | 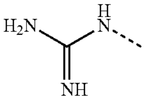 | 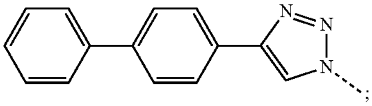 |

-continued
| | | |
|---|---|---|
| 13 | $N_3$— | 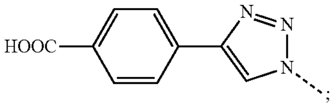 |
| 15 | $H_2N$— | 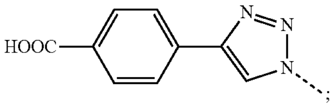 |
| 18 | 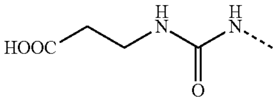 | 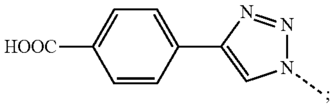 |
| 26 | HO— | 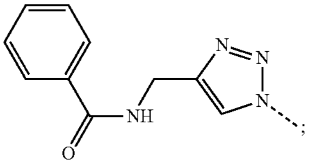 |
| 27 | HO— | 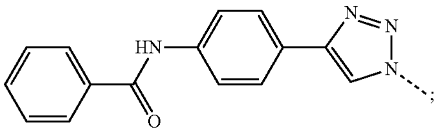 |
$R_2$ (at position C4) is HO—
| | $R_3$ (at position C5) | $R_4$ (at position C9) |
|---|---|---|
| 31 | 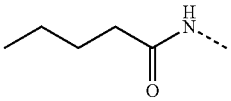 | HO—; |
| 3232 | 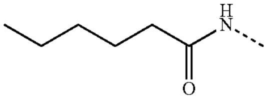 | HO—; |
| 33 | 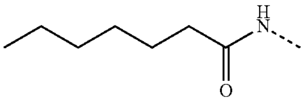 | HO—; |
| 36 | 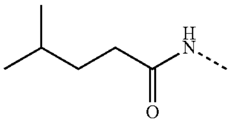 | HO—; |
| 40 | 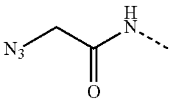 | HO—; |
| 41 | 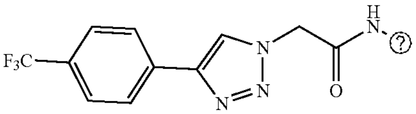 | HO—; |
| 42 | 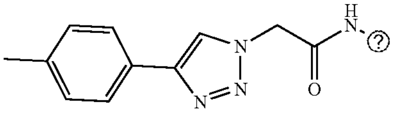 | HO—; |

-continued
| | | |
|---|---|---|
| 43 | 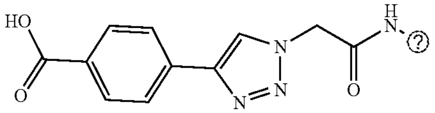 | HO—; |
| 44 | 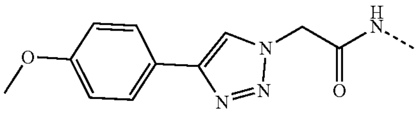 | HO—; |
| 45 | 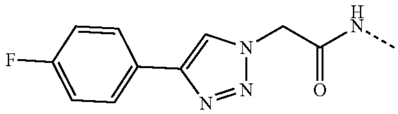 | HO—; |
| 46 | 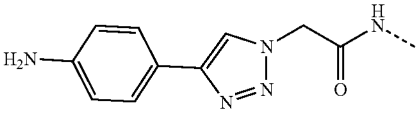 | HO—; |
| 47 | 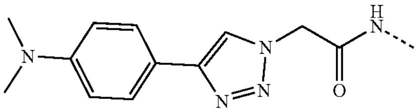 | HO—; |
| 48 | 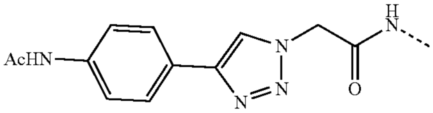 | HO—; |
| 51 | 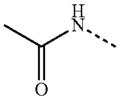 | 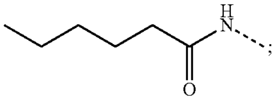 ; |
| 52 | 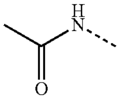 | 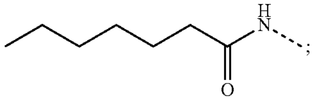 ; |
| 55 | 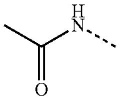 | 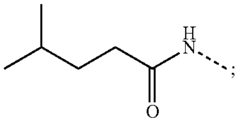 ; or |
| 57 | 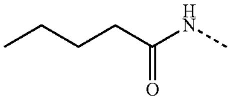 | 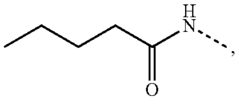 , |
or an ester, solvate, hydrate or pharmaceutical salt thereof.
Item 81. The compound of item 46, wherein $R_3$, $R_2$ and $R_4$, are as set forth below:
| $R_3$ (at position C5) is $CH_3C(O)NH$— | | |
|---|---|---|
| compound | $R_2$ (at position C4) | $R_4$ (at position C9) |
| 7i | HO— | 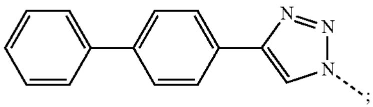 ; |

-continued
| | | |
|---|---|---|
| 7j | HO— | 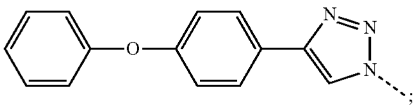 |
| 8a | 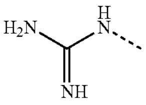 | 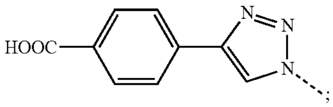 |
| 8b | 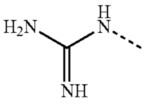 | 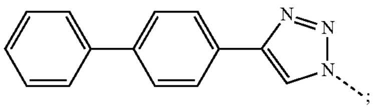 |
| 13 | $N_3$— | 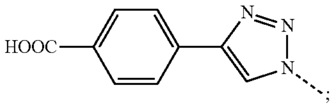 |
| 15 | $H_2N$— | 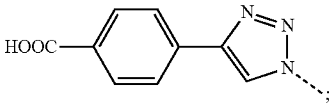 |
| 18 | 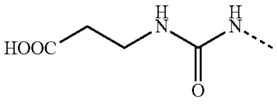 | 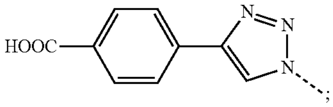 |
| 25b | 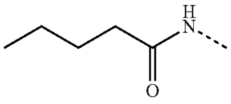 | HO—; |
| 25c | 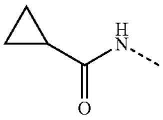 | HO—; |
| 25d | 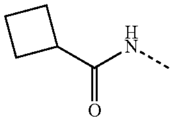 | HO—; |
| 26 | HO— | 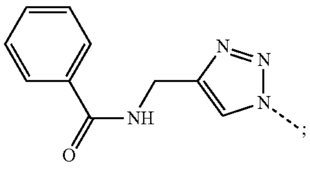 |
| 27 | HO— | 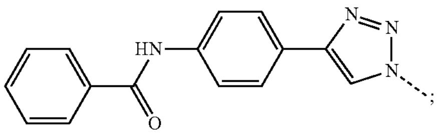 |

-continued
| $R_2$ (at position C4) is HO— | | |
|---|---|---|
| | $R_3$ (at position C5) | $R_4$ (at position C9) |
| 31 | 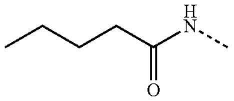 | HO—; |
| 32 | 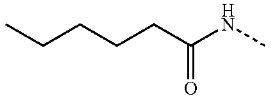 | HO—; |
| 33 | 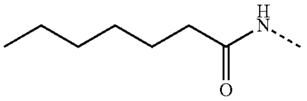 | HO—; |
| 36 | 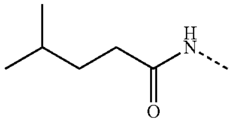 | HO—; |
| 40 | 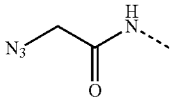 | HO—; |
| 41 | 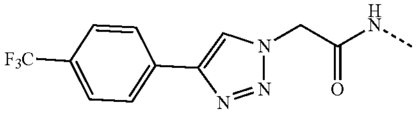 | HO—; |
| 42 | 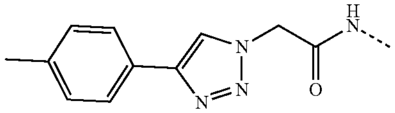 | HO—; |
| 43 | 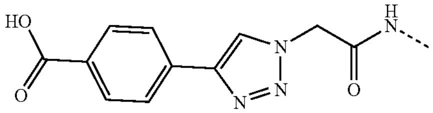 | HO—; |
| 44 | 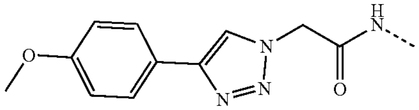 | HO—; |
| 45 | 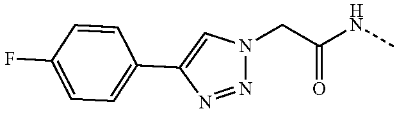 | HO—; |
| 46 | 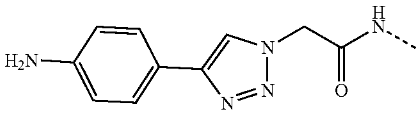 | HO—; |
| 47 | 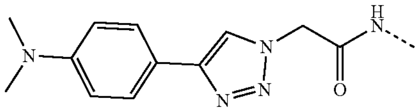 | HO—; |

-continued
| | | |
|---|---|---|
| 48 | 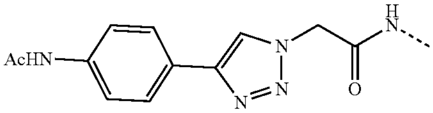 | HO—; |
| 51 | 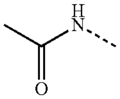 | 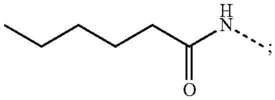 |
| 52 | 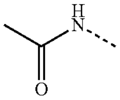 | 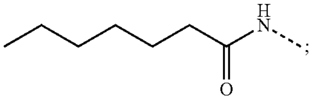 |
| 55 | 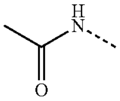 | 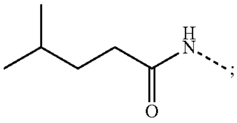 or |
| 57 | 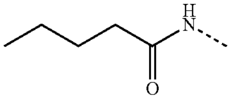 | 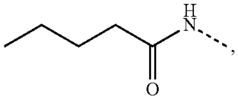 |
or an ester, solvate, hydrate or pharmaceutical salt thereof.
Item 82. The compound of item 46, wherein the compound is of formula I, wherein X is O, $R_1$ is H, and $R_3$, $R_2$ and $R_4$ are as set forth below:
| $R_3$ (at position C5) is $CH_3C(O)NH$— | | |
|---|---|---|
| compound | $R_2$ (at position C4) | $R_4$ (at position C9) |
| 7h | HO— | 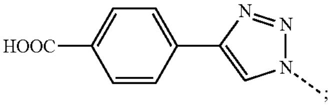 |
| 7i | HO— | 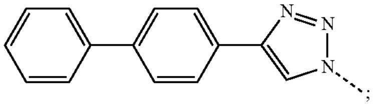 |
| 7j | HO— | 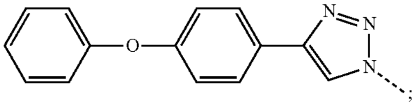 |
| 8a | 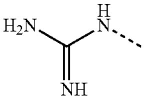 | 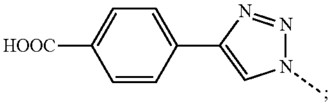 |
| 8b | 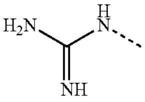 | 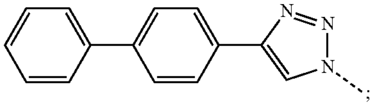 |

-continued
| $R_2$ (at position C4) is HO— | | |
|---|---|---|
| | $R_3$ (at position C5) | $R_4$ (at position C9) |
| 31 | 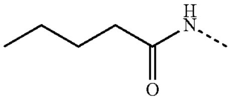 | HO—; |
| 32 | 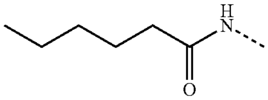 | HO—; |
| 33 | 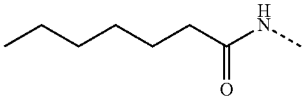 | HO—; |
| 36 | 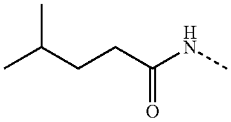 | HO—; |
| 51 | 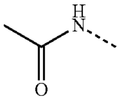 | 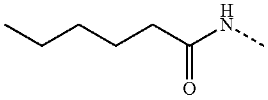 ; or |
| 57 | 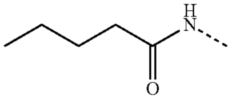 | 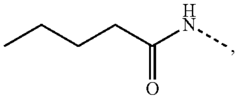 , |
or an ester, solvate, hydrate or pharmaceutical salt thereof.
Item 83. The compound of item 46, wherein the compound is of formula I, wherein X is O, $R_1$ is H, and $R_3$, $R_2$ and $R_4$ are as set forth below:
| $R_3$ (at position C5) is $CH_3C(O)NH$— | | |
|---|---|---|
| compound | $R_2$ (at position C4) | $R_4$ (at position C9) |
| 7i | HO— | 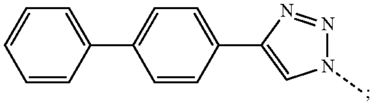 ; |
| 7j | HO— | 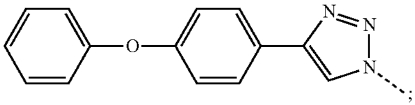 ; |
| 8a | 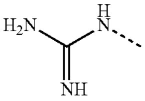 | 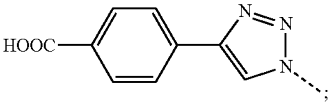 ; |
| 8b | 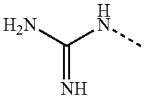 | 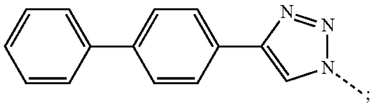 ; |

-continued

| R$_2$ (at position C4) is HO— | | |
|---|---|---|
| | R$_3$ (at position C5) | R$_4$ (at position C9) |
| 31 | 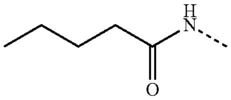 | HO—; |
| 32 | 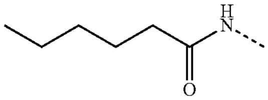 | HO—; |
| 33 | 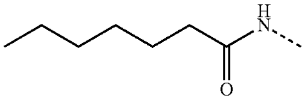 | HO—; |
| 36 | 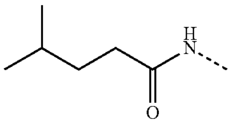 | HO—; |
| 51 | 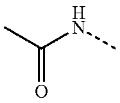 | 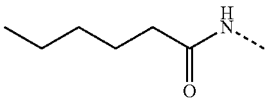; or |
| 57 | 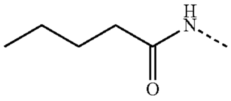 | 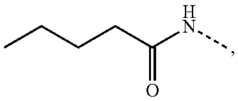, |

or an ester, solvate, hydrate or pharmaceutical salt thereof.

Item 84. The compound of any one of items 46 to 83, wherein the compound is of formula Ia:

(Ia)

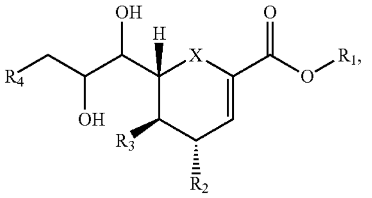

wherein $R_1$, $R_2$, $R_3$, $R_4$ and X are as defined in any one of items 46 to 83.

Item 85. The compound of any one of items 46 to 83, wherein the compound is of formula Ib:

(Ib)

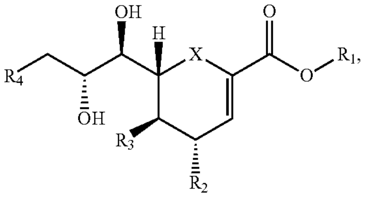

wherein $R_1$, $R_2$, $R_3$, $R_4$ and X are as defined in any one of items 46 to 83.

Item' 1. A method of preventing or treating atherosclerosis or a symptom thereof comprising administering to a subject in need thereof a therapeutically effective amount of a specific inhibitor of neuraminidase 1 (neu1); neuraminidase 3 (neu3); or a bispecific inhibitor of neu1 or neu3.

Item' 2. The method of claim' 1, wherein the inhibitor is a compound of formula I (I)

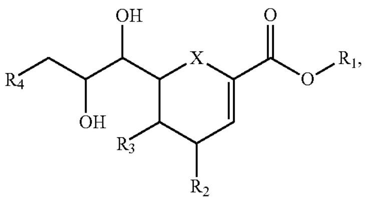

wherein $R_1$ is H; a C1-C10 alkyl; C1-C10 heteroalkyl; C3-C7 cycloalkyl; C3-C7 heterocycloalkyl; C3-C8 aryl; or C3-C8 heteroaryl; wherein the alkyl, heteroalkyl, cycloalkyl, heterocycloalkyl, aryl and heteroaryl are optionally substituted by at least one substituent, each substituent being independently a C1-C10 alkyl, a C3-C8 cycloalkyl, a C3-C7 aryl, an halogen, an amide or an hydroxyl;

$R_2$ is H; —OH, —NHC(=NH)$NH_2$; or azide;

$R_3$ is —NHC(O)$(CH_2)$n$R_5$, wherein $R_5$ is H; —OH; C1-C10 alkyl; C1-C10 heteroalkyl; C3-C7 cycloalkyl; C3-C7 heterocycloalkyl; or C3-C8 aryl;

wherein the alkyl, heteroalkyl, cycloalkyl, heterocycloalkyl, and aryl are optionally substituted by at least one substituent, each substituent being independently a C1-C10 alkyl, a C3-C8 cycloalkyl, a C3-C7 aryl, an halogen, an amide or an hydroxyl; and n is 0 or 1;

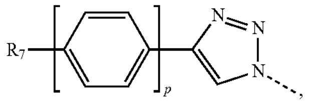

$R_4$ is H; —OH; —O-alkyl; —C(O)-alkyl-NHC(O)-aryl; —NHC(O)$R_6$; or wherein the alkyl and aryl are optionally substituted by at least one substituent, each substituent being independently a C1-C10 alkyl, a C3-C8 cycloalkyl, a C3-C7 aryl, an halogen, an amine, an amide or an hydroxyl, wherein: $R_6$ is H, C1-C10 alkyl; or C3-C7 aryl, wherein the C1-C10 alkyl and C3-C7 aryl are optionally substituted by at least one substituent, each substituent being independently a C1-C10 alkyl, a C3-C8 cycloalkyl, a C3-C7 aryl, an halogen, an amide, an amine or an hydroxyl;

$R_7$ is H; halogen; —O-alkyl; —C(O)OH; amine; acetamide; —C1-C10 alkyl; —O—C3-C7 aryl; or —$(CH_2)$qNH(CO)aryl, wherein the C1-C10 alkyl and C3-C7 aryl are optionally substituted by at least one substituent, each substituent being independently a C1-C10 alkyl, a C3-C8 cycloalkyl, a C3-C7 aryl, an halogen, an amide, an amine or an hydroxyl, wherein q is 0 or 1; and p is 0, 1, 2 or 3; and X is O, $CH_2$ or S, with the proviso that when $R_2$ and $R_4$ are OH, $R_3$ is not —NHC(O)$CH_3$, or is an ester, solvate, hydrate or pharmaceutical salt of the compound of formula I.

Item' 3. The method of claim' 2, wherein $R_3$ is —NHC(O)$(CH_2)$n$R_5$.

Item' 4. The method of claim' 2, wherein n is 0.

Item' 5. The method of claim' 4, wherein $R_5$ is cycloalkyl.

Item' 6. The method of claim' 4, wherein $R_5$ is aryl.

Item' 7. The method of claim' 4, wherein $R_5$ is C1-C10 alkyl.

Item' 8. The method of claim' 4, wherein $R_5$ is C1-C10 alkyl substituted with a C1-C10 alkyl.

Item' 9. The method of claim' 2, wherein n is 1.

Item' 10. The method of claim' 9, wherein $R_5$ is H.

Item' 11. The method of claim' 9, wherein $R_5$ is C1-C5 alkyl.

Item' 12. The method of claim' 11, wherein the C1-C5 alkyl is branched.

Item' 13. The method of any one of claims 2-12, wherein $R_2$ is OH.

Item' 14. The method of any one of claims 2-11, wherein $R_2$ is —NHC(=NH)$NH_2$.

Item' 15. The method of any one of claims 2-11, wherein $R_2$ is azido.

Item' 16. The method of any one of claims 2-15, wherein $R_4$ is —OH.

Item' 17. The method of any one of claims 2-15, wherein $R_4$ is —NHC(O)$R_6$.

Item' 18. The method of claim' 17, wherein $R_6$ is C1-C10 alkyl.

Item' 19. The method of claim' 18, wherein the C1-C10 alkyl is branched.

Item' 20. The method of claim' 17, wherein $R_6$ is C3-C7 aryl.

Item' 21. The method of claim' 20, wherein the C3-C7 aryl is substituted with an amine or an amide.

Item' 22. The method of any one of claims 2-15, wherein $R_4$ is

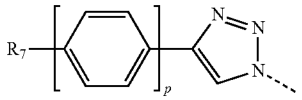

wherein $R_7$ and p are as defined in claim' 2.

Item' 23. The method of claim' 22, wherein p is 0.

Item' 24. The method of claim' 23, wherein $R_7$ is —$(CH_2)$qNH(CO)aryl.

Item' 25. The method of claim' 23, wherein $R_7$ is -hydroxy C1-C10 alkyl.

Item' 26. The method of claim' 20, wherein $R_7$ is C1-C10 alkyl.

Item' 27. The method of claim' 22, wherein p is 1.

Item' 28. The method of claim' 27, wherein $R_7$ is halogen.

Item' 29. The method of claim' 27, wherein $R_7$ is O-alkyl.

Item' 30. The method of claim' 27, wherein $R_7$ is —C(O)OH.

Item' 31. The method of claim' 27, wherein $R_7$ is amine.

Item' 32. The method of claim' 27, wherein $R_7$ is acetamide.

Item' 33. The method of claim' 27, wherein $R_7$ is —C1-C10 alkyl.

Item' 34. The method of claim' 27, wherein $R_7$ is —$CH_2$NH(CO)aryl.

Item' 35. The method of claim' 27, wherein $R_7$ is —O—C3-C7 aryl.

Item' 36. The method of claim' 22, wherein p is 2.

Item' 37. The method of claim' 36, wherein $R_7$ is H.

Item' 38. The method of any one of claims 2-15, wherein $R_4$ is —C(O)-alkyl-NHC(O)-aryl.

Item' 39. The method of claim' 38, wherein the alkyl is C1-C10 alkyl.

Item' 40. The method of claim' 38 or 39, wherein the aryl is C3-C7 aryl.

Item' 41. The method of claim' 38, wherein the C3-C7 aryl is substituted with an amide.

Item' 42. The method of claim' 2, wherein:

(i) $R_3$ is —NHC(O)$(CH_2)$n$R_5$, wherein n is 0 to 7 and wherein $R_5$ is C1-C10 alkyl, C3-C7 cycloalkyl, or C3-C8 aryl, wherein the alkyl, cycloalkyl, and aryl are optionally substituted by at least one substituent, each substituent being independently a C1-C10 alkyl, a C3-C8 cycloalkyl, a C3-C7 aryl, an halogen, an amide or an hydroxyl;

(ii) $R_2$ is —OH, —NHC(=NH)$NH_2$ or azide; and (iii) $R_4$ is —OH; —NHC(O)$R_6$, wherein $R_6$ is C1-C10 alkyl or C1-C5 aryl; —$(CH_2)$qNH(CO)aryl, wherein q is 0 or 1; or

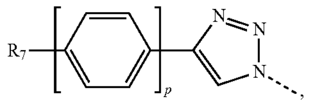

wherein p is 0, 1, 2 or 3, and $R_7$ is H, —C(=O)OH, phenyl, or phenyloxy, with the proviso that when $R_2$ and $R_4$ are OH, $R_3$ is not —NHC(O)$CH_3$.

Item' 43. The method of claim' 2, wherein:

(i) $R_3$ is —NHC(O)($CH_2$)n$CH_3$, wherein n is 0 to 7;

(ii) $R_2$ is —OH or —NHC(═NH)$NH_2$; and (iii) $R_4$ is —OH; —NHC(O)$R_6$, wherein $R_6$ is C3-C7 aryl or C1-C10 alkyl;

of

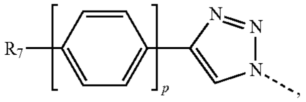

wherein p is 1, 2 or 3, and $R_7$ is H, —C(═O)OH, phenyl, or phenyloxy, with the proviso that when $R_2$ and $R_4$ are OH, $R_3$ is not —NHC(O)$CH_3$.

Item' 44. The method of any one of claims 2 to 43, wherein X is O.

Item' 45. The method of any one of claims 2 to 44, wherein $R_1$ is H or alkyl.

Item' 46. The method of claim' 2, wherein the compound is of formula I, wherein X is O, $R_1$ is H, and $R_3$, $R_2$ and $R_4$ are as set forth below:

| $R_3$ (at position C5) is $CH_3C(O)NH$— | | |
|---|---|---|
| compound | $R_2$ (at position C4) | $R_4$ (at position C9) |
| 6 | 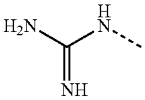 | HO—; |
| 7a | HO— | 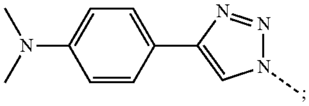 ; |
| 7b | HO— | 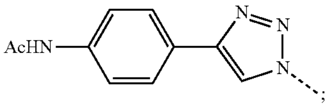 ; |
| 7c | HO— | 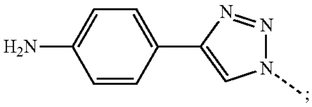 ; |
| 7d | HO— | 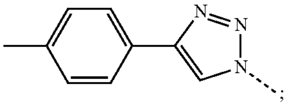 ; |
| 7e | HO— | 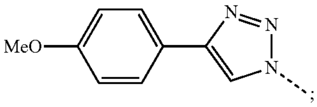 ; |
| 7f | HO— | 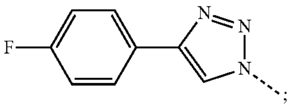 ; |
| 7g | HO— | 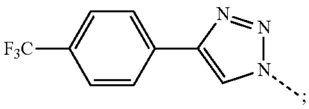 ; |
| 7h | HO— | 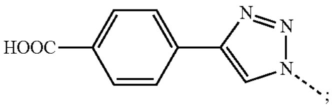 ; |

-continued
| | | |
|---|---|---|
| 7i | HO— | 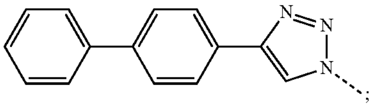 |
| 7j | HO— | 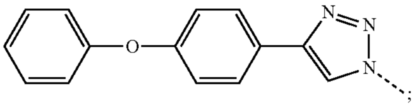 |
| 8a | 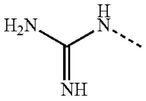 | 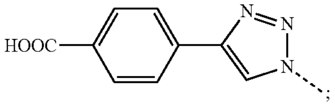 |
| 8b | 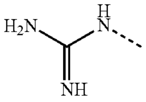 | 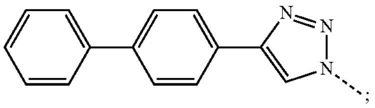 |
| 13 | $N_3$— | 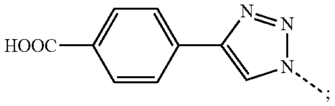 |
| 26 | HO— | 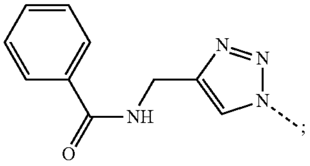 |
| 27 | HO— | 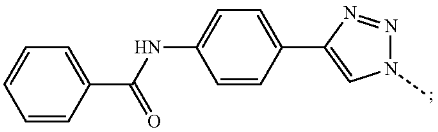 |
| C9-4HMT-DANA (28) | HO— | 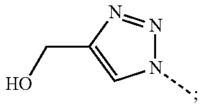 |
| 58 | HO— | 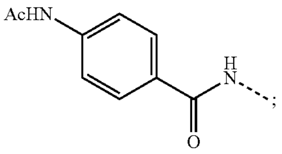 |
| 59 | HO— | 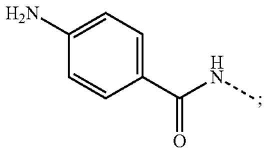 |
| 60 | HO— | 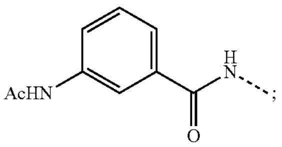 |

-continued
| | | |
|---|---|---|
| 61 | HO— | 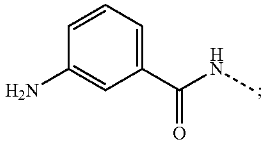 |
| 62 | HO— | 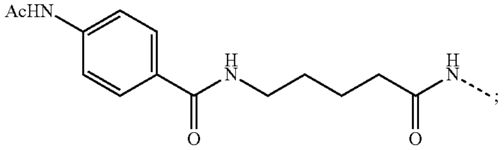 |
| 63 | HO— | 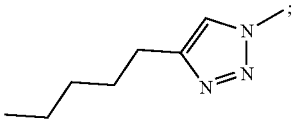 |
| R$_2$ (at position C4) is HO— | | |
|---|---|---|
| | R$_3$ (at position C5) | R$_4$ (at position C9) |
| 29 | 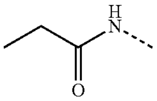 | HO—; |
| 30 | 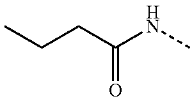 | HO—; |
| 31 | 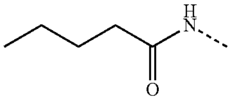 | HO—; |
| 32 | 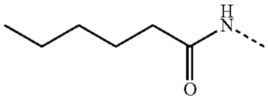 | HO—; |
| 33 | 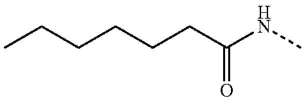 | HO—; |
| 34 | 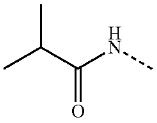 | HO—; |
| 35 | 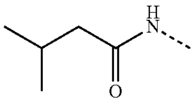 | HO—; |
| 36 | 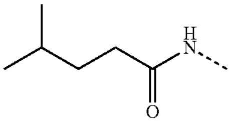 | HO—; |

-continued
| | | |
|---|---|---|
| 37 | 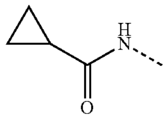 | HO—; |
| 38 | 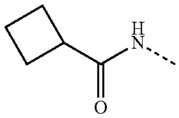 | HO—; |
| 39 | 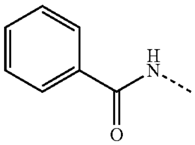 | HO—; |
| 40 | 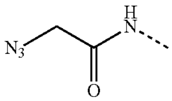 | HO—; |
| 49 | 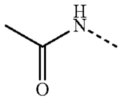 | 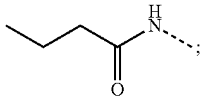 |
| 50 | 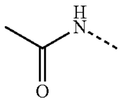 | 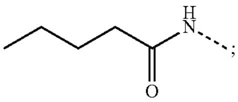 |
| 51 | 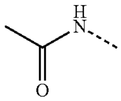 | 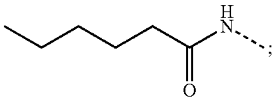 |
| 52 | 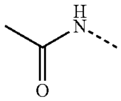 | 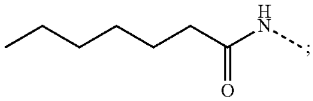 |
| 53 | 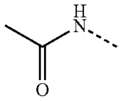 | 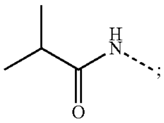 |
| 54 | 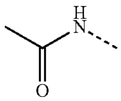 | 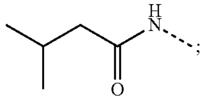 |
| 55 | 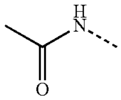 | 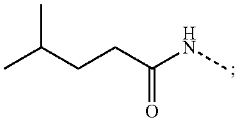 |
| 56 | 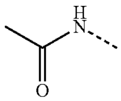 | 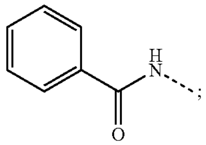 |

-continued
| | | |
|---|---|---|
| 57 | 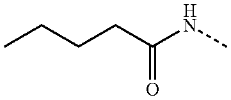 | 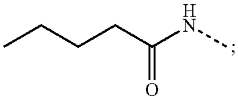 |
| 64 | 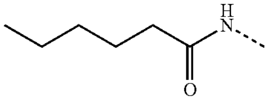 | 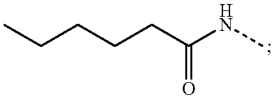 |
| 65 | 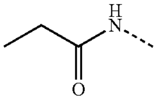 | 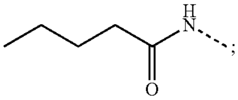 |
| 66 | 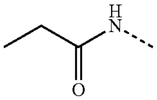 | 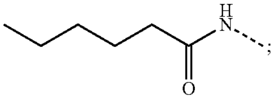 |
| 67 | 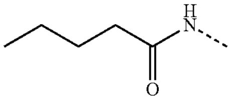 | 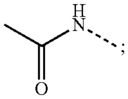 |
| 68 | 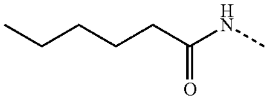 | 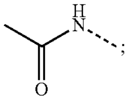 |
| 69 | 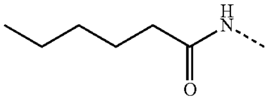 | 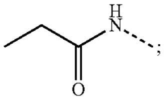 |
| 70 | 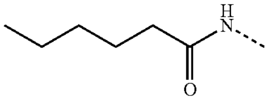 | 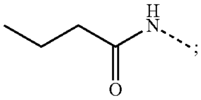 |
| 72 | 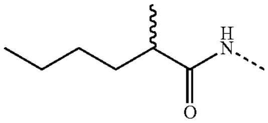 | HO—; |
| 73 | 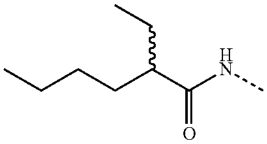 | 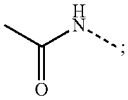 |
| 74 | 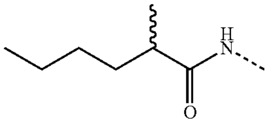 | 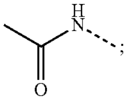 |
| 75 | 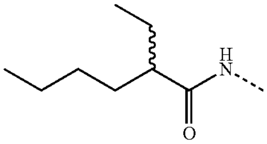 | HO—; or |

-continued

| R$_2$ (at position C4) is $NH_2C(=NH)NH$— | | |
|---|---|---|
| | R$_3$ (at position C5) | R$_4$ (at position C9) |
| 71 | 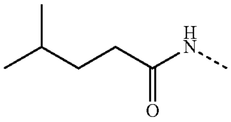 | HO—, |

or an ester, solvate, hydrate or pharmaceutical salt of the compound of formula I.

Item' 47. The method of claim' 2, wherein the compound is of formula I, wherein X is O, $R_1$ is H, and $R_3$, $R_2$ and $R_4$ are as set forth below:

| R$_3$ (at position C5) is $CH_3C(O)NH$— | | |
|---|---|---|
| compound | R$_2$ (at position C4) | R$_4$ (at position C9) |
| 7h | HO— | 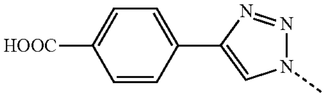; |
| 7i | HO— | 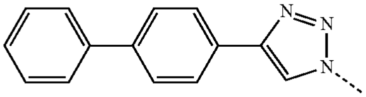; |
| 7j | HO— | 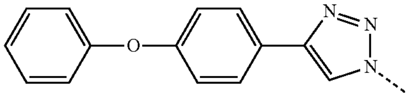; |
| 8a | 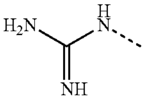 | 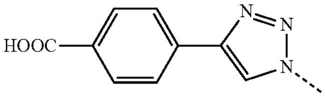; |
| 8b | 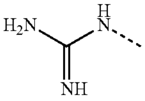 | 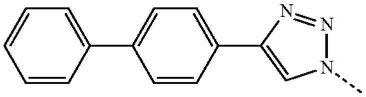; |
| R$_2$ (at position C4) is HO— | | |
| | R$_3$ (at position C5) | R$_4$ (at position C9) |
| 31 | 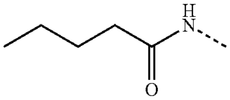 | HO—; |
| 32 | 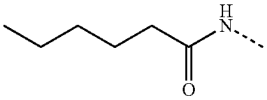 | HO—; |
| 33 | 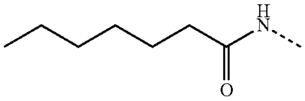 | HO—; |

-continued
| | | |
|---|---|---|
| 36 | 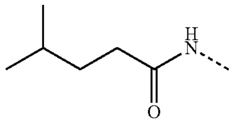 | HO—; |
| 51 | 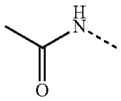 | 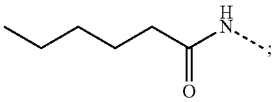 |
| 54 | 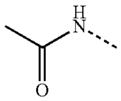 | 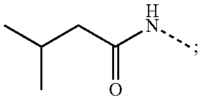 |
| 56 | 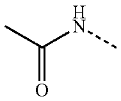 | 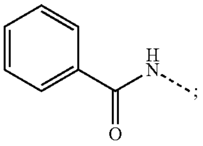 |
| 57 | 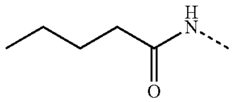 | 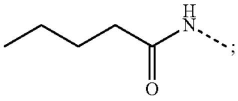 |
| 58 | HO— | 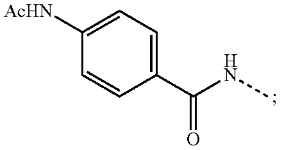 |
| 65 | 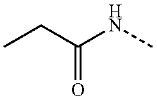 | 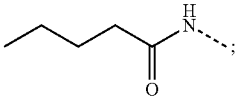 |
| 66 | 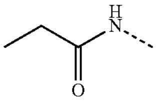 | 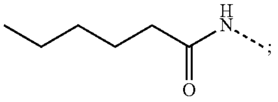 |
| 67 | 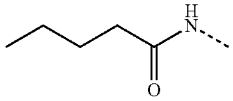 | 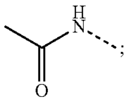 |
| 68 | 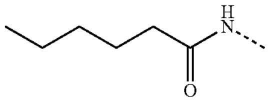 | 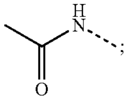 |
| 69 | 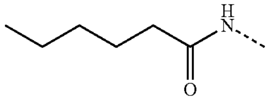 | 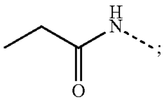 |
| 70 | 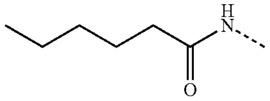 | 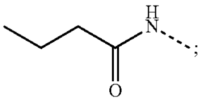 |
| 72 | 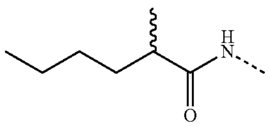 | HO—; |

-continued

| | | |
|---|---|---|
| 73 | 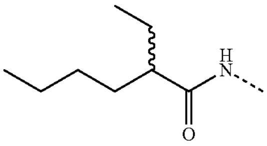 | 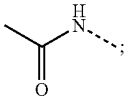 |
| 74 | 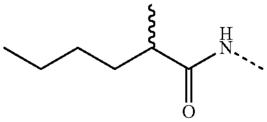 | 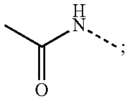 ; or |
| 75 | 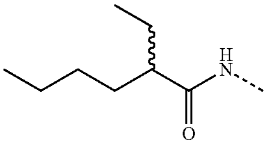 | HO—, |

or an ester, solvate, hydrate or pharmaceutical salt of the compound of formula I.

Item' 48. The method of any one of claims 2 to 47, wherein the compound of formula I is of formula Ia:

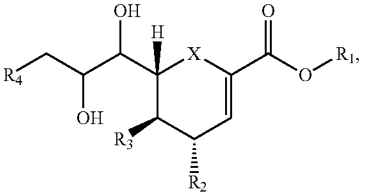

(Ia)

wherein $R_1$, $R_2$, $R_3$, $R_4$ and X are as defined in any one of claims 2 to 47.

Item' 49. The method of any one of claims 2 to 47, wherein the compound of formula I is of formula Ib:

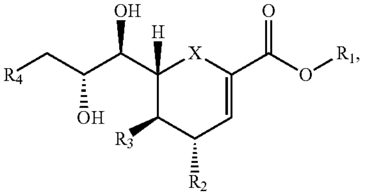

(Ib)

wherein $R_1$, $R_2$, $R_3$, $R_4$ and X are as defined in any one of claims 2 to 47.

Item' 50. The method of any one of claims 1 to 49, wherein the inhibitor is a specific or bispecific inhibitor of neu1.

Item' 51. The method of any one of claims 1 to 49, wherein the inhibitor is a specific or bispecific inhibitor of neu3.

Item' 52. The method of claim' 51, wherein the inhibitor reduces the total plasma cholesterol and/or plasma LDL.

Item' 53. A method of reducing inflammation comprising administering to a subject in need thereof a specific or bispecific inhibitor of neuraminidase 1 or neuraminidase 3.

Item' 54. The method of claims 53, wherein the specific inhibitor is as defined in any one of claims 2 to 53.

Item' 55. A compound of formula I

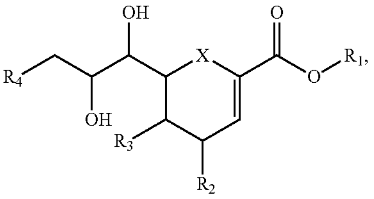

(I)

wherein $R_1$ is H, a C1-C10 alkyl, C1-C10 heteroalkyl; C3-C7 cycloalkyl; C3-C7 heterocycloalkyl; C3-C8 aryl; or C3-C8 heteroaryl; wherein the alkyl, heteroalkyl, cycloalkyl, heterocycloalkyl, aryl and heteroaryl are optionally substituted by at least one substituent, each substituent being independently a C1-C10 alkyl, a C3-C8 cycloalkyl, a C3-C7 aryl, an halogen, an amide or an hydroxyl;

$R_2$ is H; —OH; —NHC(═NH)$NH_2$; azide; or —NHC(O)R;

wherein R is —$NH(CH_2)_mCOOH$, wherein m is 1, 2 or 3;

$R_3$ is —$NHC(O)(CH_2)nR_5$, wherein $R_5$ is H; —OH; C1-C10 alkyl; C1-C10 heteroalkyl; C3-C7 cycloalkyl; C3-C7 heterocycloalkyl; C3-C8 aryl; C3-C8 heteroaryl; or

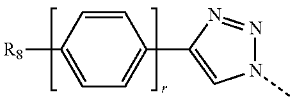 , wherein the alkyl, heteroalkyl, cycloalkyl, heterocycloalkyl, aryl and heteroaryl are optionally substituted by at least one substituent, each substituent being independently a C1-C10 alkyl; a C3-C8 cycloalkyl; a C3-C7 aryl; an halogen; a —C(O)OH; an amide; or an hydroxyl;

$R_5$ is a trifluoromethyl, a C1-C10 alkyl, a —C(O)OH, a —O—C1-C10 alkyl, an halogen, an amine, or —NH-acetamido; and r is 0, 1, 2 or 3; and n is 0 or 1;

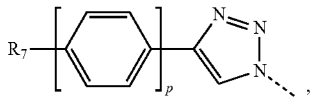

$R_4$ is H; —OH; —O-alkyl; —C(O)-alkyl-NHC(O)-aryl; —NHC(O) $R_6$; or wherein the alkyl and aryl are optionally substituted by at least one substituent, each substituent being independently a C1-C10 alkyl, a C3-C8 cycloalkyl, a C3-C7 aryl, an halogen, an amine, an amide or an hydroxyl, and wherein:

$R_6$ is H, C1-C10 alkyl; or C3-C7 aryl, wherein the C1-C10 alkyl and C3-C7 aryl are optionally substituted by at least one substituent, each substituent being independently a C1-C10 alkyl, a C3-C8 cycloalkyl, a C3-C7 aryl, an halogen, an amide, an amine or an hydroxyl;

$R_7$ is H; halogen; —O-alkyl; —C(O)OH; amine; amide; —C1-C10 alkyl; —O—C3-C7 aryl; or —$(CH_2)$qNH (CO)aryl, wherein q is 0 or 1; and p is 0, 1, 2 or 3; and X is O, $CH_2$ or S, or an ester, solvate, hydrate or pharmaceutical salt thereof, with the proviso that:

when $R_2$ and $R_4$ is —OH, $R_3$ is not —NHC(=O)$CH_3$, —NHC(=O)$CH_2CH_3$, —NHC(=O)$(CH_2)_2CH_3$, —NHC(=O)$CH(CH_3)_2$, —NHC(=O)$CH_2CH(CH_3)_2$, —NHC(=O)cyclopropyl, —NHC(=O)cyclobutyl, or —NHC(=O)phenyl;

when $R_2$ is —OH and $R_3$ is —NHC(=O)$CH_3$, $R_4$ is not -1,2,3-triazolyl-$CH_2$OH, —NHC(=O)$(CH_2)_2CH_3$, —NHC(=O)$(CH_2)_3CH_3$, —NHC(=O)$CH(CH_3)_2$, —NHC(=O)$CH_2CH(CH_3)_2$, or —NHC(=O)phenyl; and when $R_3$ is —NHC(=O)$CH_3$ and $R_4$ is OH, $R_2$ is not —NHC(=NH)$NH_2$.

Item' 56. The compound or ester, solvate, hydrate or pharmaceutical salt thereof of item' 55, with the further proviso that:

when $R_3$ is —NHC(=O)$CH_3$, $R_2$ is —OH, and $R_4$ is

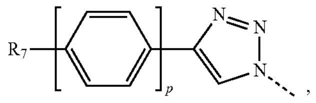

$R_7$ is not —$N(CH_3)_2$, —NHC(=O)$CH_3$, —$NH_2$, —$CH_3$, —$OCH_3$, F, —$CF_3$, or —C(=O)OH.

Item' 57. The compound or ester, solvate, hydrate or pharmaceutical salt thereof of item' 55 or 56, wherein $R_3$ is —NHC(O)$(CH_2)$n$R_5$.

Item' 58. The compound or ester, solvate, hydrate or pharmaceutical salt thereof of item' 57, wherein n is 0.

Item' 59. The compound or ester, solvate, hydrate or pharmaceutical salt thereof of item' 58, wherein $R_5$ is cycloalkyl.

Item' 60. The compound or ester, solvate, hydrate or pharmaceutical salt thereof of item' 58, wherein $R_5$ is aryl.

Item' 61. The compound or ester, solvate, hydrate or pharmaceutical salt thereof of item' 58, wherein $R_5$ is C1-C10 alkyl.

Item' 62. The compound or ester, solvate, hydrate or pharmaceutical salt thereof of item' 58, wherein $R_5$ is C1-C10 alkyl substituted with a C1-C10 alkyl.

Item' 63. The compound or ester, solvate, hydrate or pharmaceutical salt thereof of item' 57, wherein n is 1.

Item' 64. The compound or ester, solvate, hydrate or pharmaceutical salt thereof of item' 63, wherein $R_5$ is H.

Item' 65. The compound or ester, solvate, hydrate or pharmaceutical salt thereof of item' 63, wherein $R_5$ is C1-C5 alkyl.

Item' 66. The compound or ester, solvate, hydrate or pharmaceutical salt thereof of item' 65, wherein the C1-C5 alkyl is branched.

Item' 67. The compound or ester, solvate, hydrate or pharmaceutical salt thereof of item' 63, wherein $R_5$ is heteroaryl.

Item' 68. The compound or ester, solvate, hydrate or pharmaceutical salt thereof of item' 63, wherein $R_5$ is

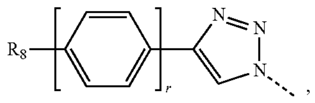

wherein $R_6$ is —$CF_3$, —$CH_3$, —C(=O)OH, —$OCH_3$, F, —$NH_2$, —$N(CH_3)_2$, or —NHC(=O)$CH_3$.

Item' 69. The compound or ester, solvate, hydrate or pharmaceutical salt thereof of item' 68, wherein r is 1.

Item' 70. The compound or ester, solvate, hydrate or pharmaceutical salt thereof of any one of items' 55-69, wherein $R_2$ is OH.

Item' 71. The compound or ester, solvate, hydrate or pharmaceutical salt thereof of any one of items' 55-69, wherein $R_2$ is —NHC(=NH)$NH_2$.

Item' 72. The compound or ester, solvate, hydrate or pharmaceutical salt thereof of any one of items' 55-69, wherein $R_2$ is azido.

Item' 73. The compound or ester, solvate, hydrate or pharmaceutical salt thereof of any one of items' 55-69, wherein $R_2$ is —NHC(O)R.

Item' 74. The compound or ester, solvate, hydrate or pharmaceutical salt thereof of any one of items' 55-69, wherein $R_2$ is —$NH(CH_2)_m$C(O)OH, wherein m is 1, 2 or 3.

Item' 75. The compound or ester, solvate, hydrate or pharmaceutical salt thereof of any one of items' 55-74, wherein $R_4$ is —OH.

Item' 76. The compound or ester, solvate, hydrate or pharmaceutical salt thereof of any one of items' 55-74, wherein $R_4$ is —NHC(O)$R_6$.

Item' 77. The compound or ester, solvate, hydrate or pharmaceutical salt thereof of item' 76, wherein $R_6$ is C1-C10 alkyl.

Item' 78. The compound or ester, solvate, hydrate or pharmaceutical salt thereof of item' 77, wherein the C1C10 alkyl is branched.

Item' 79. The compound or ester, solvate, hydrate or pharmaceutical salt thereof of item' 76, wherein $R_6$ is C3-C7 aryl.

Item' 80. The compound or ester, solvate, hydrate or pharmaceutical salt thereof of item' 79, wherein the C3-C7 aryl is substituted with an amine or an amide.

Item' 81. The compound or ester, solvate, hydrate or pharmaceutical salt thereof of any one of items' 55-75, wherein $R_4$ is

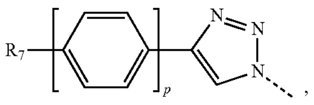

wherein $R_7$ and p are as defined in item' 55.

Item' 82. The compound or ester, solvate, hydrate or pharmaceutical salt thereof of item' 81, wherein p is 0.

Item' 83. The compound or ester, solvate, hydrate or pharmaceutical salt thereof of item' 82, wherein $R_7$ is —$(CH_2)$qNH(CO)aryl.

Item' 84. The compound or ester, solvate, hydrate or pharmaceutical salt thereof of item' 82, wherein $R_7$ is C1-C10 alkyl.

Item' 85. The compound or ester, solvate, hydrate or pharmaceutical salt thereof of item' 81, wherein p is 1.

Item' 86. The compound or ester, solvate, hydrate or pharmaceutical salt thereof of item' 85, wherein $R_7$ is halogen.

Item' 87. The compound or ester, solvate, hydrate or pharmaceutical salt thereof of item' 85, wherein $R_7$ is O-alkyl. Item' 88. The compound or ester, solvate, hydrate or pharmaceutical salt thereof of item' 85, wherein $R_7$ is —C(O)OH.

Item' 89. The compound or ester, solvate, hydrate or pharmaceutical salt thereof of item' 85, wherein $R_7$ is amine.

Item' 90. The compound or ester, solvate, hydrate or pharmaceutical salt thereof of item' 85, wherein $R_7$ is acetamide.

Item' 91. The compound or ester, solvate, hydrate or pharmaceutical salt thereof of item' 85, wherein $R_7$ is C1-C10 alkyl.

Item' 92. The compound or ester, solvate, hydrate or pharmaceutical salt thereof of item' 85, wherein $R_7$ is —$CH_2$NH(CO)aryl.

Item' 93. The compound or ester, solvate, hydrate or pharmaceutical salt thereof of item' 85, wherein $R_7$ is —O—C3-C7 aryl.

Item' 94. The compound or ester, solvate, hydrate or pharmaceutical salt thereof of item' 81, wherein p is 2.

Item' 95. The compound or ester, solvate, hydrate or pharmaceutical salt thereof of item' 94, wherein $R_7$ is H.

Item' 96. The compound or ester, solvate, hydrate or pharmaceutical salt thereof of any one of items' 55-74, wherein $R_4$ is —C(O)-alkyl-NHC(O)-aryl.

Item' 97. The compound or ester, solvate, hydrate or pharmaceutical salt thereof of item' 96, wherein the alkyl is C1-C10 alkyl.

Item' 98. The compound or ester, solvate, hydrate or pharmaceutical salt thereof of item' 96 or 97, wherein the aryl is C3-C7 aryl.

Item' 99. The compound or ester, solvate, hydrate or pharmaceutical salt thereof of item' 99, wherein the C3-C7 aryl is substituted with an amide.

Item' 100. The compound of item' 55 or 56, wherein:

(i) $R_3$ is —NHC(O)$(CH_2)$n$R_5$, wherein n is 0 to 7 and wherein $R_5$ is C1-C10 alkyl, C3-C7 cycloalkyl, or C3-C8 aryl, wherein the alkyl, cycloalkyl, and aryl are optionally substituted by at least one substituent, each substituent being independently a C1-C10 alkyl, a C3-C8 cycloalkyl, a C3-C7 aryl, an halogen, an amide or an hydroxyl;

(ii) $R_2$ is —OH, —NHC(=NH)$NH_2$ or azide; and (iii) $R_4$ is —OH; —NHC(O) $R_6$, wherein $R_6$ is C1-C10 alkyl or C1-C5 aryl; —$(CH_2)$qNH(CO)aryl, wherein q is 0 or 1; or

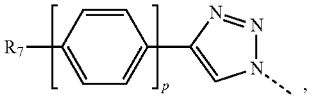

wherein p is 0, 1, 2 or 3, and $R_7$ is H, —C(=O)OH, phenyl, or phenyloxy, with the proviso that:

when $R_2$ and $R_4$ is —OH, $R_3$ is not —NHC(=O)$CH_3$, —NHC(=O)$CH_2CH_3$, —NHC(=O)$(CH_2)_2CH_3$, —NHC(=O)$CH(CH_3)_2$, —NHC(=O)$CH_2CH(CH_3)_2$, —NHC(=O)cyclopropyl, —NHC(=O)cyclobutyl, or —NHC(=O)phenyl;

when $R_2$ is —OH and $R_3$ is —NHC(=O)$CH_3$, $R_4$ is not —NHC(=O)$(CH_2)_2CH_3$, —NHC(=O)$(CH_2)_3CH_3$, —NHC(=O)$CH(CH_3)_2$, —NHC(=O)$CH_2CH(CH_3)_2$, or —NHC(=O)phenyl; and when $R_3$ is —NHC(=O)$CH_3$ and $R_4$ is OH, $R_2$ is not —NHC(=NH)$NH_2$.

Item' 101. The compound or ester, solvate, hydrate or pharmaceutical salt thereof of item' 55 or 56, wherein:

(i) $R_3$ is —NHC(O)$(CH_2)$n$CH_3$, wherein n is 0 to 7;

(ii) $R_2$ is —OH or —NHC(=NH)$NH_2$; and (iii) $R_4$ is —OH; —NHC(O) $R_6$, wherein $R_6$ is C3-C7 aryl or C1-C10 alkyl; or

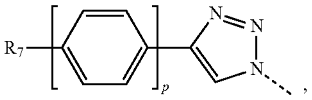

wherein p is 1, 2 or 3, and $R_7$ is H, —C(=O)OH, phenyl, or phenyloxy, with the proviso that:

when $R_2$ and $R_4$ is —OH, $R_3$ is not —NHC(=O)$CH_3$, —NHC(=O)$CH_2CH_3$, or —NHC(=O)$(CH_2)_2CH_3$;

when $R_2$ is —OH and $R_3$ is —NHC(=O)$CH_3$, $R_4$ is not —NHC(=O)$(CH_2)_2CH_3$, —NHC(=O)$(CH_2)_3CH_3$, —NHC(=O)$CH(CH_3)_2$, —NHC(=O)$CH_2CH(CH_3)_2$, or —NHC(=O)phenyl; and when $R_3$ is —NHC(=O)$CH_3$ and $R_4$ is OH, $R_2$ is not —NHC(=NH)$NH_2$.

Item' 102. The compound or ester, solvate, hydrate or pharmaceutical salt thereof of any one of items' 55 to 101, wherein X is O.

Item' 103. The compound or ester, solvate, hydrate or pharmaceutical salt thereof of any one of items' 55 to 102, wherein $R_1$ is H or alkyl.

Item' 104. The compound of item' 55, wherein the compound is of formula I, wherein X is O, $R_1$ is H, and $R_3$, $R_2$ and $R_4$ are as set forth below:

| R₃ (at position C5) is $CH_3C(O)NH—$ | | |
| --- | --- | --- |
| compound | $R_2$ (at position C4) | $R_4$ (at position C9) |
| 7a | HO— | 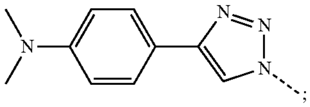 |
| 7b | HO— | 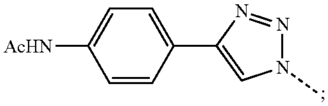 |
| 7c | HO— | 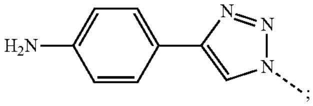 |
| 7d | HO— | 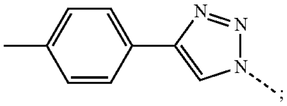 |
| 7e | HO— | 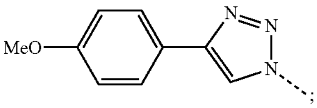 |
| 7f | HO— | 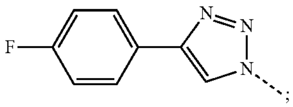 |
| 7g | HO— | 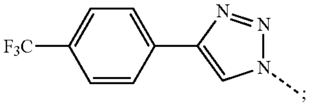 |
| 7h | HO— | 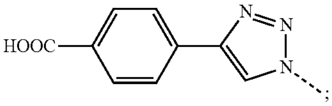 |
| 7i | HO— | 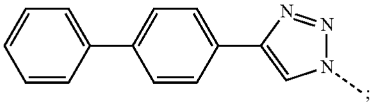 |
| 7j | HO— | 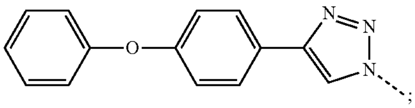 |
| 8a | 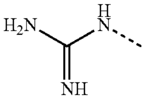 | 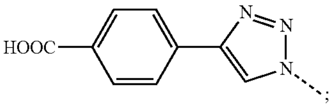 |
| 8b | 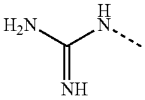 | 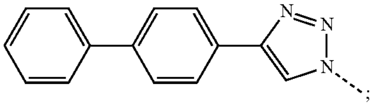 |
| 13 | $N_3—$ | 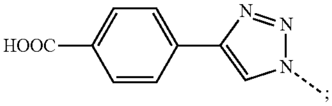 |

-continued
| | | |
|---|---|---|
| 18 | 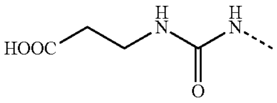 | 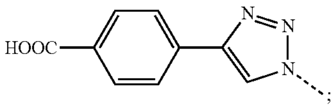 |
| 26 | HO— | 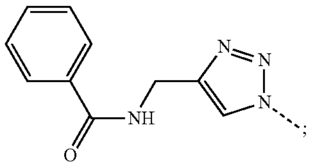 |
| 27 | HO— | 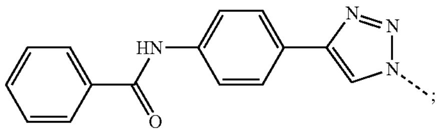 |
| 58 | HO— | 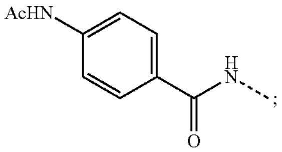 |
| 59 | HO— | 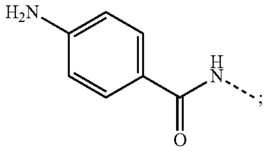 |
| 60 | HO— | 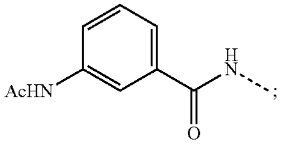 |
| 61 | HO— | 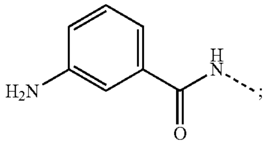 |
| 62 | HO— | 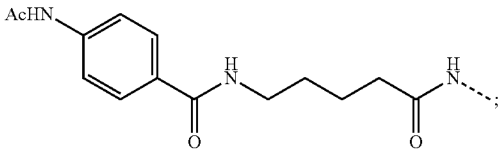 |
| 63 | HO— | 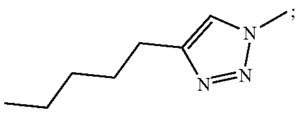 |
| $R_2$ (at position C4) is HO— | | |
|---|---|---|
| | $R_3$ (at position C5) | $R_4$ (at position C9) |
| 31 | 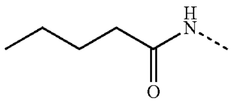 | HO—; |

-continued
| | | |
|---|---|---|
| 32 | 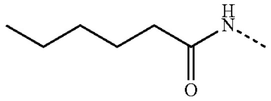 | HO—; |
| 33 | 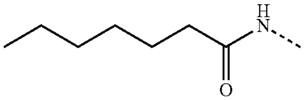 | HO—; |
| 36 | 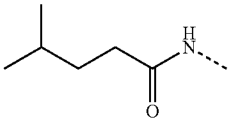 | HO—; |
| 40 | 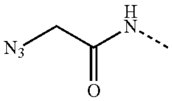 | HO—; |
| 41 | 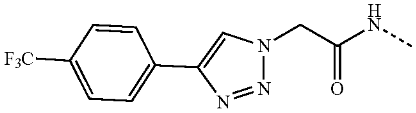 | HO—; |
| 42 | 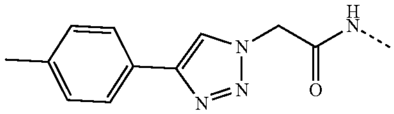 | HO—; |
| 43 | 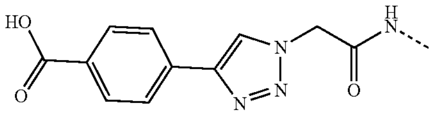 | HO—; |
| 44 | 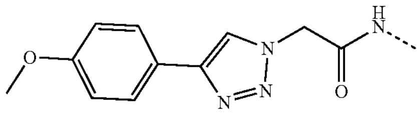 | HO—; |
| 45 | 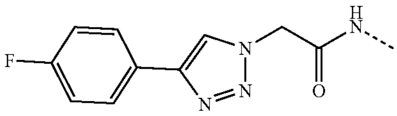 | HO—; |
| 46 | 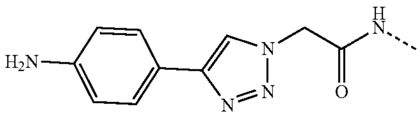 | HO—; |
| 47 | 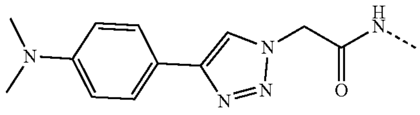 | HO—; |
| 48 | 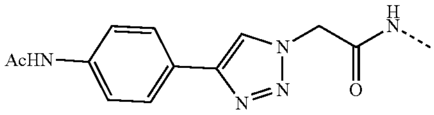 | HO—; |
| 51 | 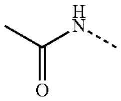 | 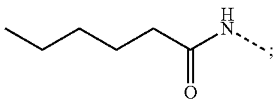; |

-continued
| | | |
|---|---|---|
| 52 | 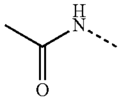 | 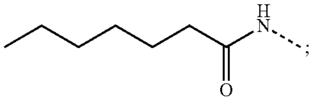 |
| 55 | 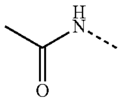 | 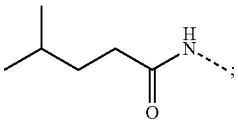 |
| 57 | 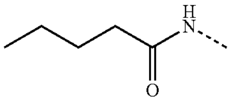 | 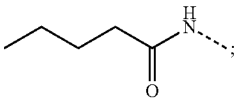 |
| 64 | 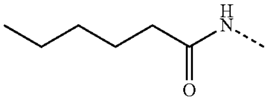 | 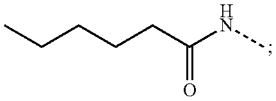 |
| 65 | 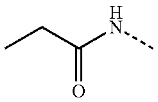 | 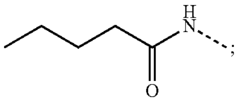 |
| 66 | 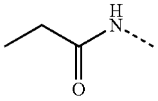 | 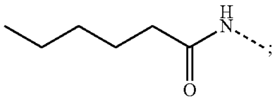 |
| 67 | 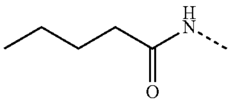 | 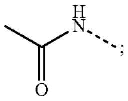 |
| 68 | 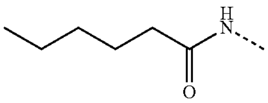 | 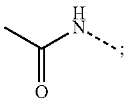 |
| 69 | 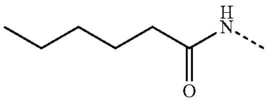 | 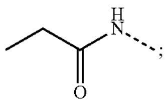 |
| 70 | 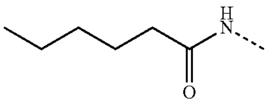 | 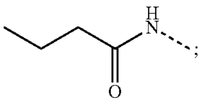 |
| 72 | 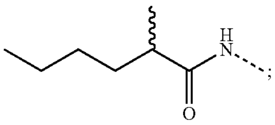 | HO—; |
| 73 | 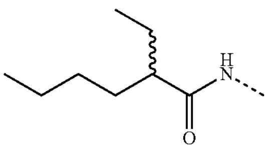 | 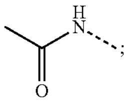 |
| 74 | 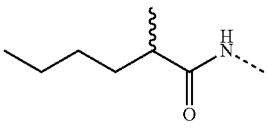 | 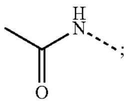 |

-continued
| | | |
|---|---|---|
| 75 | 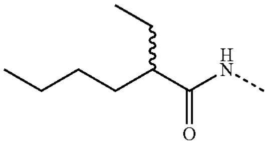 | HO—; or |
| R₂ (at position C4) is $NH_2C(=NH)NH—$ | | |
|---|---|---|
| | $R_3$ (at position C5) | $R_4$ (at position C9) |
| 71 | 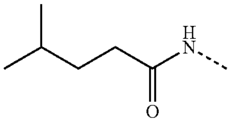 | HO—, |
or an ester, solvate, hydrate or pharmaceutical salt thereof.
Item' 105. The compound of item' 55, wherein $R_3$, $R_2$ and $R_4$ are as set forth below:
| $R_3$ (at position C5) is $CH_3C(O)NH—$ | | |
|---|---|---|
| compound | $R_2$ (at position C4) | $R_4$ (at position C9) |
| 7i | HO— | 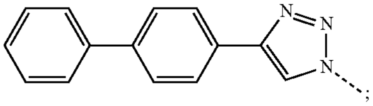 |
| 7j | HO— | 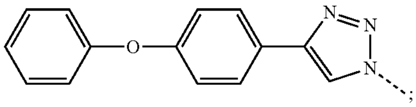 |
| 8a | 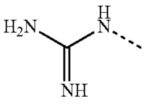 | 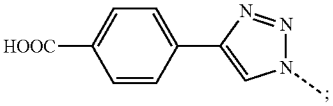 |
| 8b | 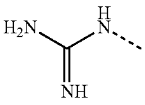 | 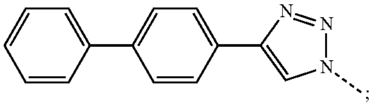 |
| 13 | $N_3$— | 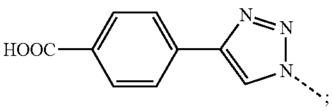 |
| 15 | $H_2N$— | 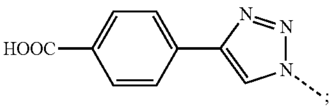 |
| 18 | 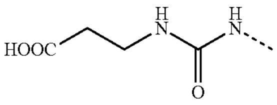 | 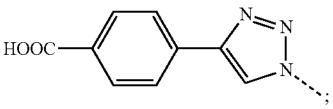 |

-continued
| | | |
|---|---|---|
| 26 | HO— | 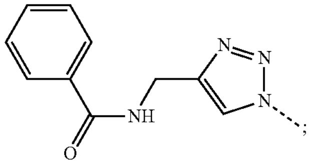 |
| 27 | HO— | 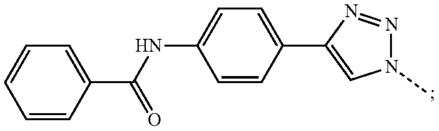 |
| 58 | HO— | 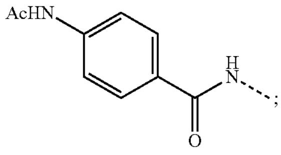 |
| 59 | HO— | 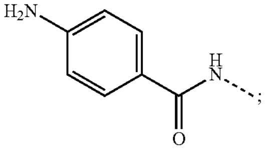 |
| 60 | HO— | 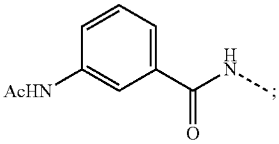 |
| 61 | HO— | 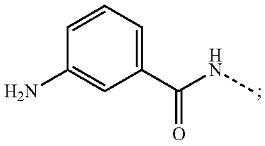 |
| 62 | HO— | 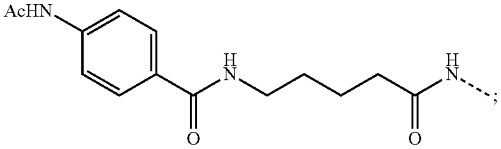 |
| 63 | HO— | 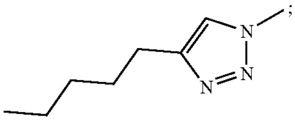 |
$R_2$ (at position C4) is HO—
| | $R_3$ (at position C5) | $R_4$ (at position C9) |
|---|---|---|
| 31 | 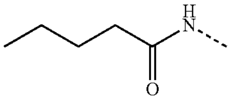 | HO—; |
| 32 | 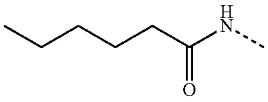 | HO—; |

-continued
| | | |
|---|---|---|
| 33 | 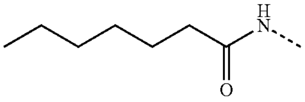 | HO—; |
| 36 | 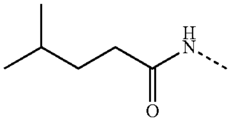 | HO—; |
| 40 | 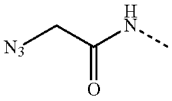 | HO—; |
| 41 | 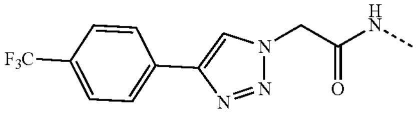 | HO—; |
| 42 | 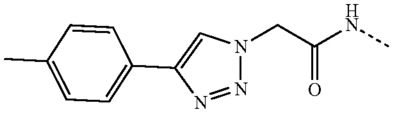 | HO— |
| 43 | 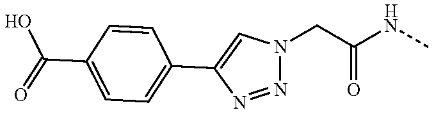 | HO—; |
| 44 | 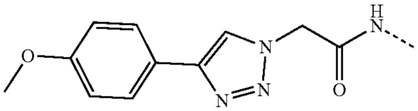 | HO—; |
| 45 | 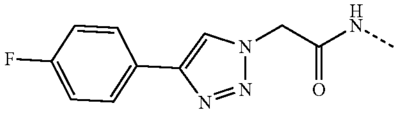 | HO—; |
| 46 | 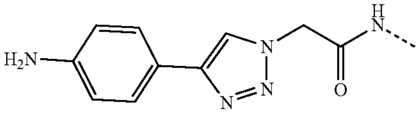 | HO—; |
| 47 | 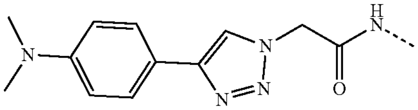 | HO—; |
| 48 | 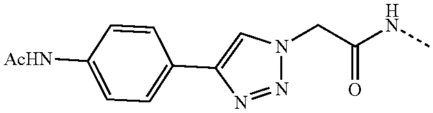 | HO—; |
| 51 | 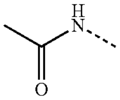 | 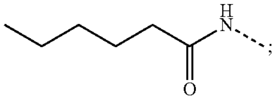 |
| 52 | 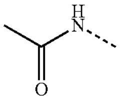 | 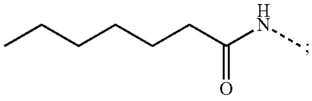 |

-continued
| | | |
|---|---|---|
| 55 | 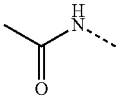 | 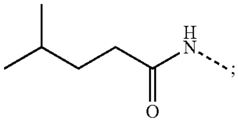; |
| 57 | 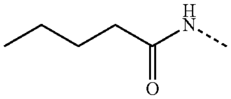 | 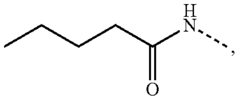, |
| 64 | 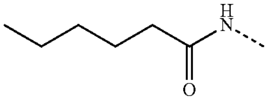 | 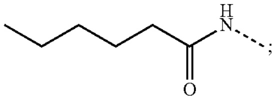; |
| 65 | 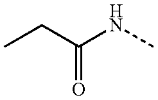 | 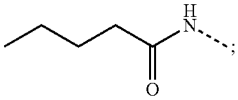; |
| 66 | 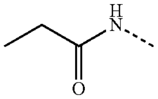 | 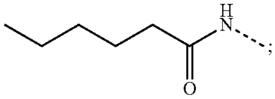; |
| 67 | 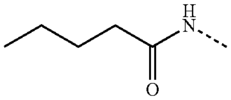 | 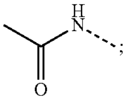; |
| 68 | 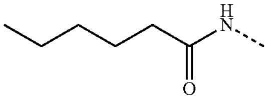 | 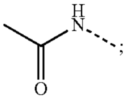; |
| 69 | 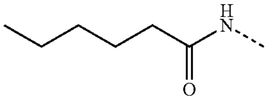 | 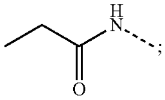; |
| 70 | 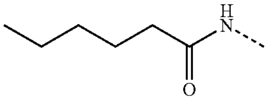 | 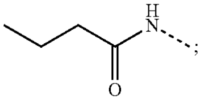; |
| 72 | 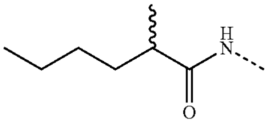 | HO—; |
| 73 | 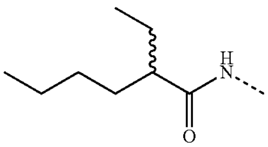 | 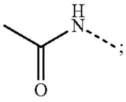; |
| 74 | 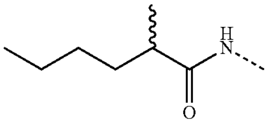 | 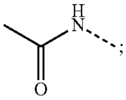; |

-continued

| | | |
|---|---|---|
| 75 | 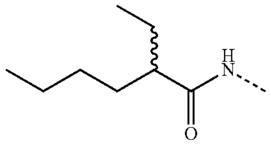 | HO—; or |
| $R_2$ (at position C4) is $NH_2C(=NH)NH—$ | | |
| | $R_3$ (at position C5) | $R_4$ (at position C9) |
| 71 | 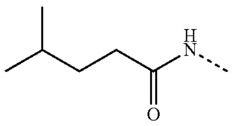 | HO—, |

or an ester, solvate, hydrate or pharmaceutical salt thereof.

Item' 106. The compound of item' 55, wherein the compound is of formula I, wherein X is O, $R_1$ is H, and $R_3$, $R_2$ and $R_4$ are as set forth below:

| $R_3$ (at position C5) is $CH_3C(O)NH—$ | | |
|---|---|---|
| compound | $R_2$ (at position C4) | $R_4$ (at position C9) |
| 7h | HO— | 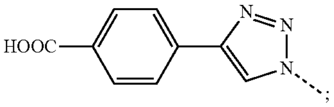 ; |
| 7i | HO— | 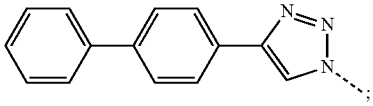 ; |
| 7j | HO— | 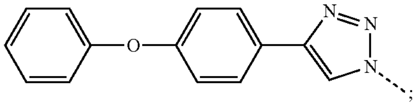 ; |
| 8a | 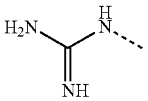 | 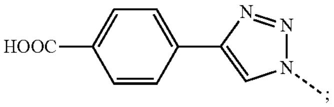 ; |
| 8b | 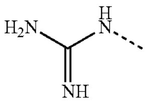 | 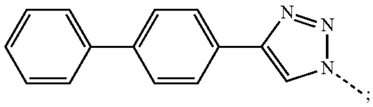 ; |
| 58 | HO— | 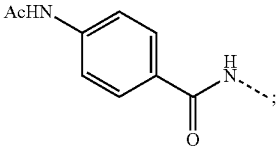 ; |
| $R_2$ (at position C4) is HO— | | |
| | $R_3$ (at position C5) | $R_4$ (at position C9) |
| 31 | 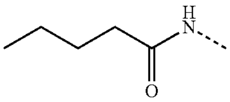 | HO—; |

-continued
| | | |
|---|---|---|
| 32 | 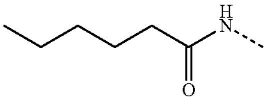 | HO—; |
| 33 | 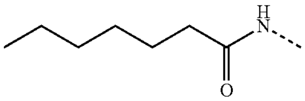 | HO—; |
| 36 | 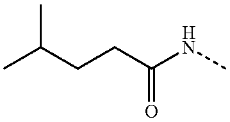 | HO—; |
| 51 | 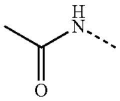 | 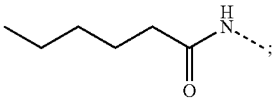; |
| 57 | 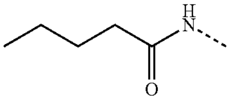 | 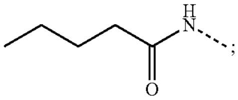; |
| 65 | 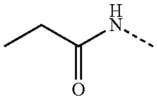 | 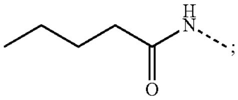; |
| 66 | 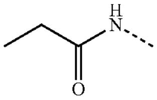 | 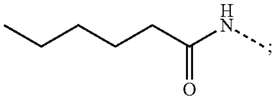; |
| 67 | 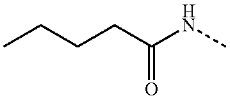 | 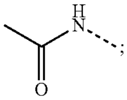; |
| 68 | 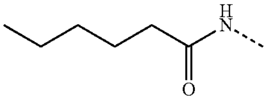 | 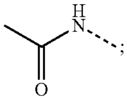; |
| 69 | 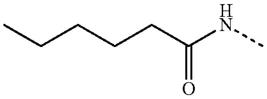 | 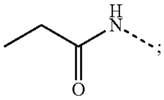; |
| 70 | 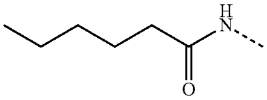 | 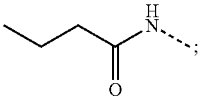; |
| 72 | 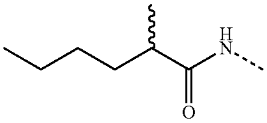 | HO—; |
| 73 | 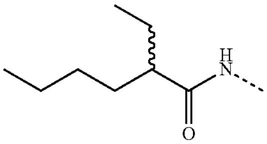 | 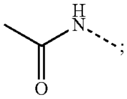; |

-continued
| | | |
|---|---|---|
| 74 | 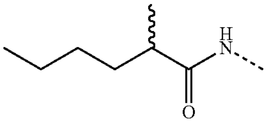 | 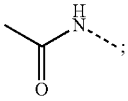 or |
| 75 | 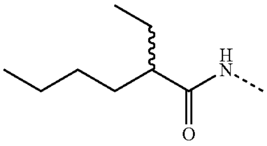 | HO—, |
or an ester, solvate, hydrate or pharmaceutical salt thereof.
Item' 107. The compound of item' 55, wherein the compound is of formula I, wherein X is O, $R_1$ is H, and $R_3$, $R_2$ and $R_4$ are as set forth below:
| $R_3$ (at position C5) is $CH_3C(O)NH$— | | |
|---|---|---|
| compound | $R_2$ (at position C4) | $R_4$ (at position C9) |
| 7i | HO— | 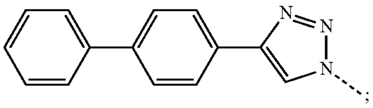 |
| 7j | HO— | 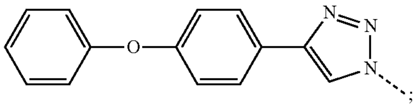 |
| 8a | 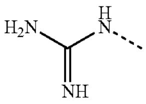 | 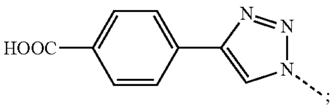 |
| 8b | 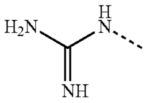 | 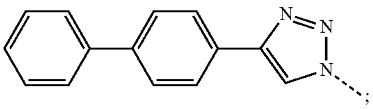 |
| 58 | HO— | 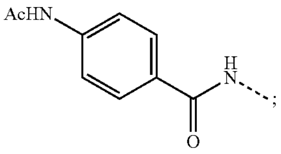 |
| $R_2$ (at position C4) is HO— | | |
|---|---|---|
| | $R_3$ (at position C5) | $R_4$ (at position C9) |
| 31 | 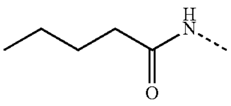 | HO—; |
| 32 | 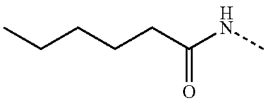 | HO—; |

-continued
| | | |
|---|---|---|
| 33 | 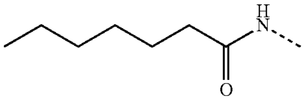 | HO—; |
| 36 | 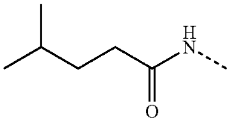 | HO—; |
| 51 | 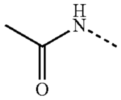 | 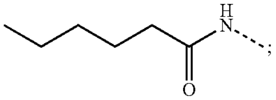 |
| 57 | 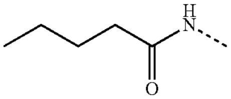 | 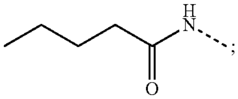 |
| 65 | 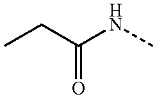 | 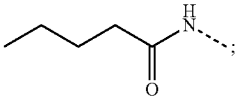 |
| 66 | 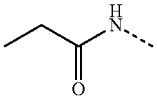 | 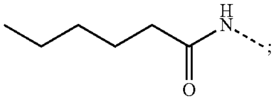 |
| 67 | 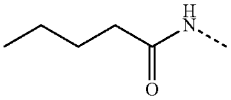 | 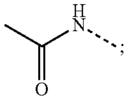 |
| 68 | 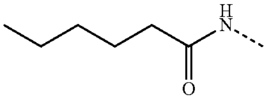 | 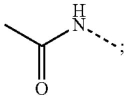 |
| 69 | 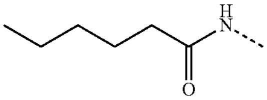 | 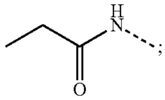 |
| 70 | 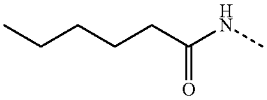 | 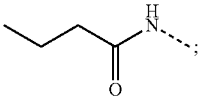 |
| 72 | 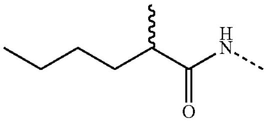 | HO—; |
| 73 | 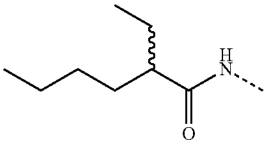 | 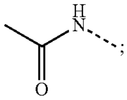 |
| 74 | 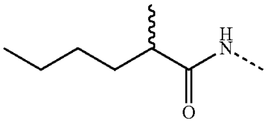 | 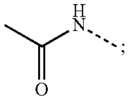 or |

-continued

| | | |
|---|---|---|
| 75 | 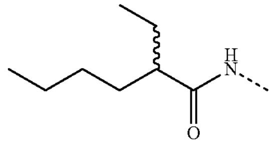 | HO—, |

or an ester, solvate, hydrate or pharmaceutical salt thereof.

Item' 108. The compound of any one of items' 55 to 107, wherein the compound is of formula Ia:

(Ia)

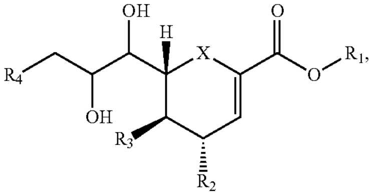

wherein $R_1$, $R_2$, $R_3$, $R_4$ and X are as defined in any one of items' 55 to 107.

Item' 109. The compound of any one of items' 55 to 107, wherein the compound is of formula Ib:

(Ib)

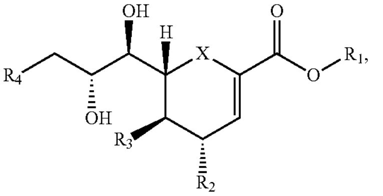

wherein $R_1$, $R_2$, $R_3$, $R_4$ and X are as defined in any one of items' 55 to 107.

Item' 110. A pharmaceutical composition comprising the compound, ester, solvate, hydrate or pharmaceutical salt thereof defined in any one of items 46-85 or any one of items' 55 to 109, and a pharmaceutically acceptable carrier.

Item' 111. A method of preventing or treating atherosclerosis or a symptom thereof comprising administering to a subject in need thereof a therapeutically effective amount of (i) the compound, ester, solvate, hydrate or pharmaceutical salt thereof defined in any one any one of items 46-85 or the compound, ester, solvate, hydrate or pharmaceutical salt thereof defined in any one of items' 55 to 109; or (ii) the pharmaceutical composition defined in item' 110.

In another specific embodiment, the specific inhibitor is a compound of formula II, wherein R2, R2 and R4 are as defined in Table III, or an ester, solvate, hydrate or pharmaceutical salt thereof.

In another specific embodiment, the specific inhibitor is a compound of formula III (III)

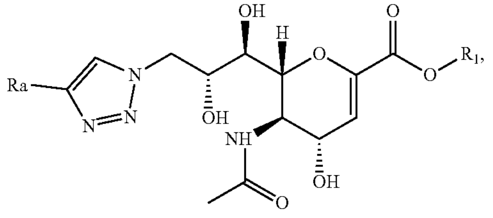

wherein $R_1$ is as defined above or H, a linear alkyl group C1-C12 (i.e. Me, Et, Pr, But, Pent, Hex, etc.), a branched alkyl group C1-C12, or an aryl group; and $R_a$ is the group shown at that position in any one of 7a-7j, and 26 to 28, or an ester, solvate, hydrate or pharmaceutical salt thereof.

In another specific embodiment, the specific inhibitor is a compound of formula IV (IV)

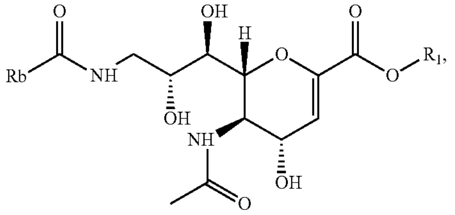

where R1 is as defined above or H, a linear alkyl group C1-C12 (i.e. Me, Et, Pr, But, Pent, Hex, etc.), a branched alkyl group C1-C12, or an aryl group; and $R_b$ is the group shown at that position in any one of compounds 49 to 56, or an ester, solvate, hydrate or pharmaceutical salt thereof.

In another specific embodiment, the specific inhibitor is a compound of formula V (V)

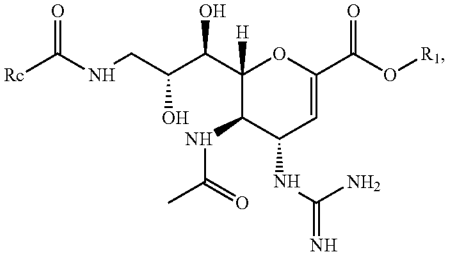

where $R_1$ is as defined above or H, a linear alkyl group C1-C12 (i.e. Me, Et, Pr, But, Pent, Hex, etc.), a branched alkyl group C1-C12, or an aryl group; and $R_c$ is the group shown at that position in any one of compounds 58-61, or an ester, solvate, hydrate or pharmaceutical salt thereof.

In another specific embodiment, the specific inhibitor is a compound of formula VI (VI)

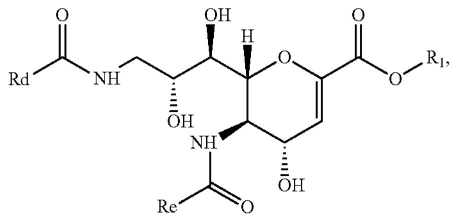

where $R_1$ is as defined above or H, a linear alkyl group C1-C12 (i.e. Me, Et, Pr, But, Pent, Hex, etc.), a branched alkyl group C1-C12, or an aryl group; and $R_d$ and $R_e$ are the groups shown at these positions in any one of compounds 49-52, 54-57, 64-70, 74-74, or an ester, solvate, hydrate or pharmaceutical salt thereof.

In another specific embodiment, the specific inhibitor is a compound of formula VII (VII)

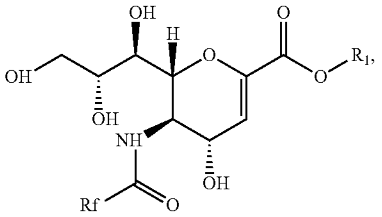

where R1 is as defined above or H, a linear alkyl group C1-C12 (i.e. Me, Et, Pr, But, Pent, Hex, etc.), a branched alkyl group C1-C12, or an aryl group; and fir is the group shown at that position in any one of compounds 29 to 48, or an ester, solvate, hydrate or pharmaceutical salt thereof.

In another specific embodiment, the specific inhibitor is a compound of formula VIII (VIII)

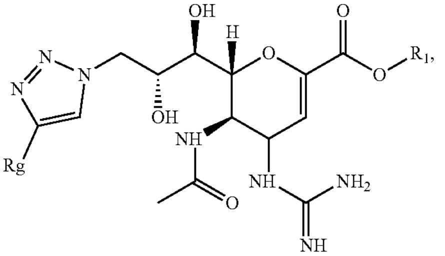

where R1 is as defined above or H, a linear alkyl group C1-C12 (i.e. Me, Et, Pr, But, Pent, Hex, etc.), a branched alkyl group C1-C12, or an aryl group; and $R_g$ is an C3-C7 aryl group substituted or not with a C3-C10 aryl group (substituted or not with an halogen, an amine, a C1-C10 alkyl, a C1-C10 alkyloxy, a trifluoromethyl, a —COOH, a C3-C7 aryl); a C1-C10 alkyl group; or a —COOH group. In a more specific embodiment, it is a group as shown at that position in any one of compounds 8a and 8b, or an ester, solvate, hydrate or pharmaceutical salt thereof.

In another specific embodiment, there is provided a pharmaceutical composition comprising a specific inhibitor that is a compound of any one of formulas I, Ia, Ib, and II-VIII, or any specific inhibitor disclosed in Table III, or an ester, solvate, hydrate or pharmaceutical salt thereof, and a pharmaceutically acceptable carrier. In a specific embodiment, the specific inhibitor has an IC50 against a neuraminidase that is lower than 1 NM (e.g., compound 7i, 8b or 68).

In another specific embodiment, there is provided a pharmaceutical composition comprising a neu1/neu3 specific inhibitor that is a compound of any one of formulas I, Ia, Ib, and II-VIII, or any specific inhibitor disclosed in Table III, or an ester, solvate, hydrate or pharmaceutical salt thereof, and a pharmaceutically acceptable carrier. In a specific embodiment, the specific inhibitor has an IC50 against a neu1/neu3 that is lower than 1 μM (e.g., 7i, 8a and 8b, 31-32, 67-69, 72, 74 and 75, preferably compound 7i, 8b or 68).

In another specific embodiment, there is provided a pharmaceutical composition comprising a neu1 specific inhibitor that is a compound of any one of formulas I, Ia, Ib, and II-VIII, or any specific inhibitor disclosed in Table III, or an ester, solvate, hydrate or pharmaceutical salt thereof, and a pharmaceutically acceptable carrier. In a specific embodiment, the specific inhibitor has an IC50 against a neu1 that is lower than 1 μM (e.g., compounds 31-32, 67-69, 72, 74 and 75, preferably compound 68).

In another specific embodiment, there is provided a pharmaceutical composition comprising a neu3 specific inhibitor that is a compound of any one of formulas I, Ia, Ib, and II-VIII, or any specific inhibitor disclosed in Table III, or an ester, solvate, hydrate or pharmaceutical salt thereof, and a pharmaceutically acceptable carrier. In a specific embodiment, the specific inhibitor has an IC50 against a neu3 that is lower than 1 μM (e.g., compounds 31-32, 67-69, 72, 74 and 75, preferably compound 68).

In another specific embodiment, there is provided a method of preventing or treating atherosclerosis or a symptom thereof comprising administering to a subject in need thereof a therapeutically effective amount of (i) a specific neu1/neu3 inhibitor of the present invention that is a compound of any one of formulas I, Ia, Ib, and II-VIII, or any specific neu1/neu3 inhibitor disclosed in Table III, or an ester, solvate, hydrate or pharmaceutical salt thereof; or (ii) a pharmaceutical composition comprising (i) and a pharmaceutically acceptable carrier. (e.g., 7i, 8a and 8b, 31-32, 67-69, 72, 74 and 75, preferably compound 7i, 8b or 68).

In another specific embodiment, there is provided a method of preventing or treating atherosclerosis or a symptom thereof comprising administering to a subject in need thereof a therapeutically effective amount of (i) a specific neu1 inhibitor of the present invention that is a compound of any one of formulas I, Ia, Ib, and II-VIII, or any specific neu1 inhibitor disclosed in Table III, or an ester, solvate, hydrate or pharmaceutical salt thereof; or (ii) a pharmaceutical composition comprising (i) and a pharmaceutically acceptable carrier. (e.g., compounds 31-32, 67-69, 72, 74 and 75, preferably compound 68).

In another specific embodiment, there is provided a method of preventing or treating atherosclerosis or a symptom thereof comprising administering to a subject in need thereof a therapeutically effective amount of (i) a specific neu3 inhibitor of the present invention that is a compound of any one of formulas I, Ia, Ib, and II-VIII, or any specific neu3 inhibitor disclosed in Table III, or an ester, solvate, hydrate or pharmaceutical salt thereof; or (ii) a pharmaceutical composition comprising (i) and a pharmaceutically acceptable carrier. (e.g., compounds 31-32, 67-69, 72, 74 and 75, preferably compound 68).

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1A. Sialylation of ApoB is analyzed by blotting with lectin from *Sambucus nigra* (SNA) specific to α-2,6 linked Sia. FIG. 1B. Sialylation of ApoB is analyzed by blotting with *Maackia amurensis* lectin (MAL-II) specific for α-2,3 linked Sia. FIG. 1C. Treatment with Neu3 results in the recognition of ApoB by PNA specific to carbohydrate sequence Gal-β (1-3)-GalNAc confirming removal of the terminal Sia residues form the glycan chains. FIGS. 1D-E: Analysis of glycosylation changes to native human LDL ApoB and ApoB treated with human recombinant NEU3. FIG. 1D: A glycopeptide analysis of ApoB was conducted using nanoscale liquid chromatography coupled to tandem mass spectrometry (nano LC-MS/MS). The primary sequence of ApoB is represented, with the N and C termini labeled at the bottom. Domains of the protein are indicated in pale grey and dark grey. Predicted N-link sites are indicated by a black arrow. Individual glycopeptides were identified, those containing Sia residues were localized to specific sites in ApoB (represented by a diamond; second row). NEU3-treated ApoB (dApoB) was also analyzed (top row). A previous analysis of native ApoB, reported by Haranzo et al., is shown in the third row for comparison. FIG. 1E: glycan profiling experiment was performed to quantitate changes in Sia content between ApoB and dApoB. The glycan was cleaved using PNGaseF, and labeled with Rapifluor (Waters, Milford MA). Peaks were then separated by ion exchange, allowing separation by charge. Each peak was analyzed for glycan sequence, and classified by the average number of Sia per sequence observed. A shift of glycans from 1-3 Sia to 0-1 Sia is observed (note peaks 11, 7, and 4).

FIG. 2A. After incubation cells were washed, fixed and analyzed by confocal microscopy. Relative fluorescence intensities of the cells were measured by ImageJ™ software. Enzymatically desialylated LDL in contrast to native LDL are engulfed by cultured monocyte-derived macrophages at a rate comparable or even higher than that for oxidized LDL. FIG. 2B. Accumulation of Alexa-labeled LDL. FIG. 2C. Accumulation of Dil-labeled LDL. Bar graphs show average fluorescence intensities of cells treated with Alexa-labeled (FIG. 2B) and Dil-labeled LDL (FIG. 2C). Data show mean values ±SD of three independent experiments. (*** p<0.001 as compared with native LDL by t-test).

FIG. 3A. Relative fluorescence intensities of the cells were measured by ImageJ™ software. FIG. 3B. Accumulation of Alexa-labeled LDL. FIG. 3C. Accumulation of Dil-labeled LDL. Bar graphs show average fluorescence intensities of cells treated with Alexa-labeled (FIG. 3B) and Dil-labeled LDL (FIG. 3C). Data show mean values ±SD of three independent experiments.

FIG. 4A. Cells were washed, fixed and analyzed by fluorescence microscopy. FIG. 4B. Relative fluorescence intensities of the cells were measured by ImageJ™ software. Data show mean values ±SD of three independent experiments. Inhibition of desLDL uptake by oxLDL is significantly different from that by desLDL (P<0.01).

FIG. 5A. Accumulation of Alexa-labeled nLDL and desLDL. FIGS. 5B-C. Accumulation of Dil-labeled nLDL and desLDL. FIGS. 5B and C show the results of quantification of Alexa and Dil dye in the aorta wall. Data show mean values ±SD of three independent experiments. (, * significantly different with nLDL uptake; P<0.01 and <0.001 respectively).

FIG. 6A. Representative images of aortic root sections from female mice stained with Red Oil O. FIGS. 6B-C. Graphs showing atherosclerotic lesion size in the aortic roots ($\mu m^2$) measured by ImageJ™' software in female (F) and male (M) mice. FIG. 6C expresses the same data as FIG. 6B but in a different format with the exclusion of images of lesser quality or when less than 4 heart sections were analyzed were excluded.

FIGS. 7A-B, Representative photomicrographs (x40) (FIG. 7A) and quantitative analysis (FIG. 7B) of T cell infiltration (number of CD3 positive cells/$mm^2$).

FIG. 9A shows the image of a representative blot performed with 0.7, 0.5 and 2.8 μg of LDL protein. FIG. 9B shows results of quantification (mean values ±SD) performed on 3 individual blots by ImageJ™' software. *Significantly different from ApoE$^{-/-}$ (P<0.05) according to one-way ANOVA test.

FIGS. 11A-B: Fourteen-week-old ApoE KO female mice fed normal diet were treated intraperitoneally with compound 50 (30 mg/kg, for 4 (n=6) and 2 (n=3) weeks, respectively). Ten- μm serial sections of aortic root were collected using a cryostat and stained with Red Oil O to visualize atherosclerotic lesions. Representative images of aortic root sections of mice treated 2 weeks with compound 50, the sections being stained with Red Oil O (FIG. 11A). Bar graph shows atherosclerotic lesion size in the aortic roots (μm$^2$) of mice treated with compound 50 for 2 and 4 weeks, measured by ImageJ™' software (FIG. 11B). Data show means±SD. (, * Significantly different from control; P<0.01 and <0.005, respectively) according to t-test.

FIG. 12A: Representative images of aortic root sections of compound 7i and 2% DMSO-treated mice stained with Red Oil O (FIGS. 12B-C: Bar graph showing atherosclerotic lesion size in the aortic roots (μm$^2$) of mice treated with compound 7i (FIG. 12B), compounds 8b and 31 (FIG. 12C) and their respective control, measured by ImageJ™' software. Data show means±SD. *, ***—significantly different from control (p<0.05, and 0.001, respectively) according to t-test.

FIG. 16: Amino acid of human neuraminidase 1 (SEQ ID NO: 1); human neuraminidase 2 (SEQ ID NO: 2); human neuraminidase 3, isoform 1 (SEQ ID NO: 3); human neuraminidase 3, isoform 2 (SEQ ID NO: 4); human neuraminidase 4, isoform 1 (SEQ ID NO: 5); human neuraminidase 4, isoform 2 (SEQ ID NO: 6); and human neuraminidase 4, isoform 3 (SEQ ID NO: 7).

FIGS. 17A-B: Alignment of neuraminidase proteins of FIG. 16, and consensus sequence derived therefrom (SEQ ID NO: 8). In this alignment, "*" denotes that the residues in that column are identical in all sequences of the alignment, ":" denotes that conserved substitutions have been observed, and"." denotes that semi-conserved substitutions have been observed. Consensus sequences derived from these alignments are also presented wherein X is any amino acid.

FIG. 18: Presents the general form of compounds 7a-j, 8a and 8b.

FIG. 19: Presents the general synthetic route for generation of compounds 7a-j.

DETAILED DESCRIPTION OF THE INVENTION

Figures 1A, 1B:
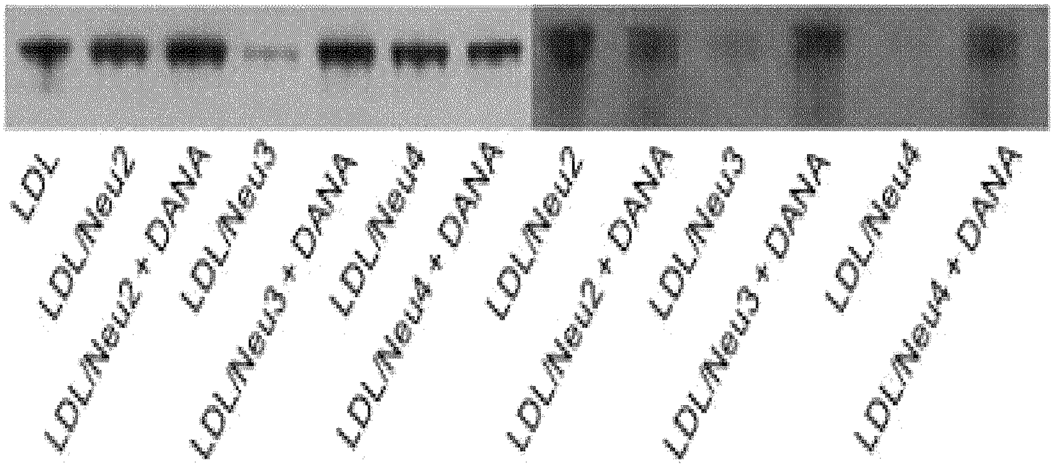
FIGS. 1A-E: Neuraminidases 3 and 4 remove sialic acids from the glycan chains of ApoB molecule. Low-density lipoproteins (LDL) were incubated with human recombinant neuraminidases 2, 3 or 4 either with or without the neuraminidase inhibitor DANA (2,3-Dehydro-2-deoxy-N-acetylneuraminic acid—compound 1).

The present invention relates to specific inhibitors of human neuraminidase enzymes. It also relates to the use of a therapeutically effective amount of a specific neuraminidase 1, a specific neuraminidase 3, or a bispecific neuraminidase 1 (e.g., neu1/neu2 or neu1/neu4) or a bispecific neuraminidase 3 inhibitor (e.g., neu3/neu2 or neu3/neu4) to prevent or treat atherosclerosis or a symptom thereof in a subject in need thereof.

As used herein, the term "specific inhibitor" encompasses bispecific inhibitors and refers to any inhibitor that specifically inhibits at least one of neu1, neu2, neu2 and neu4.

As used herein, the term "specific neu1/neu3 inhibitor" is used herein to refer to "a specific inhibitor of neuraminidase 1 (neu1); neuraminidase 3 (neu3); or a bispecific inhibitor of neu1 or neu3". It refers to at least one of a "specific neuraminidase 1 inhibitor", "specific neuraminidase 3 inhibitor", "bispecific neuraminidase 1 inhibitor" and "bispecific neuraminidase 3 inhibitor". For convenience, the term. It refers to an agent able to reduce, the case being, Neu1 and/or Neu3 expression and/or activity. Without being so limited, such inhibitors include small molecules including but not limited those of any one of formulas I, Ia, Ib, and II-VIII and those identified as such in in Table III, dsRNA (e.g., RNAi, siRNA, miRNA), peptides, antibodies or antibody fragments (e.g., antibodies that specifically binds to neu1 or neu3 or are bispecific against neu1 or neu3 and against another neuraminidase enzyme, and antibody fragments that specifically binds to neu1 or neu3 or are bispecific against neu1 or neu3 and another neuraminidase enzyme). In more specific embodiments, such inhibitors are those identified as such in Table III.

Typically, specific inhibitors advantageously avoid certain deleterious side effects that could be present when using inhibitors with less selectivity.

As used herein the terms "specific neuraminidase 1 inhibitor" refer to an inhibitor that is more active against neuraminidase 1 than against neuraminidase 2, 3, or 4. In a specific embodiment, the inhibitor has an IC50 against neu1 that is at least 2×lower than the IC50 against at least one of neu2, neu3, and neu4 (in a specific embodiment, against at least two of neu2, neu3, and neu4 and in another specific embodiment against all three of neu2, neu3, and neu4). In another specific embodiment, its IC50 against neu1 is at least 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, or 46× lower than its IC50 against at least one of neu2, neu3, and neu4 (in a specific embodiment, against at least two of neu2, neu3, and neu4 and in another specific embodiment against all three of neu2, neu3, and neu4).

As used herein the terms "specific neuraminidase 3 inhibitor" refer to an inhibitor that is more active against neuraminidase 3 than against neuraminidase 1, 2 or 4. In a specific embodiment, it has an IC50 against neu3 that is at least 2×lower than the IC50 against at least one of neu1, neu2 and neu4 (in a specific embodiment, against at least two of neu1, neu2, and neu4 and in another specific embodiment against all three of neu1, neu2, and neu4). In another specific embodiment, its IC50 against neu3 is at least 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, or 46× lower than its IC50 against at least one of neu1, neu2 and 4 (in a specific embodiment, against at least two of neu1, neu2, and neu4 and in another specific embodiment against all three of neu1, neu2, and neu4).

As used herein the terms "bispecific neuraminidase 1 inhibitor" refer to "bispecific neuraminidase 1/neuraminidase 2 inhibitor" (or "bispecific neu1/2 inhibitor"), "bispecific neuraminidase 1/neuraminidase 3 inhibitor" (or "bispecific neu1/3 inhibitor") or "bispecific neuraminidase 1/neuraminidase 4 inhibitor" (or "bispecific neu1/4 inhibitor").

As used herein the terms "bispecific neuraminidase 1/neuraminidase 2 inhibitor" or "bispecific neu1/2 inhibitor" refer to an inhibitor that has activity against neuraminidase 1 and neuraminidase 2, and is less active against neuraminidase 3 and/or 4. In a specific embodiment, such an inhibitor has an IC50 against neu1 that is of from 3:1 to 1:3 against neu2. In a specific embodiment, such an inhibitor has an IC50 against neu1 and neu2 that is at least 2×lower than the IC50 against at least one of neu3 and neu4 (in a specific embodiment, against both of neu3 and neu4). In another specific embodiment, its IC50 against neu1 and neu2 is at least 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, or 46× lower than its IC50 against at least one of neu3 and neu4 (in a specific embodiment, against both of neu3 and neu4).

As used herein the terms "bispecific neuraminidase 1/neuraminidase 3 inhibitor" or "bispecific neu1/3 inhibitor" refer to an inhibitor that has activity against neuraminidase 1 and neuraminidase 3, and is less active against neuraminidase 2 and/or 4. In a specific embodiment, such an inhibitor has an IC50 against neu1 that is of from 3:1 to 1:3 against neu3. In a specific embodiment, such an inhibitor has an IC50 against neu1 and neu3 that is at least 2×lower than the IC50 against at least one of neu2 and neu4 (in a specific embodiment, against both of neu2 and neu4). In another specific embodiment, its IC50 against neu1 and neu3 is at least 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, or 46× lower than its IC50 against at least one of neu2 and neu4 (in a specific embodiment, against both of neu2 and neu4).

As used herein the terms "bispecific neuraminidase 1/neuraminidase 4 inhibitor" or "bispecific neu1/4 inhibitor" refer to an inhibitor that has activity against neuraminidase 1 and neuraminidase 4, and is less active against neuraminidase 2 and/or 3. In a specific embodiment, such an inhibitor has an IC50 against neu1 that is of from 3:1 to 1:3 against neu4. In a specific embodiment, such an inhibitor has an IC50 against neu1 and neu4 that is at least 2×lower than the IC50 against at least one of neu2 and neu3 (in a specific embodiment, against both of neu2 and neu3). In another specific embodiment, its IC50 against neu1 and neu4 is at least 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, or 46×lower than its IC50 against at least one of neu2 and neu3 (in a specific embodiment, against both of neu2 and neu3).

As used herein the terms "bispecific neuraminidase 3 inhibitor" refer to "bispecific neuraminidase 3/neuraminidase 2 inhibitor" (or "bispecific neu3/2 inhibitor") or "bispecific neuraminidase 3/neuraminidase 4 inhibitor" (or "bispecific neu3/4 inhibitor").

As used herein the terms "bispecific neu3/4 inhibitor" refer to an inhibitor that has activity against neuraminidase 3 and neuraminidase 4, and is less active against neuraminidase 1 and/or 2. In a specific embodiment, such an inhibitor has an IC50 against neu3 that is of from 3:1 to 1:3 against neu4. In a specific embodiment, such an inhibitor has an IC50 against neu3 and neu4 that is at least 2×lower than the IC50 against at least one of neu1 and neu2 (in a specific embodiment, against both of neu1 and neu2). In another specific embodiment, its IC50 against neu3 and neu4 is at least 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, or 46×lower than its IC50 against at least one of neu1 and neu2 (in a specific embodiment, against both of neu1 and neu2).

As used herein the terms "bispecific neuraminidase 3/neuraminidase 2 inhibitor" or "bispecific neu3/2 inhibitor" refer to an inhibitor that has activity against neuraminidase 3 and neuraminidase 2, and is less active against neuraminidase 1 and/or 4. In a specific embodiment, such an inhibitor has an IC50 against neu3 that is of from 3:1 to 1:3 against neu2. In a specific embodiment, such an inhibitor has an IC50 against neu3 and neu2 that is at least 2×lower than the IC50 against at least one of neu1 and neu4 (in a specific embodiment, against both of neu1 and neu4). In another specific embodiment, its IC50 against neu1 and neu4 is at least 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, or 46×lower than its IC50 against at least one of neu1 and neu4 (in a specific embodiment, against both of neu1 and neu4).

As used herein the term "atherosclerosis or symptom thereof" refers to a specific form of arteriosclerosis in which an artery wall thickens as a result of invasion and accumulation of white blood cells (foam cells) and proliferation of intimal-smooth-muscle cell creating an atheromatous (fibro-fatty) plaque. As used herein a symptom of atherosclerosis includes ApoB desialylation (e.g., in plasma), LDL uptake by macrophage, formation of foam cells, LDL incorporation in arterial walls, increase of fatty streak regions number on arterial walls, increase of fatty streak regions size on arterial walls, infiltration of T cell in atherosclerotic lesions, infiltration of macrophages, vascular smooth muscle cells or leucocytes in atherosclerotic lesions, production of extra-cellular matrix molecules, collagen and elastin, formation of a fibrous cap covering the plaque, cellular necrosis, plaque rupture and thrombosis.

The present invention also relates to the use of specific neu1, and neu3 inhibitors, and bispecific neu1 or neu3 inhibitors (e.g., neu3/neu4 inhibitors) to reduce inflammation in a subject in need thereof.

A "therapeutically effective amount" or "effective amount" or "therapeutically effective dosage" of a specific inhibitor of the invention or composition thereof can result in a reduction of atherosclerosis in a subject; a decrease in severity of at least one atherosclerosis symptom (e.g., a decrease in ApoB desialylation, a decrease in LDL uptake by macrophage, or a decrease in number and/or size of atherosclerotic lesions); an increase in frequency and duration of atherosclerosis symptom-free periods; a delay in appearance of atherosclerosis or a symptom thereof in a subject, or a prevention of impairment or disability due to the atherosclerosis in the subject.

Small Molecule Inhibitors

The structure of specific small molecules of the present invention are shown in FIGS. 19-22 and/or Examples 7 to 97. Their names are also indicated in Examples 7 to 97. In case of discrepancies between the name and structure presented, the structure shall prevail.

In specific embodiments of the present invention, small molecule inhibitors of the present invention (e.g., formulas I, Ia, Ib, and II-VIII) have an IC50 against neu1 or neu3 that is of 100 μM or lower, 20 μM or lower, 10 μM or lower, 3 μM or lower, 1 μM or lower or lower than 1 μM. In specific embodiments, small molecule inhibitors of the present invention are the compounds of Table III that have an IC50 against neu1 or neu3 that is lower than 1 μM (e.g., compounds with neu3 specificity or bispecificity: 7i, 8a and 8b; and compounds with neu1 specificity or bispecificity: compounds 31, 32, 67-69, 72, 74 and 75), 1 μM or lower (e.g., the foregoing compounds and compound 7j (neu3 specificity or bispecificity)), 3 μM or lower (e.g., the foregoing compounds and compounds 7h and 27 (neu3 specificity or bispecificity); and compounds 54, 56, 33, 57, 36, 51, 58, 65, 66, 70 and 73 (neu1 specificity or bispecificity)), 10 μM or lower (e.g., the foregoing compounds and compounds 7e, 7c, 7a, 7b, 7d, 7g, 27, zanamivir (6), 40, 63 (neu3 specificity or bispecificity); and compounds 55, 50, 30, 34, 37, 49, 52, 60-61, 64 (neu1 specificity or bispecificity)), 20 μM or lower (e.g., the foregoing compounds and compounds 7f, 26, and 13 (neu3 specificity or bispecificity); and compounds 29, 38, 39 and 71 (neu1 specificity or bispecificity)) or 100 μM or lower (e.g., the foregoing compounds and compounds 53, 28, 59 and 62 (neu3 specificity or bispecificity); and compounds 35 and 59 (neu1 specificity or bispecificity)).

Chemical Groups

As used herein, the term "alkyl" refers to a monovalent straight or branched chain, saturated or unsaturated aliphatic hydrocarbon radical having a number of carbon atoms in the specified range. Thus, for example, "C1-10 alkyl" (or "C1-C10 alkyl") refers to any of the hexyl alkyl and pentyl alkyl isomers as well as n-, iso-, sec- and t-butyl, n- and iso-propyl, ethyl, and methyl. As another example, "C1-4 alkyl" refers to n-, iso-, sec- and t-butyl, n- and isopropyl, ethyl, and methyl. As another example, "C1-3 alkyl" refers to n-propyl, isopropyl, ethyl, and methyl. Alkyl include unsaturated aliphatic hydrocarbon including alkyne (R—C≡C—R); and/or alkene (R—C═C—R).

The term "halogen" (or "halo") refers to fluorine, chlorine, bromine and iodine (alternatively referred to as fluoro, chloro, bromo, and iodo). The term "haloalkyl" refers to an alkyl group as defined above in which one or more of the hydrogen atoms have been replaced with a halogen (i.e., F, Cl, Br and/or I). Thus, for example, "C1-10 haloalkyl" (or "C1-C6 haloalkyl") refers to a C1 to C10 linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "heteroalkyl" is given its ordinary meaning in the art and refers to alkyl groups as described herein in which one or more carbon atoms is replaced with a heteroatom (e.g., oxygen, nitrogen, sulfur, or derivatives thereof, and the like). Examples of heteroalkyl groups include, but are not limited to, alkoxy, alkyl-substituted amino, thiol such as methionine side group. Up to two heteroatoms may be consecutive. When a prefix such as C2-6 is used to refer to a heteroalkyl group, the number of carbons (2-6, in this example) is meant to include the heteroatoms as well.

The term "aminoalkyl" refers to an alkyl group as defined above in which one or more of the hydrogen or carbon atoms has been replaced with a nitrogen or an amino derivative. Thus, for example, "C1-6 aminoalkyl" (or "C1-C6 aminoalkyl") refers to a C1 to C6 linear or branched alkyl group as defined above with one or more amino derivatives (e.g., NH, amide, diazirin, azide, etc.).

The term "thioalkyl" refers to an alkyl group as defined above in which one or more of the hydrogen or carbon atoms has been replaced with a sulfur atom or thiol derivative. Thus, for example, "C1-6 aminoalkyl" (or "C1-C6 aminoalkyl") refers to a C1 to C6 linear or branched alkyl group as defined above with one or more sulfur atoms or thiol derivatives (e.g., S, SH, etc.).

Aminoalkyl and thioalkyls are specific embodiments of and encompassed by the term "heteroalkyl" or substituted alkyl depending on the heteroatom replaces a carbon atom or an hydrogen atom.

The term "cycloalkyl" refers to saturated alicyclic hydrocarbon consisting of saturated 3-8 membered rings optionally fused with additional (1-3) aliphatic (cycloalkyl) or aromatic ring systems, each additional ring consisting of a 3-8 membered ring. It includes without being so limited cyclopropane, cyclobutane, cyclopentane, and cyclohexane.

The term "heterocyclyl" refers to (i) a 4- to 7-membered saturated heterocyclic ring containing from 1 to 3 heteroatoms independently selected from N, O and S, or (ii) is a heterobicyclic ring (e.g., benzocyclopentyl). Examples of 4- to 7-membered, saturated heterocyclic rings within the scope of this invention include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

The terms "C(O)" and —CO refer to carbonyl. The terms "$S(O)_2$" and "$SO_2$" each refer to sulfonyl. The term "S(O)" refers to sulfinyl.

The term "aryl" refers to aromatic (unsaturated) compounds consisting of 3-8 membered rings, optionally fused with additional (1-3) aliphatic (cycloalkyl) or aromatic ring systems, each additional ring consisting of 3-8 membered ring. In a specific embodiment, it refers to phenyl, benzocyclopentyl, or naphthyl. The aryl of particular interest is phenyl.

The term "heteroaryl" refers to (i) a 3-, 4-, 5- or 6-membered heteroaromatic ring containing from 1 to 4 heteroatoms independently selected from N, O and S, or (ii) is a heterobicyclic ring selected from quinolinyl, isoquinolinyl, and quinoxalinyl. Suitable 3-, 4-, 5- and 6-membered heteroaromatic rings include, for example, diazirin, pyridyl (also referred to as pyridinyl), pyrrolyl, diazine (e.g., pyrazinyl, pyrimidinyl, pyridazinyl), triazinyl, thienyl, furanyl, imidazolyl, pyrazolyl, triazolyl (e.g., 1, 2, 3 triazolyl), tetrazolyl (e.g., 1, 2, 3, 4 tetrazolyl), oxazolyl, iso-oxazolyl, oxadiazolyl, oxatriazolyl, thiazolyl, isothiazolyl, and thiadiazolyl. Heteroaryls of particular interest are pyrrolyl, imidazolyl, pyridyl, pyrazinyl, quinolinyl (or quinolyl), isoquinolinyl (or isoquinolyl), and quinoxalinyl. Suitable heterobicyclic rings include indolyl.

As used herein, and unless otherwise specified, the terms "alkyl", "haloalkyl", "aminoalkyl", "cycloalkyl", "heterocyclyl", "aryl", "heteroalkyl" and "heteroaryl" and the terms designating their specific embodiments (e.g., butyl, fluoropropyl, aminobutyl, cyclopropane, morpholine, phenyl, pyrazole, etc.) encompass the substituted (i.e. in the case of haloalkyl and aminoalkyl, in addition to their halogen and nitrogen substituents, respectively) and unsubstituted embodiments of these groups. Hence for example, the term "phenyl" encompasses unsubstituted phenyl as well as fluorophenyl, hydroxyphenyl, methylsulfonyl phenyl (or biphenyl), trifluoromethyl-diazirin-phenyl, isopropyl-phenyl, trifluorohydroxy-phenyl. Similarly, the term pyrazole, encompass unsubstituted pyrazole as well as methylpyrazole. The one or more substituents may be an amine, halogen, hydroxyl, C1-6 aminoalkyl, C1-6 heteroalkyl, C1-6 alkyl, C3-8 cycloalkyl, C1-6 haloalkyl, aryl, heteroaryl and heterocyclyl groups (etc.).

It is understood that the specific rings listed above are not a limitation on the rings which can be used in the present invention. These rings are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results.

Isomers, Tautomers and Polymorphs

As used herein, the term "isomers" refers to optical isomers (enantiomers), diastereoisomers as well as the other known types of isomers.

The compounds of the invention have at least five asymmetric carbon atoms and can therefore exist in the form of optically pure enantiomers (optical isomers), as racemates and as mixtures thereof. Some of the compounds have at least two asymmetric carbon atoms and can therefore exist in the form of pure diastereoisomers and as mixtures thereof. It is to be understood, that, unless otherwise specified, the present invention embraces the racemates, the enantiomers and/or the diastereoisomers of the small molecule inhibitors of the invention as well as mixtures thereof.

In addition, the present invention embraces all geometric isomers. For example, when a compound of the invention incorporates a double bond or a fused ring, both the cis- and trans-forms, as well as mixtures, are embraced within the scope of the invention.

Within the present invention, it is to be understood that a compound of the invention may exhibit the phenomenon of tautomerism and that the formula drawings within this specification can represent only one of the possible tautomeric forms. It is to be understood that the invention encompasses any tautomeric form and is not to be limited merely to any one tautomeric form utilized within the formula drawings.

It is also to be understood that certain small molecule inhibitors of the invention may exhibit polymorphism, and that the present invention encompasses all such forms.

Salts

The present invention relates to the small molecule inhibitors of the invention as hereinbefore defined as well as to salts thereof. The term "salt(s)", as employed herein, denotes basic salts formed with inorganic and/or organic bases. Salts for use in pharmaceutical compositions will be pharmaceutically acceptable salts, but other salts may be useful in the production of the compounds of the invention. The term "pharmaceutically acceptable salts" refers to salts of compounds of the present invention that are pharmacologically acceptable and substantially non-toxic to the subject to which they are administered. More specifically, these salts retain the biological effectiveness and properties of the anti-atherosclerosis compounds of the invention and are formed from suitable non-toxic organic or inorganic acids or bases.

For example, where the small molecule inhibitors of the invention are sufficiently acidic, the salts of the invention include base salts formed with an inorganic or organic base. Such salts include alkali metal salts such as sodium, lithium, and potassium salts; alkaline earth metal salts such as calcium and magnesium salts; metal salts such as aluminum salts, iron salts, zinc salts, copper salts, nickel salts and a cobalt salts; inorganic amine salts such as ammonium or substituted ammonium salts, such as e.g., trimethylammonium salts; and salts with organic bases (for example, organic amines) such as chloroprocaine salts, dibenzylamine salts, dicyclohexylamine salts, dicyclohexylamines, diethanolamine salts, ethylamine salts (including diethylamine salts and triethylamine salts), ethylenediamine salts, glucosamine salts, guanidine salts, methylamine salts (including dimethylamine salts and trimethylamine salts), morpholine salts, morpholine salts, N,N'-dibenzylethylenediamine salts, N-benzyl-phenethylamine salts, N-methylglucamine salts, phenylglycine alkyl ester salts, piperazine salts, piperidine salts, procaine salts, t-butyl amines salts, tetramethylammonium salts, t-octylamine salts, tris-(2-hydroxyethyl) amine salts, and tris(hydroxymethyl)aminomethane salts. Preferred salts include those formed with sodium, lithium, potassium, calcium and magnesium.

Such salts can be formed routinely by those skilled in the art using standard techniques. Indeed, the chemical modification of a pharmaceutical compound (i.e. drug) into a salt is a technique well known to pharmaceutical chemists, (See, e.g., H. Ansel et. al., Pharmaceutical Dosage Forms and Drug Delivery Systems (6th Ed. 1995) at pp. 196 and 1456-1457, incorporated herein by reference). Salts of the compounds of the invention may be formed, for example, by reacting a compound of the invention with an amount of acid or base, such as an equivalent amount, in a medium such as one in which the salt precipitates or in an aqueous medium followed by lyophilization.

Esters

The present invention relates to the small molecule inhibitors of the invention as hereinbefore defined as well as to the esters thereof. The term "ester(s)", as employed herein, refers to compounds of the invention or salts thereof in which hydroxy groups have been converted to the corresponding esters using, for example, inorganic or organic anhydrides, acids, or acid chlorides. Esters for use in pharmaceutical compositions will be pharmaceutically acceptable esters, but other esters may be useful in the production of the compounds of the invention.

The term "pharmaceutically acceptable esters" refers to esters of the compounds of the present invention that are pharmacologically acceptable and substantially non-toxic to the subject to which they are administered. More specifically, these esters retain the biological effectiveness and properties of the anti-atherosclerosis small molecule inhibitors of the invention and act as prodrugs which, when absorbed into the bloodstream of a warm-blooded animal, cleave in such a manner as to produce the parent alcohol small molecule inhibitor.

Esters of the small molecule inhibitors of the present invention include among others the following groups (1) carboxylic acid esters obtained by esterification of the hydroxy groups, in which the non-carbonyl moiety of the carboxylic acid portion of the ester grouping is selected from straight or branched chain alkyl (for example, ethyl, n-propyl, t-butyl, n-butyl, methyl, propyl, isopropyl, butyl, isobutyl, or pentyl), alkoxyalkyl (for example, methoxymethyl, acetoxymethyl, and 2,2-dimethylpropionyloxymethyl), aralkyl (for example, benzyl), aryloxyalkyl (for example, phenoxymethyl), aryl (for example, phenyl optionally substituted with, for example, halogen, $C_{1-4}$ alkyl, or $C_{1-4}$ alkoxy, or amino); (2) sulfonate esters, such as alkyl- or aralkylsulfonyl (for example, methanesulfonyl); (3) amino acid esters (for example, L-valyl or L-isoleucyl); (4) phosphonate esters; (5) mono-, di- or triphosphate esters (including phosphoramidic cyclic esters). The phosphate esters may be further esterified by, for example, a $C_{1-20}$ alcohol or reactive derivative thereof, or by a 2,3-di($C_{6-24}$)acyl glycerol. (6) Carbamic acid ester (for example N-methylcarbamic ester); and (7) Carbonic acid ester (for example methylcabonate).

Further information concerning examples of and the use of esters for the delivery of pharmaceutical compounds is available in Design of Prodrugs. Bundgaard H ed. (Elsevier, 1985) incorporated herein by reference. See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191; Jarkko Rautio et a, Nat. Rev. Drug Discov., 7, pp. 255-270 (2008); and Pen-Wei Hsieh et al., Curr. Pharm. Des., 15 (19), pp. 2236-2250 (2009), all incorporated herein by reference.

The small molecule inhibitors of this invention may be esterified by a variety of conventional procedures including reacting the appropriate anhydride, carboxylic acid or acid chloride with an alcohol group of a compound of this invention. For example, an appropriate anhydride may be reacted with an alcohol in the presence of a base, such as 1,8-bis[dimethylamino]naphthalene or N,N-dimethylaminopyridine, to facilitate acylation. Also, an appropriate carboxylic acid can be reacted with an alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and, optionally, an acylation catalyst. Esterification can also be effected using the appropriate carboxylic acid. Reaction of an acid chloride with an alcohol can also be carried out. When a compound of the invention contains a number of free hydroxy group, those groups not being converted into a prodrug functionality may be protected (for example, using a t-butyl-dimethylsilyl group), and later deprotected. Also, enzymatic methods may be used to selectively phosphorylate or dephosphorylate alcohol functionalities. One skilled in the art would readily know how to successfully carry out these as well as other known methods of esterification of alcohols.

Esters of the small molecule inhibitors of the invention may form salts. Where this is the case, this is achieved by conventional techniques as described above.

In a specific embodiment, esters of the present invention are compounds of formulas I, Ia, Ib, and II-VIII of the present invention with a methyl, ethyl, propyl, or butyl at position R1.

Solvates

The small molecule inhibitors of the invention may exist in unsolvated as well as solvated forms with solvents such as water, ethanol, and the like, and it is intended that the invention embrace both solvated and unsolvated forms.

"Solvate" means a physical association of a small molecule inhibitor of this invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates. Solvates for use in pharmaceutical compositions will be pharmaceutically acceptable solvates, but other solvates may be useful in the production of the compounds of the invention.

As used herein, the term "pharmaceutically acceptable solvates" means solvates of small molecule inhibitors of the present invention that are pharmacologically acceptable and substantially non-toxic to the subject to which they are administered. More specifically, these solvates retain the biological effectiveness and properties of the anti-atherosclerosis small molecule inhibitors of the invention and are formed from suitable non-toxic solvents.

Non-limiting examples of suitable solvates include ethanolates, methanolates, and the like, as well as hydrates, which are solvates wherein the solvent molecules are $H_2O$.

Preparation of solvates is generally known. Thus, for example, Caira, 2004, incorporated herein by reference, describe the preparation of the solvates of the antifungal fluconazole in ethyl acetate as well as from water. Similar preparations of solvates, hemisolvate, hydrates and the like are described by van Tonder, 2004; Bingham, 2001, both incorporated herein by reference.

A typical, non-limiting, process for preparing a solvate involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, can be used to show the presence of the solvent (or water) in the crystals as a solvate (or hydrate).

Antibodies

The present invention also encompasses the use of antibodies that specifically bind to either of neuraminidase 1 (NP_000425.1); or to neuraminidase 3 (isoform 1 (Q9UQ49-1); or 2 (Q9UQ49-2). (see FIG. 16). Antibodies that specifically bind to either of neu1 or neu3 can be prepared by using epitopes present specifically in either of these proteins. See alignments of neuraminidase 1 to 4 in FIGS. 17A-B.

As indicated above, illustrative human neuraminidase amino acid sequences are presented in FIGS. 17-B. Antibodies that specifically bind to neuraminidase 1 or 3 may be devised by targeting epitope regions of these neuraminidases that are specifically found in each of these enzymes. An epitope of a protein/polypeptide is defined as a fragment of said protein/polypeptide of at least about 4 or 5 amino acids in length, capable of eliciting a specific antibody and/or an immune cell (e.g., a T cell or B cell) bearing a receptor capable of specifically binding said epitope. Two different kinds of epitopes exist: linear epitopes and conformational epitopes. A linear epitope comprises a stretch of consecutive amino acids. A conformational epitope is typically formed by several stretches of consecutive amino acids that are folded in position and together form an epitope in a properly folded protein. An immunogenic fragment as used herein refers to either one, or both, of said types of epitopes. Without being so limited, epitopes in a sequence may be predicted with softwares such as BCPred™, AAP™, FBCPredn™ and ABCPredN™.

Methods for making antibodies are well known in the art. Polyclonal antibodies can be prepared by immunizing a suitable subject (e.g., rabbit, goat, mouse, or other mammal) with the polypeptide/protein of interest or a fragment thereof as an immunogen. A polypeptide/protein "fragment" "portion" or "segment" is a stretch of amino acid residues of at least about 5, 7, 10, 14, 15, 20, 21 or more amino acids of the polypeptide noted above. The antibody titer in the immunized subject can be monitored over time by standard techniques, such as with an enzyme linked immunosorbent assay (ELISA) using immobilized exosomal marker polypeptide or a fragment thereof. At an appropriate time after immunization, e.g., when the antibody titers are highest, antibody-producing cells can be obtained from the animal, usually a mouse, and can be used to prepare monoclonal antibodies by standard techniques, such as the hybridoma technique originally described by Kohler and Milstein (1975) Nature 256: 495-497, the human B cell hybridoma technique (Kozbor et al. (1983) Immunol. Today 4: 72), the EBV-hybridoma technique (Cole et al. (1985) in Monoclonal Antibodies and Cancer Therapy, ed. Reisfeld and Sell (Alan R. Liss, Inc., New York, NY), pp. 77-96) or trioma techniques. The technology for producing hybridomas is well known (see generally Coligan et al., eds. (1994) Current Protocols in Immunology, John Wiley & Sons, Inc., New York, NY).

Alternatively, to preparing monoclonal antibody-secreting hybridomas, a monoclonal antibody can be identified and isolated by screening a recombinant combinatorial immunoglobulin library (e.g., an antibody phage display library) with a polypeptide or a fragment thereof to thereby isolate immunoglobulin library members that bind the polypeptide. Kits for generating and screening phage display libraries are commercially available (e.g., the Pharmacia Recombinant Phage Antibody System™, Catalog No. 27-9400-01; and the Stratagene SurfZAP™ Phage Display Kit, Catalog No. 240612).

Without being so limited, anti-neuraminidase 1 (lysosomal sialidase) antibodies include: Anti-NEU1/NEU Antibody (aa172-221) IHC-Plus™ from LifeSpan BioScience; Human NEU-1/Sialidase-1 Antibody (MAB6860) from R & D Systems; Human NEU-1/Sialidase-1 Antibody (MAB6860-SP) from R & D systems; NEU-1/Sialidase-1 Antibody (3D4) (NBP2-46152) from Novus Biologicals; NEU-1/Sialidase-1 Antibody (H00004758-1302P-50ug) from Novus Biologicals; anti-Neuraminidase, NEU (NEU) (Internal Region) antibody (ABIN964880); Monoclonal Antibody to Neuraminidase (NEU) (MAB611Hu21) from Cloud-Clone; Anti-NEU1 (HPA015634) from Atlas antibody.

Without being so limited, anti-neuraminidase 3 (membrane sialidase) antibodies include Anti-NEU3 Antibody (clone 11B) (LS-C179421-100) from Lifespans BioScience; anti-Neu3 antibody (ABIN1449196) from Antibodies online; NEU3 Antibody (NBP2-48694) from Novus Biologicals; Anti-NEU3 Antibody (HPA038730) from Atlas Antibodies; Anti-NEU3 (Human) mAb (D164-3) from MBL International; Sialidase 3 antibody (orb186135) from Biorbyt, etc.

Nucleic Acid Inhibitors

In a specific embodiment, the specific inhibitor of the present invention is a double-stranded RNA (dsRNA) molecule (or a molecule comprising region of double-strandedness). The dsRNA comprises a subsequence of a neu1 and/or neu3 polynucleotide (e.g., a subsequence of the sequence encoding neu1 or neu3 disclosed in FIGS. 21 and 22A-B). In some embodiments, the dsRNA is about 15, 16, 17, 18, 19, 20, 21, 22, 23, 24, 25 or more duplex nucleotides in length. in some embodiments, the dsRNA is a small interfering RNA (siRNA), a short-hairpin RNA (shRNA), or a micro RNA (miRNA). Also provided herein are double-stranded RNA (dsRNA) molecules, comprising a portion of the mature polypeptide coding sequence of any one of the coding sequences of the polypeptides disclosed herein of inhibiting expression of that polypeptide in a cell. While the present disclosure is not limited by any particular mechanism of action, in some embodiments, the dsRNA enters a cell and causes the degradation of a single-stranded RNA (ssRNA) of similar or identical sequences, including endogenous mRNAs. When a cell is exposed to dsRNA, mRNA from the homologous gene is selectively degraded by a process called RNA interference (RNAi). In some embodiments, dsRNAs provided herein are used in gene-silencing methods. In one aspect, methods are provided to selectively degrade RNA using the dsRNAi's disclosed herein. In some embodiments, the specific inhibitor of the present invention is a shRNA expressed by a DNA vector transfected or transduced into a target cell. In some embodiments, the specific inhibitor of the present invention is a virus encoding a shRNA. In some embodiments, the specific inhibitor of the present invention is a vector encoding a shRNA. The process is alternatively practiced in vitro, ex vivo or in vivo. In one aspect, the dsRNA molecules are used to generate a lossof-function mutation in a cell, an organ or an organism. Methods for making and using dsRNA molecules to selectively degrade RNA are described in the art, see, for example, U.S. Pat. Nos. 6,506,559; 6,511,824; 6,515,109; and 6,489,127.

Generation of Anti-Neu1 or Anti-Neu3 dsRNA Molecules

In some embodiments, an anti-neu1 or anti-neu3 double stranded RNA molecule with sequences complementary to a target is generated. The synthesis of an anti-neu1 or anti-neu3 dsRNA molecule comprises: (a) synthesis of two complementary strands of the dsRNA molecule; and (b) annealing the two complementary strands together under conditions suitable to obtain a double-stranded RNA molecule. In another embodiment, synthesis of the two complementary strands of the RNA molecule is by solid phase oligonucleotide synthesis. In yet another embodiment, synthesis of the two complementary strands of the RNA molecule is by solid phase tandem oligonucleotide synthesis. In some embodiments, a nucleic acid molecule described herein is synthesized separately and joined together post-synthetically, for example, by ligation or by hybridization following synthesis and/or deprotection. Oligonucleotides (e.g., certain modified oligonucleotides or portions of oligonucleotides lacking ribonucleotides) are synthesized using any suitable method. dsRNA constructs can be purified by gel electrophoresis or can be purified by high pressure liquid chromatography.

Design of RNAi Molecules

In some embodiments, an anti-neu1 or anti-neu3 dsRNA molecule (e.g., RNAi molecules, siRNA molecules, miRNA molecules, and analogues thereof) is about 20-25 bp. In some embodiments, the 20-25 bp dsRNA molecule (e.g., RNAi molecules, siRNA molecules, miRNA molecules, and analogues thereof) has 2-5 bp overhangs on the 3' end of each strand, and a 5' phosphate terminus and a 3' hydroxyl terminus. In some embodiments, the 20-25 bp dsRNA molecule (e.g., RNAi molecules, siRNA molecules, miRNA molecules, and analogues thereof) has blunt ends.

In some embodiments, an anti-neu1 or anti-neu3 dsRNA molecule (e.g., RNAi molecules, siRNA molecules, miRNA molecules, and analogues thereof) is assembled from two separate oligonucleotides, where one strand is the sense strand and the other is the anti-sense strand, wherein the anti-sense and sense strands are self-complementary (i.e. each strand comprises nucleotide sequence that is complementary to nucleotide sequence in the other strand; such as where the anti-sense strand and sense strand form a duplex or double stranded structure, for example wherein the double stranded region is about 19 base pairs). In some embodiments, the anti-sense strand of an anti-neu1 or anti-neu3 dsRNA molecule (e.g., siRNA molecules, miRNA molecules, and analogues thereof) comprises a nucleotide sequence that is complementary to a nucleotide sequence in a target nucleic acid molecule or a portion thereof, and the sense strand comprises a nucleotide sequence corresponding to the target nucleic acid sequence or a portion thereof. In some embodiments, an anti-neu1 or anti-neu3 dsRNA molecule (e.g., RNAi molecules, siRNA molecules, miRNA molecules, and analogues thereof) is assembled from a single oligonucleotide, where the self-complementary sense and anti-sense regions of the dsRNA molecule (e.g., RNAi molecules, siRNA molecules, miRNA molecules, and analogues thereof) are linked by means of a nucleic acid-based or non-nucleic acid-based linker(s).

In some embodiments, an anti-neu1 or anti-neu3 dsRNA molecule (e.g., RNAi molecules, siRNA molecules, miRNA molecules, and analogues thereof) comprises a single stranded polynucleotide having nucleotide sequence complementary to nucleotide sequence in a target nucleic acid molecule or a portion thereof (for example, where such dsRNA molecule (e.g., RNAi molecules, siRNA molecules, miRNA molecules, and analogues thereof) does not require the presence within the dsRNA molecule (e.g., RNAi molecules, siRNA molecules, miRNA molecules, and analogues thereof) of nucleotide sequence corresponding to the target nucleic acid sequence or a portion thereof), wherein the single stranded polynucleotide further comprises a terminal phosphate group, such as a 5'-phosphate, or 5',3'-diphosphate.

In other embodiments, an anti-neu1 or anti-neu3 dsRNA molecule (e.g., RNAi molecules, siRNA molecules, miRNA molecules, and analogues thereof) comprises separate sense and anti-sense sequences or regions, wherein the sense and anti-sense regions are covalently linked by nucleotide or non-nucleotide linker molecules, or are alternately non-covalently linked by ionic interactions, hydrogen bonding, van der Waals interactions, hydrophobic interactions, and/or stacking interactions.

The terminal structure of dsRNA molecules described herein is either blunt or cohesive (overhanging). In some embodiments, the cohesive (overhanging) end structure is a 3' overhang or a 5' overhang. In some embodiments, the number of overhanging nucleotides is any length as long as the overhang does not impair gene silencing activity. In some embodiments, an overhang sequence is not complementary (anti-sense) or identical (sense) to the neu1 or neu3 sequence. In some embodiments, the overhang sequence contains low molecular weight structures (for example a natural RNA molecule such as tRNA, rRNA or tumor or CTC RNA, or an artificial RNA molecule).

The total length of dsRNA molecules having cohesive end structure is expressed as the sum of the length of the paired double-stranded portion and that of a pair comprising overhanging single-strands at both ends. For example, in the exemplary case of a 19 bp double-stranded RNA with 4 nucleotide overhangs at both ends, the total length is expressed as 23 bp.

In some embodiments, the terminal structure of an anti-neu1 or anti-neu3 dsRNA molecule (e.g., RNAi molecules, siRNA molecules, miRNA molecules, and analogues thereof) has a stem-loop structure in which ends of one side of the double-stranded nucleic acid are connected by a linker nucleic acid, e.g., a linker RNA. In some embodiments, the length of the double-stranded region (stem-loop portion) is 15 to 49 bp, often 15 to 35 bp, and more commonly about 21 to 30 bp long.

In some embodiments, an anti-neu1 or anti-neu3 dsRNA molecule is a polynucleotide with a duplex, asymmetric duplex, hairpin or asymmetric hairpin secondary structure, having self-complementary sense and anti-sense regions, wherein the anti-sense region comprises a nucleotide sequence that is complementary to a nucleotide sequence in a separate target nucleic acid molecule or a portion thereof, and the sense region comprises a nucleotide sequence corresponding to the target nucleic acid sequence or a portion thereof.

In some embodiments, an anti-neu1 or anti-neu3 dsRNA molecule (e.g., RNAi molecules, siRNA molecules, miRNA molecules, and analogues thereof) comprises a circular nucleic acid molecule, wherein the dsRNA molecule (e.g., RNAi molecules, siRNA molecules, miRNA molecules, and analogues thereof) is about 38 to about 70 (e.g., about 38, 40, 45, 50, 55, 60, 65, or 70) nucleotides in length having about 18 to about 23 (e.g., about 18, 19, 20, 21, 22, or 23) base pairs wherein the circular oligonucleotide forms a dumbbell shaped structure having about 19 base pairs and 2 loops.

In some embodiments, a circular dsRNA molecule (e.g., RNAi molecules, siRNA molecules, miRNA molecules, and analogues thereof) contains two loop motifs, wherein one or both loop portions of the dsRNA molecule (e.g., RNAi molecules, siRNA molecules, miRNA molecules, and analogues thereof) is biodegradable. In some embodiments, degradation of the loop portions of a circular dsRNA molecule (e.g., RNAi molecules, siRNA molecules, miRNA molecules, and analogues thereof) generates a double-stranded dsRNA molecule (e.g., RNAi molecules, siRNA molecules, miRNA molecules, and analogues thereof) with 5-terminal overhangs, such as 3'-terminal nucleotide overhangs comprising about 2 nucleotides.

The sense strand of a double stranded dsRNA molecule (e.g., RNAi molecules, siRNA molecules, miRNA molecules, and analogues thereof) may have a terminal cap moiety such as an inverted deoxybasic moiety, at the 3'-end, 5-end, or both 3' and 5'-ends of the sense strand.

In some embodiments, the 3'-terminal nucleotide overhangs of an anti-neu1 or anti-neu3 dsRNA molecule (e.g., RNAi molecules, siRNA molecules, miRNA molecules, and analogues thereof) comprise ribonucleotides or deoxyribonucleotides that are chemically-modified at a nucleic acid sugar, base, or backbone. In some embodiments, the 5-terminal nucleotide overhangs comprises one or more universal base ribonucleotides. In some embodiments, the 3'-terminal nucleotide overhangs comprises one or more acyclic nucleotides.

Selection of RNAi Molecules

In some embodiments, an anti-neu1 or anti-neu3 dsRNA molecule (e.g., RNAi molecules, siRNA molecules, miRNA molecules, and analogues thereof) disclosed herein is capable of specifically binding to desired neu1 or neu3 variants while being incapable of specifically binding to non-desired neu1 or neu3 variants.

In some embodiments, an anti-neu1 or anti-neu3 dsRNA molecule (e.g., RNAi molecules, siRNA molecules, miRNA molecules, and analogues thereof) is selected for use in a method disclosed herein based on predictions of the stability of molecule. In some embodiments, a prediction of stability is achieved by employing a theoretical melting curve wherein a higher theoretical melting curve indicates an increase in the molecule's stability and a concomitant decrease in cytotoxic effects. In some embodiments, stability of an anti-neu1 or anti-neu3 dsRNA molecule (e.g., RNAi molecules, siRNA molecules, miRNA molecules, and analogues thereof) is determined empirically by measuring the hybridization of a single modified RNA strand containing one or more universal-binding nucleotide(s) to a complementary neu1 or neu3 sequence within, for example, a polynucleotide array. In some embodiments, the melting temperature (i.e., the Tm value) for each modified RNA and complementary RNA immobilized on the array is determined and, from this Tm value, the relative stability of the modified RNA pairing with a complementary RNA molecule determined.

In some embodiments, an anti-neu1 or anti-neu3 dsRNA molecule (e.g., RNAi molecules, siRNA molecules, miRNA molecules, and analogues thereof) is selected for use in a method disclosed herein based on "off-target" profiling whereby one or more dsRNA molecules is administered to a cell(s), either in vivo or in vitro, and total mRNA is collected, and used to probe a microarray comprising oligonucleotides having one or more nucleotide sequence from a panel of known genes, including non-target genes. The "off-target" profile of the modified dsRNA molecule (e.g., RNAi molecules, siRNA molecules, miRNA molecules, and analogues thereof) is quantified by determining the number of non-target genes having reduced expression levels in the presence of the RNAi molecule. The existence of "off target" binding indicates an anti-neu1 or anti-neu3 dsRNA molecule (e.g., RNAi molecules, siRNA molecules, miRNA molecules, and analogues thereof) that is capable of specifically binding to one or more non-target gene. Ideally, an anti-neu1 or anti-neu3 dsRNA molecule (e.g., RNAi molecules, siRNA molecules, miRNA molecules, and analogues thereof) applicable to therapeutic use will exhibit a high Tm value while exhibiting little or no "off-target" binding.

In some embodiments, an anti-neu1 or anti-neu3 dsRNA molecule (e.g., RNAi molecules, siRNA molecules, miRNA molecules, and analogues thereof) is selected for use in a method disclosed herein by use of a report gene assay. In some embodiments, a reporter gene construct comprises a constitutive promoter, for example the cytomegalovirus (CMV) or phosphoglycerate kinase (PGK) promoter, operably fused to, and capable of modulating the expression of, one or more reporter gene such as, for example, a luciferase gene, a chloramphenicol (CAT) gene, and/or a β-galactosidase gene, which, in turn, is operably fused in-frame with an oligonucleotide (typically between about 15 base-pairs and about 40 base-pairs, more typically between about 19 base-pairs and about 30 base-pairs, most typically 20, 21, 22, 23, 24, 25, 26, 27, 28, or 29 base-pairs) that contains a target sequence for the one or more RNAi molecules. In some embodiments, individual reporter gene expression constructs are co-transfected with one or more RNAi molecules. In some embodiments, the capacity of a given dsRNA molecule (e.g., RNAi molecules, siRNA molecules, miRNA molecules, and analogues thereof) to reduce the expression level of each of the contemplated gene variants is determined by comparing the measured reporter gene activity from cells transfected with and without the modified RNAi molecule.

In some embodiments, an anti-neu1 or anti-neu3 dsRNA molecule (e.g., RNAi molecules, siRNA molecules, miRNA molecules, and analogues thereof) is selected for use in a method disclosed herein by assaying its ability to specifically bind to an mRNA, such as an mRNA expressed by a target tumor cell or circulating tumor cell (CTC).

The present invention also relates to the use of the above-mentioned inhibitors of the invention and in the case of small molecule inhibitors, their pharmaceutically acceptable salts, esters, and solvates thereof in the preparation of a medicament, a combination or a kit.

Compositions, Combination and kits

Compositions

The present invention also relates to pharmaceutical compositions comprising the above-mentioned inhibitors of the invention or, in the case of small molecule inhibitors, their pharmaceutically acceptable salts, esters and solvates thereof.

Without being so limited, the medicaments/pharmaceutical compositions of the invention may be administered orally, for example in the form of tablets, coated tablets, dragees, hard or soft gelatin capsules, solutions, emulsions or suspensions. Administration can also be carried out rectally, for example using suppositories; locally, topically, or percutaneously, for example using ointments, creams, gels or solutions; or parenterally, e.g., intravenously, intramuscularly, subcutaneously, intrathecally or transdermally, using for example injectable solutions. Furthermore, administration can be carried out sublingually, nasally, or as ophthalmological preparations or an aerosol, for example in the form of a spray, such as a nasal spray.

For the preparation of tablets, coated tablets, dragees or hard gelatin capsules, the compounds of the present invention may be admixed with any known pharmaceutically inert, inorganic or organic excipient and/or carrier. Examples of suitable excipients/carriers include lactose, maize starch or derivatives thereof, talc or stearic acid or salts thereof.

Suitable excipients for use with soft gelatin capsules include for example vegetable oils, waxes, fats, semi-solid or liquid polyols etc. According to the nature of the active ingredients it may however be the case that no excipient is needed at all for soft gelatin capsules.

For the preparation of solutions and syrups, excipients which may be used include for example water, polyols, saccharose, invert sugar and glucose.

For injectable solutions, excipients which may be used include for example water, saline, alcohols, polyols, glycerine, vegetable oils and other appropriate excipients.

For suppositories, and local or percutaneous application, excipients which may be used include for example natural or hardened oils, waxes, fats and semi-solid or liquid polyols.

The medicaments/pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically active agents.

Intravenous, or oral administrations are preferred forms of use. The dosages in which the inhibitors of the invention are administered in effective amounts depend on the nature of the specific active ingredient, the age and the requirements of the patient and the mode of application.

As mentioned above, the pharmaceutical compositions of the invention can contain a pharmaceutically acceptable carrier including, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Pharmaceutically acceptable carriers also can include physiologically acceptable aqueous vehicles (e.g., physiological saline) or other known carriers appropriate to specific routes of administration.

The inhibitors of the invention may be incorporated into dosage forms in conjunction with any of the vehicles which are commonly employed in pharmaceutical preparations, e.g., talc, gum arabic, lactose, starch, magnesium searate, cocoa butter, aqueous or non-aqueous solvents, oils, paraffin derivatives or glycols. Emulsions such as those described in U.S. Pat. No. 5,434,183, incorporated herein by reference, may also be used in which vegetable oil (e.g., soybean oil or safflower oil), emulsifying agent (e.g., egg yolk phospholipid) and water are combined with glycerol. Methods for preparing appropriate formulations are well known in the art (see e.g., Remington's Pharmaceutical Sciences, 16th Ed., 1980, A. Oslo Ed., Easton, Pa. incorporated herein by reference).

In cases where parenteral administration is elected as the route of administration, preparations containing the inhibitors of the invention may be provided to patients in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringers solution containing lactose, or fixed oils. Intravenous vehicles may include fluid and nutrient replenishers, electrolyte replenishers, such as those based upon Ringers dextrose, and the like.

It is a prerequisite that all adjuvants used in the manufacture of the preparations, such as carriers, are non-toxic and more generally pharmaceutically acceptable.

As used herein, "pharmaceutically acceptable" such as pharmaceutically acceptable carrier, excipient, etc., means pharmacologically acceptable and substantially non-toxic to the subject to which the particular inhibitor is administered.

Any amount of a pharmaceutical composition can be administered to a subject. The dosages will depend on many factors including the mode of administration. Typically, the amount of the inhibitor of the invention contained within a single dose will be an amount that effectively prevent, delay or treat the disease or condition to be treated, delayed or prevented without inducing significant toxicity.

The effective amount of the inhibitors of the invention may also be measured directly. The effective amount may be given daily or weekly or fractions thereof. Typically, a pharmaceutical composition of the invention can be administered in an amount from about 0.001 mg up to about 500 mg per kg of body weight per day (e.g., 10 mg, 50 mg, 100 mg, or 250 mg). Dosages may be provided in either a single or multiple dosage regimen. For example, in some embodiments the effective amount may range from about 1 mg to about 25 grams of the composition per day, about 50 mg to about 10 grams of the composition per day, from about 100 mg to about 5 grams of the composition per day, about 1 gram of the composition per day, about 1 mg to about 25 grams of the composition per week, about 50 mg to about 10 grams of the composition per week, about 100 mg to about 5 grams of the composition every other day, and about 1 gram of the composition once a week.

These are simply guidelines since the actual dose must be carefully selected and titrated by the attending physician based upon clinical factors unique to each patient. The optimal daily dose will be determined by methods known in the art and will be influenced by factors such as the age of the patient and other clinically relevant factors. In addition, patients may be taking medications for other diseases or conditions. The other medications may be continued during the time that the pharmaceutical composition of the invention is given to the patient, but it is particularly advisable in such cases to begin with low doses to determine if adverse side effects are experienced.

Combinations

In accordance with another aspect, there is provided a combination of at least one of the inhibitors described herein (e.g., a specific neu1 inhibitor, a specific neu3 inhibitor or a bispecific neu1 or neu3 inhibitor (e.g., neu3/neu4 inhibitor)) with another of the inhibitors described herein and/or with another anti-atherosclerotic inhibitor and/or with a non-pharmaceutical treatment/regimen. Without being so limited, such anti-atherosclerotic inhibitors include statin, dihydropyridine calcium antagonists, ACE inhibitors containing the sulphydryl group, highly lipophilic beta-blockers, cholesterol transport inhibitors, bile acid transport inhibitors, inhibitors of acyl coenzyme A:cholesterol acyltransferase, PCSK9 inhibitors, etc. and such non-pharmaceutical means includes stopping smoking, practicing regular exercise, following a diet high in fruits and vegetables (e.g., Mediterranean diet), etc.

In accordance with an aspect, there is provided a composition comprising at least one of the inhibitors as defined herein, and (i) another of the inhibitors described herein; (ii) another anti-atherosclerotic agent; (iii) a pharmaceutically acceptable carrier; or (iv) a combination of at least two of (i) to (iii). In accordance with another aspect, there is provided a method for preventing or treating atherosclerosis or a symptom thereof comprising administering an effective amount of at least one of the inhibitors described herein (e.g., a specific neu1 inhibitor, a specific neu3 inhibitor or a bispecific neu1 or neu3 inhibitor (e.g., neu3/neu4 inhibitor)); and (i) another of the inhibitors described herein (e.g., a specific neu3 (or bispecific neu1 or neu3 inhibitor (e.g., neu3/neu4 inhibitor)); (ii) another anti-atherosclerotic compound; and/or (iii) a non-pharmaceutical means.

In a specific embodiment, said composition is a pharmaceutical composition. In another specific embodiment, the composition comprises (i) an inhibitor as defined herein; and (ii) another anti-atherosclerotic agent.

Kits

In accordance with another aspect of the present invention, there is provided a kit comprising the inhibitor defined herein or the above-mentioned composition, and instructions to use same in the prevention or treatment of atherosclerosis or of a symptom thereof.

In a specific embodiment of the kit, the kit comprises: (i) another of the inhibitors described herein; (ii) another anti-atherosclerotic agent; (iii) instructions to use same in the prevention or treatment of atherosclerosis or of a symptom thereof; or (iv) a combination of at least two of (i) to (iii).

Screening Methods

In accordance with another aspect of the present invention, there is provided a method of identifying an anti-atherosclerosis agent, said method comprising contacting a neuraminidase 1 or a neuraminidase 3 (or a cell expressing same) with a candidate compound (and eventually a neuraminidase 1 or neuraminidase 3 substrate such as a sialylated substrate)) and determining the effect of said candidate compound on the neuraminidase 1 or 3 expression and/or activity (e.g., ability of compound to prevent neuraminidase 1 or a neuraminidase 3 to desialylated ApoB), wherein a decrease in the expression and/or activity of the neuraminidase 1 or 3 in the presence as compared to in the absence of said candidate compound is an indication that said candidate compound may prevent or treat atherosclerosis or a symptom thereof.

As used herein the terms "neuraminidase 1 or neuraminidase 3 activity" refers to ApoB desialylation (e.g., in plasma) and to events downstream of this desialylation such as LDL uptake by macrophage, formation of foam cells, LDL incorporation in arterial walls, increase of fatty streak regions number on arterial walls, increase of fatty streak regions size on arterial walls, infiltration of T cell in atherosclerotic lesions, infiltration of macrophages, vascular smooth muscle cells or leucocytes in atherosclerotic lesions, production of extracellular matrix molecules, collagen and elastin, formation of a fibrous cap that covers the plaque, cellular necrosis, plaque rupture and thrombosis. Neuraminidase 1 or neuraminidase 3 activity can further be measured in vitro and in situ using substrates such as sialylated ApoB, 4-Mu-5NeuAc, sialyllactose or other knows substrates of neuraminidases/sialidases.

As used herein the terms "subject in need thereof" refer to a subject who would benefit from receiving an effective amount of the inhibitor of the present invention. It refers to an animal and to a human. The inhibitors of the present invention may be used for veterinary applications and be used in pets or other animals (e.g., pets such as cats, dogs, horses, etc.; and cattle, fishes, swine, poultry, etc.).

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% of the numerical value qualified.

Unless otherwise defined, all technical and scientific terms used herein have the same meaning as commonly understood by one of ordinary skill in the art to which this invention belongs.

Other objects, advantages and features of the present invention will become more apparent upon reading of the following non-restrictive description of specific embodiments thereof, given by way of example only with reference to the accompanying drawings.

Description of Illustrative Embodiments

The present invention is illustrated in further details by the following non-limiting examples.

Example 1: Material and Methods—Biological

Isolation of LDL and LPDS

Low density lipoproteins (LDL) ($1.020<d<1.063$ g/ml) were isolated from EDTA-anticoagulated blood plasma obtained from healthy normolipidemic human donors by sequential ultracentrifugation as described (Levy, 1990). The isolated LDL fraction was dialyzed against phosphate-buffered saline (PBS) containing 1 mM EDTA at 4° C. Lipoprotein-deficient serum (LPDS) was prepared by ultracentrifugation at density of 1.25 g/ml (Levy, 1990) and dialyzed against PBS at 4° C. Protein concentration was measured using a Bio-Rad™ Bradford reagent.

LDL Modification and Labeling

Isolated LDL were desialylated by overnight treatment at 37° C. with human recombinant neuraminidases (Smutova, 2014) in a ratio of 1 mU of enzyme per 10 μg of LDL. Before adding the enzyme pH of LDL fraction was adjusted to the pH optimal for the corresponding neuraminidase (4.5 for Neu1, Neu3, and Neu4; and 5.5 for Neu2). Desialylation of LDL was confirmed by lectin blot as described below. To prepare oxidized LDL the sample was dialyzed against PBS supplemented with 5 μmol/L $CuSO_4$ and incubated at 37° C. for 24 hours. All LDL fractions were used within 2 weeks after isolation and filtered (0.22 μm pore size) before each experiment.

Native and modified LDL were labeled with a fluorescent 3,3'-dioctadecylindocarbocyanine (Dil) dye (Molecular Probes) essentially as described (Pitas, 1981) with minor changes. Briefly, Dil dissolved in dimethyl sulfoxide (DMSO) at a concentration of 3 mg/ml was added to 2 ml of LPDS containing 1 mg of LDL to a final concentration of 300 μg of Dil per 1 mg of LDL protein. The sample was then incubated at 37° C. for 24 h in the dark. Then, the density of the incubation mixture was increased to 1.063 g/ml by adding KBr and sample was subjected to ultracentrifugation to re-isolate LDL. Labeling of native or modified LDL with Alexa Fluor 488 (Invitrogen) was performed following the manufacture's protocol. After the labeling all LDL fractions were dialyzed against PBS.

Production and purification of human neuraminidases 1-4 Neu1 was purified from mouse kidney by affinity chromatography on a concanavalin A-Sepharose™ column followed by fast protein liquid chromatography gel filtration on Superose-6™ column, as previously described (Pshezhetsky, 1996), or expressed as a His-tagged protein in HEK293 transduced with lentiviral bicistronic vector containing human Neu1-$(His)_6$ and CathA cDNA at the multiplicity of infection 10. Two weeks after transduction cells were harvested and a crude lysate showing ~200 nmol/h mg of sialidase activity used in experiments. NEU3 and NEU2 were expressed as N-terminal MBP fusion protein in *E. coli* and purified as previously reported (Albohy, 2010). NEU4 was expressed as a GST fusion protein in *E. coli* and purified as previously reported (Albohy, 2011). Inhibition assays against 4-methylumbelliferyl alpha-D-N-acetylneuraminic acid (4MU-NANA) cleavage and GM3 cleavage was performed using protocols reported previously (Zhang, 2013). In vitro assays were conducted in 0.1 M sodium acetate buffer at optimum pH for each enzyme (4.5 for NEU1, NEU3 and NEU4; 5.5 for NEU2) (Zhang, 2013). To get comparable IC50 among the four isoenzymes, similar activity units of each enzyme were used in the assay.

Lectin Blotting

LDL samples were subjected to NuPAGE™ using 3-8% Novex™ Bis-Tris gels (Invitrogen) and transferred to nitrocellulose membrane. Blots were blocked in 50 mM Tris-HCl (pH 7.4) containing 150 mM NaCl, 3% BSA, and 0.05% Tween™ 20 at room temperature for 1 h and then incubated overnight with biotinylated *Maackia amurensis* lectin (MAL) II, *Sambucus nigra* agglutinin (SNA) or peanut (*Arachis hypogaea*) agglutinin (PNA) (all Vector Laboratories) in the same buffer containing 1% BSA at 4° C. After the washing with TBS-Tween™ (0.05%), blots were incubated with HRP-conjugated streptavidin for 1 h at room temperature. Following washing, blots were developed using ECL chemiluminescence reagent (Thermo Fisher Scientific).

Analysis of LDL Uptake by Cultured Human Monocyte-Derived Macrophages

Peripheral blood mononuclear cells were isolated by leukophoresis of blood from human immunodeficiency virus, type 1, and hepatitis B and C seronegative donors followed by centrifugation over Ficoll-Paque™ Plus (Amersham Biosciences) gradient. Monocytes were isolated from the mononuclear cells using of EasySep™ Human Monocyte Isolation Kit (Stemcell). Cells were plated at a density of $2\times10^5$ monocytes per $cm^2$ on glass coverslips in 24-well plates in RPMI 1640 medium containing 10% FBS gold, 1% antibiotic-antimicotic and 20 ng/ml of human recombinant macrophage colony-stimulating factor (M-CSF, eBioscience). After 7 days in culture, differentiated macrophages (larger and more granular than monocytes as seen by light microscopy) were confirmed to have characteristic macrophage cell surface phenotypic markers (CD14, CD206) by flow cytometry.

Human monocyte-derived macrophages were cultured overnight with RPMI medium 1640, containing 5% Lipoprotein Deficient Serum (LPDS) and 20 ng/ml M-CSF, supplemented with 30 μg/ml of labeled LDL and incubated at 37° C. for 3 h. To study the competition between the uptake of desialylated and oxidized LDL, macrophages were incubated for 3 hours with 30 μg/ml of Dil-labeled oxidized or desialylated LDL in the absence or in the presence of 5, 10 or 20-fold excess of non-labeled oxidized or desialylated LDL. To study the uptake of LDL by HepG2, the cells grown on glass coverslips coated with poly-1-lysine in 24-well plates were incubated for 20 min in DMEM containing 5% LPDS and 30 μg/ml of native or modified labeled LDL. After the incubation, all cells were washed three times with ice-cold PBS and incubated on ice with 2 mg/ml of heparin (Sigma) in PBS for 2 h. Cells were further rinsed with PBS and fixed for 20 min with 4% paraformaldehyde/4% sucrose solution on ice. The cover slips were mounted on the slides with ProLong™ Gold antifade reagent (Thermofisher) and analyzed by the fluorescence microscopy using a Leica™ DM 5500 Q upright confocal microscope (40× dry objective).

Analysis of LDL Incorporation in the Wall of Aortic Root

Sixteen-week-old C57B16 male mice kept on a normal diet were injected through the tail vein with 200 μg of native or desialylated Alexa- or Dil-labeled LDL in 100 μl of saline (n=6 animals for each group). Eight hours after injection, mice were euthanized and perfused with 4% paraformaldehyde solution. Accumulation of Alexa or Dil was quantified on cross-sections of the aorta starting at the level of the aortic sinus. For that, isolated hearts were embedded with optimum cutting temperature (OCT) compound (Tissue-Tek). Forty sections with 10-μm thickness were prepared from the top of the left ventricle, where the aortic valves were first visible, up to the position in the aorta where the valve cusps were just disappearing from the field. Fluorescence was analyzed using a Leica™ DM 5500 Q upright confocal microscope (40× dry objective). The captured images were quantified using ImageJ™ software.

Analysis of Atherosclerotic Lesions in $ApoE^{-/-}$ Mice Deficient in Neuraminidases 1, 3 or 4

To generate $ApoE^{-/-}$ mice with deficiencies of neuraminidases 1, 3 and 4, $ApoE^{-/-}$ (JaxLab) mice were crossed with previously described Neu3 KO ($Neu3^{-/-}$) or Neu4 KO ($Neu4^{-/-}$), mice or with CathA hypomorph mice with secondary 90% reduction of the Neu1 activity in tissues ($Cath^{AS190A\text{-}Neo}$). All mice had the same C5761/6J genetic background. Mice were housed in an enriched environment with continuous access to food and water, under constant temperature and humidity, on a 12 h light/dark cycle. Approval for the animal experimentation was granted by the Animal Care and Use Committee of the Ste-Justine Hospital Research Center. Mice were kept on normal chow diet. Between 8 and 20 female mice were analyzed for each genotype.

At the age of 16 weeks, mice were sacrificed and areas of atherosclerotic lesions in aortic root analyzed as described previously (Gayral, 2014). Briefly, isolated hearts were washed and incubated overnight in PBS at 4° C., frozen in a cryostat mount with OCT compound (Tissue-Tek) and stored at −80° C. Surface lesion area at the aortic root was measured by computer-assisted image quantification after staining with Oil Red O.

To analyze inflammatory cell infiltration within atherosclerotic lesions, frozen sections from the aortic root were air-dried, fixed in acetone/methanol (1:1) mix, and incubated with 3% hydrogen peroxide in methanol for 10 min to eliminate endogenous peroxidase. The sections were then blocked in 3% BSA for 30 minutes and in 2% normal rabbit serum (Vector Laboratories) for 3 min. The sections were further stained with either rat monoclonal anti-mouse macrophage antibody (clone MOMA-2 from Serotec; 1:50 dilution) or goat polyclonal anti-mouse CD3 antibody (clone M-20 from Santa Cruz Biotechnology, 1:200 dilution); both in 2% mouse serum. Then, sections were incubated with corresponding secondary biotinylated antibodies (Vector Laboratories) in 3% BSA and visualized with a streptavidin horseradish peroxidase complex (Sigma) and DAB peroxidase substrate (Sigma). Counter-staining was performed using Mayer's haematoxylin method.

LDL, cholesterol, triglycerides, and HDL levels in the mouse plasma were measured by Sainte-Justine University Hospital central biochemistry laboratory using the glycerol phosphate oxidase technique and enzymatic method of the cholesterol esterase as described by Allain, 1974; and Roeschlau, 1974, respectively.

Histochemical Assay of Neuraminidase Activity in Mouse Tissues

Five μm-thick sections were cut from OCT-embedded frozen mouse tissues using a CM3050 S Microtome (Leica). The slices were incubated with 0.2 mM sialidase substrate 1,5-bromo-4-chloroindol-3-yl 5-acetamido-3,5-dideoxy-α-d-glycero-d-galacto-2-nonulopyranosidonic acid (X-Neu5Ac, Sigma) and Fast Red™ Violet LB Salt (Sigma), at pH 4.7 for 1 h. Then the sections were rinsed in PBS, mounted on glass slides using Vectashield™ mounting medium and scanned using Axioscan™ slide scanner (Zeiss).

Statistical Analysis

Figure 4A:
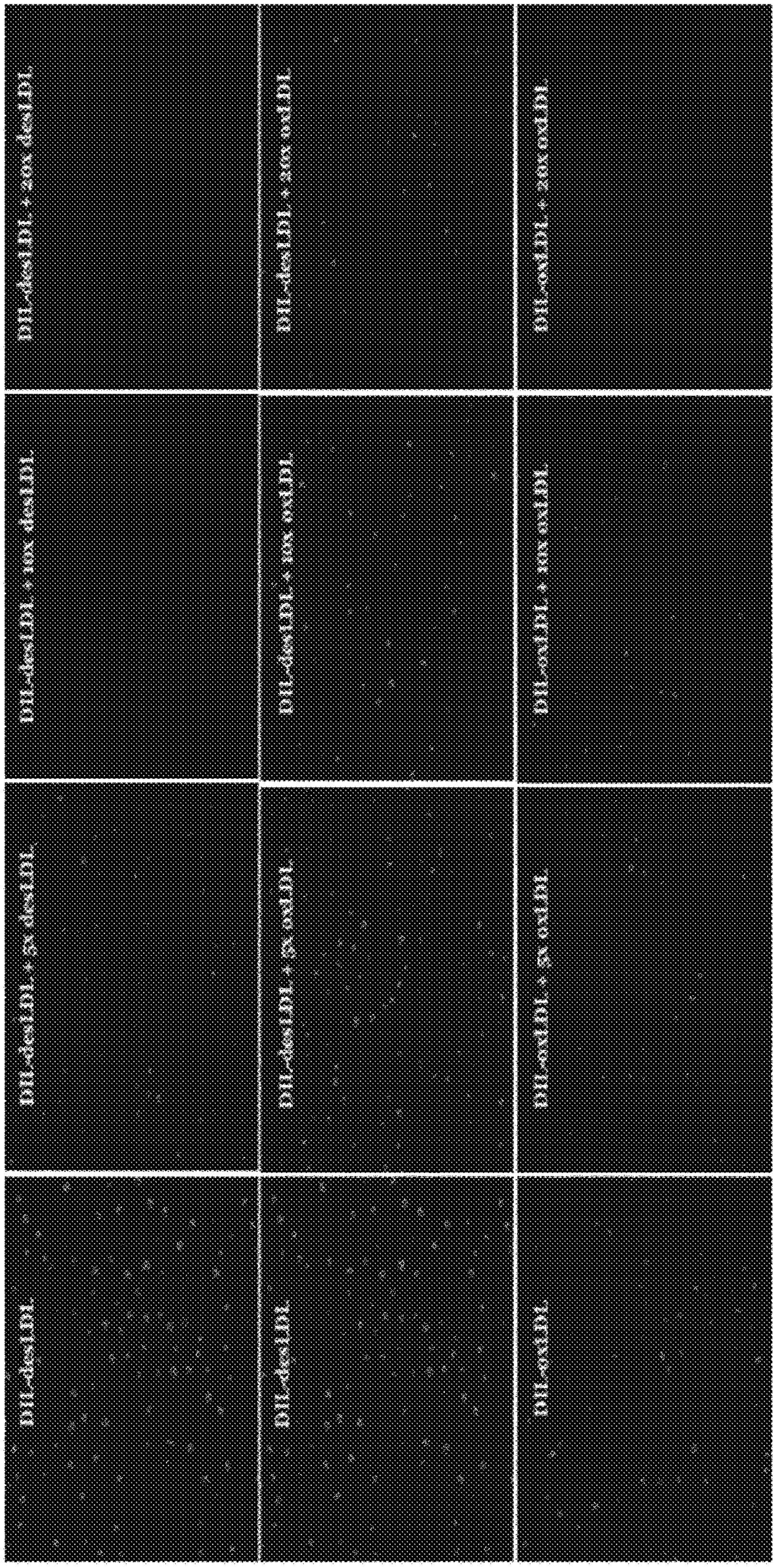
FIGS. 4A-B: Oxidized LDL only partially blocks the uptake of desialylated LDL by macrophages. Cultured macrophages where incubated for 3 h at 37° C. with Dil-labeled desialylated or oxidized LDL with or without 5, 10 or 20-fold excess of non-labeled oxidized or desialylated LDL.
Figure 4B:
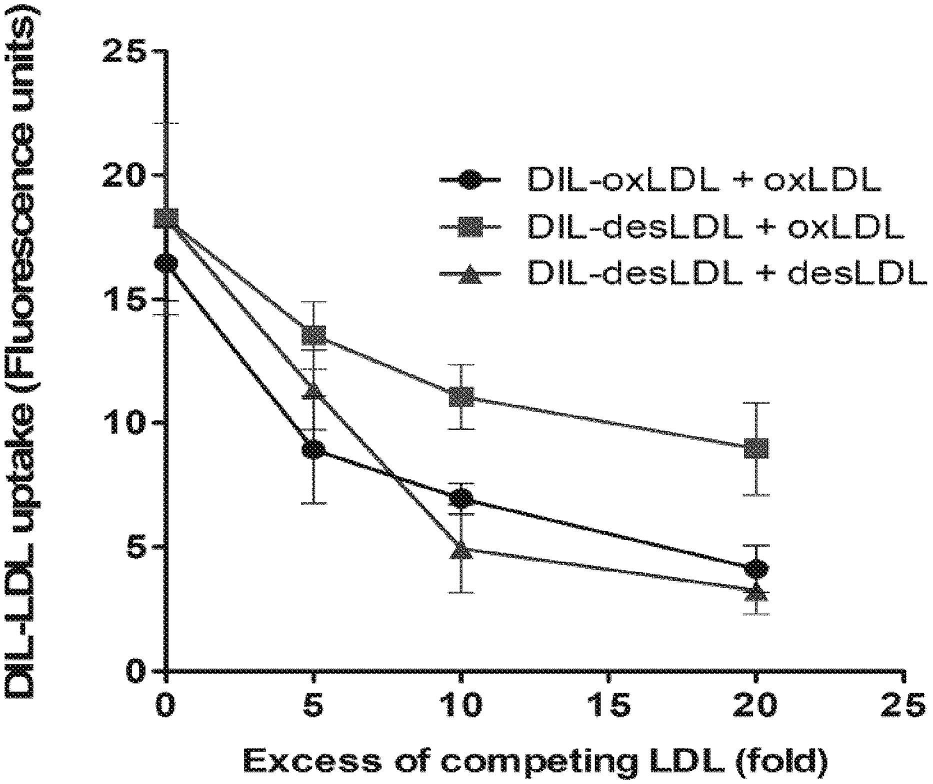

Statistical analyses were performed using an unpaired t-test (FIGS. 2, 3, 5, 9 and 11), one-way ANOVA (FIGS. 6 and 8) or two-way ANOVA ((FIG. 4) and Prism Graphpad™ software. P-value of 0.05 or less was considered significant. Bonferroni post-hoc test was used to compare specific means, if significance was determined.

Example 2: ApoB in Human LDL can be Desialylated In Vitro by Neuraminidases 3 and 4

Figure 1C:
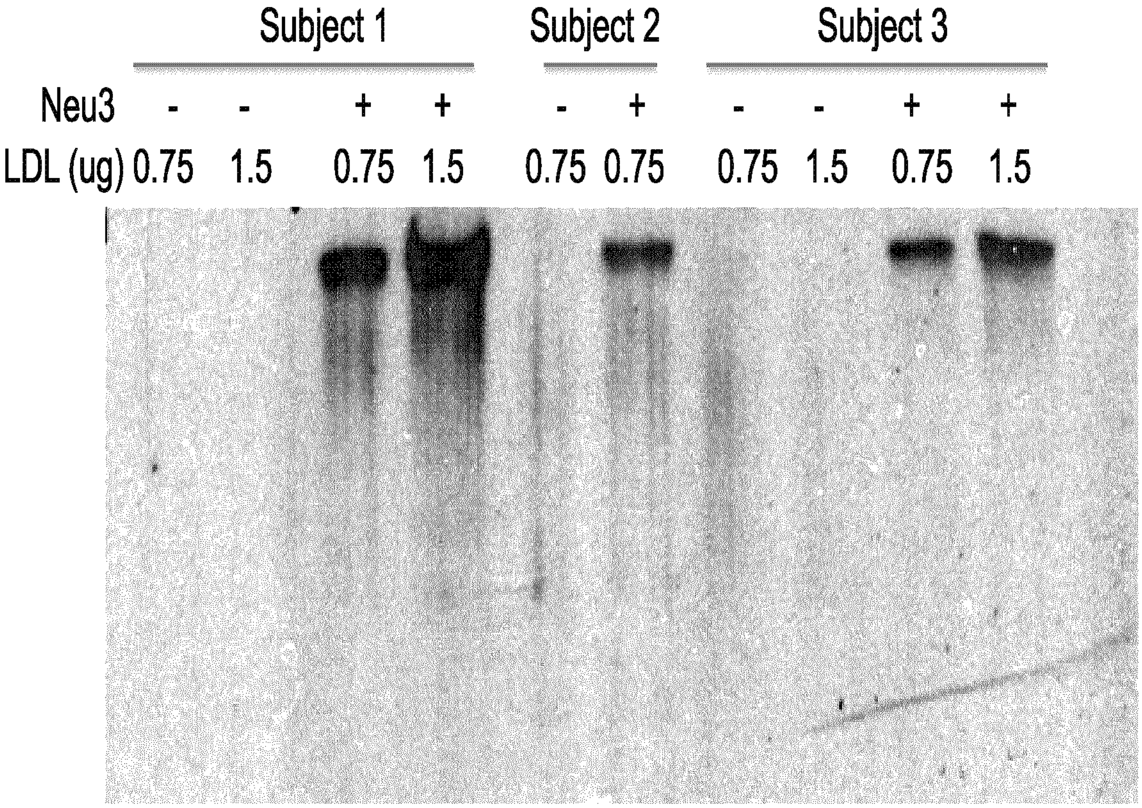

The inventors first tested if human neuraminidases can remove sialic acid residues from ApoB in LDL in vitro. LDL fraction from healthy human subjects was isolated by preparative ultracentrifugation in the density gradient (from 1.019 to 1.063 g/mL) (Steinbrecher, 1987). Purity of the isolated LDL fraction was confirmed by PAGE analysis, which detected a single protein band with a molecular weight of 500 kDa corresponding to that of the major LDL glycoprotein, ApoB. Purified LDL were incubated for 12 h with recombinant human neuraminidases 2, 3 and 4 at the pH corresponding to their pH optimum and the sialylation of ApoB was analyzed by blotting with lectins derived from *Sambucus nigra* (SNA), and *Maackia amurensis* (MAL-II), that have affinity to Sia in α-2,6 and α-2,3 linkages, respectively (Shibuya, 1987; Knibbs, 1991) (FIGS. 1A-B). The data showed that incubation of LDL with Neu3 resulted in removal of both α-2,3 nor α-2,6 attached Sia from the glycan chains of ApoB, whereas Neu4 removed mostly α-2,3 attached Sia chains (FIG. 1A). The recombinant human Neu2 was not active against neither α-2,3 nor α-2,6 attached Sia in ApoB glycans (FIGS. 1A-B). Treatment of LDL with Neu3 also resulted in ApoB staining with peanut agglutinin (PNA) specific to carbohydrate sequence Gal-13 (1-3)-GaINAc again confirming removal of the terminal Sia residues form the glycan chains (FIG. 1C). Importantly, desialylation of ApoB did not occur in the presence of the inhibitor of neuraminidases N-Acetyl-2,3-dehydro-2-deoxyneuraminic acid, (DANA, 1 mM concentration in the reaction mixture) or when active Neu3 has been replaced with the mutant enzyme lacking an active site Tyr residue essential for its activity (Neu3 Y370F) confirming that Sia residues on ApoB are specifically removed by the enzymatic action of neuraminidases.

Figure 1D:
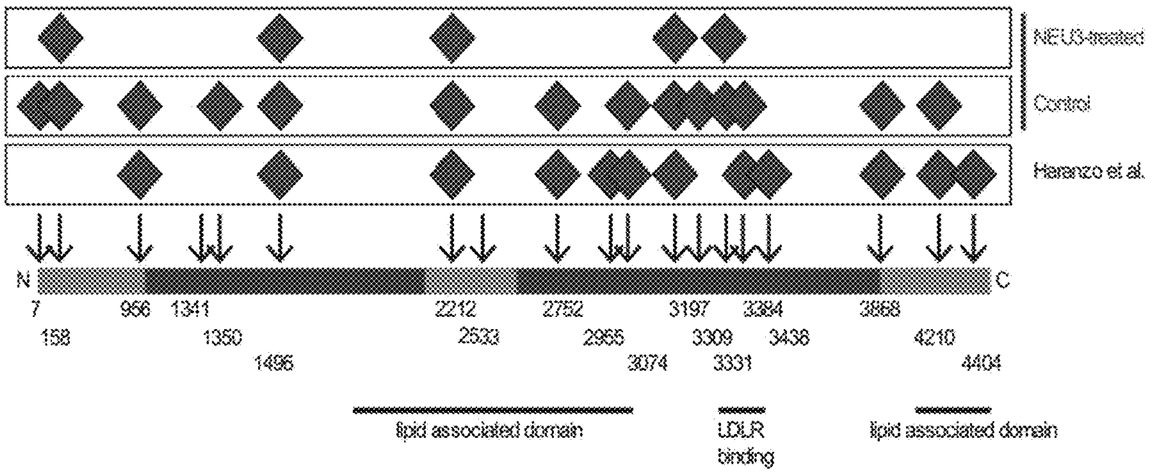
Figure 1E:
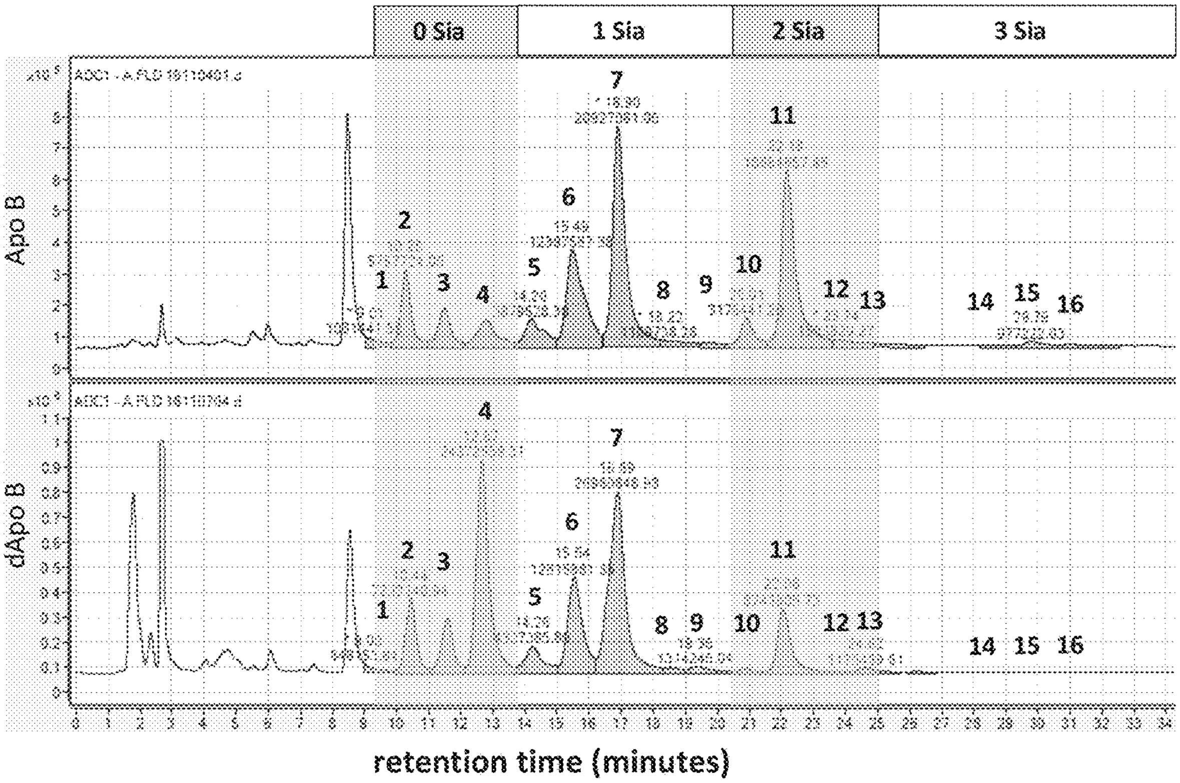

Structure of the glycan chains of ApoB in native LDL or those treated with Neu3 was further analyzed by tandem mass spectroscopy. For this, the LDL proteins were resolved by PAGE and gel pieces containing ApoB bands were treated with endoglycosidase, PNGase F. The released ApoB N-glycans were extracted from the gel pieces and their structure was determined using Waters Q-TOF Premier nanoAcquity™ UPLC-MS/MS instrument with an ESI source. The identification of peptides containing N-glycosylation was performed after in-gel trypsin digestion of ApoB followed by extraction of peptides and their analysis by LC-MS/MS. Analysis of ApoB glycan chains has directly shown that Neu3 removes Sia from the complex glycan chains linked to Asn1523, Asn2976, Asn3095, Asn3353 and Asn4488/4489 residues, reducing the total sialylation of glycan chains from 96% to 36% (FIGS. 1D-E and Tables I, and IA below).

TABLE I

Desialylation of LDL ApoB glycan chains by recombinant human Neu3

| peak | RT (min) | ApoB | dApoB | | % ApoB [b] | % dApoB |
|---|---|---|---|---|---|---|
| 1 | 0.01 | 1.3% | 0.0% | 0 Sia[a] | 13.0% | 40.4% |
| 2 | 10.28 | 7.2% | 7.5% | | | |
| 3 | 11.47 | 4.7% | 6.5% | | | |
| 4 | 12.79 | 4.8% | 25.4% | | | |
| 5 | 14.20 | 4.8% | 4.5% | 1 Sia | 48.6% | 48.2% |
| 6 | 15.49 | 15.4% | 13.4% | | | |
| 7 | 16.90 | 26.1% | 28.1% | | | |
| 8 | 18.23 | 1.5% | 0.8% | | | |
| 9 | 19.75 | 0.8% | 1.4% | | | |
| 10 | 20.81 | 4.0% | 0.7% | 2 Sia | 30.5% | 11.4% |
| 11 | 22.18 | 23.3% | 9.1% | | | |
| 12 | 23.71 | 1.0% | 1.2% | | | |
| 13 | 24.81 | 1.2% | 0.3% | | | |
| 14 | 28.82 | 0.6% | 0.0% | 3 Sia | 2.9% | 0.0% |
| 15 | 29.79 | 1.2% | 0.0% | | | |
| 16 | 31.03 | 1.0% | 0.0% | | | |

TABLE IA

Summary of changes in sialic content of human ApoB100

| Sample | Number of glycopeptides | Total # Sia residues | % containing Sia | Avg # Sia glycan |
|---|---|---|---|---|
| Control | 28 | 30 | 96% | 1.1 |
| Neu3-treated | 28 | 10 | 36% | 0.4 |

Figure 2A:
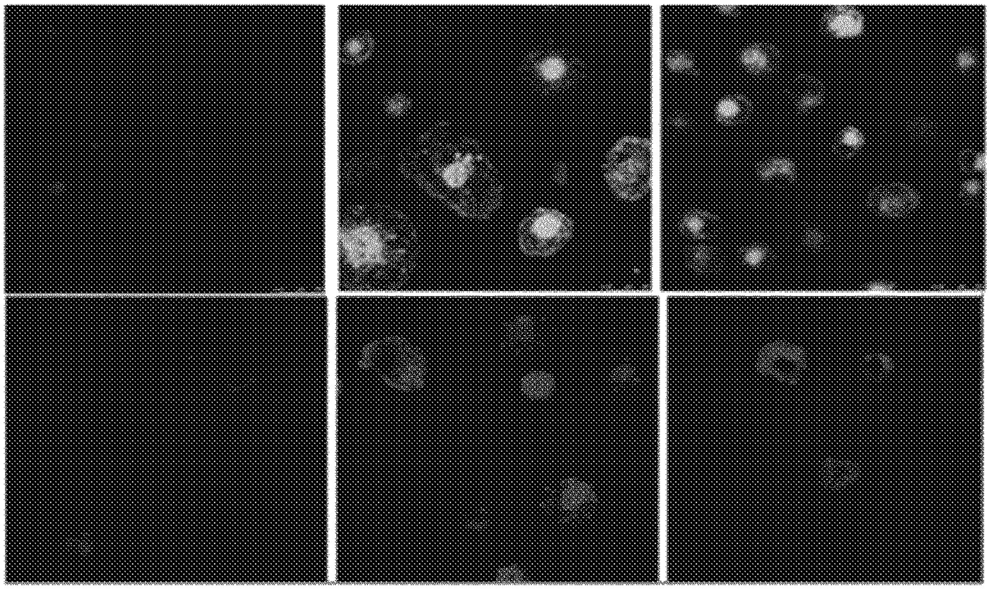
FIGS. 2A-C: Desialylation of LDL increases their uptake by human monocyte-derived macrophages. Human monocyte-derived macrophages were incubated in LPDS with 30 μg/ml of labeled LDL for 3 h at 37° C.
Figure 2B:
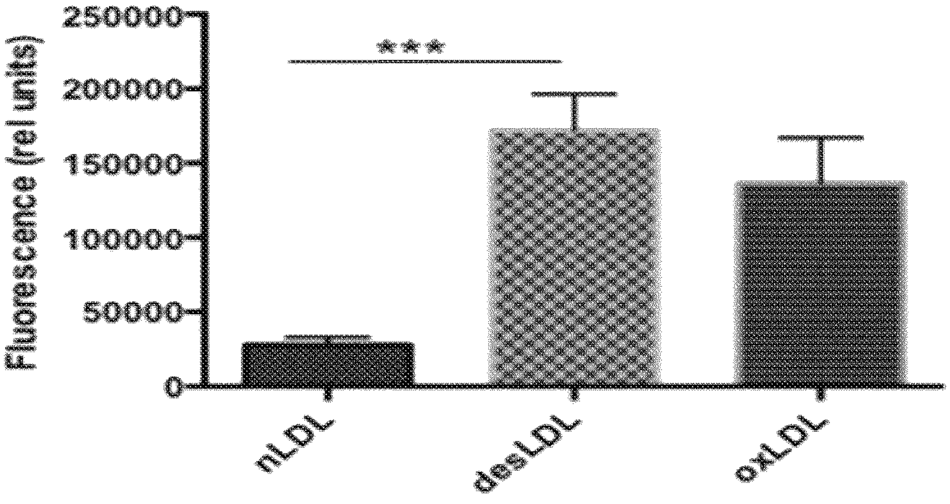
Figure 2C:
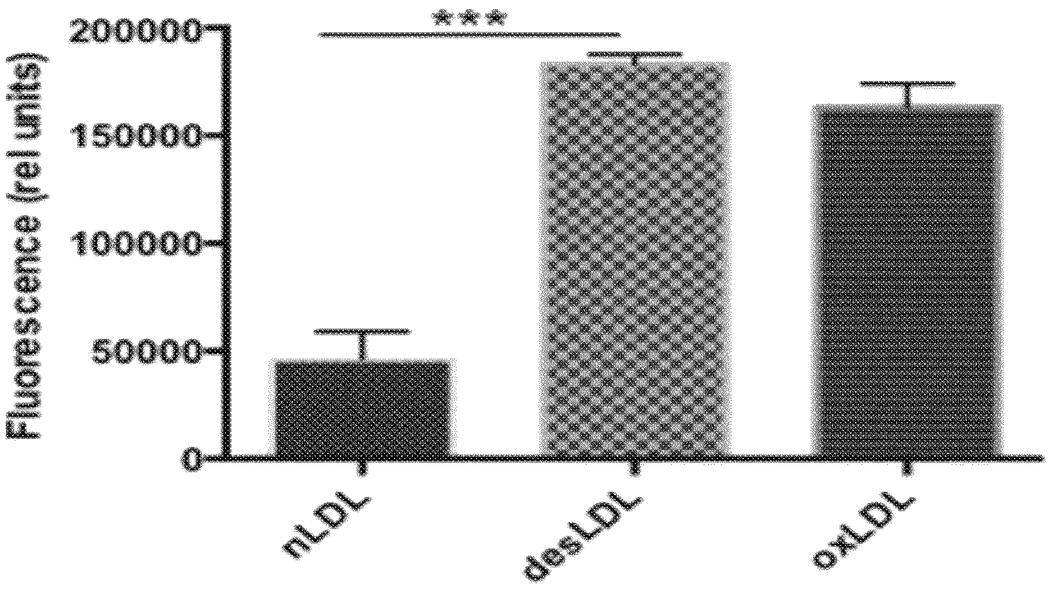
Figure 3A:
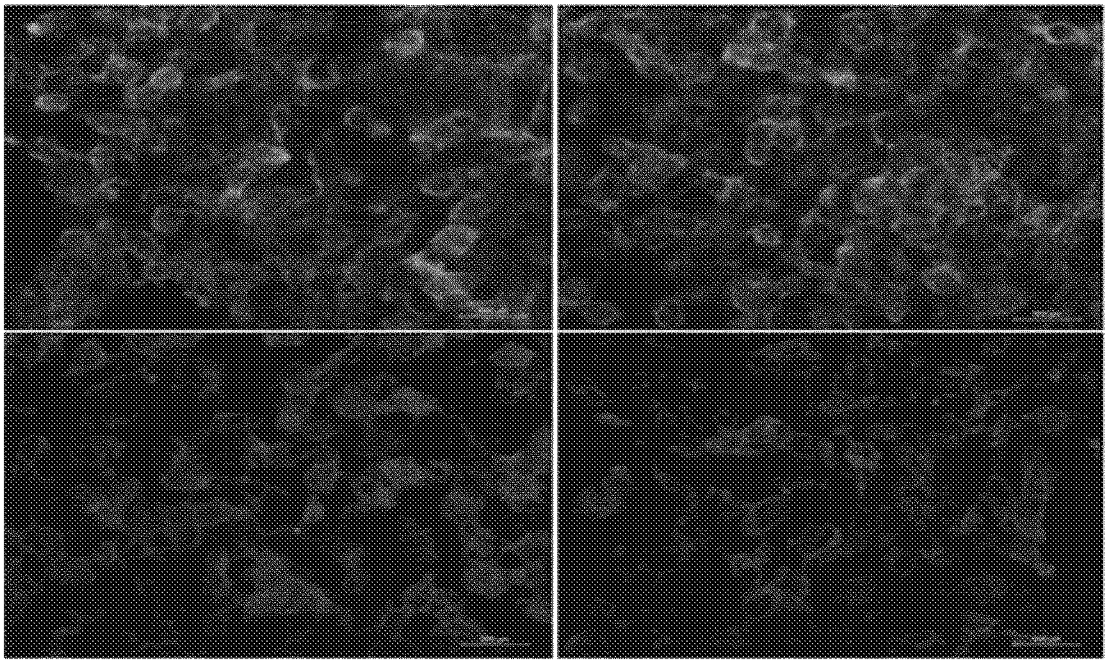
FIGS. 3A-C: Desialylation of LDL does not affect their uptake by cultured hepatocytes. HepG2 cells were incubated with 30 μg/ml of labeled LDL for 20 min at 37° C., and then after washing and fixation analyzed by fluorescent microscopy.
Figure 3B:
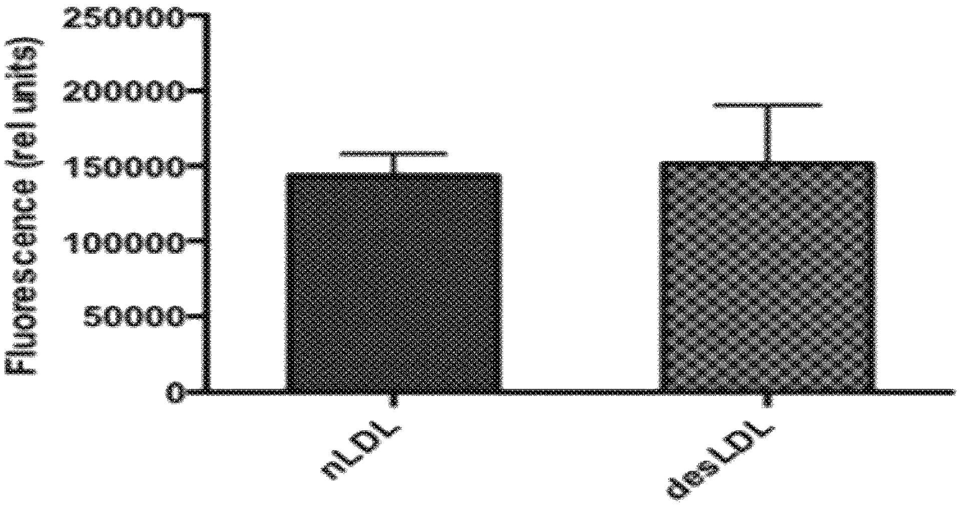
Figure 3C:
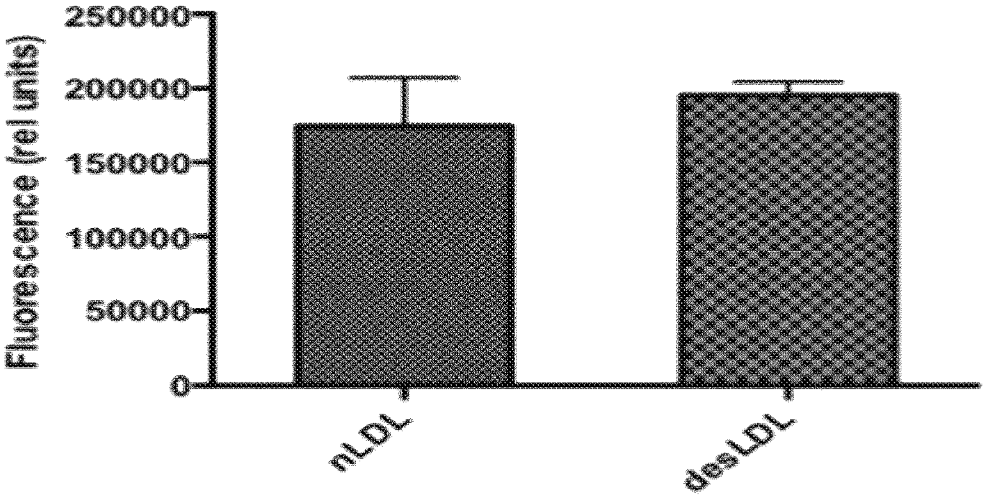

Example 3: Desialylation of LDL Increases their Uptake by Cultured Human Monocyte-Derived Macrophages Via Lectin-Dependent Pathway To test whether removal of sialic acids from glycan chains of ApoB affects the uptake of LDL by macrophages the inventors compared the uptake of fluorescently labeled native LDL, LDL desialylated by Neu3 treatment (desLDL) or oxidized LDL (oxLDL) by cultured human blood monocyte-derived macrophages. Two types of labels were used, Alexa-fluo, that covalently binds to the ApoB molecule, and DiI (1,1'-dioctadecyl-3,3,3',3'-tetramethylindocarbocyanine perchlorate), that incorporates into the lipid core of LDL due to its hydrophobicity. Using two types of labeling allowed to analyze simultaneously the uptake of both the LDL particles and cholesterol. Human blood monocytes were purified from the blood of healthy volunteers and differentiated into macrophages by culturing for 7 days in the presence of GM-CSF. To test the uptake, the cells cultured on glass coverslips were starved overnight in the medium containing human lipoprotein-deficient serum instead of FBS. Then the cell medium was supplemented with either modified or native LDL and cells were incubated for 3 h at 37° C., washed, fixed and studied by fluorescent microscopy. The data (FIGS. 2A-C) show that incubation of human macrophages with desLDL, resulted in significantly higher accumulation of both Alexa and DiI labels as compared with the cells incubated in the presence of similarly labeled native LDL. Desialylated LDL were engulfed at a rate similar or even higher than that for oxidized LDL (FIGS. 2A-C). Together the data suggested that removal of Sia from the ApoB by neuraminidases dramatically increases their uptake by cultured macrophages.

Example 4: Desialylation of LDL does not Change the Rate of their Uptake by HepG2 Cells To analyze if desialylation of ApoB affects affinity of LDL towards hepatocyte LDL receptor the uptake of native LDL and desLDL was tested by cultured human liver carcinoma cells, HepG2. Similarly, to primary hepatocytes, HepG2 cells express high levels of LDLR and are routinely used to study the LDL uptake by LDLR-mediated pathway. Cultured HepG2 were incubated for 20 min in the presence of 30 µg/ml of native or desialylated LDL labeled with Alexa or DiI and then the uptake of the dye into the cells was quantified as described above for macrophages. The data show that native and desialylated LDL were taken up by cultured HepG2 cells at a similar rate (FIGS. 3A-C) indicating that desialylation of LDL did not change their affinity to LDL receptors.

In order to study if endocytosis of desialylated and oxidized LDL occurred through the same or different surface receptors human monocyte-derived macrophages were incubated with 30 µg/mL of DiI-labeled desLDL and a 5, 10 or 20 times excess of unlabeled desialylated or oxidized LDL. As before, the cells were analyzed by confocal microscopy and the fluorescence intensity quantified with ImageJ™ software. The data (FIGS. 4A-B) show that the uptake of labeled fluorescent desLDL was completely blocked by the excess of unlabeled desLDL, but only partially inhibited by the excess of unlabeled oxLDL. This indicates that endocytosis of desLDL occurs through several pathways both common for desialylated and oxidized LDL and those specific for desialylated particles.

Figure 5A:
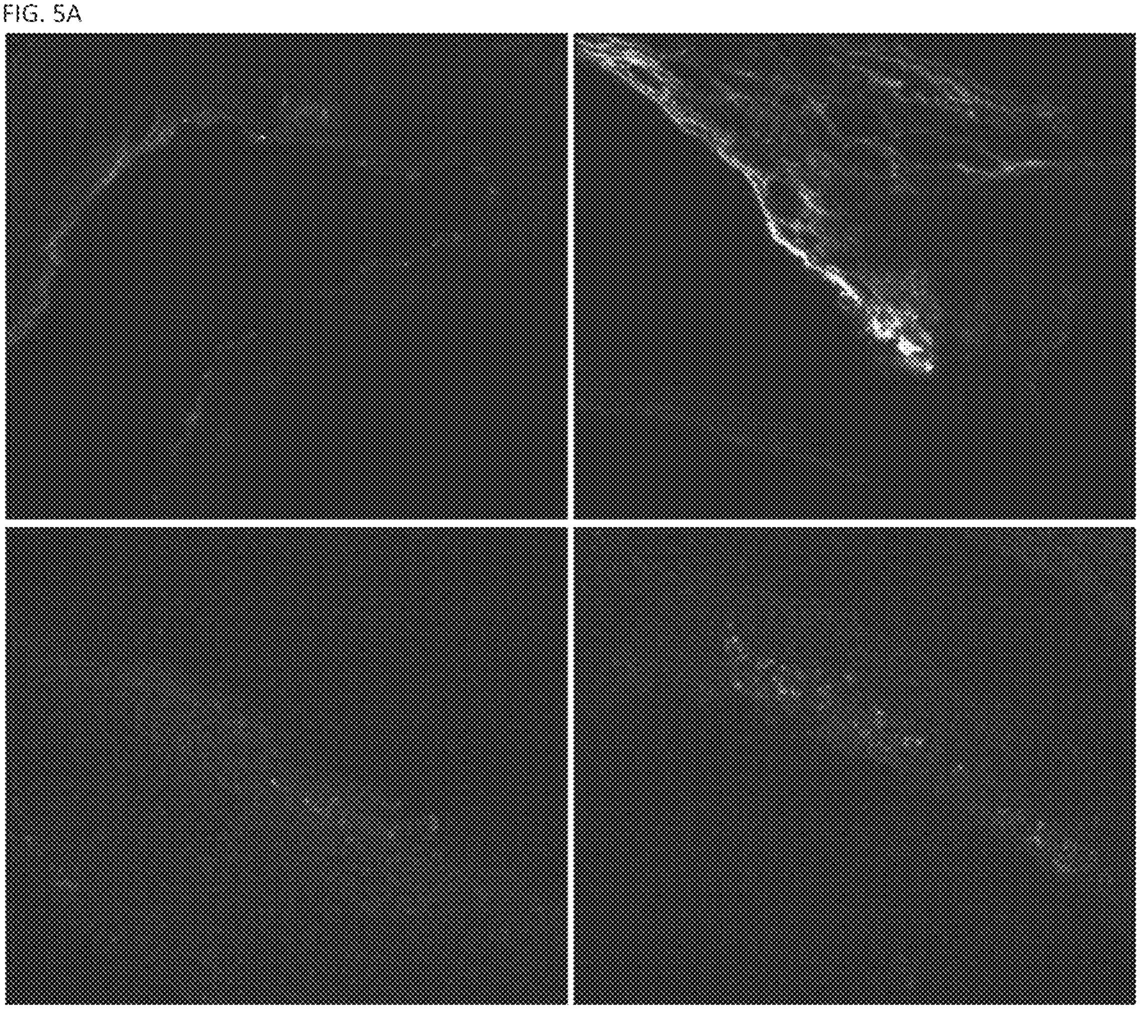
FIGS. 5A-C: Desialylation increases incorporation of LDL into the mouse aortic wall. Accumulation of native and desLDL in the aortic root wall of mice was studied 8 h after injection of 200 μg of labeled LDL into their tail vain. Sectioned aortic root was analyzed by fluorescent confocal microscopy. Relative fluorescence intensities were measured by ImageJ™ software (FIG. 5A).
Figure 5B:
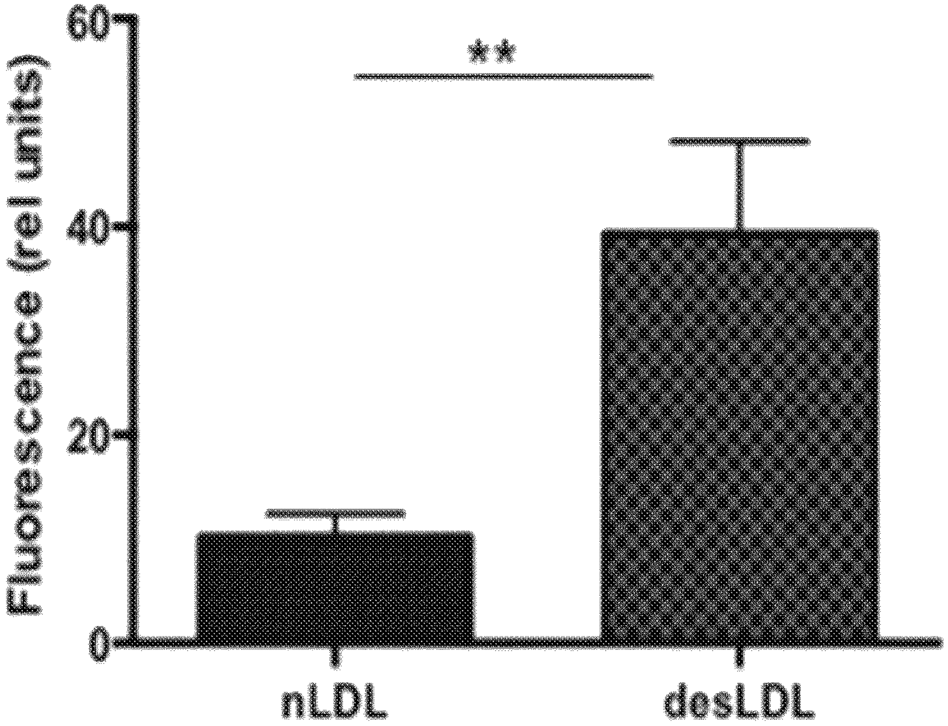
Figure 5C:
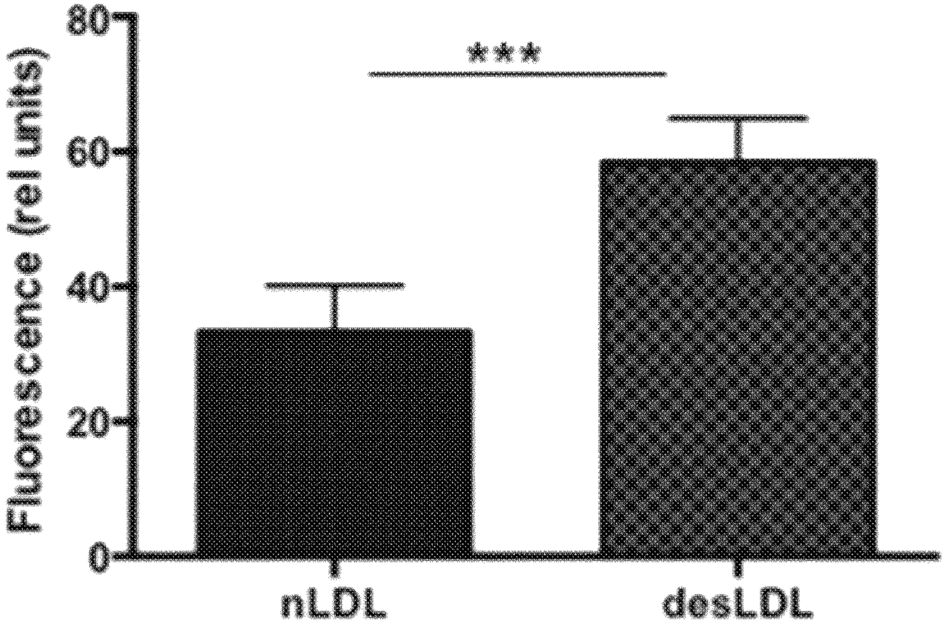

Example 5: Desialylation of LDL Increases its Incorporation into the Mouse Aortic Root Wall after Systemic Injection The inventors further studied if in addition to increasing the LDL uptake by macrophages in vitro desialylation also increases their incorporation into the arterial wall in live mice. For that, sixteen weeks old C57Bl/6J male mice were injected via the tail vein with 200 µg of native or desialylated LDL fluorescently labeled with Alexa or DiI and dissolved in 200 µl of saline. Control mice were injected with the same volume of saline only. Eight hours after injection mice were sacrificed, their hearts collected and aortic roots analyzed for the presence of LDL particles in the aortic wall. Eight hours after LPS injection, mice were euthanized, perfused with 4% paraformaldehyde solution, and their hearts isolated and dissected to collect the aortic root area. The OCT-embalmed blocks with aortic roots were sectioned on cryostat and 10-µm thick slices analyzed by confocal microscopy (FIG. 5A). The quantification of the fluorescence intensity with ImageJ™ software demonstrated that the incorporation of Alexa or DiI dye into the aortic wall was significantly higher (4 and 2 times, respectively, $P<0.05$)) when mice were injected with desialylated LDL as compared with those injected with native LDL (FIGS. 5B-C).

Example 6: Early Stage of Atherosclerosis is Delayed in Gene-Targeted Neuraminidase 1 and Neuraminidase 3 Deficient Mice To evaluate whether neuraminidases play a role in atheroma progression in vivo genetic inactivation of individual neuraminidases was performed in Apolipoprotein E-knockout mice ($ApoE^{-/-}$), the commonly used spontaneous murine model of atherosclerosis. As compared with WT C5761/6J black mice $ApoE^{-/-}$ mice have significantly increased level of total cholesterol and LDL cholesterol in blood (Jawien, 2004) even when they are fed a regular diet. Approximately at 15 weeks of life they develop intermediate aortic lesions containing both foam and smooth muscle cells (Meir, 2004). ApoE/Neu3 and ApoE/Neu4 double-knockout mice were generated by crossing homozygous $ApoE^{-/-}$ mice with homozygous Neu3 and Neu4 KO mice, respectively (Yamaguchi, 2012; Seyrantepe, 2008a). To assess the role of Neu1 in atherosclerosis, $ApoE^{-/-}$ mice were crossed with previously described cathepsin A-hypomorph mice ($CathA^{S190A-Neo}$). These mice have a −90% reduction in Neu1 activity in tissues (Seyrantepe, 2008b) but do not develop a rapidly progressing neurologic disease occurring in a NEU1 KO due to the lysosomal storage of sialoglycoconjugates in neurons (de Geest, 2002), which makes the Neu1 KO strain unsuitable for physiological studies. All mice had the same C5781/6J background, were fertile and had normal development with the increase of body weight over age similar to that of normal mice. In order to analyze if neuraminidases are involved in the initial stage of atherosclerosis mice were kept on a normal diet and were sacrificed at 16 weeks when the intermediate lesions already become apparent in the aortic root. After sacrifice mouse hearts were collected, frozen in OCT-embalmed blocks and the aortic root regions were sectioned into 10-µm thick slices.

Figure 6A:
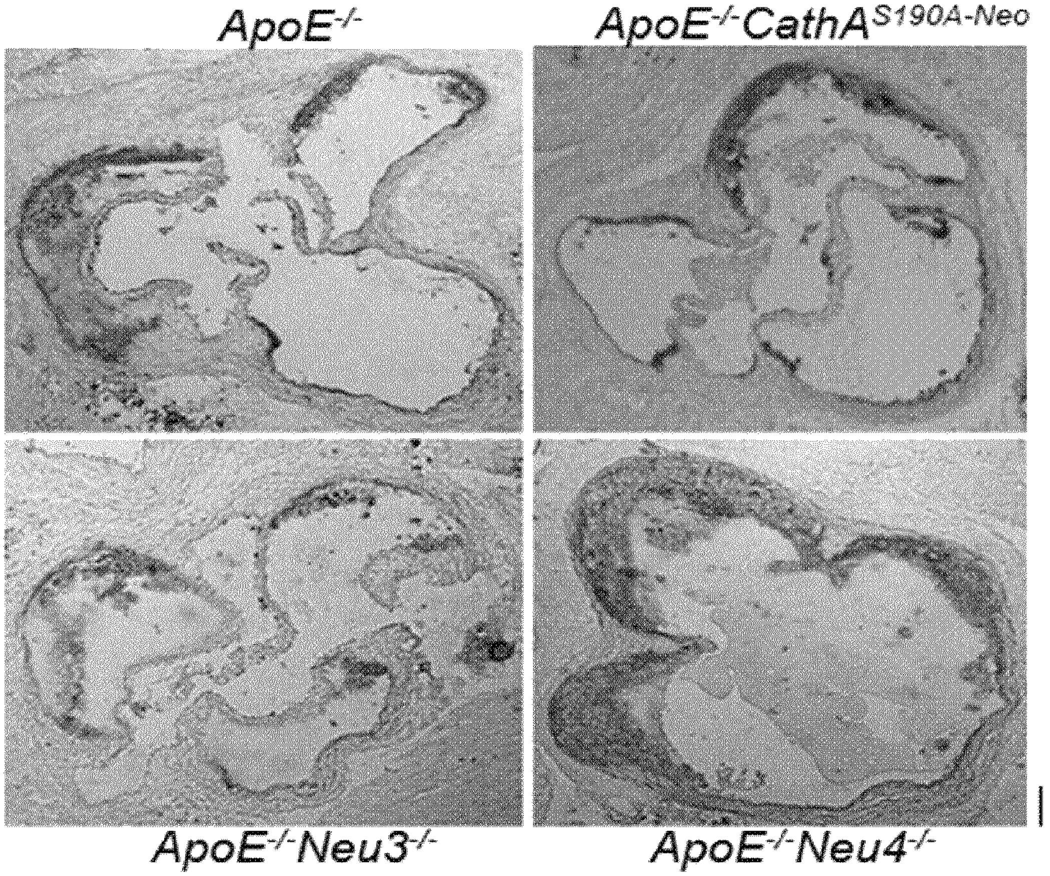
FIGS. 6A-C: Reduced size of fatty streaks in the aortic root of $ApoE^{-/-}$ mice deficient in Neu1 and Neu3. $ApoE^{-/-}$ mice deficient in Neu1 ($ApoE^{-/-}CathA^{S190A\text{-}Neo}$), Neu3 ($ApoE^{-/-}$-$Neu3^{-/-}$) or Neu4 ($ApoE^{-/-}$ $Neu4^{-/-}$), were fed with normal diet and sacrificed at the age of 16 weeks. Atherosclerosis was analyzed by staining fatty streaks in the thin sections of mouse aortic roots with Red Oil O.
Figure 6B:
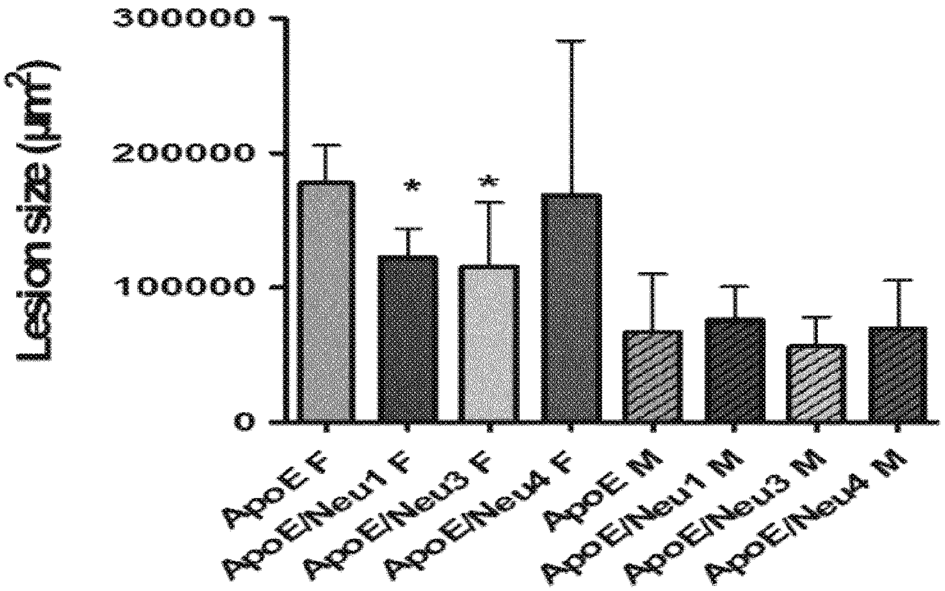
Figure 6C:
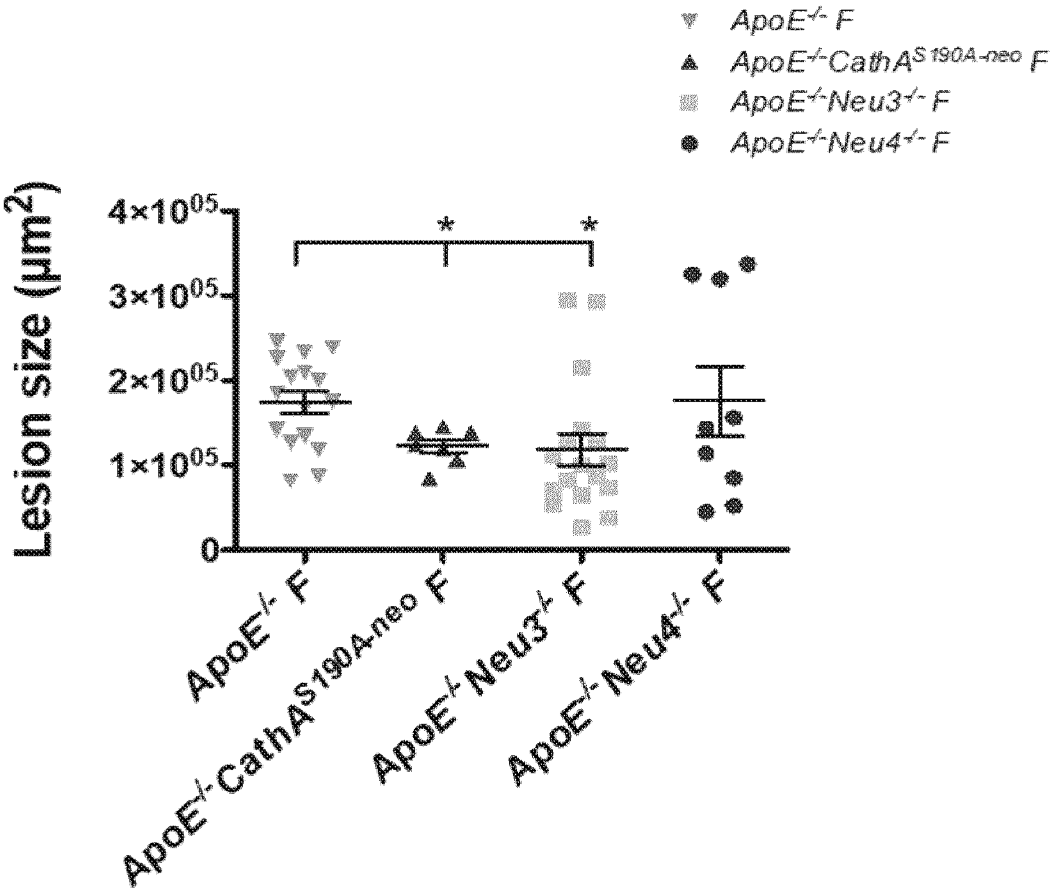

Analysis of lipid deposition in the aortic root sections of control $ApoE^{-/-}$ female mice showed fatty streak lesions with a significantly higher average area than in $ApoE^{-/-}$ $CathA^{S190A-Neo}$ female mice ($P<0.05$) (FIGS. 6A-C). While decreased activity of Neu1 and Neu3 causes a dramatic decrease of the lesion size in ApoE KO female mice, it does not in the male group. In the ApoE KO mice male animals have significantly slower progression of atherosclerosis lesions as compared with females. Applicant suggest therefore, without being limited by this hypothesis, that the effect of neuraminidase deficiency on the atherosclerotic plaque progression in the male mice has to be analyzed at an older age such as at 5 or 6 months. Average lesion size of $ApoE^{-/-}$ females was 177000±9900 $\mu m^2$ vs. average lesion size of 125000±6000 $\mu m^2$ for $ApoE^{-/-}CathA^{S190A\text{-}Neo}$ mice. The mean size of lesions in $ApoE^{-/-}Neu3^{-/-}$ mice was also significantly lower than that in $ApoE^{-/-}$ mice although variability between the individual lesion size values in $ApoE^{-/-}Neu3^{-/-}$ animals was higher than that in $ApoE^{-/-}CathA^{S190A\text{-}Neo}$ mice. This result clearly demonstrates that deficiency of Neu1 or Neu3 is associated with dramatic reduction of the lesion size in $ApoE^{-/-}$ mice. At the same time, the size of atherosclerotic lesions in $ApoE^{-/-}Neu4^{-/-}$ was similar to that in $ApoE^{-/-}$ animals. No significant difference was found in the progression of atherosclerosis between $ApoE^{-/-}$ and double mutant male mice (not shown).

Figure 7A:
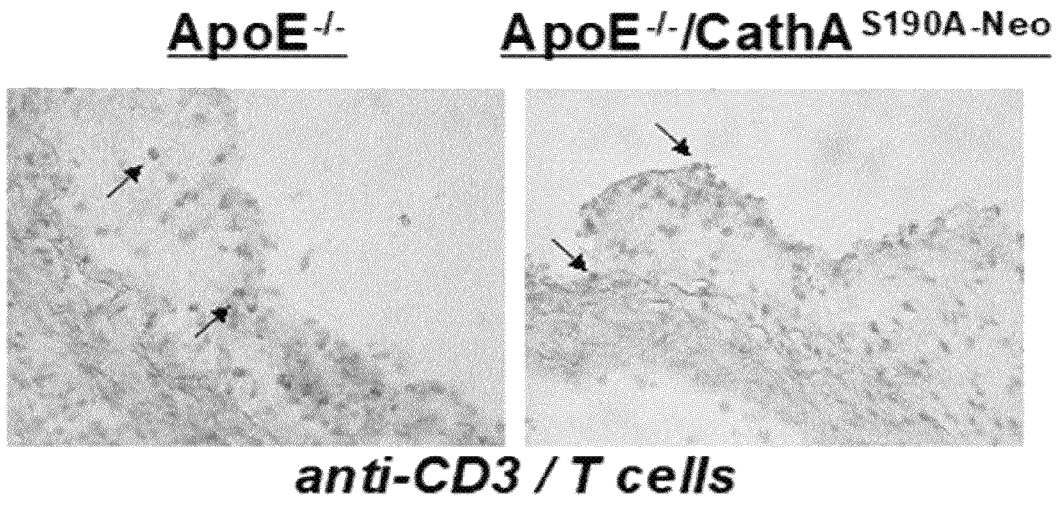
FIGS. 7A-B: Inflammatory cell infiltration within atherosclerotic aortic root lesions from $ApoE^{-/-}$ and $ApoE^{-/-}$/$CathA^{S190a\text{-}Neo}$ (Neu1 deficient) mice. Spontaneous early atherosclerosis was studied in 16-week old $ApoE^{-/-}$ (n=7) and $ApoE^{-/-}$/$CathA^{S190A\text{-}Neo}$ (n=6) mice.
Figure 7B:
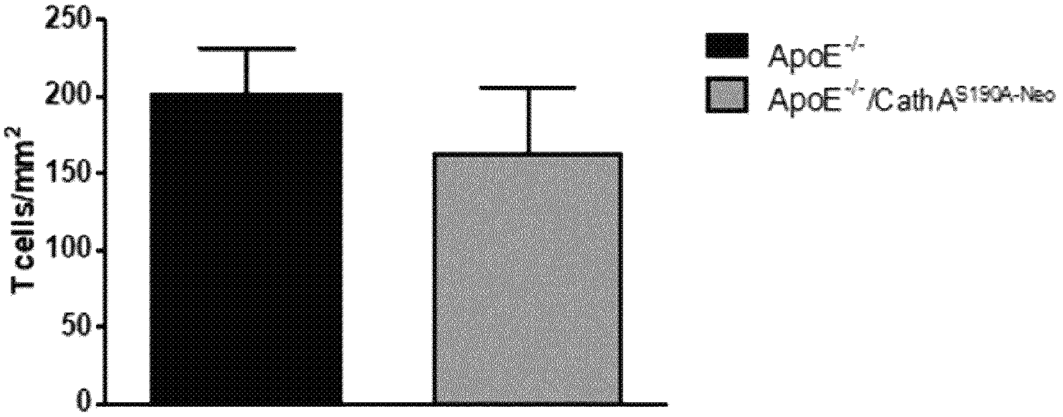
Figure 7C:
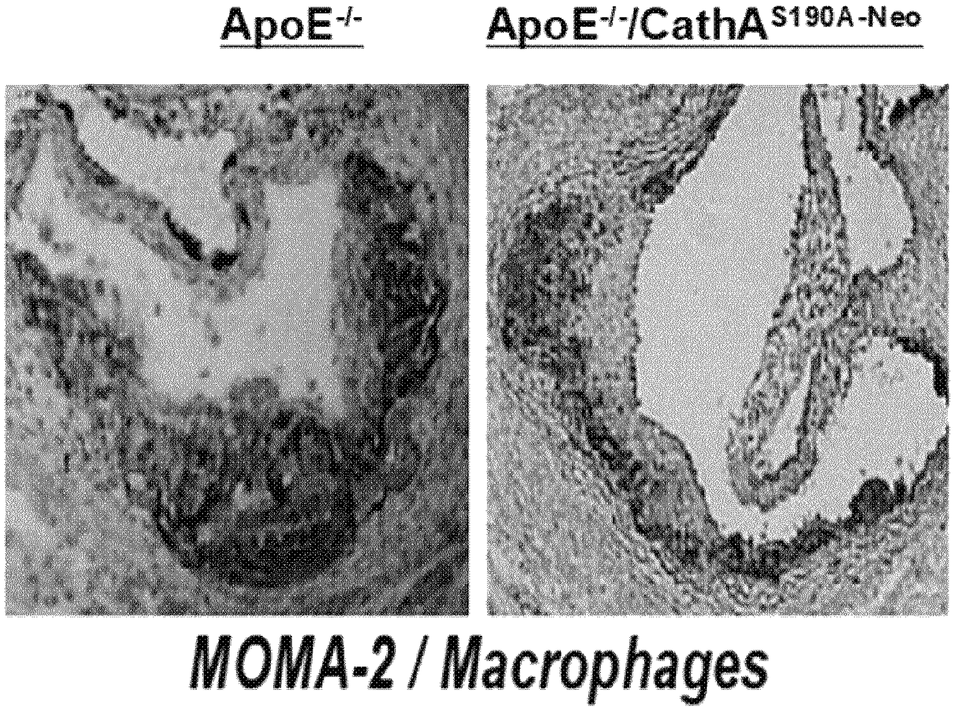
FIG. 7C-D, Representative photomicrographs (x40) (FIG. 7C) and quantitative analysis (FIG. 7D) of macrophage content as revealed MOMA-2 staining. At least 4 sections per mouse were examined for each immunostaining. Data represent means±s.e.m. significantly different, ** P<0.01.
Figure 7D:
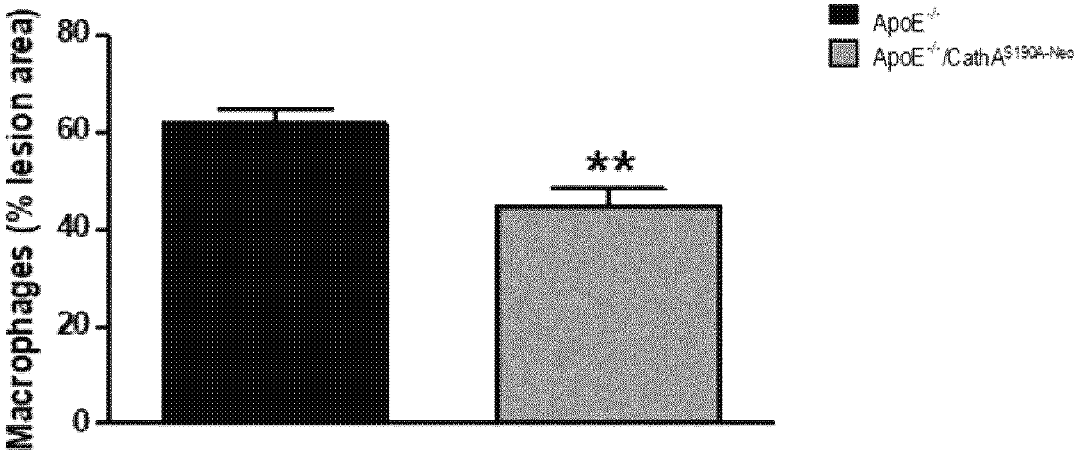
Figure 8A:
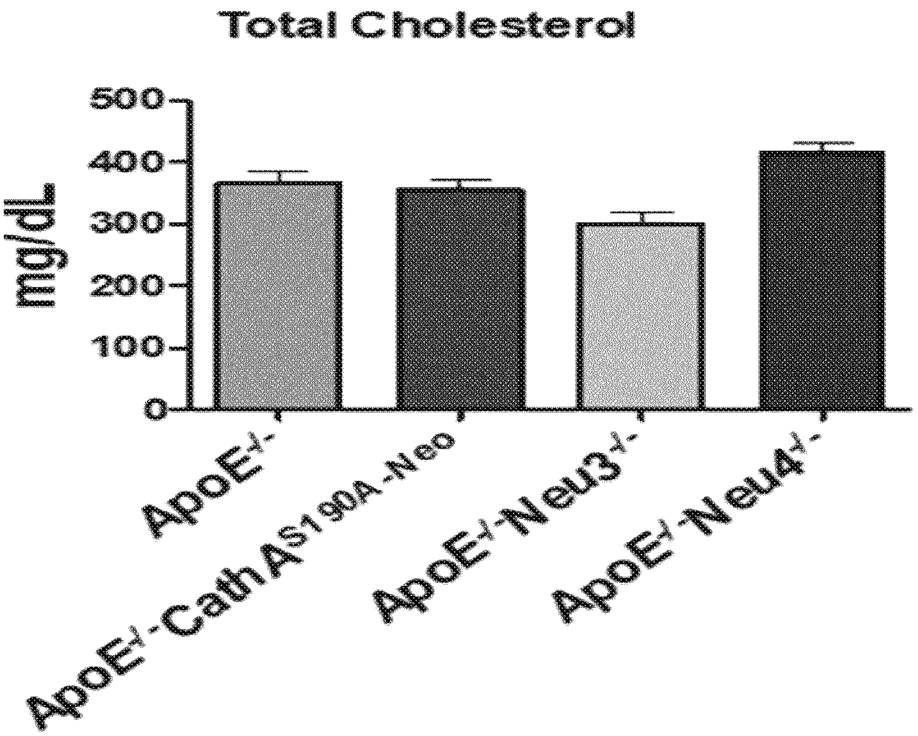
FIGS. 8A-D: Lipid plasma composition of 16-week-old $ApoE^{-/-}$ mice deficient in individual neuraminidases. Total cholesterol (FIG. 8A), triglyceride (FIG. 8B), HDL cholesterol (FIG. 8C), and LDL cholesterol (FIG. 8D) levels were measured in mouse plasma samples. Data represent means±SEM (* significantly different, P<0.05) as compared with $ApoE^{-/-}$ mice.
Figure 8B:
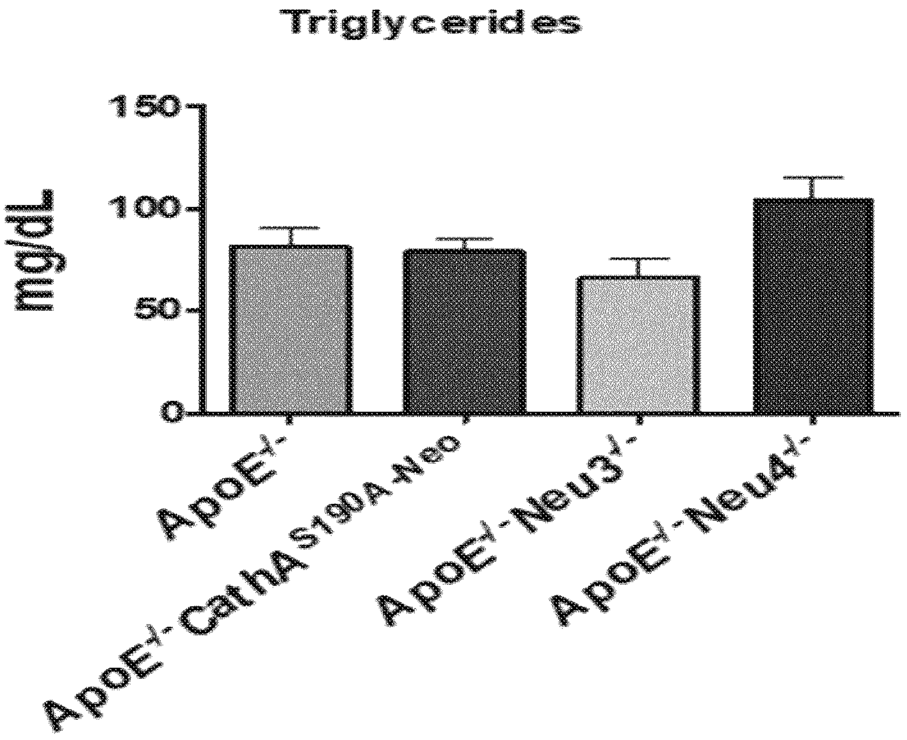
Figure 8C:
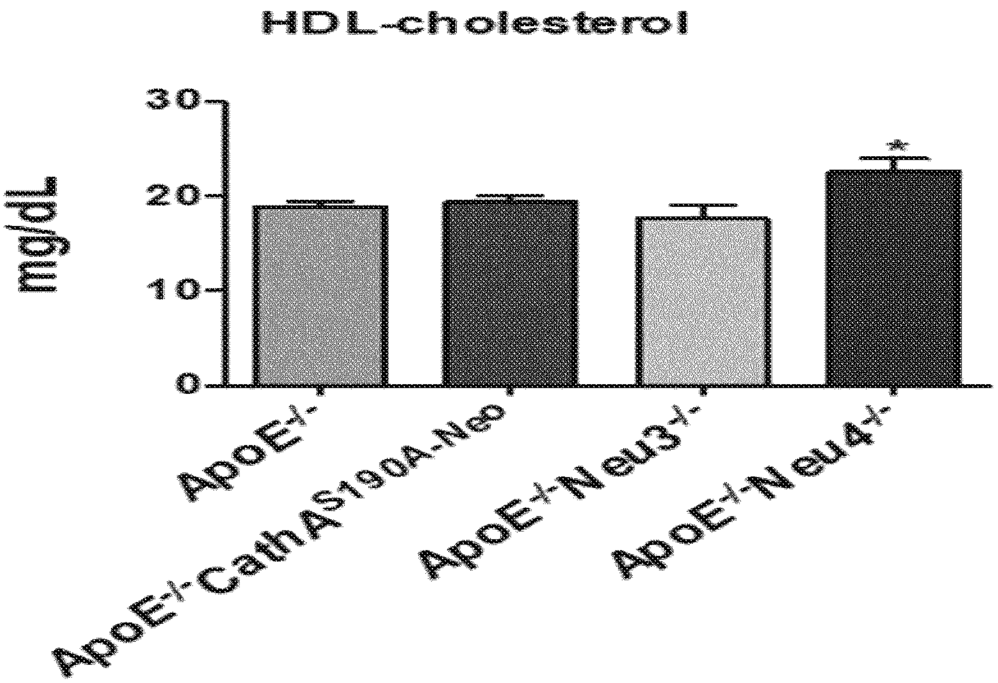
Figure 8D:
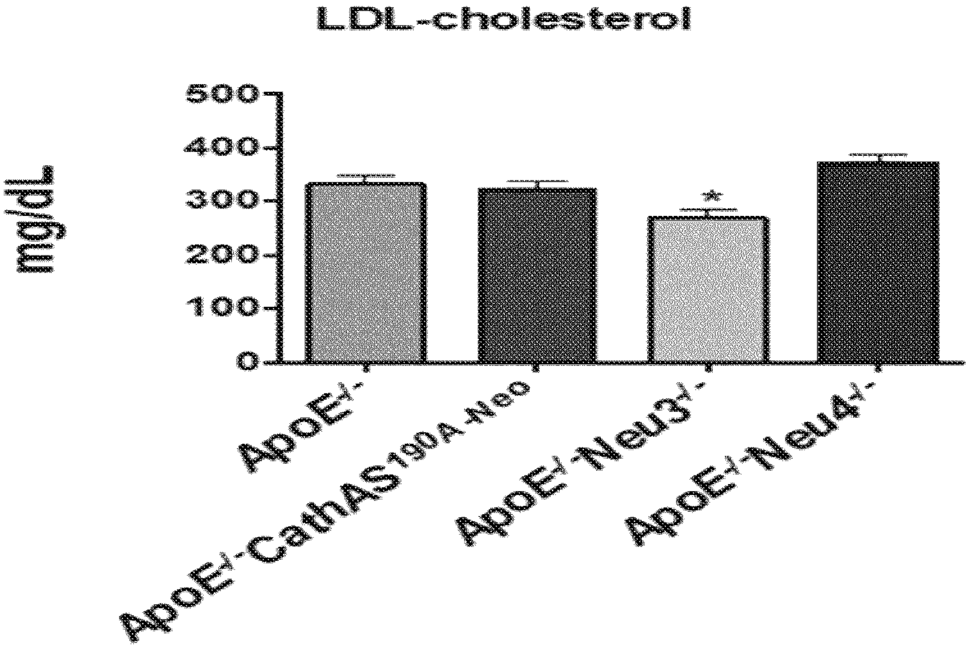
Figure 9A:
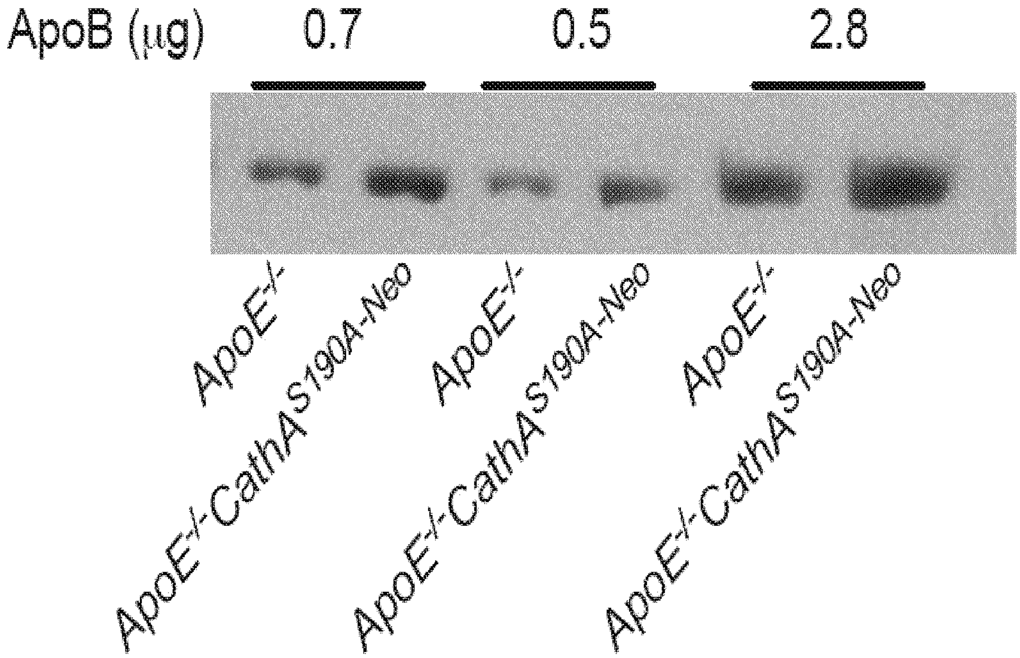
FIGS. 9A-B: Increased sialylation of LDL ApoB in the blood of Neu1-deficient mice. Blood was collected by cardiac puncture into EDTA-coated tubes from ten female 16-week-old ApoE-CathA$^{S190A-Neo}$ mice and the same number of ApoE$^{-/-}$ mice with matching age and sex. For each group LDL (d=1.019 to 1063 g/mL) was isolated from 4 mL of pooled plasma by sequential density gradient ultracentrifugation as has been described previously. Sialylation of the major LDL protein, ApoB-100 ("ApoB") (~500 kDa) was analyzed by blotting using biotinylated *Sambucus nigra* lectin (Vector Labs; dilution 1:20,000).
Figure 9B:
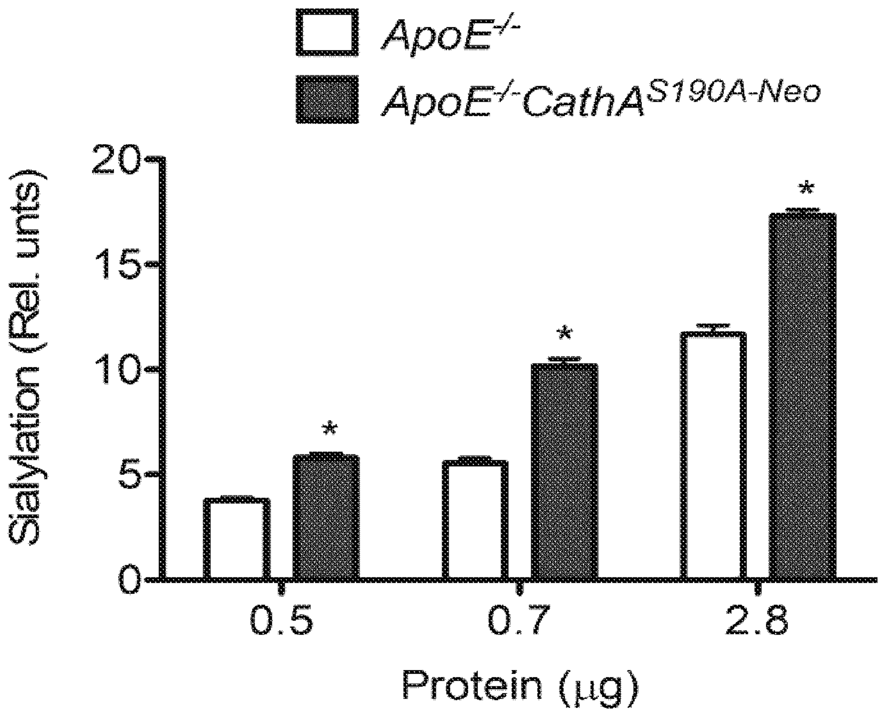

Infiltration of T cell and macrophages in atherosclerotic lesions was further tested by immunohistochemistry using monoclonal Anti-Monocyte+Macrophage (MOMA-2) antibody or goat polyclonal anti-mouse CD3 antibody (FIGS. 7A-B). Significantly reduced MOMA-2 staining was found in the atherosclerotic lesions from $ApoE^{-/-}CathA^{S190A\text{-}Neo}$ as compared with ApoE KO mice consistent with reduced infiltration of macrophages (FIGS. 7C-D).

The analysis of mouse plasma did not reveal any significant difference in the levels of total cholesterol, LDL cholesterol, HDL-cholesterol or triglycerides between $ApoE^{-/-}$ and $ApoE^{-/-}CathA^{S190A\text{-}Neo}$ mice (FIGS. 8A-D) suggesting that the decrease in the size of the atherosclerotic lesions in female $ApoE^{-/-}CathA^{S190A\text{-}Neo}$ mice was not caused by changes in plasma cholesterol levels. HDL cholesterol levels were increased in the $ApoE^{-/-}Neu4^{-/-}$ mice whereas both total cholesterol level and LDL-cholesterol level were slightly reduced in Neu3-deficient mice (FIGS. 8A-D). Finally, the sialylation of ApoB in the plasma of Neu1-deficient mice that showed slower rate of atherosclerosis was analyzed by lectin blot. Proteins from LDL fraction isolated from pooled blood obtained by cardiac puncture from ten 16-week-old $ApoE^{-/-}$ or $ApoE^{-/-}CathA^{S190A\text{-}Neo}$ mice were resolved by SDS PAGE, transferred to a nitrocellulose membrane and blotted with biotinylated SNL as described above for the human LDL fraction (FIGS. 9A-B). Quantitation of the intensity of lectin-stained ApoB bands showed that ApoB sialylation in the blood of $ApoE^{-/-}CathA^{S190A\text{-}Neo}$ mice was significantly increased as compared with that in $ApoE^{-/-}$ group.

Example 7: Inhibitors Design and Synthesis

A series of compounds were designed, synthesized and their inhibitory effects were tested against the four isoenzymes of human neuraminidases. The inventors first varied the aromatic ring of a C9-triazole DANA derivative, including electron-withdrawing and electron-donating groups, negatively and positively charged groups, as well as larger phenyl and phenoxyl groups (7, FIG. 14).

Figure 14:
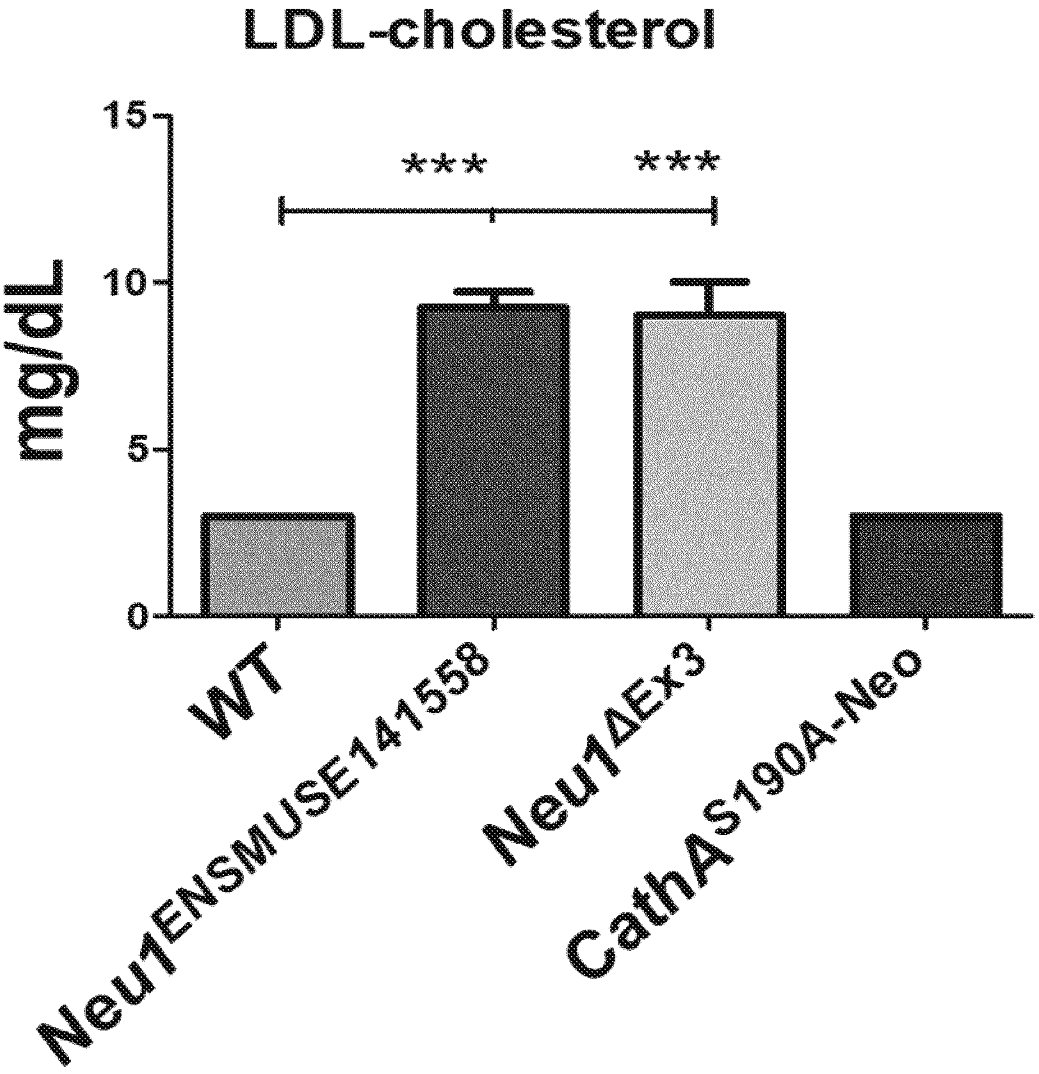
FIG. 14. LDL levels are increased in the plasma of Neu1 KO mice. LDL cholesterol levels were measured in plasma samples of 8-week-old C57B16J (WT) and NEU1-deficient CathA$^{S190A-Neo}$ Neu1$^{ENSMUSE141558}$ and Neu1$^{\Delta Ex3}$ mice. Data represent means±SEM (*** significantly different, P<0.005) as compared with WT mice.

The inventors also synthesized compounds with different phenyltriazole groups at C9; nitrogen-containing groups at C4, including guanidine (6), azido, amino groups; and combinations with modifications at both C9 and C4 (8, FIGS. 14; and 13, 15, etc.).

Figure 15:
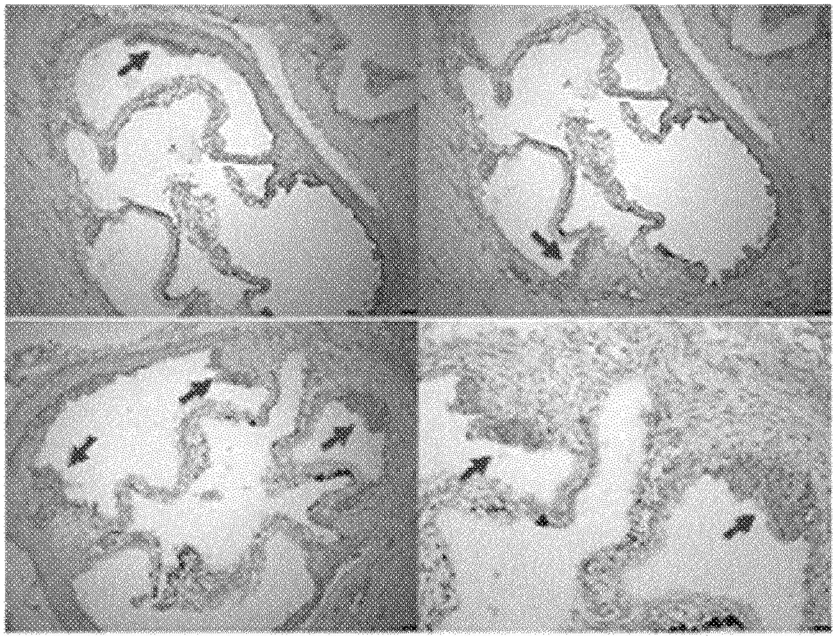
FIG. 15: Inflammatory cell infiltration within atherosclerotic aortic root lesions from 16-week-old ApoE$^{-/-}$ mice treated for 4 weeks with NEU1-specific inhibitor compound 31 (n=3) or control (n=4). Representative photomicrographs (x40) of macrophage content in Compound 31 treated tissue as revealed MOMA-2 staining. At least 4 sections per mouse were examined for each immunostaining.

Compounds with phenyltriazole groups at C9 were synthesized using C9-azido-DANA methyl ester (9), which could be obtained from Neu5Ac in 6 steps (Zou, 2010). CuCAAC (copper-catalyzed azide—alkyne cycloaddition) was applied with para-substituted phenylalkynes to introduce the various C9 modifications (7a-7j, FIG. 15).

For compounds with combined C4 and C9 modifications, two strategies were adopted (synthetic routes shown in FIGS. 16-17). Compound 8a started from the C9-modified derivative (10h, FIG. 16). C4 modifications were then realized through a previously reported strategy (Shidmoossavee, 2013): an azide was introduced to the C4 position via nucleophilic ring opening of an oxazoline intermediate (11). The Staudinger reduction (Staudinger, 1919) then gave the C4-amino derivative (14), which could be converted to a guanidino group using N,N'-di-Boc-1H-pyrazole-1-carboxamidine, providing the final C4, C9 modified compound 8a after deprotection. The C4-azido and C4-amino derivatives were also deprotected to give corresponding compounds (13 and 15) for testing. Compound 14 was treated with 1,1'-Carbonyldiimidazole and 8-alanine methyl ester to form a urea moiety at C4. The methyl esters were then hydrolyzed to give compound 18. To prepare compound 8b, the inventors started from a fully protected C4-amino-DANA derivative (19, FIG. 17), which can be synthesized from Neu5Ac in several steps as reported (Shidmoossavee, 2013). C9-azido group was introduced via a two-step strategy of tosylation (20, 21), followed by displacement with $NaN_3$ to give the C9-azido, C4-amino derivative, 22. At this point, the guanidino group was introduced at C4, then a subsequent CuAAC was applied to introduce the biphenyltriazole group at C9, 24. The final product (8b) was obtained after deprotection.

To generate compounds with only C4 amide moieties, compound 19 was treated with different anhydrides or acyl chlorides to form the desired amides (synthetic route shown in FIG. 18; 25). Final products (25a-d) were obtained by hydrolyzing the C1-methyl ester with sodium hydroxide.

General Synthetic Procedures. All reagents and solvents were purchased from Sigma-Aldrich unless otherwise noted and used without further purification. Reactions were monitored with TLC (Merck TLC Silica gel 60 $F_{254}$) and spots were visualized under UV light (254 nm) or by charring with 0.5% $H_2SO_4$/EtOH. Compounds were purified by flash column chromatography with silica gel (SiliaFlash™ F60, 40-63 μm particle size) or recrystallization with the solvent mixtures specified in the corresponding experiments. Proton (1H) and carbon ($^{13}C$) NMR spectra were recorded on Varian™ 400 (400 MHz for $^1H$; 100 MHz for $^{13}C$) or Varian™ 500 (500 MHz for $^1H$; 125 MHz for $^{13}C$). High-resolution mass spectrometry (HR-MS) analysis was performed on Agilent Technologies™ 6220 TOF spectrometer. Purity of all final products used for inhibitor assays was determined to be ≥95% by HPLC.

Example 8: 5-Acetamido-2,6-Anhydro-3,5-Dideoxy-D-Glycero-D-Galacto-Non-2-Enonic Acid (DANA, 1)

Was synthesized as previously reported. (Zou, 2010) $^1H$ NMR (500 MHz, $cd_3od$) δ 5.67 (d, J=2.3 Hz, 1H, H-3), 4.36 (dd, J=8.6, 2.3 Hz, 1H, H-4), 4.10 (dd, J=10.9, 1.1 Hz, 1H, H-6), 3.99 (dd, J=10.9, 8.6 Hz, 1H, H-5), 3.87 (ddd, J 9.1, 5.4, 3.1 Hz, 1H, H-8), 3.80 (dd, J=11.4, 3.1 Hz, 1H, H-9), 3.65 (dd, J=11.4, 5.4 Hz, 1H, H-9'), 3.52 (dd, J=9.1, 1.1 Hz, 1H, H-7), 2.02 (s, 3H, $COCH_3$). $^{13}C$ NMR (125 MHz, $cd_3od$) δ 174.68, 170.02 (C═O), 149.95 (C-2), 108.34

(C-3), 77.24 (C-6), 71.29 (C-8), 70.22 (C-7), 68.70 (C-4), 64.94 (C-9), 51.96 (C-5), 22.82 ($COCH_3$). HR-MS (ESI) calcd. for $C_{11}N_{16}NO_8$ $[M-H]^-$, 290.0876; found 290.0879.

Example 9: 5-Acetamido-2,6-Anhydro-4-Guanidino-3,4,5-Trideoxy-n-Glycero-D-galacto-Non-2-Enonic Acid (Zanamivir (6))

Was synthesized as previously reported (von Itzstein, 1994; von Itzstein, 1993). $^1H$ NMR (500 MHz, $d_2o$) δ 5.70 (d, J=1.9 Hz, 1H, H-3), 4.54 (dd, J=9.3, 1.9 Hz, 1H, H-4), 4.46 (m, 1H, H-6), 4.29 (dd, J=10.5, 9.3 Hz, 1H, H-5), 4.02 (ddd, J=9.1, 6.2, 2.5 Hz, 1H, H-8), 3.96 (dd, J=11.9, 2.5 Hz, 1H, H-9), 3.77-3.69 (m, 2H, H-7, H-9'), 2.11 (s, 3H, $COCH_3$). $^{13}C$ NMR (125 MHz, $d_2o$) δ 175.38, 170.10 (C═O), 157.99 (C═N), 150.19 (C-2), 104.79 (C-3), 76.33 (C-6), 70.74 (C-8), 69.11 (C-7), 64.03 (C-9), 52.11 (C-4), 48.71 (C-5), 22.93 ($COCH_3$). HR-MS (ESI) calcd. for $C_{12}H_{21}N_4O_7$ $[M+H]^+$, 333.1405; found 333.1400.

Example 10: General Procedure of CuAAC Reaction and Hydrolyzation of Methyl Ester To a solution of Methyl 5-acetamido-9-azido-2,6-anhydro-3,5-dideoxy-D-glycero-D-galacto-non-2-enonate (9) (Zou, 2010) (1 eq) and the corresponding alkyne (1.5 eq) in THF-$H_2O$ (2:1), sodium L-ascorbate (0.5 eq) and copper (II) sulfate (0.5 eq) were added sequentially. The reaction was kept stirring at room temperature and monitored by TLC until no azide was remained. Silica gel was then added to the reaction mixture and the solvent was removed under reduced pressure. The residue was separated by flash chromatography to provide the desired products with yields of 42%-88%. To hydrolyze the C1-methyl ester, the product was dissolved in MeOH, and 0.5 M NaOH was added. The mixture was kept stirring at room temperature. After completion, the mixture was neutralized with Amberlite IR-120 ($H^+$ form), filtered and purified by flash chromatography to provide the desired products with yields of 45%-88%.

Example 11: 5-Acetamido-9-(4-(dimethylamino) phenyl)-2,6-anhydro-3,5-dideoxy-D-glycero-D-galacto-non-2-enonic acid (7a)

Compound 7a was prepared as above in 75% yield (86 mg). $^1H$ NMR (500 MHz, $CD_3OD$) δ 8.11 (s, 1H, Triazole-H5), 7.64 (d, J=8.9 Hz, 2H, Ar—H), 6.81 (d, J=8.9 Hz, 2H, Ar—H), 5.90 (d, J=2.3 Hz, 1H, H-3), 4.49 (dd, J=14.0, 7.5 Hz, 1H, H-9'), 4.40 (dd, J=8.7, 2.3 Hz, 1H, H-4), 4.31-4.25 (m, 1H, H-8), 4.14 (dd, J=10.9, 1.0 Hz, 1H, H-6), 3.99 (dd, J=10.9, 8.7 Hz, 1H, H-5), 3.41 (dd, J=9.2, 1.0 Hz, 1H, H-7), 2.96 (s, 6H, $N(CH_3)_2$), 1.99 (s, 3H, $COCH_3$). $^{13}C$ NMR (125 MHz, $CD_3OD$) δ 175.16 (C═O), 152.12, 127.59, 120.10, 113.93 (Ar—C), 149.18 (Triazole-C4), 121.83 (Triazole-C5), 77.67 (C-6), 71.23 (C-7), 69.79 (C-4), 68.01 (C-8), 55.13 (C-9), 51.96 (C-5), 40.78 (N—$CH_3$), 22.65 ($COCH_3$). HR-MS (ESI) calcd. for $C_{21}H_{26}N_5O_7$ $[M-H]^-$, 460.1832; found 460.1834.

Example 12: 5-Acetamido-9-(4-acetamidophenyl)-2,6-anhydro-3,5-dideoxy-n-glycero-D-galacto-non-2-enonic acid (7b)

Compound 7b was prepared as above in 79% yield (90 mg). $^1H$ NMR (500 MHz, $CD_3OD$) δ 8.28 (s, 1H, Triazole-H5), 7.76 (d, J=8.2 Hz, 2H, Ar—H), 7.62 (d, J=8.2 Hz, 2H, Ar—H), 5.70 (s, 1H, H-3), 4.50 (dd, J=13.5, 7.7 Hz, 1H, H-9'), 4.35 (d, J=8.6 Hz, 1H, H-4), 4.30-4.27 (m, 1H, H-8), 4.10 (d, J=10.7 Hz, 1H, H-6), 4.04-3.96 (m, 1H, H-5), 3.39 (d, J=7.7 Hz, 1H, H-7), 2.13, 1.98 (2×s, 3H, 2×$COCH_3$). $^{13}C$ NMR (125 MHz, $d_6$-DMSO) δ 172.10, 168.34, 168.25 (C═O), 165.18 (C═O), 147.63 (C-2), 145.74 (Triazole-C4), 121.67 (Triazole-C5), 138.80, 138.69, 125.72, 125.44, 119.20, 119.11 (Ar—C), 108.60 (C-3), 75.66 (C-6), 69.95 (C-7), 68.10 (C-4), 65.90 (C-8), 53.70 (C-9), 50.81 (C-5), 22.97, 22.49 ($COCH_3$). HR-MS (ESI) calcd. for $C_{21}H_{24}N_5O_8$ $[M-H]^-$, 474.1625; found 474.1636.

Example 13: 5-Acetamido-9-(4-amidophenyl)-2,6-anhydro-3,5-dideoxy-b-glycero-D-galacto-non-2-enonic acid (7c)

Compound 7c was prepared as above in 77% yield (80 mg). $^1H$ NMR (500 MHz, $CD_3OD$) δ 8.09 (s, 1H, Triazole-H5), 7.55 (d, J=8.6 Hz, 2H), 6.79 (d, J=8.6 Hz, 2H), 5.88 (d, J=2.4 Hz, 1H, H-3), 4.82 (dd, J=14.1, 2.6 Hz, 1H, H-9), 4.48 (dd, J=14.1, 7.6 Hz, 1H, H-9'), 4.41 (dd, J=8.7, 2.4 Hz, 1H, H-4), 4.28 (ddd, J=9.5, 7.6, 2.6 Hz, 1H, H-8), 4.14 (dd, J=10.9, 1.0 Hz, 1H, H-6), 4.00 (dd, J=10.9, 8.7 Hz, 1H, H-5), 3.41 (dd, J=9.5, 1.0 Hz, 1H, H-7), 1.98 (s, 3H, $COCH_3$). $^{13}C$ NMR (125 MHz, $CD_3OD$) δ 175.13, 166.94 (C═O), 149.13, 148.42 (Ar—C, Triazole-C4), 146.69 (C-2), 127.77, 116.96 (Ar—C), 122.01, 121.94 (Ar—C, Triazole-C5), 112.19 (C-3), 77.57 (C-6), 71.24 (C-7), 69.81 (C-4), 68.08 (C-8), 55.14 (C-9), 51.93 (C-5), 22.72 ($COCH_3$). HR-MS (ESI) calcd. for $C_{19}H_{22}N_5O_7$ $[M-H]^-$, 432.1529; found 432.1513.

Example 14: 5-Acetamido-9-(4-methylphenyl)-2,6-anhydro-3,5-dideoxy-b-glycero-D-galacto-non-2-enonic acid (7d)

Compound 7d was prepared as above in 86% yield (100 mg). $^1H$ NMR (500 MHz, $CD_3OD$) δ 8.24 (s, 1H, Trizole-H), 7.68 (d, J=8.0 Hz, 2H, Ar—H), 7.22 (d, J=8.0 Hz, 2H, Ar—H), 5.79 (s, 1H, H-3), 4.50 (dd, J=13.9, 7.4 Hz, 1H, H-9'), 4.39 (d, J=8.2 Hz, 1H, H-4), 4.29 (brs, 1H, H-8), 4.13 (d, J=10.9 Hz, 1H, H-6), 4.06-3.97 (m, 1H, H-5), 3.42 (d, J=9.0 Hz, 1H, H-7), 2.34 (s, 3H, $PhCH_3$), 1.98 (s, 3H, $COCH_3$). $^{13}C$ NMR (125 MHz, $CD_3OD$) δ 175.00 (C═O), 148.64 (Triazole-C4), 123.08 (Triazole-C5), 139.31, 130.58, 129.01, 126.62 (Ar—C), 110.40 (C-3), 77.27 (C-6), 71.24 (C-7), 69.84 (C-4), 68.35 (C-8), 55.16 (C-9), 51.95 (C-5), 22.76 ($COCH_3$), 21.31 ($PhCH_3$). HR-MS (ESI) calcd. for $C_{20}H_{23}N_4O_7$ $[M-H]^-$, 431.1567; found 431.1568.

Example 15: 5-Acetamido-(4-methoxyphenyl)-2,6-anhydro-3,5-dideoxy-b-glycero-D-galacto-non-2-enonic acid (7e)

Compound 7e was prepared as above in 74% yield (80 mg). $^1H$ NMR (500 MHz, $CD_3OD$) δ 8.20 (s, 1H, Triazole-H5), 7.72 (d, J=8.9 Hz, 2H), 6.97 (d, J=8.9 Hz, 2H), 5.77 (d, J=2.0 Hz, 1H, H-3), 4.49 (dd, J=14.0, 7.6 Hz, 1H, H-9'), 4.39 (dd, J=8.7, 2.0 Hz, 1H, H-4), 4.32-4.25 (m, 1H, H-8), 4.12 (d, J=10.8 Hz, 1H, H-6), 4.00 (dd, J=10.8, 8.7 Hz, 1H, H-5), 3.81 (s, 3H, $COCH_3$), 3.41 (d, J=9.2 Hz, 1H, H-7), 1.98 (s, 3H, $COCH_3$). $^{13}C$ NMR (125 MHz, $CD_3OD$) δ 174.96 ($COCH_3$), 161.27, 128.00, 124.40, 115.37 (Ar—C), 148.49 (Triazole-C4), 122.59 (Triazole-C5), 109.95 (C-3), 77.20 (C-6), 71.26 (C-7), 69.86 (C-4), 68.38 (C-8), 55.80 ($PhOCH_3$), 55.15 (C-9), 51.97 (C-5), 22.74 ($COCH_3$). HR-MS (ESI) calcd. for $C_{20}H_{23}N_4O_8$ $[M-H]^-$, 447.1516; found 447.1527.

Example 16: 5-Acetamido-9-(4-fluorophenyl)-2,6-anhydro-3,5-dideoxy-b-glycero-D-galacto-non-2-enonic acid (7f)

Compound 7f was prepared as above in 83% yield (80 mg). $^{1}$H NMR (500 MHz, $CD_3OD$) δ 8.28 (s, 1H, Triazole-H5), 7.87-7.80 (m, 2H, Ar—H), 7.20-7.13 (m, 2H, Ar—H), 5.92 (d, J=2.4 Hz, 1H, H-3), 4.86 (dd, J=14.0, 2.6 Hz, 1H, H-9), 4.51 (dd, J=14.0, 7.7 Hz, 1H, H-9'), 4.41 (dd, J=8.7, 2.4 Hz, 1H, H-4), 4.29 (ddd, J=9.6, 7.7, 2.6 Hz, 1H, H-8), 4.14 (dd, J=10.8, 1.1 Hz, 1H, H-6), 3.99 (dd, J=10.8, 8.7 Hz, 1H, H-5), 3.43 (dd, J=9.6, 1.1 Hz, 1H, H-7), 1.99 (s, 3H, $COCH_3$). $^{13}$C NMR (125 MHz, $CD_3OD$) δ 175.15 (C═O), 164.09 (d, J=245.9 Hz, Ar—C), 147.63 (Triazole-C4), 123.31 (Triazole-C5), 128.61 (d, J=8.2 Hz, Ar—C), 128.34 (d, J=3.2 Hz, Ar—C), 116.77 (d, J=22.0 Hz, Ar—C), 112.86 (C-3), 77.70 (C-6), 71.30 (C-7), 69.80 (C-4), 67.95 (C-8), 55.25 (C-9), 51.96 (C-5), 22.64 ($COCH_3$). HR-MS (ESI) calcd. for $C_{19}H_{20}FN_4O_7$[M−H]$^-$, 435.1316; found 435.1324.

Example 17: 5-Acetamido-9-(4-(trifluoromethyl) phenyl)-2,6-anhydro-3,5-dideoxy-D-glycero-D-galacto-non-2-enonic acid (7g)

Compound 7g was prepared as above in 45% yield (40 mg). $^{1}$H NMR (500 MHz, $CD_3OD$) δ 8.44 (s, 1H, Triazole-C), 8.02 (d, J=8.2 Hz, 2H, Ar—H), 7.72 (d, J=8.2 Hz, 2H, Ar—H), 5.95 (d, J=2.4 Hz, 1H, H-3), 4.90 (dd, J=14.0, 2.6 Hz, 1H, H-9), 4.53 (dd, J=14.0, 7.7 Hz, 1H, H-9'), 4.42 (dd, J=8.7, 2.4 Hz, 1H, H-4), 4.37-4.21 (m, 1H, H-8), 4.16 (dd, J=10.8, 1.0 Hz, 1H, H-6), 4.00 (dd, J=10.8, 8.7 Hz, 1H, H-5), 3.45 (dd, J=9.1, 1.0 Hz, 1H, H-7), 1.99 (s, 3H, $COCH_3$). $^{13}$C NMR (125 MHz, $CD_3OD$) δ 175.20 (C═O), 147.04 (Triazole-C4), 124.50 (Triazole-C5), 135.81 (Ar—C), 130.90 (q, J=32.3 Hz, Ar—C), 127.01 (Ar—C), 126.89 (q, J=3.8 Hz), 113.43 (C-3), 77.81 (C-6), 71.35 (C-7), 69.80 (C-4), 67.88 (C-8), 55.34 (C-9), 51.95 (C-9), 22.65 ($COCH_3$). HR-MS (ESI) calcd. for $C_{20}H_{20}F_3N_4O_7$ [M−H]$^-$, 485.1284; found 485.1282.

Example 18: 5-Acetamido-9-(4-carboxyphenyl)-2,6-anhydro-3,5-dideoxy-D-glycero-D-galacto-non-2-enonic acid (7h)

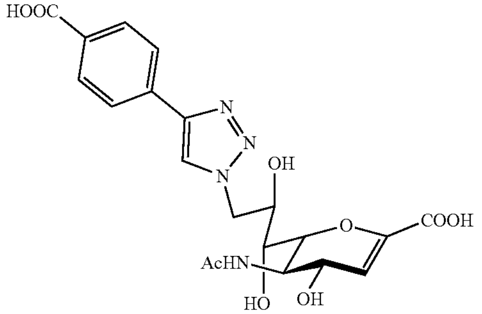

Compound 7h was prepared as above in 83% yield (100 mg). $^{1}$H NMR (500 MHz, $CD_3OD$) δ 8.42 (s, 1H, C═CH—N), 8.06 (d, J=8.5 Hz, 2H, Ar—H), 7.90 (d, J=8.5 Hz, 2H, Ar—H), 5.84 (d, J=1.9 Hz, 1H, H-3), 4.88 (dd, J=14.0, 2.1 Hz, 1H, H-9), 4.54 (dd, J=14.0, 7.6 Hz, 1H, H-9'), 4.43 (dd, J=8.7, 1.9 Hz, 1H, H-4), 4.31 (t, J=7.6 Hz, 1H, H-8), 4.15 (d, J=10.9 Hz, 1H, H-6), 4.03 (dd, J=10.9, 8.7 Hz, 1H, H-5), 3.44 (d, J=7.6 Hz, 1H, H-7), 1.99 (s, 3H, $COCH_3$). $^{13}$C NMR (125 MHz, $CD_3OD$) δ 175.08, 169.69, 167.90 (C═O), 147.50, 124.53 (Triazole-C), 136.19, 131.49, 126.44 (Ar—C), 111.19 (C-3), 77.37 (C-6), 71.31 (C-7), 69.84 (C-4), 68.24 (C-8), 55.29 (C-9), 51.90 (C-5), 22.82 ($COCH_3$). HR-MS (ESI) calcd. for $C_{20}H_{21}N_4O_9$ [M−H]$^-$, 461.1309; found 461.1316.

Example 19: 5-Acetamido-9-(4-biphenyl)-2,6-anhydro-3,5-dideoxy-D-glycero-D-galacto-non-2-enonic acid (7i)

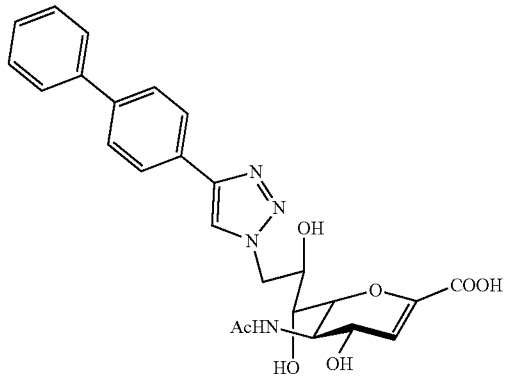

CuAAC reaction gave 77 mg crude protected product, which was deprotected to give the desired final product 52 mg (75%). $^{1}$H NMR (500 MHz, $CD_3OD$) δ 8.34 (s, 1H, Triazole-H), 7.88 (d, J=8.1 Hz, 2H, Ar—H), 7.65 (d, J=8.1 Hz, 3H, Ar—H), 7.42 (t, J=7.5 Hz, 2H, Ar—H), 7.32 (t, J=7.5 Hz, 1H, Ar—H), 5.74 (d, J=1.9 Hz, 1H, H-3), 4.88 (dd, J=13.9, 2.2 Hz, 1H, H-9), 4.52 (dd, J=13.9, 7.7 Hz, H-9'), 4.39 (dd, J=8.7, 1.9 Hz, H-4), 4.37-4.21 (m, 1H, H-8), 4.13 (d, J=10.8 Hz, 1H, H-6), 4.02 (dd, J=10.8, 8.7 Hz, 1H, H-5), 3.42 (d, J=9.3 Hz, 1H, H-7), 2.00 (s, 3H, $COCH_3$). $^{13}$C NMR (125 MHz, $CD_3OD$) δ 174.93, 169.51 (C═O), 149.28, 123.47 (Triazole-C), 148.20 (C-2), 142.24, 141.76, 130.84, 129.94, 128.54, 128.48, 127.86, 127.10 (Ar—C), 77.14 (C-6), 71.34 (C-7), 69.83 (C-4), 68.49 (C-8), 55.25 (C-9), 52.00 (C-5), 22.77 ($COCH_3$). HR-MS (ESI) calcd. for $C_{25}H_{25}N_4O_7$[M−H]$^-$, 493.1723; found 493.1729.

Example 20: 5-Acetamido-9-(4-phenoxyphenyl)-2,6-anhydro-3,5-dideoxy-D-glycero-D-galacto-non-2-enonic acid (7j)

Click reaction gave 77 mg crude protected product, which was deprotected to give the desired final product 40 mg (43%). $^{1}$H NMR (500 MHz, $CD_3OD$) δ 8.24 (s, 1H, Triazole-H5), 8.24 (s, 1H), 7.78 (d, J=8.7 Hz, 2H, Ar—H), 7.35 (dd, J=8.7, 7.4 Hz, 2H, Ar—H), 7.12 (t, J=7.4 Hz, 1H, Ar—H), 7.05-6.98 (m, 4H, Ar—H), 5.93 (d, J=2.4 Hz, 1H, H-3), 4.85 (dd, J=14.0, 2.5 Hz, 1H, H-9), 4.50 (dd, J=14.0, 7.7 Hz, 1H, H-9'), 4.42 (dd, J=8.7, 2.4 Hz, 1H, H-4), 4.30 (ddd, J=10.0, 7.7, 2.5 Hz, 1H, H-8), 4.16 (m, 1H, H-6), 4.01 (dd, J=10.8, 8.8 Hz, 1H, H-5), 3.47-3.41 (m, 1H, H-7), 2.00 (s, 3H, $COCH_3$). $^{13}$C NMR (125 MHz, $CD_3OD$) δ 175.18, 166.12 (C═O), 158.95, 158.31, 131.00, 128.28, 126.98, 124.77, 120.19, 119.98 (Ar—C), 148.06 (Triazole-C4), 123.10 (Triazole-C5), 145.90 (C-2), 113.04 (C-3), 77.73 (C-6), 71.32 (C-7), 69.83 (C-4), 67.95 (C-8), 55.25 (C-9), 51.95 (C-5), 22.70 ($COCH_3$). HR-MS (ESI) calcd. for $C_{25}H_{25}N_4O_8$ $[M-H]^-$, 509.1672; found 509.1674.

Example 21: 5-Acetamido-9-(3-(4-(benzamidomethyl))-2,6-anhydro-3,5-dideoxy-D-glycero-D-galacto-non-2-enonic acid (26)

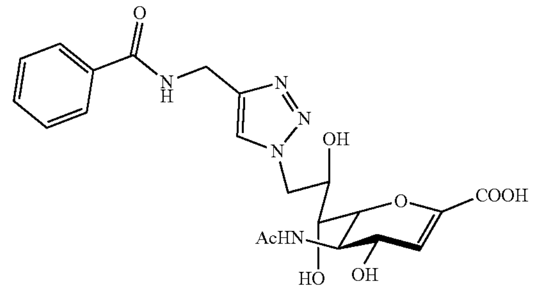

$^1$H NMR (500 MHz, $CD_3OD$) δ 7.93 (s, 1H, Triazole-H), 7.86-7.80 (m, 2H, Ar—H), 7.53 (t, J=7.4 Hz, 1H, Ar—H), 7.45 (t, J=7.6 Hz, 2H, Ar—H), 5.94 (d, J=2.5 Hz, 1H, H-3), 4.86-4.81 (m, 1H, H-9), 4.64 (s, 2H, N—$CH_2$-Triazole), 4.46-4.38 (m, 2H, H-9', H-4), 4.22 (td, J=8.4, 2.4 Hz, 1H, H-8), 4.14 (d, J=11.1 Hz, 1H, H-6), 3.97 (dd, J=11.1, 8.8 Hz, 1H, H-5, H-5), 3.43 (d, J=8.4 Hz, 1H, H-7), 2.01 (s, 3H, $COCH_3$). $^{13}$C NMR (126 MHz, $CD_3OD$) δ 175.30 (N—C═O), 132.88, 129.62, 128.40 (Ar—C), 113.51 (C-3), 77.73 (C-6), 71.36 (C-7), 69.87 (C-4), 67.85 (C-8), 55.16 (C-9), 51.90 (C-5), 36.21 (N—$CH_2$-Triazole), 22.69 ($COCH_3$). HR-MS (ESI) calcd. for $C_{21}H_{24}N_5O_8$ $[M-H]^-$, 474.1630; found 474.1624.

Example 22: 5-Acetamido-9-(3-(4-(4-benzamidophenyl))-2,6-anhydro-3,5-dideoxy-D-glycero-D-galacto-non-2-enonic acid (27)

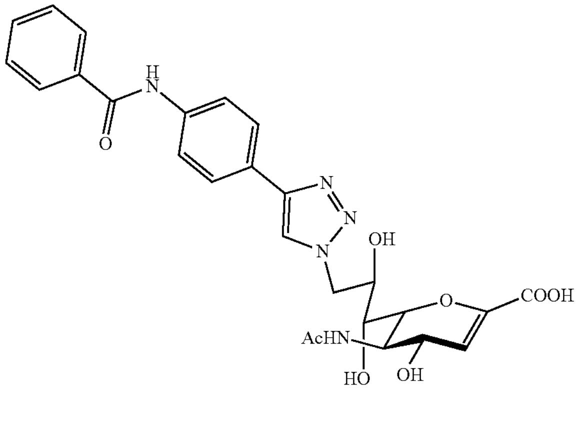

$^1$H NMR (500 MHz, $CD_3OD$) δ 8.31 (d, J=7.4 Hz, 1H, Triazole-H), 7.93 (d, J=7.3 Hz, 2H, Ar—H), 7.86-7.80 (m, 2H, Ar—H), 7.79 (d, J=8.7 Hz, 2H, Ar—H), 7.61-7.57 (m, 1H, Ar—H), 7.53 (d, J=6.5 Hz, 2H, Ar—H), 5.97 (s, 1H, H-3), 4.87 (d, J=11.9 Hz, 1H, H-9), 4.54 (dd, J=14.1, 7.4 Hz, 1H, H-9'), 4.44 (d, J=9.2 Hz, 1H, H-4), 4.35-4.27 (m, 1H, H-8), 4.17 (d, J=10.2 Hz, 1H, H-6), 4.03-3.95 (m, 1H, H-5), 3.44 (d, J=8.7 Hz, 1H, H-7), 2.01 (d, J=3.4 Hz, 3H, $COCH_3$). $^{13}$C NMR (126 MHz, $CD_3OD$) δ 133.10, 129.76, 128.66, 127.17, 122.63, 116.42 (Ar—C), 113.69 (C-3), 77.70 (C-6), 71.10 (C-7), 69.76 (C-4), 67.85 (C-8), 55.15 (C-9), 51.85 (C-5), 22.75 ($COCH_3$). HR-MS (ESI) calcd. for $C_{26}H_{26}N_5O_8$ $[M-H]^-$, 536.1787; found 536.1782.

Example 23: 2-Methyl-4,5-dihydro-(methyl(7,8-di-O-acetyl-9-(4-(methoxycarbonyl)phenyl)-2,6-anhydro-3,4,5-trideoxy-D-glycero-D-talo-non-2-en)onate)[5,4-d]-1,3-oxazole (11)

A solution of compound 10 h (250 mg, 1 eq) in anhydrous pyridine was cooled down to 0° C., followed by dropwise addition of acetic anhydride (230 μl, 4.5 eq). The reaction mixture was allowed to warm to room temperature and kept stirring overnight. After completion, the reaction was quenched with methanol and the solvents were removed under reduced pressure. The residue was dissolved in ethyl acetate and carefully washed with 0.05 M HCl, water, and brine sequentially and dried over $Na_2SO_4$. The solution was then concentrated and purified by flash chromatography, providing a crude fully protected product, which was used in the next step without further purification. The obtained crude protected product (800 mg, 1 eq, several batches' product of last step) was dissolved in 10 ml ethyl acetate. The solution was warmed to 40° C. and TMSOTf (408 μl, 3 eq) was added dropwisely. The resulting solution was kept stirring at 50° C. for 4 hours. After completion, the solution was added to a vigorously stirred cold saturated sodium bicarbonate solution. The aqueous phase was separated and extracted with ethyl acetate. The organic phase was combined, dried over $Na_2SO_4$, concentrated and purified by flash chromatography to give the desired product (430 mg, 60%). $^1$H NMR (500 MHz, $CD_3OD$) δ 8.49 (s, 1H, Triazole-H5), 8.03-7.97 (d, J=8.5 Hz, 2H, Ar—H), 7.88 (d, J=8.5 Hz, 2H, Ar—H), 6.39 (d, J=4.0 Hz, 1H, H-3), 5.65-5.57 (m, 2H, H-7, H-8), 5.22 (dd, J=14.8, 2.6 Hz, 1H, H-9), 4.94 (dd, J=9.5, 4.0 Hz, 1H, H-4), 4.79 (m, 1H, H-9'), 4.02 (t, J=9.5 Hz, 1H, H-5), 3.87, 3.79 (2×s, 2×3H, 2×$COOCH_3$), 3.60 (dd, J=9.5, 2.3 Hz, 1H, H-6), 2.17 (s, 3H, oxazole-$CH_3$), 1.97, 1.95 (2×s, 2×3H, 2×$COOCH_3$). $^{13}$C NMR (125 MHz, $CD_3OD$) δ 171.55, 171.32, 168.03, 163.34 (C═O), 170.12 (oxazole-O—C═N), 148.09 (Triazole-C4), 124.39 (Triazole-C5), 147.66 (C-2), 136.30, 131.27, 130.78, 126.55 (Ar—C), 109.05 (C-3), 78.35 (C-6), 74.22 (C-4), 73.52 (C-8), 70.86 (C-7), 62.68 (C-5), 53.27, 52.81 ($COOCH_3$), 51.09 (C-9), 20.73, 20.67 ($COCH_3$), 14.06 (oxazole-$CH_3$). HR-MS (ESI) calcd. for $C_{26}H_{28}N_4NaO_{10}[M+Na]^+$, 579.1703; found 579.1697.

Example 24: Methyl 5-acetamido-7,8-di-O-acetyl-9-(4-(methoxycarbonyl)phenyl)-2,6-anhydro-4-azido-3,4,5-trideoxy-D-glycero-D-galacto-non-2-enonate (12)

To a solution of compound 11 (430 mg, 1 eq) in dry $^t$BuOH, $TMSN_3$ (507 μl, 5 eq) was added and the resulting solution was stirred at 80° C. under a nitrogen atmosphere for 12 hours. After completion, the solution was cooled down to room temperature, concentrated and purified by flash chromatography to give the desired product. 470 mg (quant.). $^1$H NMR (500 MHz, $CD_3OD$) δ 8.51 (s, 1H, Triazole-H5), 8.07-8.02 (m, 2H, Ar—H), 7.92-7.87 (m, 2H, Ar—H), 5.97 (d, J=2.2 Hz, 1H, H-3), 5.57-5.56 (dd, J=3.3, 2.2 Hz, 1H, H-4), 5.52 (dt, J=9.1, 2.9 Hz, 1H, H-8), 5.29 (dd, J=14.8, 2.7 Hz, 1H, H-9), 4.71 (dd, J=14.8, 9.1 Hz, 1H, H-9'), 4.49 (dd, J=10.3, 1.9 Hz, 1H, H-6), 4.27-4.18 (m, 2H, H-5, H-7), 3.89, 3.80 (2×s, 2×3H, 2×$COOCH_3$), 2.13, 1.93, 1.92 (3×s, 3×3H, 3×$COCH_3$). $^{13}$C NMR (125 MHz, $CD_3OD$) δ 173.49, 171.83, 171.42, 168.09, 163.07 (C═O), 147.64 (Triazole-C4), 124.51 (Triazole-C5), 146.32 (C-2), 136.25, 131.26, 130.85, 126.54 (Ar—C), 109.74 (C-3), 78.44 (C-6), 73.96 (C-8), 69.60 (C-7), 60.46 (C-4), 53.21, 52.74 ($COOCH_3$), 51.17 (C-9), 48.39 (C-5), 22.89, 20.88, 20.63 ($COCH_3$). HR-MS (ESI) calcd. for $C_{26}H_{29}N_7NaO_{10}$ $[M+Na]^+$, 622.1874; found 622.1866.

Example 25: 5-Acetamido-9-(4-(methoxycarbonyl) phenyl)-2,6-anhydro-4-azido-3,4,5-trideoxy-D-glycero-D-galacto-non-2-enonic acid (13)

60 mg compound 12 was dissolved in 2 ml 0.5 N NaOH, the solution was stirred under room temperature for 1 hour. After completion, Amberlite IR 120 ($H^+$) was added to neutralize the solution. The suspension was then filtered, and the filtrate was concentrated and purified by flash chromatography to give the desired product. 32 mg (66%). $^1H$ NMR (500 MHz, $CD_3OD$) δ 8.43 (s, 1H, Triazole-H5), 8.06 (d, J=8.2 Hz, 2H, Ar—H), 7.91 (d, J=8.2 Hz, 2H, Ar—H), 5.73 (s, 1H), 4.53 (dd, J=14.0, 7.6 Hz, 1H, H-9'), 4.32-4.25 (m, 2H, H-4, H-8), 4.23 (d, J=10.8 Hz, 1H, H-6), 4.18-4.10 (m, 1H, H-5), 3.45 (d, J=9.3 Hz, 1H, H-7), 1.98 (s, 3H, $COCH_3$). $^{13}C$ NMR (125 MHz, $CD_3OD$) δ 174.32 (C═O), 147.53 (Triazole-C4), 124.47 (Triazole-C5), 136.17, 131.48, 126.42 (Ar—C), 104.50 (C-3), 77.02 (C-6), 71.03 (C-8), 69.86 (C-7), 60.23 (C-4), 55.25 (C-9), 48.53 (C-5), 22.78 ($COCH_3$). HR-MS (ESI) calcd. for $C_{20}H_{20}ON_7O_8$ $[M-H]^-$, 486.1373; found 486.1378.

Example 26: Methyl 5-acetamido-7,8-di-O-acetyl-9-(4-(methoxycarbonyl)phenyl)-2,6-anhydro-4-amino-3,4,5-trideoxy-D-glycero-D-galacto-non-2-enonate (14)

To a solution of compound 12 (50 mg, 1 eq) in THF (2 ml), 0.5 N HCl (200 μl, 2 eq) was added, followed by triphenylphosphine (29 mg, 1.1 eq). The resulting mixture was stirred at room temperature overnight. After completion, solvents were removed under reduced pressure and the residue was purified by flash chromatography, providing the desired product 39 mg (84%). $^1H$ NMR (500 MHz, $CD_3OD$) δ 8.57 (s, 1H, Triazole-H5), 8.05 (d, J=8.4 Hz, 2H, Ar—H), 7.92 (d, J=8.4 Hz, 2H, Ar—H), 6.06 (d, J=2.3 Hz, 1H, H-3), 5.63-5.55 (m, 2H, H-7, H-8), 5.29-5.21 (m, 1H, H-9), 4.74 (dd, J=14.7, 8.4 Hz, 1H, H-9'), 4.64 (dd, J=10.0, 1.1 Hz, 1H, H-6), 4.35 (t, J=10.0 Hz, 1H, H-5), 4.15 (dd, J=10.0, 2.3 Hz, 1H, H-4), 3.90, 3.81 (2×s, 2×3H, $2\times COOCH_3$), 2.12, 1.97, 1.95 (3×s, 3×3H, $3\times COCH_3$). $^{13}C$ NMR (125 MHz, $CD_3OD$) δ 174.28, 171.71, 171.31, 168.15, 162.80 (C═O), 147.66 (Triazole-C4), 124.59 (Triazole-C5), 147.29, 136.28, 130.84, 126.56 (Ar—C), 107.15 (C-3), 77.96 (C-6), 73.34 (C-8), 69.49 (C-7), 53.34, 52.78 ($COOCH_3$), 51.67 (C-4), 51.31 (C-9), 46.73 (C-5), 23.14, 20.89, 20.66 ($COCH_3$). HR-MS (ESI) calcd. for $C_{26}H_{31}N_5NaO_{10}$ $[M+Na]^+$, 596.1969; found 596.1967.

Example 27: 5-acetamido-7,8-di-O-acetyl-9-(4-(methoxycarbonyl)phenyl)-2,6-anhydro-4-amino-3,4,5-trideoxy-D-glycero-D-galacto-non-2-enonic acid (15)

35 mg compound 14 was dissolved in 400 μL 1N NaOH and the solution was kept stirring at r.t. for 1 h. After completion, the reaction mixture was neutralized with Amberlite IR 120 ($H^+$). The suspension was then filtered, and the filtrate was concentrated and purified by flash chromatography to give the desired product. 20 mg (71%). $^1H$ NMR (500 MHz, $CD_3OD$) δ 8.47 (s, 1H, Triazole-H5), 8.08 (d, J=8.2 Hz, 2H, Ar—H), 7.94 (d, J=8.2 Hz, 2H, Ar—H), 5.84 (s, 1H, H-3), 4.89 (d, J=14.4 Hz, 1H, H-9), 4.56 (dd, J=14.0, 7.5 Hz, 1H, H-9'), 4.41-4.26 (m, 3H, H-8, H-6, H-5), 4.18 (d, J=7.1 Hz, 1H, H-4), 3.56 (d, J=9.1 Hz, 1H, H-7), 2.03 (s, 3H, $COCH_3$). $^{13}C$ NMR (125 MHz, $CD_3OD$) δ 174.86, 169.48 (C═O), 147.50 (Triazole-C4), 124.66 (Triazole-C5), 136.29, 131.48, 131.25, 126.45 (Ar—C), 103.03 (C-3), 77.01 (C-6), 70.71 (C-8), 70.03 (C-7), 55.19 (C-9), 51.29 (C-4), 47.54 (C-5), 23.03 ($COCH_3$). HR-MS (ESI) calcd. for $C_{20}H_{22}N_5O_8[M-H]^-$, 460.1468; found 460.1482.

Example 28: Methyl 5-acetamido-9-(4-(methoxycarbonyl)phenyl-1H-1,2,3-triazol-1-yl))-4-[2,3-bis (tert-butoxycarbonyl)guanidino]-7,8-di-O-acetyl-2,6-anhydro-3,4,5-trideoxy-D-glycero-D-galacto-non-2-enonate (16)

To a solution of compound 14 (40 mg, 1 eq) in 2 ml anhydrous DCM, TEA (40 μl, 4 eq) was added. The solution was cooled down to 0° C. and N, N'-Di-Boc-1H-pyrazole-1-carboxamidine (42 mg, 2 eq) added. The reaction mixture was allowed to warm up to room temperature and kept stirring overnight. After completion, the reaction was quenched with water, extracted with ethyl acetate. The organic phase was washed with brine, dried over $Na_2SO_4$, concentrated and purified by flash chromatography to give the desired product. Crude product, 40 mg (72%). $^1H$ NMR (500 MHz, $CD_3OD$) δ 8.55 (s, 1H, Triazole-H5), 8.06 (d, J=8.3 Hz, 2H, Ar—H), 7.92 (d, J=8.3 Hz, 2H), 6.00 (d, J=2.3 Hz, 1H, H-3), 5.58 (d, J=1.5 Hz, 1H, H-7), 5.56-5.52 (m, 1H, H-8), 5.31 (dd, J=14.8, 2.4 Hz, 1H, H-9), 5.02 (dd, J=10.2, 2.3 Hz, 1H, H-4), 4.74 (dd, J=14.8, 9.0 Hz, 1H, H-9'), 4.53 (dd, J=10.2, 1.5 Hz, 1H, H-6), 4.27 (t, J=10.2 Hz, 1H, H-5), 3.91, 3.80 (2×s, 3H, $COOCH_3$), 2.12, 1.94, 1.85 (3×s, 3×3H, $3\times COCH_3$), 1.51, 1.46 (2×s, 2×9H, 2×Boc). $^{13}C$ NMR (125 MHz, $CD_3OD$) δ 173.57, 171.77, 171.41, 168.07, 164.32, 163.39, 158.01 (C═O), 153.82 (C═N), 147.64 (Triazole-C4), 124.50 (Triazole-C5), 145.61 (C-2), 136.34, 131.27, 131.27, 126.55 (Ar—C), 111.83 (C-3), 84.84, 80.57 ($^t$Boc-$C(CH_3)_3$), 78.89 (C-6), 74.00 (C-8), 69.87 (C-7), 53.07, 52.74 ($COOCH_3$), 51.27 (C-9), 50.84 (C-4), 47.90 (C-5), 28.59, 28.26 ($^t$Boc-$C(CH_3)_3$), 22.77, 20.86, 20.65 ($COCH_3$). HR-MS (ESI) calcd. for $C_{37}H_{49}N_7NaO_{14}$ $[M+Na]^+$, 838.3235; found 838.3226.

Example 29: 5-Acetamido-9-(4-carboxyphenyl)-2,6-anhydro-4-guanidino-3,4,5-trideoxy-D-glycero-D-galacto-non-2-enonic acid (8a)

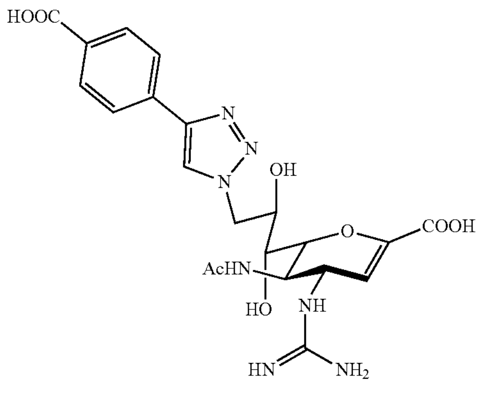

To a solution of compound 16 (40 mg) in 1 ml DCM, 100 μl TFA was added. The solution was then stirred at room temperature for 2 hours. After completion, DCM and TFA were removed under reduced pressure. The residue was dissolved in 2 ml 0.1 N NaOH, and stirred at room temperature for 1 hour. After completion, the reaction mixture was added with Amberlite IR 120 ($H^+$) to adjust the pH of the solution as 7. The suspension was then filtered, and the filtrate was concentrated and purified by flash chromatography to give the desired product. 10 mg (41%). $^1$H NMR (500 MHz, $D_2O$) δ 8.49 (s, 1H, Triazole-H), 8.02 (d, J=8.2 Hz, 2H, Ar—H), 7.93 (d, J=8.2 Hz, 2H, Ar—H), 5.68 (d, J=2.1 Hz, 1H, H-3), 4.91 (dd, J=14.4, 2.8 Hz, 1H, H-9), 4.72 (dd, J=14.4, 6.7 Hz, 1H, H-9'), 4.48 (dd, J=9.5, 2.1 Hz, 1H, H-4), 4.46-4.41 (m, 1H, H-8), 4.40 (d, J=11.0 Hz, 1H, H-7), 4.26 (t, J=9.5 Hz, 1H, H-5), 3.53 (d, J=9.5 Hz, 1H, H-6), 1.99 (s, 3H, $COCH_3$). $^{13}$C NMR (125 MHz, $D_2O$) δ 175.37, 169.94, 163.66 (C═O), 157.96 (C═N), 150.14 (C-2), 147.81, 124.65 (Triazole-C), 133.00, 130.62, 126.33 (Ar—C), 104.76 (C-3), 76.02 (C-6), 69.79 (C-8), 69.00 (C-7), 54.41 (C-9), 51.83 (C-4), 48.65 (C-5), 22.75 ($COCH_3$). HR-MS (ESI) calcd. for $C_{21}H_{24}N_7O_8$ $[M-H]^-$, 502.1686; found 502.1683.

Example 30: Methyl 5-acetamido-9-(4-(methoxycarbonyl)phenyl-1H-1,2,3-triazol-1-yl))-4-(3-(3-methoxy-3-oxopropyl)ureido)-7,8-di-O-acetyl-2,6-anhydro-3,4,5-trideoxy-D-glycero-D-galacto-non-2-enonate (17)

A solution of compound 14 (100 mg, 1 eq) and TEA (56 mg, 2 eq) in anhydrous DCM was cooled down to 0° C., and added with 1,1'-Carbonyldiimidazole (39 mg, 1.2 eq). The reaction mixture was then warmed to room temperature and kept stirring for 2 hours until TLC results showed no amine remained. The solution was then cooled down to 0° C., and β-alanine methyl ester (56 mg, 2 eq) was added. The solution was warmed to room temperature and kept stirring overnight. After completion, the reaction was quenched with water, extracted by ethyl acetate. The organic layer was washed with water, brine, dried over $Na_2SO_4$. After concentrated, the residue was purified by flash chromatography to give the desired product. 140 mg (quant.). $^1$H NMR (500 MHz, $CD_3OD$) δ 8.54 (s, 1H, Triazole-H5), 8.07 (d, J=8.7 Hz, 2H, Ar—H), 7.92 (d, J=8.7 Hz, 2H, Ar—H), 5.92 (d, J=2.5 Hz, 1H, H-3), 5.55 (m, 2H, H-8, H-4), 5.31 (dd, J=14.8, 2.6 Hz, 1H, H-9), 4.73 (dd, J=14.8, 8.9 Hz, 1H, H-9'), 4.55 (dd, J=9.9, 2.5 Hz, 1H, H-7), 4.46 (dd, J=10.2, 2.0 Hz, 1H, H-6), 4.10 (t, J=10.2 Hz, 1H, H-5), 3.91, 3.78, 3.66 (3×s, 3×3H, 3×$COOCH_3$), 3.36 (td, J=6.6, 1.9 Hz, 2H, $CH_2$), 2.48 (t, J=6.5 Hz, 2H, $CH_2$), 2.10, 1.93, 1.87 (3×s, 3×3H, 3×$COCH_3$). $^{13}$C NMR (125 MHz, $CD_3OD$) δ 174.12, 173.59, 171.79, 171.41, 168.13, 163.56, 160.42 (C═O), 147.66 (C-2), 145.10 (Triazole-C4), 124.46 (Triazole-C5), 136.30, 131.26, 130.88, 126.54 (Ar—C), 114.06 (C-1), 79.10 (C-6), 73.99 (C-8), 69.97 (C-7), 52.96, 52.70, 52.15 ($COOCH_3$), 51.26 (C-9), 50.38 (C-5), 36.92, 35.64 ($CH_2CH_2$), 22.85, 20.84, 20.59 ($COCH_3$). HR-MS (ESI) calcd. for $C_{31}H_{39}N_7N_6O_{13}$ $[M+Na]^+$, 703.2575; found 703.2571.

Example 31: 5-Acetamido-9-(4-carboxyphenyl)-2,6-anhydro-4-(3-(2-carboxyethyl)ureido)-3,4,5-trideoxy-D-glycero-D-galacto-non-2-enonic acid (18)

140 mg compound 17 was dissolved in 5 ml 0.1 N NaOH, and stirred at room temperature for 1 hour. After completion, the reaction mixture was added with Amberlite IR 120 ($H^+$) to neutralize the solution. The suspension was then filtered, and the filtrate was concentrated and purified by flash chromatography to give the desired product. 88 mg (77%). $^1$H NMR (500 MHz, $CD_3OD$) δ 8.44 (s, 1H, Triazole-H5), 8.07 (d, J=8.4 Hz, 2H, Ar—H), 7.93 (d, J=8.4 Hz, 2H, Ar—H), 5.66 (d, J=1.9 Hz, 1H, H-3), 4.57 (dd, J=9.8, 1.9 Hz, 1H, H-4), 4.52 (dd, J=14.0, 7.7 Hz, 1H, H-9'), 4.30 (dd, J=12.1, 4.8 Hz, 1H, H-8), 4.19 (d, J=10.8 Hz, 1H, H-6), 4.02 (t, J=10.3 Hz, 1H, H-5), 3.44 (d, J=9.3 Hz, 1H, H-7), 3.37 (t, J=6.4 Hz, 2H, $CH_2$), 2.46 (t, J=6.4 Hz, 2H, $CH_2$), 1.94 (s, 3H, $COCH_3$). $^{13}$C NMR (125 MHz, $CD_3OD$) δ 175.74, 174.73, 160.76, 169.64 (C═O), 147.51 (Triazole-C4), 124.40 (Triazole-C5), 136.24, 131.68, 131.45, 126.42 (Ar—C), 109.35 (C-3), 77.81 (C-6), 71.36 (C-8), 69.80 (C-7), 55.31 (C-9), 37.00, 35.78 ($CH_2CH_2$), 22.74 ($COCH_3$). HR-MS (ESI) calcd. for $C_{24}H_{27}N_6O_{11}$ $[M-H]^-$, 575.1738; found 575.1738.

Example 32: Methyl 5-(acetylamino)-4-(tert-butoxycarbonyl)amino-2,6-anhydro-3,5-dideoxy-D-glycero-D-galacto-non-2-enonate (20)

To a solution of compound 19 (600 mg, 1 eq) and TEA (389 μl, 2 eq) in 20 ml anhydrous DCM at 0° C., di-tert-butyl dicarbonate (456 mg, 1.5 eq) was added in dropwise. The mixture was them warmed up to room temperature and kept stirring overnight. After completion, solvent was removed and the residue was purified by flash chromatography to give the desired compound 350 mg (crude product, 47%). The crude product (350 mg, 1 eq) was dissolved in 10 ml methanol, and cooled down to 0° C., followed by addition of NaOMe (92 mg, 3 eq). The solution was kept stirring at 0° C. for about 1 hour until no starting material remained. Amberlite IR 120 ($H^+$) was added to neutralize the solution. The suspension was then filtered, and the filtrate was concentrated and purified by flash chromatography to give the desired product. 190 mg (71%). $^1$H NMR (500 MHz, $CD_3OD$) δ 5.82 (d, J=2.2 Hz, 1H, H-3), 4.46 (d, J=10.1 Hz, 1H, H-4), 4.23 (d, J=10.1 Hz, 1H, H-6), 4.05 (t, J=10.1 Hz, 1H, H-5), 3.88 (ddd, J=9.2, 5.4, 2.9 Hz, 1H, H-8), 3.81 (dd, J=11.4, 2.9 Hz, 1H, H-9), 3.65 (dd, J=11.4, 5.4 Hz, 1H, H-9'), 3.58 (dd, J=9.3, 1.1 Hz, 1H, H-7), 1.98 (s, 3H, $COOCH_3$), 1.44 (s, 9H, $^t$Boc-$C(CH_3)_3$). $^{13}$C NMR (125 MHz, $CD_3OD$) δ 174. 65, 164.26, 158.35 (C═O), 145.71 (C-2), 112.19 (C-3), 80.56 ($^t$Boc-$C(CH_3)_3$), 78.62 (C-6), 71.13 (C-8), 70.00 (C-7), 64.90 (C-9), 52.79 (C-4), 50.26 (C-5), 28.70 ($^t$Boc-$C(CH_3)_3$), 22.70 ($COCH_3$). HR-MS (ESI) calcd. for $C_{17}H_{29}N_2O_9$ $[M+H]^+$, 405.1873; found 405.1875.

Example 33: Methyl 4-(tert-butoxycarbonyl)amino-5-acetylamino-9-(4-methylbenzenesulfonate)-2,6-anhydro-3,5-dideoxy-D-glycero-D-galacto-non-2-enonate (21)

A solution of compound 20 (190 mg, 1 eq) in anhydrous pyridine was cooled down to 0° C., TsCl (98 mg, 1.1 eq) was then added slowly under stirring. The solution was warmed room temperature and kept stirring overnight. After completion, the reaction was quenched by methanol. The solution was concentrated and purified by flash chromatography to give the desired product. 200 mg (76%). $^1$H NMR (500 MHz, $CDCl_3$) δ 7.78 (d, J=8.1 Hz, 2H, Ar—H), 7.33 (d, J=8.1 Hz, 2H, Ar—H), 6.93, 5.23, 5.11, 3.59 (4×d, 4H, 2×NH, 2×OH), 5.82 (d, J=2.3 Hz, 1H, H-3), 4.55 (td, J=9.6, 2.2 Hz, 1H, H-8), 4.40-4.31 (m, 1H, H-6), 4.21-4.17 (m, 1H, H-5), 4.15-4.11 (m, 2H, H-9', H-4), 4.01-3.95 (m, 1H, H-9'), 3.71 (s, 3H, $COOCH_3$), 3.56-3.48 (m, 1H, H-7), 2.43 (s, 3H, $PhCH_3$), 2.00 (s, 3H, $COCH_3$), 1.42 (s, 9H, $^t$Boc-$C(CH_3)_3$). $^{13}$C NMR (125 MHz, $CDCl_3$) δ 174.01, 162.21, 156.80 (C═O), 145.07 (C-2), 144.86, 132.59, 129.91, 128.02 (Ar—C), 109.92 (C-3), 80.60 ($^t$Boc-$C(CH_3)_3$), 72.56 (C-9), 68.53 (C-7), 67.90 (C-8), 52.38 (C-6), 50.19 (C-4), 48.68 (C-5), 28.26 ($^t$Boc-$C(CH_3)_3$), 22.86, 21.63 ($COCH_3$, $PhCH_3$). HR-MS (ESI) calcd. for $C_{24}H_{35}N_2O_{11}S$ $[M+H]^+$, 559.1962; found 559.1966.

Example 34: Methyl 5-acetamido-7,8-di-O-acetyl-9-azido-2,6-anhydro-4-[2,3-bis(tert-butoxycarbonyl) guanidino]-3,4,5-trideoxy-D-glycero-D-galacto-non-2-enonate (23)

Compound 21 (200 mg, 1 eq) was dissolved in 3 ml acetone-water (2:1) and $NaN_3$ (117 mg, 5 eq) was added. The solution was heated at 67° C. under $N_2$ for two days. After completion, the solution was concentrated and purified by flash chromatography to give 100 mg compound 22 (crude product, 75%) which was used in the next step without further purification. The crude product was dissolved in 2 ml anhydrous DCM, and 200 μl TFA was added. The solution was kept stirring at room temperature until no starting material remained. Solvents was then removed under vacuum and the residue was dissolved in 2 ml anhydrous DCM, and TEA (140 μl, 4 eq) was added. After the solution was cooled down to 0° C., N,N'-Di-Boc-1H-pyrazole-1-carboxamidine (150 mg, 2 eq) was added. The reaction mixture was allowed to warm up to room temperature and kept stirring overnight. After completion, the reaction was quenched with water, extracted with ethyl acetate. The organic phase was washed with brine, dried over $Na_2SO_4$, concentrated and purified by flash chromatography to give the desired product. 108 mg (82%). $^1$H NMR (500 MHz, $CDCl_3$) δ 8.63, 8.15, 7.70, 6.43 (2×d, 2×brs, 4H, 2×NH, 2×OH), 5.82 (d, J=2.4 Hz, 1H, H-3), 5.20 (ddd, J=10.2, 8.1, 2.4 Hz, 1H, H-4), 4.22-4.15 (m, 2H, H-6, H-5), 4.02 (td, J=10.2, 6.1 Hz, 1H, H-8), 3.72 (dd, J=12.6, 2.8 Hz, 1H, H-9), 3.60-3.53 (m, 2H, H-9', H-7), 2.04 (s, 3H, $COCH_3$), 1.52 (2×s, 2×9H, 2×$^t$Boc-$C(CH_3)_3$). $^{13}$C NMR (125 MHz, $CDCl_3$) δ 174.04, 162.29, 162.08, 157.56 (C═O), 152.70 (C═N), 146.31 (C-2), 107.51 (C-3), 84.39, 80.11 ($^t$Boc-$C(CH_3)_3$), 69.14 (C-6), 54.89 (C-9), 52.53 (C-7), 51.53 (C-8), 48.33 (C-5), 28.23, 28.04 ($^t$Boc-$C(CH_3)_3$), 22.96 ($COCH_3$). HR-MS (ESI) calcd. for $C_{23}H_{38}N_7O_{10}$$[M+H]^+$, 572.2680; found 572.2681.

Example 35: Methyl 5-acetamido-9-(4-biphenyl-1H-1,2,3-triazol-1-yl))-4-[2,3-bis(tert-butoxycarbonyl)guanidino]-2,6-anhydro-4-[2,3-bis(tert-butoxycarbonyl)guanidino]-3,4,5-trideoxy-D-glycero-D-galacto-non-2-enonate (24)

Compound 23 (200 mg, 1 eq) and 4-ethynylbiphenyl (32 mg, 1.5 eq) were taken in to click-reaction as mentioned earlier to give the desired product. 180 mg (69%). $^1$H NMR (700 MHz, $CDCl_3$) δ 8.55, 8.06 (2×d, 2H, 2×NH), 7.94 (s, 1H, Triazole-H5), 7.81 (d, J=8.3 Hz, 2H, Ar—H), 7.57 (dd, J=13.1, 7.8 Hz, 4H, Ar—H), 7.39 (t, J=7.7 Hz, 2H, Ar—H), 7.31 (t, J=7.4 Hz, 1H, Ar—H), 5.75 (d, J=2.3 Hz, 1H, H-3), 5.51 (brs, 1H, OH), 5.16-5.10 (m, 1H, H-4), 4.90 (dd, J=14.0, 1.7 Hz, 1H, H-9), 4.54 (dd, J=14.0, 6.7 Hz, 1H, H-9'), 4.48-4.43 (m, 1H, H-8), 4.20 (d, J=10.4 Hz, 1H, H-6), 3.96 (td, J=10.4, 6.2 Hz, 1H, H-5), 3.69 (s, 3H, $COOCH_3$), 3.34 (d, J=9.0 Hz, 1H, H-7), 1.90 (s, 3H), 1.47, 1.43 (2×s, 2×9H, 2×$^t$Boc-$C(CH_3)_3$). $^{13}$C NMR (176 MHz, $CDCl_3$) δ 174.10 ($COCH_3$), 162.26, 162.03 ($^t$Boc-OCO), 157.37 (C-1), 152.66 (C═N), 146.98 (C-2), 146.26 (Triazole-C4), 121.69 (Triazole-C5), 140.63, 140.43, 129.41, 128.77, 127.37, 126.86, 125.99 (Ar—C), 107.54 (C-3), 84.22, 79.96 ($^t$Boc-$C(CH_3)_3$), 69.33 (C-6), 68.54 (C-4), 53.90 (C-9), 52.42 (C-8), 51.58 (C-7), 48.37 (C-5), 28.17, 27.99 ($^t$Boc-$C(CH_3)_3$), 22.86 ($COCH_3$). HR-MS (ESI) calcd. for $C_{37}H_{48}N_7O_{10}$$[M+H]^+$, 750.3463; found 750.3454.

Example 36: 5-Acetamido-9-(4-biphenyl-1H-1,2,3-triazol-1-yl))-4-guanidino-2,6-anhydro-4-[2,3-bis (tert-butoxycarbonyl)guanidino]-3,4,5-trideoxy-b-glycero-D-galacto-non-2-enonic acid (8b)

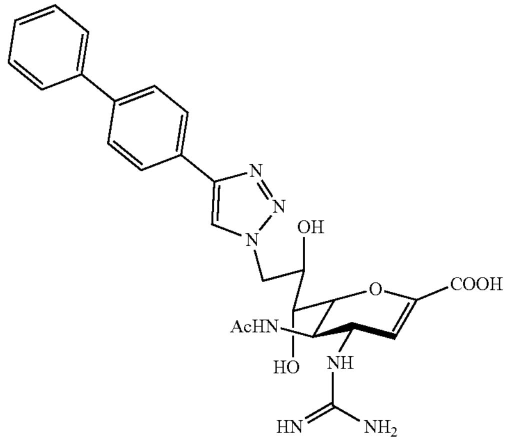

300 μl TFA was added to a solution of compound 24 (180 mg) in 3 ml DCM and the solution was then stirred at room temperature for about 2 hours. After completion, DCM and TFA were removed under reduced pressure. The residue was dissolved in 3 ml 0.1 N NaOH, and stirred at room temperature for 1 hour. After completion, Amberlite IR 120 ($H^+$) was added to neutralize the solution. The suspension was then filtered, and the filtrate was concentrated and purified by flash chromatography to give the desired product. 10 mg (31%). $^1$H NMR (500 MHz, $CD_3OD$) δ 8.34 (s, 1H, Triazole-H), 7.87 (d, J=8.1 Hz, 2H, Ar—H), 7.66 (d, J=8.1 Hz, 2H, Ar—H), 7.61 (d, J=7.5 Hz, 2H, Ar—H), 7.41 (t, J=7.6 Hz, 2H, Ar—H), 7.32 (t, J=7.3 Hz, 1H, Ar—H), 5.89 (s, 1H, H-3), 4.88 (d, J=14.3 Hz, 1H, H-9), 4.60-4.47 (m, 2H, H-9', H-6), 4.42 (d, J=10.0 Hz, 1H, H-4), 4.28 (m, 2H, H-5, H-8), 3.57 (d, J=9.0 Hz, 1H, H-7), 1.98 (s, 3H, $COCH_3$). $^{13}$C NMR (125 MHz, $CD_3OD$) δ 174.56, 165.08 (C═O), 158.96 (C═N), 148.25 (C-2), 146.68, 123.70 (Triazole-C), 142.30, 141.70, 130.71, 129.95, 128.58, 128.50, 127.85, 127.12 (Ar—C), 109.14 (C-3), 77.79 (C-6), 71.21 (C-8), 70.06 (C-7), 55.19 (C-9), 51.53 (C-4), 22.72 ($COCH_3$). HR-MS (ESI) calcd. for $C_{26}H_{28}N_7O_6$ $[M-H]^-$, 534.2101; found 534.2105.

Example 37: General Procedure for Synthesis of Compounds 25a-d

A solution of compound 19 (1 eq) and TEA (3 eq) in anhydrous DCM was cooled down to 0° C. and corresponding anhydrides or acyl chlorides (3 eq) was added in dropwise. The resulting mixture was warmed to room temperature and kept stirring overnight. After completion, the reaction was quenched with water and extracted with ethyl acetate. The organic layer was collected and washed with saturated $NaHCO_3$, brine sequentially and dried with $NaSO_4$. Solvents were removed under reduced pressure and the residue was separated by flash chromatography to give desired crude products. For hydrolysis of the C1-methyl ester, the product obtained above was dissolved in MeOH, and 0.5 M NaOH was added. The mixture was kept stirring at room temperature. After completion, the mixture was neutralized with Amberlite IR-120 ($H^+$), filtrated and purified by flash chromatography to provide the desired products with yields of 42%-68% (two steps).

Example 38: 5-Acetamido-2,6-anhydro-4-propionamido-3,4,5-trideoxy-D-glycero-D-galacto-non-2-enonic acid (25a)

(28 mg, 68%) $^1H$ NMR (500 MHz, $CD_3OD$) δ 5.49 (d, J=2.0 Hz, 1H, H-3), 4.75 (dd, J=9.7, 2.0 Hz, 1H, H-4), 4.20 (d, J=10.8 Hz, 1H, H-6), 4.10-4.06 (m, 1H, H-5), 3.86-3.85 (m, 1H, H-8), 3.79 (dd, J=11.4, 3.0 Hz, 1H, H-9), 3.63 (dd, J=11.4, 5.4 Hz, 1H, H-9'), 3.55 (d, J=9.0 Hz, 1H, H-7), 2.17 (q, J=7.6 Hz, 2H, (α-$CH_2$), 1.93 (s, 3H, $COCH_3$), 1.09 (t, J=7.6 Hz, 3H, μ-$CH_3$). $^{13}C$ NMR (125 MHz, $CD_3OD$) δ 177.40, 174.17 (C═O), 106.15 (C-3), 77.49 (C-6), 71.46 (C-8), 70.05 (C-7), 64.88 (C-9), 49.64 (C-5), 30.40 (α-$CH_2$), 22.78 ($COCH_3$), 10.59 (β-$CH_3$). HR-MS (ESI) calcd. for $C_{14}H_{21}N_2O_8$[M−H]$^-$, 345.1298; found 345.1302.

Example 39: 5-Acetamido-2,6-anhydro-4-pentanamido-3,4,5-trideoxy-D-glycero-D-galacto-non-2-enonic acid (25b)

(25 mg, 56%). $^1H$ NMR (500 MHz, $CD_3OD$) δ 5.47 (d, J=2.2 Hz, 1H, H-3), 4.76 (dd, J=9.8, 2.2 Hz, 1H, H-4), 4.19 (d, J=10.8 Hz, 1H, H-6), 4.09-4.05 (m, 1H, H-5), 3.87-3.85 (m, 1H, H-8), 3.78 (dd, J=11.5, 3.1 Hz, 1H, H-9), 3.66 (dd, J=11.5, 5.1 Hz, 1H, H-9'), 3.57 (t, J=7.8 Hz, 1H, H-7), 2.17 (t, J=7.5 Hz, 2H, α-$CH_2$), 1.94 (s, 3H, $COCH_3$), 1.60-1.51 (m, 2H, β-$CH_2$), 1.34-1.29 (m, 2H, γ-$CH_2$), 0.90 (t, J=7.4 Hz, 3H, δ—$CH_3$). $^{13}C$ NMR (125 MHz, $CD_3OD$) δ 176.55, 174.18, 170.01 (3×C═O), 151.02 (C-2), 105.96 (C-3), 77.51 (C-6), 71.55 (C-8), 69.91 (C-7), 64.71 (C-9), 49.60 (C-4), 49.00 (C-5), 37.02 (α-$CH_2$), 29.24 (β-$CH_2$), 23.31 (γ-$CH_2$), 23.31 ($COCH_3$), 14.19 (δ—$CH_3$). HR-MS (ESI) calcd. for $C_16H_{25}N_2O_8$[M−H]$^-$, 373.1611; found 373.1612.

Example 40: 5-Acetamido-2,6-anhydro-4-cyclopropanecarboxamido-3,4,5-trideoxy-b-glycero-D-galacto-non-2-enonic acid (25c)

(22 mg, 44%). $^1H$ NMR (500 MHz, $CD_3OD$) δ 5.54 (d, J=2.1 Hz, 1H, H-3), 4.77 (dd, J=9.8, 2.1 Hz, 1H, H-4), 4.20 (d, J=10.7 Hz, 1H, H-6), 4.11-4.07 (m, 1H, H-5), 3.90-3.82 (m, 1H, H-8), 3.79 (dd, J=11.4, 3.0 Hz, 1H, H-9), 3.66 (dd, J=11.4, 5.2 Hz, 1H, H-9'), 3.57 (d, J=9.0 Hz, 1H, H-7), 1.94 (s, 3H, $COCH_3$), 1.58-1.53 (m, 1H, α-CH), 0.88-0.78 (m, 2H, β-$CH_2$), 0.74-0.72 (m, 2H, β-$CH_2$). $^{13}C$ NMR (125 MHz, $CD_3OD$) δ 176.90, 174.36, 169.54 (3×C═O), 150.41 (C-2), 106.92 (C-3), 77.64 (C-6), 71.52 (C-8), 69.95 (C-7), 64.77 (C-9), 49.92 (C-4), 49.28 (C-5), 22.87 ($COCH_3$), 15.05 (α-CH), 7.57, 7.49 (2×β-$CH_2$). HR-MS (ESI) calcd. for $C_{15}H_{21}N_2O_8$ [M−H]$^-$, 357.1298; found 357.1305.

Example 41: 5-Acetamido-2,6-anhydro-4-cyclobutanecarboxamido-3,4,5-trideoxy-D-glycero-D-galacto-non-2-enonic acid (25d)

(19 mg, 42%). $^1H$ NMR (500 MHz, $CD_3OD$) δ 5.49 (d, J=2.2 Hz, 1H, H-3), 4.75 (dd, J=9.8, 2.2 Hz, 1H, H-4), 4.21 (d, J=10.8 Hz, 1H, H-6), 4.10-4.06 (m, 1H, H-5), 3.88-3.84 (m, m, 1H, H-8), 3.78 (dd, J=11.5, 3.1 Hz, 1H, H-9), 3.66 (dd, J=11.5, 5.2 Hz, 1H, H-9'), 3.56 (d, J=9.3 Hz, 1H, H-7), 3.09-3.02 (m, 1H, α-CH), 2.27-1.77 (m, 6H, 3×$CH_2$), 1.93 (s, 3H, $COCH_3$). $^{13}C$ NMR (125 MHz, $CD_3OD$) δ 178.06, 174.20, 169.63 (3×C═O), 150.52 (C-2), 106.54 (C-3), 77.53 (C-6), 71.55 (C-8), 69.94 (C-7), 64.77 (C-9), 49.57 (C-4), 49.14 (C-5), 40.90 (α-CH), 26.44, 26.02, 19.09 (3×$CH_2$), 22.88 ($COCH_3$). HR-MS (ESI) calcd. for $C_{16}H_{23}N_2O_8$ [M−H]$^-$, 371.1454; found 371.1458.

Example 42: General Procedure for Synthesis of C9-Amido Compounds

C9-azido DANA methyl ester was dissolved in THF-$H_2O$, and cooled down to 0° C. with ice water bath. Triphenyl phosphate was then added followed with activated carboxylic acids. The solution was allowed to warm to room temperature and kept stirring overnight. After completion, the reaction was quenched with water, concentrated and purified by flash chromatography to give the desired product. The product was then dissolved in MeOH, and 0.5 M NaOH was added (FIG. 19). The mixture was kept stirring at room temperature. After completion, the mixture was neutralized with Amberlite IR-120 ($H^+$ form), filtered and purified by flash chromatography to provide the desired products.

Example 43: 5-Acetamido-9-butyramido-2,6-anhydro-3,5-dideoxy-D-glycero-D-galacto-non-2-enonic acid (49)

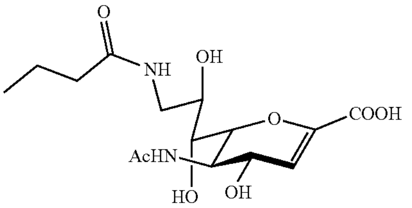

$^1H$ NMR (500 MHz, $CD_3OD$) δ 5.93 (d, J=2.5 Hz, 1H, H-3), 4.41 (dd, J=8.7, 2.5 Hz, 1H, H-4), 4.20-4.15 (m, 1H, H-6), 3.96 (dd, J=10.7, 8.7 Hz, 1H, H-5), 3.94-3.88 (m, 1H, H-8), 3.57 (dd, J=14.0, 3.3 Hz, 1H, H-9), 3.41 (dd, J=9.1, 1.1 Hz, 1H, H-7), 2.22-2.15 (m, 2H, α-$CH_2$), 2.00 (d, J=9.2 Hz, 3H, $COCH_3$), 1.62 (dd, J=14.8, 7.4 Hz, 2H, β-$CH_2$), 0.93 (t, J=7.4 Hz, 3H, γ-$CH_3$). $^{13}C$ NMR (126 MHz, $CD_3OD$) δ 177.13, 174.87 ((N—C═O)), 165.51 (C-1), 113.36 (C-3), 77.83 (C-6), 71.49 (C-7), 70.17 (C-4), 67.96 (C-8), 52.01 (C-5), 44.40 (C-9), 38.97 (C-α), 22.73 ($COCH_3$), 20.45 (C-β), 14.05 (C-γ).

Example 44: 5-Acetamido-9-pentanamido-2,6-anhydro-3,5-dideoxy-D-glycero-D-galacto-non-2-enonic acid (50)

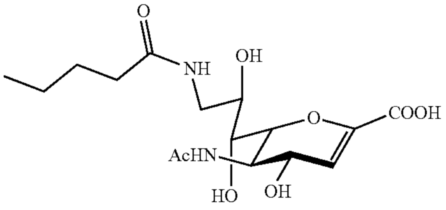

$^1$H NMR (500 MHz, $CD_3OD$) δ 5.93 (d, J=1.7 Hz, 1H, H-3), 4.43 (dd, J=8.6, 1.7 Hz, 1H, H-4), 4.18 (d, J=10.8 Hz, 1H, H-6), 4.02-3.95 (m, 1H, H-5), 3.95-3.87 (m, 1H, H-8), 3.59 (dd, J=13.9, 2.9 Hz, 1H, H-9), 3.43 (d, J=9.0 Hz, 1H, H-7), 3.32-3.27 (m, 1H, H-9'), 2.22 (t, J=7.6 Hz, 2H, α-$CH_2$), 2.03 (s, 3H, $COCH_3$), 1.64-1.54 (m, 2H, δ—$CH_2$), 1.35 (dd, J=15.0, 7.5 Hz, 2H, γ-$CH_2$), 0.92 (t, J=7.4 Hz, 3H, δ—$CH_2$). $^{13}$C NMR (126 MHz, $CD_3OD$) δ 177.26, 174.88 (N—C═O), 165.81 (C-1), 145.81 (C-2), 113.17 (C-3), 77.79 (C-6), 71.50 (C-7), 70.24 (C-4), 68.03 (C-8), 51.97 (C-5), 44.40 (C-9), 36.87 (C-α), 29.28 (C-6), 23.44 (γ), 22.86 ($COCH_3$), 14.22 (C-6). HRMS (ESI) calcd. for $C_{16}H_{25}N_2O_8$ $[M-H]^-$, 373.1616; found 373.1614.

Example 45: 5-Acetamido-9-hexanamido-2,6-anhydro-3,5-dideoxy-D-glycero-D-galacto-non-2-enonic acid (51)

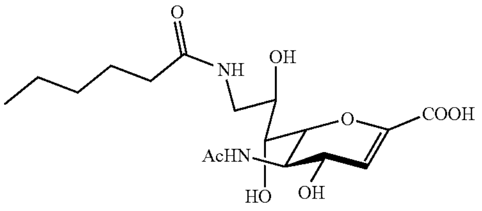

$^1$H NMR (500 MHz, $CD_3OD$) δ 5.92 (d, J=2.5 Hz, 1H, H-3), 4.42 (dd, J=8.7, 2.5 Hz, 1H, H-4), 4.17 (dd, J=10.7, 1.0 Hz, 1H, H-6), 3.97 (dd, J=10.7, 8.7 Hz, 1H, H-5), 3.94-3.88 (m, 1H, H-8), 3.59 (dd, J=13.9, 3.3 Hz, 1H, H-9), 3.42 (dd, J=9.0, 1.0 Hz, 1H, H-7), 3.31-3.27 (m, 1H, H-9'), 2.23-2.16 (m, 2H, α-$CH_2$), 2.01 (s, 3H, $COCH_3$), 1.59 (dt, J=15.0, 7.6 Hz, 2H, β-$CH_2$), 1.39-1.25 (m, 4H, γ-$CH_2$, δ—$CH_2$), 0.89 (t, J=7.1 Hz, 3H, ε-$CH_3$). $^{13}$C NMR (126 MHz, $CD_3OD$) δ 177.25, 174.87 (N—C═O), 165.63 (C-1), 113.30 (C-3), 77.82 (C-6), 71.55 (C-7), 70.24 (C-4), 67.98 (C-8), 51.97 (C-5), 44.41 (C-9), 37.09 (C-α), 32.58 (C-13), 26.81 (C-γ), 23.45 (C-6), 22.81 ($COCH_3$), 14.32 (C-ε). HRMS (ESI) calcd. for $C_{17}H_{27}N_2O_8[M-H]^-$, 387.1773; found 387.1766.

Example 46: 5-Acetamido-9-heptanamido-2,6-anhydro-3,5-dideoxy-D-glycero-D-galacto-non-2-enonic acid (52)

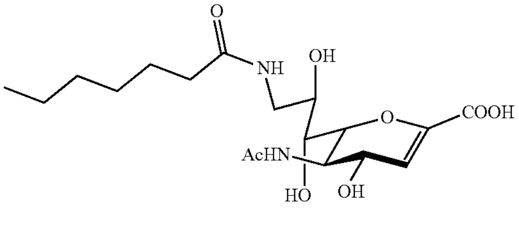

$^1$H NMR (500 MHz, $CD_3OD$) δ 5.77 (d, J=2.3 Hz, 1H, H-3), 4.37 (dd, J=8.6, 2.3 Hz, 1H, H-4), 4.16-4.08 (m, 1H, H-6), 3.97 (dd, J=10.7, 8.7 Hz, 1H, H-5), 3.89 (ddd, J=8.7, 7.1, 3.4 Hz, 1H, H-8), 3.58 (dd, J=13.8, 3.4 Hz, 1H, H-9), 3.40 (d, J=8.7 Hz, 1H, H-7), 3.28-3.23 (m, 1H, H-9'), 2.26-2.13 (m, 2H, α-$CH_2$), 2.01 (s, 3H, $COCH_3$), 1.64-1.52 (m, 2H, β-$CH_2$), 1.37-1.23 (m, 6H, γ-$CH_2$, δ—$CH_2$, ε-$CH_3$), 0.88 (dd, J=8.8, 5.1 Hz, 3H, —$CH_3$). $^{13}$C NMR (126 MHz, $CD_3OD$) δ 177.04, 174.70 (N—C═O), 110.32 (C-3), 77.35 (C-6), 71.50 (C-7), 70.44 (C-4), 68.36 (C-8), 51.99 (C-5), 44.23 (C-9), 37.15 (C-α), 32.73 (C-13), 30.07 (C-γ), 27.10 (C-6), 23.58 (C-ε), 22.80 (C-4), 14.39 ($COCH_3$). HRMS (ESI) calcd. for $C_{18}H_{29}N_2O_8[M-H]^-$, 401.1929; found 401.1931.

Example 47: 5-Acetamido-9-isobutyramido-2,6-anhydro-3,5-dideoxy-D-glycero-D-galacto-non-2-enonic acid (53)

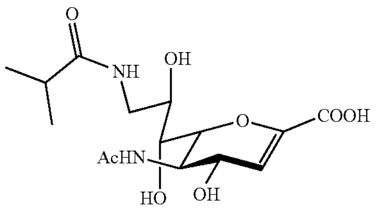

$^1$H NMR (700 MHz, $CD_3OD$) δ 5.74 (d, J=2.3 Hz, 1H, H-3), 4.37 (dd, J=8.7, 2.3 Hz, 1H, H-4), 4.14 (dd, J=10.8, 1.0 Hz, 1H, H-6), 3.99 (dd, J=10.8, 8.7 Hz, 1H, H-5), 3.91 (ddd, J=9.1, 6.9, 3.4 Hz, 1H, H-8), 3.58 (dd, J=13.8, 3.4 Hz, 1H, H-9), 3.40 (dd, J=9.1, 1.0 Hz, 1H, H-7), 3.33 (dd, J=13.8, 6.9 Hz, 1H, H-9'), 2.49 (dt, J=13.8, 6.9 Hz, 1H, α-$CH_2$), 2.02 (s, 3H, $COCH_3$), 1.12 (dd, J=6.9, 0.5 Hz, 6H, 2×p-$CH_3$). $^{13}$C NMR (176 MHz, $CD_3OD$) δ 180.76, 174.56 (N—C═O), 109.51 (C-3), 77.30 (C-6), 71.67 (C-7), 70.20 (C-4), 68.50 (C-8), 52.07 (C-5), 44.23 (C-9), 36.28 (C-α), 22.73, 19.96, 19.90 (2×C-β, $COCH_3$). HRMS (ESI) calcd. for $C_{15}H_{23}N_2O_8[M-H]^-$, 359.1460; found 359.1458.

Example 48: 5-Acetamido-9-(3-methylbutanamido)-2,6-anhydro-3,5-dideoxy-D-glycero-D-galacto-non-2-enonic acid (54)

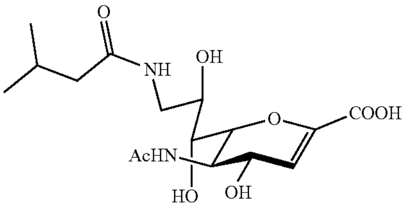

$^1$H NMR (700 MHz, $CD_3OD$) δ 5.74 (d, J=2.3 Hz, 1H, H-3), 4.37 (dd, J=8.7, 2.3 Hz, 1H, H-4), 4.13 (dd, J=10.8, 1.0 Hz, 1H, H-6), 3.99 (dd, J=10.8, 8.7 Hz, 1H, –5), 3.91 (ddd, J=9.0, 6.9, 3.4 Hz, 1H, H-8), 3.60 (dd, J=13.8, 3.4 Hz, 1H, H-9), 3.43-3.39 (dd, J=13.8, 6.9 Hz, 1H, H-9'), 3.33 (m, 1H, H-7), 2.10-2.09 (m, 2H, α-$CH_2$), 2.08-2.03 (m, 1H, β-CH), 2.02 (s, 3H, $COCH_3$), 0.96 (dd, J=6.4, 1.6 Hz, 6H, 2×γ-$CH_3$). $^{13}$C NMR (176 MHz, $CD_3OD$) δ 176.27, 174.60 (N—C═O), 109.43 (C-3), 77.30 (C-6), 71.71 (C-7), 70.26 (C-4), 68.51 (C-8), 52.08 (C-5), 46.32 (C-9), 44.18 (C-α), 27.42 (C-β), 22.77, 22.75, 22.74 (2 λC-γ, $COCH_3$). HRMS (ESI) calcd. for $C_{16}H_{25}N_2O_8$ $[M-H]^-$, 373.1616; found 373.1617.

Example 49: 5-Acetamido-9-(4-methylpentanamido)-2,6-anhydro-3,5-dideoxy-D-glycero-D-galacto-non-2-enonic acid (55)

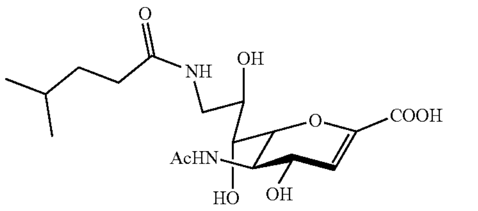

$^1$H NMR (500 MHz, $CD_3OD$) δ 5.69 (d, J=2.3 Hz, 1H, H-3), 4.36 (dd, J=8.7, 2.3 Hz, 1H, H-4), 4.10 (dd, J=10.8, 0.8 Hz, 1H, H-6), 3.97 (dd, J=10.8, 8.7 Hz, 1H, H-5), 3.92-3.85 (m, 1H, H-8), 3.58 (dd, J=13.8, 3.3 Hz, 1H, H-9), 3.38 (dd, J=8.9, 0.8 Hz, 1H, H-7), 3.28-3.21 (m, 1H, H-9'), 2.25-2.18 (m, 2H, α-$CH_2$), 2.01 (s, 3H, $COCH_3$), 1.60-1.44 (m, 3H, β-$CH_2$, γ-CH), 0.90 (d, J=6.5 Hz, 6H, 2×6-$CH_3$). $^{13}$C NMR (126 MHz, $CD_3OD$) δ 177.19, 174.68 (N—C═O), 108.93 (C-3), 77.12 (C-6), 71.55 (C-7), 70.35 (C-4), 68.59 (C-8), 52.00 (C-5), 44.22 (C-9), 36.12 (C-α), 35.23 (C-β), 29.04 (C-γ), 22.86, 22.74 (2×C-6, $COCH_3$). HRMS (ESI) calcd. for $C_{17}H_{27}N_2O_8$ $[M-H]^-$, 387.1773; found 387.1765.

Example 50: 5-Acetamido-9-benzamido-2,6-anhydro-3,5-dideoxy-D-glycero-D-galacto-non-2-enonic acid (56)

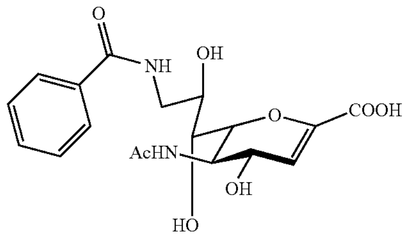

$^1$H NMR (500 MHz, $CD_3OD$) δ 7.85-7.79 (m, 2H, Ar—H), 7.54-7.48 (m, 1H, Ar—H), 7.43 (dd, J=10.3, 4.7 Hz, 2H, Ar—H), 5.84 (d, J=2.3 Hz, 1H, H-3), 4.40 (dd, J=8.7, 2.3 Hz, 1H, H-4), 4.18 (d, J=10.8 Hz, 1H, H-6), 4.07-3.96 (m, 2H, H-8, H-5), 3.77 (dd, J=13.8, 3.4 Hz, 1H, H-9), 3.55 (dd, J=13.8, 6.8 Hz, 1H, H-9'), 3.48 (d, J=8.9 Hz, 1H, H-7), 1.96 (s, 3H, $COCH_3$). $^{13}$C NMR (126 MHz, $CD_3OD$) δ 174.79, 170.91 (N—C═O), 135.63, 132.71, 129.57, 128.36 (Ar—C), 111.64 (C-3), 77.53 (C-6), 71.60 (C-7), 70.35 (C-4), 68.20 (C-8), 51.92 (C-5), 45.02 (C-9), 22.74 ($COCH_3$). HRMS (ESI) calcd. for $C_{18}H_{21}N_2O_8$$[M-H]^-$, 393.1303; found 393.13.

Example 51: General Procedure for Synthesis of C5-Amido Compounds

Figure 20:
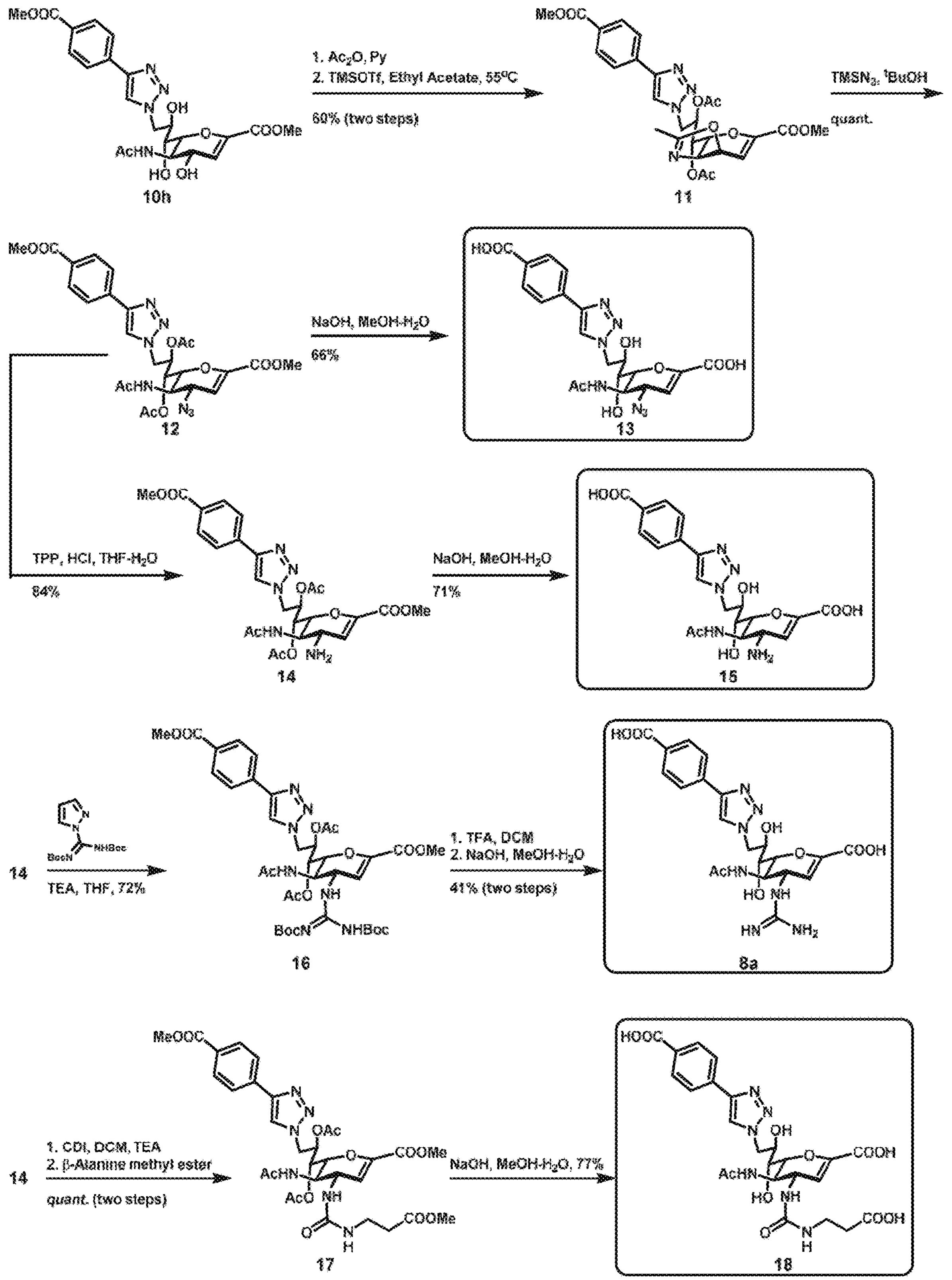
FIG. 20: Presents the synthetic route for compounds 8a, 13, 15, 18.

Compound I-25 was dissolved in anhydrous DCM and TEA was added. The mixture was then cooled down to 0° C. and activated carboxylic acids was added in dropwise. The solution was allowed to warm to room temperature and kept stirring overnight. After completion, the reaction was quenched with water, concentrated and purified by flash chromatography to give the desired product. The product was then dissolved in MeOH, and 0.5 M NaOH was added (FIG. 20). The mixture was kept stirring at room temperature. After completion, the mixture was neutralized with Amberlite IR-120 ($H^+$ form), filtered and purified by flash chromatography to provide the desired products.

Figure 21:
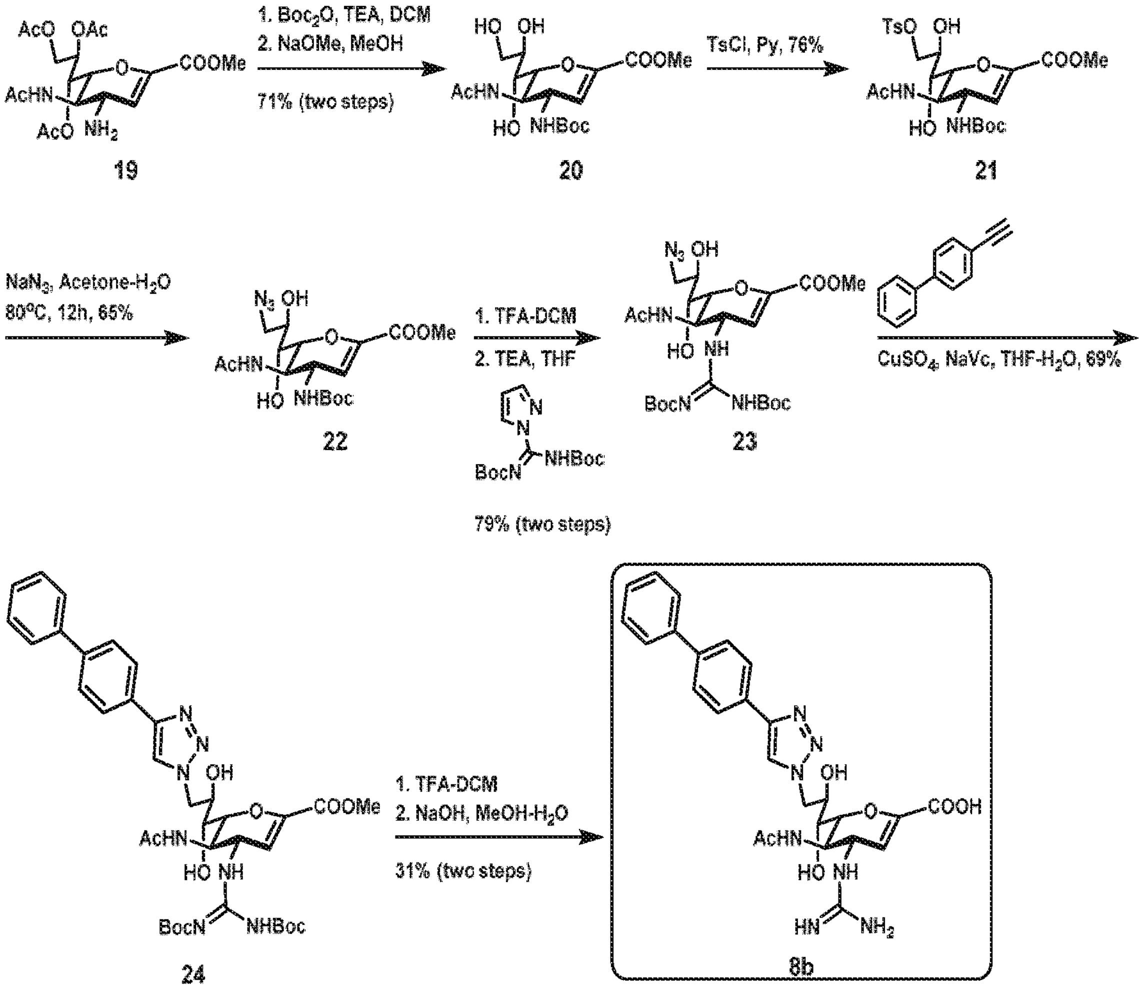
FIG. 21: Presents the synthetic route for compound 8b.

To synthesize compounds 40-48, fully protected 40 was taken to CuAAC as described before with alkynes to give desired product, which was then hydrolyzed using NaOH to give desired final products for enzymatic assay (FIG. 21).

Example 52: 5-Propionamido-2,6-anhydro-3,5-dideoxy-D-glycero-D-galacto-non-2-enonic acid (29)

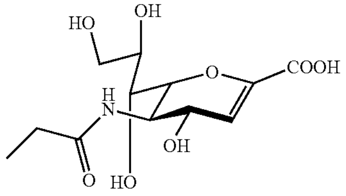

$^1$H NMR (500 MHz, $CD_3OD$) δ 5.90 (d, J=2.4 Hz, 1H, H-3), 4.43 (dd, J=8.7, 2.4 Hz, 1H, H-4), 4.15 (dd, J=10.8, 0.9 Hz, 1H, H-6), 4.01-3.95 (m, 1H, H-5), 3.91-3.86 (m, 1H, H-8), 3.81 (dd, J=11.4, 3.0 Hz, 1H, H-9), 3.65 (dd, J=11.4, 5.4 Hz, 1H, H-9'), 3.55 (dd, J=9.2, 0.9 Hz, 1H, H-7), 2.31 (q, J=7.6 Hz, 2H, $CH_2$), 1.15 (t, J=7.6 Hz, 3H, $CH_3$). $^{13}$C NMR (126 MHz, $CD_3OD$) δ 178.80 (N—C═O), 166.46 (C-1), 112.52 (C-3), 77.98 (C-6), 71.17 (C-8), 70.17 (C-7), 68.10 (C-4), 64.93 (C-9), 51.80 (C-5), 30.20 (C-α), 10.33 (C-β). HRMS (ESI) calcd. for $C_{12}H_{18}NO_8$ $[M-H]^-$, 304.1032; found 304.1039.

Example 53: 5-Butyramido-2,6-anhydro-3,5-dideoxy-n-glycero-n-galacto-non-2-enonic acid (30)

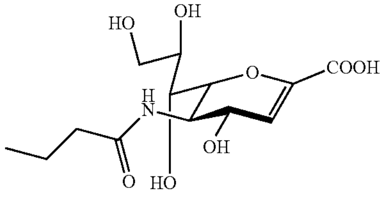

$^1$H NMR (500 MHz, $CD_3OD$) δ 5.89 (d, J=2.4 Hz, 1H, H-3), 4.42 (dd, J=8.7, 2.4 Hz, 1H, H-4), 4.15 (d, J=10.8 Hz, 1H, H-6), 3.99 (dd, J=10.8, 8.7 Hz, 1H, H-5), 3.89 (ddd, J=9.0, 5.3, 3.0 Hz, 1H, H-8), 3.81 (dd, J=11.4, 3.0 Hz, 1H, H-9), 3.63 (dd, J=11.4, 5.3 Hz, 1H, H-9'), 3.56 (d, J=9.0 Hz, 1H, H-7), 2.29-2.23 (m, 2H, $CH_2$), 1.66 (dt, J=13.4, 7.0 Hz, 2H, $CH_2$), 0.97 (t, J=7.0 Hz, 3H, $CH_3$). $^{13}$C NMR (126 MHz, $CD_3OD$) δ 177.98 (N—C═O), 166.50 (C-1), 112.47 (C-3), 78.00 (C-6), 71.17 (C-7), 70.26 (C-4), 68.09 (C-8), 64.99 (C-9), 51.85 (C-5), 39.04 (C-α), 20.31 (C-β), 14.11 (C-γ). HRMS (ESI) calcd. for $C_{13}H_{20}NO_8$ $[M-H]^-$, 318.1189; found 318.1196.

Example 54: 5-Pentanamido-9-(4-biphenyl)-2,6-anhydro-3,5-dideoxy-D-glycero-D-galacto-non-2-enonic acid (31)

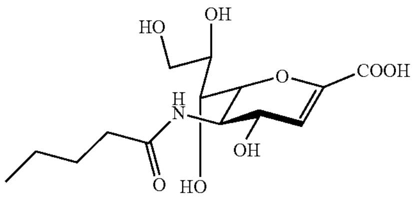

$^1$H NMR (500 MHz, $CD_3OD$) δ 5.88 (d, J=2.1 Hz, 1H, H-3), 4.44 (dd, J=8.8, 2.1 Hz, 1H, H-4), 4.15 (d, J=10.8 Hz, 1H, H-6), 3.99 (dd, J=10.8, 8.8 Hz, 1H, H-5), 3.89 (m, 1H, H-8), 3.81 (dd, J=11.4, 2.9 Hz, 1H, H-9), 3.64 (dd, J=11.4, 5.3 Hz, 1H, H-9'), 3.57 (d, J=9.0 Hz, 1H, H-7), 2.29 (t, J=7.6 Hz, 2H, α-$CH_2$), 1.62 (m, 2H, β-$CH_2$), 1.37 (dq, J=14.8, 7.4 Hz, 2H, γ-$CH_2$), 0.93 (t, J=7.4 Hz, 3H, $CH_3$). $^{13}$C NMR (126 MHz, $CD_3OD$) δ 178.13 (N—C═O), 166.89 (C-1), 146.72 (C-2), 112.33 (C-3), 77.91 (C-6), 71.30 (C-7), 70.18 (C-4), 68.09 (C-8), 64.90 (C-9), 51.76 (C-5), 36.92 (C-α), 29.08 (C-β), 23.46 (C-γ), 14.21 (C-6). HRMS (ESI) calcd. for $C_{14}H_{22}NO_8$ [M−H]$^-$, 332.1345; found 332.1348.

Example 55: 5-Hexanamido-2,6-anhydro-3,5-dideoxy-D-glycero-D-galacto-non-2-enonic acid (32)

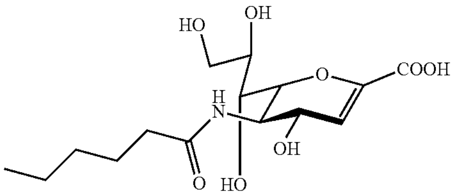

$^1$H NMR (700 MHz, $CD_3OD$) δ 5.95 (d, J=2.3 Hz, 1H, H-3), 4.43 (dd, J=8.7, 2.3 Hz, 1H, H-4), 4.16 (dd, J=10.8, 0.8 Hz, 1H, H-6), 3.99 (dd, J=10.8, 8.7 Hz, 1H, H-5), 3.91 (brs, 1H, H-8), 3.83 (dd, J=11.4, 2.9 Hz, 1H, H-9), 3.63 (dd, J=11.4, 5.5 Hz, 1H, H-9'), 3.56 (dd, J=9.3, 0.7 Hz, 1H, H-7), 2.29 (t, J=7.5 Hz, 2H, α-$CH_2$), 1.69-1.62 (m, 2H, p-$CH_2$), 1.35 (m, 2×2H, γ-$CH_2$, δ—$CH_2$), 0.93 (t, J=7.0 Hz, 3H, $CH_3$). $^{13}$C NMR (176 MHz, $CD_3OD$) δ 178.20 (N—C═O), 113.34 (C-3), 78.14 (C-6), 71.06 (C-7), 70.27 (C-4), 67.95 (C-8), 65.03 (C-9), 51.81 (C-5), 37.06 (C-α), 32.56 (C-0), 26.59 (C-γ), 23.44 (C-6), 14.27 (C-ε). HRMS (ESI) calcd. for $C_{15}H_{25}NO_8$ [M−H]$^-$, 346.1507; found 346.1506.

Example 56: 5-Heptanamido-2,6-anhydro-3,5-dideoxy-D-glycero-D-galacto-non-2-enonic acid (33)

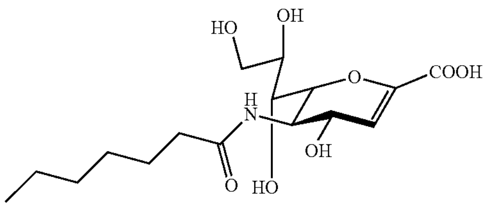

$^1$H NMR (500 MHz, $CD_3OD$) δ 5.93 (d, J=2.1 Hz, 1H, H-3), 4.40 (dd, J=8.7, 2.1 Hz, 1H, H-4), 4.13 (d, J=10.8 Hz, 1H, H-6), 3.98 (dd, J=10.8, 8.7 Hz, 1H, H-5), 3.89 (brs, 1H, H-8), 3.81 (dd, J=11.4, 2.7 Hz, 1H, H-9), 3.61 (dd, J=11.4, 5.5 Hz, 1H, H-9'), 3.53 (d, J=8.8 Hz, 1H, H-7), 2.27 (t, J=7.5 Hz, 2H, α-$CH_2$), 1.69-1.55 (m, 2H, β-$CH_2$), 1.42-1.16 (m, 3×2H, γ-$CH_2$, δ—$CH_2$, ε-$CH_2$), 0.89 (t, J=7.0 Hz, 3H). $^{13}$C NMR (126 MHz, $CD_3OD$) δ 178.23 (N—C═O), 113.38 (C-3), 78.18 (C-6), 71.07 (C-7), 70.32 (C-4), 67.98 (C-8), 65.06 (C-9), 51.84 (C-5), 37.12 (C-α), 32.72 (C-β), 30.06 (C-γ), 26.89 (C-6), 23.58 (C-ε), 14.40 (C-Q. HRMS (ESI) calcd. for $C_{16}H_{26}NO^8$ [M−H]$^-$, 360.1664; found 360.1665.

Example 57: 5-isobutyramido-2,6-anhydro-3,5-dideoxy-D-glycero-D-galacto-non-2-enonic acid (34)

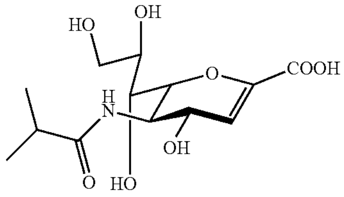

$^1$H NMR (500 MHz, $CD_3OD$) δ 5.93 (d, J=2.5 Hz, 1H, H-3), 4.43 (dd, J=8.7, 2.5 Hz, 1H, H-4), 4.15 (dd, J=10.8, 1.1 Hz, 1H, H-6), 3.95 (dd, J=10.8, 8.7 Hz, 1H, H-5), 3.88 (s, 1H, H-8), 3.80 (dd, J=11.4, 2.9 Hz, 1H, H-9), 3.62 (dd, J=11.4, 5.4 Hz, 1H, H-9'), 3.52 (dd, J=9.2, 1.1 Hz, 1H, H-7), 2.57-2.46 (m, 1H, α-CH), 1.14 (dd, J=6.9, 2.4 Hz, 6H, 2×13-$CH_3$). $^{13}$C NMR (126 MHz, $CD_3OD$) δ 182.10 (N—C═O), 165.49 (C-1), 113.48 (C-3), 78.20 (C-6), 71.05 (C-7), 70.21 (C-4), 67.89 (C-8), 64.98 (C-9), 51.68 (C-5), 36.41 (C-α), 20.10, 19.70 (2×C-13). HRMS (ESI) calcd. for $C_{13}H_{21}NO_8$ [M−H]$^-$, 318.1194; found 318.1193.

Example 58: 5-(3-methylbutanamido)-2,6-anhydro-3,5-dideoxy-D-glycero-D-galacto-non-2-enonic acid (35)

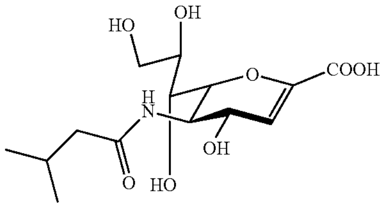

$^1$H NMR (500 MHz, $CD_3OD$) δ 5.93 (d, J=2.5 Hz, 1H, H-3), 4.40 (dd, J=8.7, 2.5 Hz, 1H, H-4), 4.14 (dd, J=10.8, 1.1 Hz, 1H, H-6), 3.98 (dd, J=10.8, 8.7 Hz, 1H, H-5), 3.89 (s, 1H, H-8), 3.80 (dd, J=11.4, 2.9 Hz, 1H, H-9), 3.61 (dd, J=11.4, 5.5 Hz, 1H, H-9'), 3.57 (dd, J=9.3, 1.1 Hz, 1H, H-7), 2.17-2.04 (m, 3H, α-$CH_2$, β-$CH_2$), 0.96 (dd, J=6.5, 3.8 Hz, 6H, 2×γ-$CH_3$). $^{13}$C NMR (126 MHz, $CD_3OD$) δ 177.53 (N—C═O), 113.50 (C-3), 78.18 (C-6), 71.05 (C-7), 70.34 (C-4), 67.95 (C-8), 65.04 (C-9), 51.87 (C-5), 46.33 (C-α), 27.43 (C-β), 22.89, 22.83 (2×C-γ). HRMS (ESI) calcd. for $C_{14}H_{22}NO_8$ [M−H]$^-$, 332.1351; found 333.1348.

Example 59: 5-(4-Methylpentanamido)-2,6-anhydro-3,5-dideoxy-D-glycero-D-galacto-non-2-enonic acid (36)

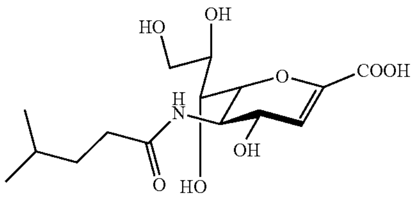

$^1$H NMR (500 MHz, $CD_3OD$) δ 5.93 (d, J=2.3 Hz, 1H, H-3), 4.42 (dd, J=8.7, 2.3 Hz, 1H, H-4), 4.14 (d, J=10.8 Hz, 1H, H-6), 3.96 (dd, J=10.8, 8.8 Hz, 1H, H-5), 3.89 (s, 1H, H-8), 3.81 (dd, J=11.4, 2.8 Hz, 1H, H-9), 3.62 (dd, J=11.4, 5.4 Hz, 1H, H-9'), 3.54 (d, J=8.7 Hz, 1H, H-7), 2.32-2.25 (m, 2H, α-$CH_2$), 1.62-1.47 (m, 3H, β-$CH_2$, γ-CH), 0.91 (dd, J=6.4, 1.1 Hz, 6H, 2×δ—$CH_3$). $^{13}$C NMR (126 MHz, $CD_3OD$) δ 178.46 (N—C═O), 113.46 (C-3), 78.14 (C-6), 71.07 (C-7), 70.22 (C-4), 67.97 (C-8), 64.99 (C-9), 51.81 (C-5), 35.86 (C-α), 35.19 (C-0), 29.00 (C-γ), 22.75, 22.67 (2× C-δ). HRMS (ESI) calcd. for $C_{15}H_{24}NO_8$ $[M-H]^-$, 346.1507; found 346.1496.

Example 60: 5-Cyclopropanecarboxamido-2,6-anhydro-3,5-dideoxy-D-glycero-D-galacto-non-2-enonic acid (37)

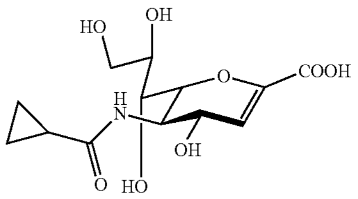

$^1$H NMR (500 MHz, $CD_3OD$) δ 8.26 (d, J=8.4 Hz, 1H, NH), 5.88 (d, J=1.5 Hz, 1H, H-3), 4.47 (d, J=8.7 Hz, 1H, H-4), 4.16 (d, J=10.8 Hz, 1H, H-6), 4.01 (m, 1H, H-5), 3.93-3.85 (m, 1H, H-8), 3.80 (dd, J=11.4, 2.6 Hz, 1H, H-9), 3.69-3.62 (m, 1H, H-9), 3.56 (d, J=9.0 Hz, 1H, H-7), 1.69-1.66 (m, 1H, CH), 0.92-0.88 (m, 2H, $CH_2$), 0.81-0.78 (m, 5 2H, $CH_2$). $^{13}$C NMR (126 MHz, $CD_3OD$) δ 178.35 (N—C═O), 166.87 (C-1), 112.31 (C-3), 78.06 (C-6), 71.28 (C-7), 70.10 (C-4), 68.19 (C-8), 64.84 (C-9), 51.96 (C-5), 15.10 (C-α), 8.10 (C-β), 7.75 (C-β'). HRMS (ESI) calcd. for $C_{13}H_{18}NO_8$ $[M-H]^-$, 316.1032; found 316.1030.

Example 61: 5-Cyclobutanecarboxamido-2,6-anhydro-3,5-dideoxy-D-glycero-D-galacto-non-2-enonic acid (38)

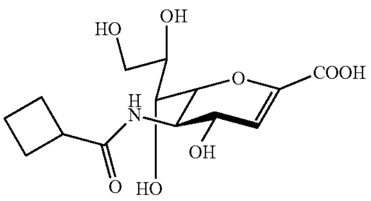

$^1$H NMR (500 MHz, $CD_3OD$) δ 5.89 (d, J=1.7 Hz, 1H, H-3), 4.44 (dd, J=8.9, 1.7 Hz, 1H, H-4), 4.15 (d, J=10.6 Hz, 1H, H-6), 3.99 (dd, J=10.6, 8.9 Hz, 1H, H-5), 3.88 (m, 1H, H-8), 3.80 (dd, J=11.4, 2.7 Hz, 1H, H-9), 3.65 (dd, J=11.4, 5.2 Hz, 1H, H-9'), 3.53 (d, J=9.0 Hz, 1H, H-7), 3.19 (p, J=8.5 Hz, 1H, CH), 2.30-2.22 (m, 2H, $CH_2$), 2.20-2.10 (m, 2H, $CH_2$), 1.89-1.82 (m, 2H, $CH_2$). $^{13}$C NMR (126 MHz, $CD_3OD$) δ 179.57 (N—C═O), 166.68 (C-1), 112.52 (C-3), 77.96 (C-6), 71.26 (C-7), 70.10 (C-4), 68.04 (C-8), 64.87 (C-9), 51.69 (C-5), 40.83 (C-α), 26.42 (C-6), 26.09 (C-t3'), 19.08 (C-γ). HRMS (ESI) calcd. for $C_{14}H_{20}NO_8$ $[M-H]^-$, 330.1189; found 330.1195.

Example 62: 5-Benzamido-2,6-anhydro-3,5-dideoxy-D-glycero-D-galacto-non-2-enonic acid (39)

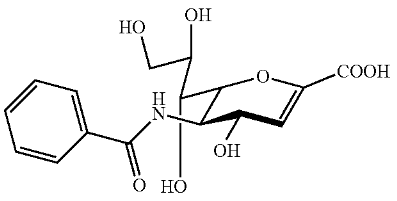

$^1$H NMR (500 MHz, $CD_3OD$) δ 7.88 (dd, J=8.3, 1.2 Hz, 2H, Ar—H), 7.57-7.50 (m, 1H, Ar—H), 7.49-7.41 (m, 2H, Ar—H), 5.98 (d, J=2.3 Hz, 1H, H-3), 4.64 (dd, J=8.7, 2.3 Hz, 1H, H-4), 4.32 (d, J=11.0 Hz, 1H, H-6), 4.24 (dd, J=11.0, 8.7 Hz, 1H, H-5), 3.92 (s, 1H, H-8), 3.80 (dd, J=11.5, 2.8 Hz, 1H, H-9), 3.68-3.59 (m, 2H, H-9', H-7). $^{13}$C NMR (126 MHz, $CD_3OD$) δ 171.74 (N—C═O), 135.08, 133.05, 129.55, 128.67 (Ar—C), 113.62 (C-3), 78.17 (C-6), 71.16 (C-7), 70.17 (C-4), 68.06 (C-8), 64.86 (C-9), 52.47 (C-5). HRMS (ESI) calcd. for $C_{1}6H_{1}8NO^{8}$ $[M-H]^-$, 352.1038; found 352.1035.

Example 63: 5-(N-2-azidoacetyl)-2, 3, 5-trideoxy-D-glycero-D-galacto-2-nonulopyranosonic acid (40)

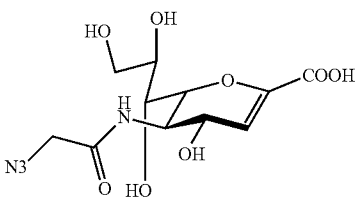

$^1$H NMR (500 MHz, $CD_3OD$) δ 5.86 (d, J=1.5 Hz, 1H, H-3), 4.46 (dd, J=8.7, 1.5 Hz, 1H, H-4), 4.24 (d, J=10.8 Hz, 1H, H-6), 4.07 (dd, J=10.8, 8.7 Hz, 1H, H-5), 3.97 (q, J=16.1 Hz, 2H, N—$CH_2$—CO), 3.88 (br, 1H, H-8), 3.81 (dd, J=11.4, 2.6 Hz, 1H, H-9), 3.66 (dd, J=11.4, 5.2 Hz, 1H, H-9'), 3.57 (d, J=9.0 Hz, 1H, H-7). $^{13}$C NMR (126 MHz, $CD_3OD$) δ 171.55 (C═O), 111.68 (C-3), 77.43 (C-6), 71.41 (C-8), 70.04 (C-7), 68.23 (C-4), 64.86 (C-9), 53.01 ($CH_2N_3$), 51.93 (C-5). HRMS (ESI) calcd. for $C_{11}H_{15}N_4O_8$ $[M-H]^-$, 331.0890; found 331.0894.

Example 64: 5-(2-(4-(4-(trifluoromethyl)phenyl)-1H-1,2,3-triazol-1-yl)acetamido))-2, 3, 5-trideoxy-D-glycero-D-galacto-2-nonulopyranosonic acid (41)

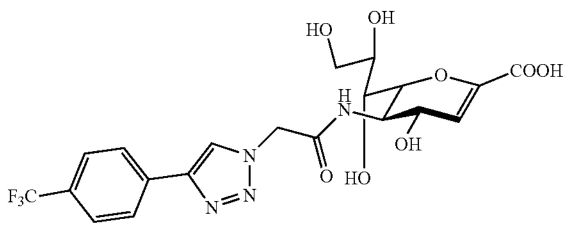

$^1$H NMR (500 MHz, $CD_3OD$) δ 8.47 (s, 1H, N—CH═C), 7.97 (d, J=8.1 Hz, 2H, Ar—H), 7.68 (d, J=8.3 Hz, 2H, Ar—H), 5.76 (s, 1H, H-3), 5.32 (s, 2H, N—$CH_2$—CO), 4.47 (dd, J=8.6, 1.5 Hz, 1H, H-4), 4.27 (d, J=10.8 Hz, 1H, H-6), 4.12 (dd, J=10.8, 8.6 Hz, 1H, H-5), 3.89 (br, 1H, H-8), 3.84-3.76 (m, 1H, H-9), 3.69 (dd, J=11.4, 5.1 Hz, 1H, H-9'), 3.64 (d, J=8.9 Hz, 1H, H-7). $^{13}$C NMR (126 MHz, $CD_3OD$) δ 168.79 (C═O), 147.36, 125.07 (Triazole-C), 135.56 (Ar—C), 130.94 (q, J=32.3 Hz, Ar—C), 127.05 (Ar—C), 127.87 (q, J=3.7 Hz, Ar—C), 109.19 (C-3), 76.99 (C-6), 71.60 (C-8), 70.06 (C-7), 68.68 (C-4), 64.80 (9), 53.36 ($CH_2N_3$), 52.24 (C-5). HRMS (ESI) calcd. for $C_{20}H_{20}F_3N_4O_8$ [M−H]$^-$, 501.1233; found 501.1243.

Example 65: 5-(2-(4-(4-p-tolyl)-1H-1,2,3-triazol-1-yl) acetamido))-2, 3, 5-trideoxy-D-glycero-D-galacto-2-nonulopyranosonic acid (42)

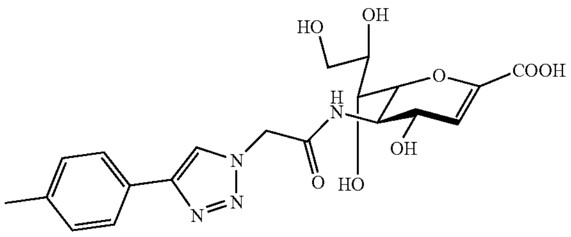

$^1$H NMR (500 MHz, $CD_3OD$) δ 8.31 (s, 1H, NC═CH), 7.70 (d, J=8.1 Hz, 2H, Ar—H), 7.24 (d, J=8.0 Hz, 2H), 5.87 (d, J=2.2 Hz, 1H, H-3), 5.29 (s, 2H, N—$CH_2$—CO), 4.49 (dd, J=8.7, 2.2 Hz, 1H, H-4), 4.29 (d, J=10.8 Hz, 1H, H-6), 4.10 (dd, J=10.7, 8.7 Hz, 1H, H-5), 3.91-3.84 (m, 1H, H-8), 3.81 (dd, J=11.4, 2.9 Hz, 1H, H-9), 3.67 (dd, J=11.4, 5.3 Hz, 1H, H-9'), 3.64 (d, J=9.1 Hz, 1H, H-7), 2.35 (s, 3H, $PhCH_3$). $^{13}$C NMR (126 MHz, $CD_3OD$) δ 168.97 (C═O), 167.13 (C-1), 148.95, 123.68 (Triazole-C), 146.97 (C-2), 139.45, 130.64, 128.89, 126.71 (Ar—C), 111.62 (C-3), 77.42 (C-6), 71.51 (C-8), 70.06 (C-7), 68.30 (C-4), 64.86 (C-9), 53.29 ($CH_2N_3$), 52.18 (C-5), 21.37 ($PhCH_3$). HRMS (ESI) calcd. for $C_{20}H_{23}N_4O_8$[M−H]$^-$, 447.1516; found 447.1520.

Example 66: 5-(2-(4-(4-carboxyphenyl)-1H-1,2,3-triazol-1-yl) acetamido))-2, 3, 5-trideoxy-D-glycero-D-galacto-2-nonulopyranosonic acid (43)

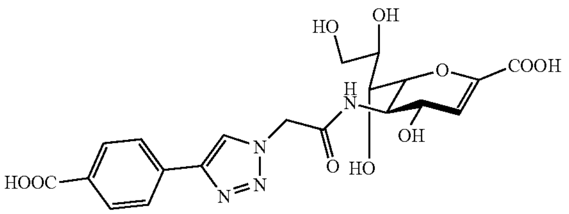

$^1$H NMR (500 MHz, $CD_3OD$) δ 8.48 (s, 1H, C═CH—N), 8.10-8.04 (m, 2H, Ar—H), 7.95-7.90 (m, 2H, Ar—H), 5.88 (d, J=2.4 Hz, 1H, H-3), 5.32 (s, 2H, N—$CH_2$—CO), 4.49 (dd, J=8.7, 2.4 Hz, 1H, H-4), 4.30 (dd, J=10.8, 0.6 Hz, 1H, H-6), 4.11 (dd, J=10.8, 8.7 Hz, 1H, H-5), 3.91-3.86 (m, 1H, H-8), 3.82 (dd, J=11.4, 3.0 Hz, 1H, H-9), 3.68 (dd, J=11.5, 5.4 Hz, 1H, H-9'), 3.64 (dd, J=9.2, 0.6 Hz, 1H, H-7). $^{13}$C NMR (126 MHz, DMSO-$d_6$) δ 169.44, 168.85 (C═O), 167.00 (C-1), 147.83, 125.04 (Triazole-C), 146.85 (C-2), 136.10, 131.60, 131.48, 126.53 (Ar—C), 111.73 (C-3), 77.44 (C-6), 71.45 (C-8), 70.09 (C-7), 68.32 (C-4), 64.88 (C-9), 53.32 ($CH_2N_3$), 52.21 (C-5). HRMS (ESI) calcd. for $C_{20}H_{21}N_4O_{10}$ [M−H]$^-$, 477.1258; found 477.1268.

Example 67: 5-(2-(4-(4-methoxyphenyl)-1H-1,2,3-triazol-1-yl)acetamido))-2, 3, 5-trideoxy-D-glycero-D-galacto-2-nonulopyranosonic acid (44)

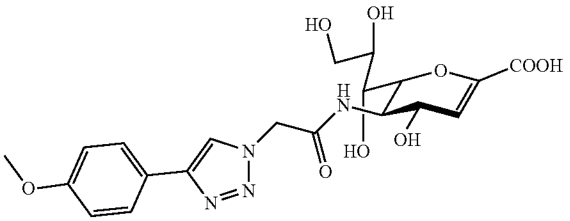

$^1$H NMR (500 MHz, $CD_3OD$) δ 8.27 (s, 1H, C═CH—N), 7.74 (d, J=8.7 Hz, 2H, Ar—H), 7.01 (d, J=8.7 Hz, 2H, Ar—H), 5.89 (d, J=1.8 Hz, 1H, H-3), 5.31 (s, 2H, N—$CH_2$—CO), 4.56-4.45 (m, 1H, H-4), 4.33 (d, J=10.8 Hz, 1H, H-6), 4.11 (dd, J=10.5, 8.9 Hz, 1H, H-5), 3.92-3.86 (m, 1H, H-8), 3.85-3.83 (m, 4H, H-9, $OCH_3$), 3.70-3.63 (m, 2H, H-7, H-9'). $^{13}$C NMR (126 MHz, $CD_3OD$) δ 169.15 (C═O), 167.27 (C-1), 148.92, 123.53 (Triazole-C), 146.62 (C-2), 161.19, 128.28, 124.06 115.61 (Ar—C), 112.08 (C-3), 77.26 (C-6), 71.38 (C-8), 69.81 (C-7), 68.41 (C-4), 64.77 (C-9), 56.20 ($PhOCH_3$), 53.38 ($CH_2N_3$), 52.02 (C-5). HRMS (ESI) calcd. for $C_{20}H_{23}N_4O_9$[M−H]$^-$, 463.1465; found 463.1471.

Example 68: 5-(2-(4-(4-fluorophenyl)-1H-1,2,3-triazol-1-yl)acetamido))-2,3,5-trideoxy-D-glycero-D-galacto-2-nonulopyranosonic acid (45)

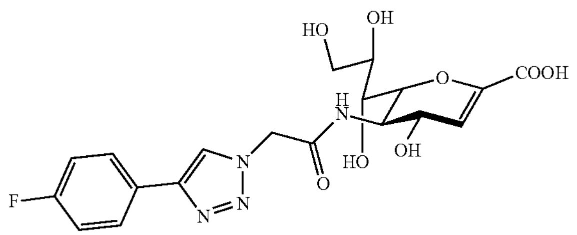

$^1$H NMR (500 MHz, $CD_3OD$) δ 8.33 (s, 1H, C═CH—N), 7.81 (dd, J=8.6, 5.4 Hz, 2H, Ar—H), 7.14 (t, J=8.7 Hz, 2H, Ar—H), 5.80 (s, 1H, H-3), 5.29 (s, 2H, N—$CH_2$—CO), 4.48 (d, J=8.2 Hz, 1H, H-4), 4.27 (d, J=10.7 Hz, 1H, H-6), 4.14-4.07 (m, 1H, H-5), 3.88 (m, 1H, H-8), 3.81 (d, J=11.0 Hz, 1H, H-9), 3.73-3.60 (m, 2H, H-9', H-7). $^{13}C$ NMR (126 MHz, $CD_3OD$) δ 168.94 (C-1), 168.64 (C═O), 165.11, 163.15 (d, J=246.3 Hz), 148.28 (C-2), 147.97, 123.91 (Triazole-C), 128.70 (d, J=8.2 Hz, Ar—C), 128.11 (d, J=3.2 Hz, Ar—C), 116.78 (d, J=22.0 Hz, Ar—C), 110.10 (C-3), 77.12 (C-6), 71.64 (C-8), 69.99 (C-7), 68.50 (C-4), 64.75 (C-9), 53.32 ($CH_2N_3$), 52.18 (C-5). HRMS (ESI) calcd. for $C_{19}H_{20}N_4O_8$ $[M-H]^-$, 451.1265; found 451.1271.

Example 69: 5-(2-(4-(4-aminophenyl)-1H-1,2,3-triazol-1-yl) acetamido))-2, 3, 5-trideoxy-D-glycero-D-galacto-2-nonulopyranosonic acid (46)

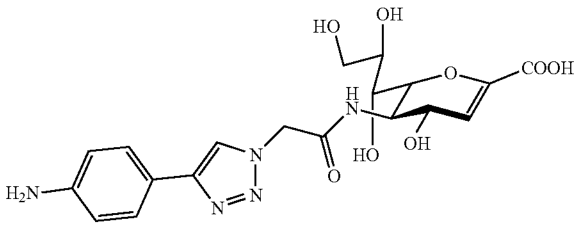

$^1$H NMR (500 MHz, $CD_3OD$) δ 8.18 (s, 1H, C═CH—N), 7.57 (d, J=8.6 Hz, 2H, Ar—H), 6.81 (d, J=8.5 Hz, 2H, Ar—H), 5.70 (d, J=2.2 Hz, 1H, H-3), 5.28 (s, 2H, N—$CH_2$—CO), 4.47 (dd, J=8.7, 2.2 Hz, 1H, H-4), 4.25 (d, J=10.8 Hz, 1H, H-6), 4.09 (dd, J=10.8, 8.7 Hz, 1H, H-5), 3.93-3.86 (m, 1H, H-8), 3.83 (dd, J=11.6, 2.8 Hz, 1H, H-9), 3.66 (dd, J=11.6, 5.7 Hz, 1H, H-9'), 3.60 (d, J=9.3 Hz, 1H, H-7). $^{13}C$ NMR (126 MHz, $CD_3OD$) δ 169.93 (C-1), 169.04 (C═O), 149.58, 122.78 (Triazole-C), 148.93 (C-2), 127.94, 121.52, 117.07 (Ar—C), 108.57 (C-3), 76.73 (C-6), 71.42 (C-8), 70.02 (C-7), 68.81 (C-4), 64.87 (C-9), 53.35 ($CH_2N_3$), 52.19 (C-5). HRMS (ESI) calcd. for $C_{19}H_{22}N_5O_8$ $[M-H]^-$, 448.1468; found 448.1481.

Example 70: 5-(2-(4-(4-(dimethylamino)phenyl-1H-1,2,3-triazol-1-yl)acetamido))-2,3,5-trideoxy-D-glycero-D-galacto-2-nonulopyranosonic acid (47)

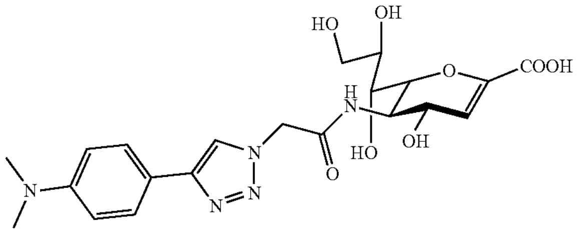

$^1$H NMR (500 MHz, $CD_3OD$) δ 8.18 (s, 1H, C═CH—N), 7.57 (d, J=8.6 Hz, 2H, Ar—H), 6.81 (d, J=8.5 Hz, 2H, Ar—H), 5.70 (d, J=2.2 Hz, 1H, H-3), 5.28 (s, 2H, N—$CH_2$—CO), 4.47 (dd, J=8.7, 2.2 Hz, 1H, H-4), 4.25 (d, J=10.8 Hz, 1H, H-6), 4.09 (dd, J=10.8, 8.7 Hz, 1H, H-5), 3.93-3.86 (m, 1H, H-8), 3.83 (dd, J=11.6, 2.8 Hz, 1H, H-9), 3.66 (dd, J=11.6, 5.7 Hz, 1H, H-9'), 3.60 (d, J=9.3 Hz, 1H, H-7). $^{13}C$ NMR (126 MHz, $CD_3OD$) δ 169.93 (C-1), 169.04 (C═O), 149.58, 122.78 (Triazole-C), 148.93 (C-2), 127.94, 121.52, 117.07 (Ar—C), 108.57 (C-3), 76.73 (C-6), 71.42 (C-8), 70.02 (C-7), 68.81 (C-4), 64.87 (C-9), 53.35 ($CH_2N_3$), 52.19 (C-5). HRMS (ESI) calcd. for $C_{19}H_{22}N_5O_8$ $[M-H]^-$, 448.1468; found 448.1481.

Example 71: 5-(2-(4-(4-acetamidophenyl)-1H-1,2,3-triazol-1-yl) acetamido))-2, 3, 5-trideoxy-D-glycero-D-galacto-2-nonulopyranosonic acid (48)

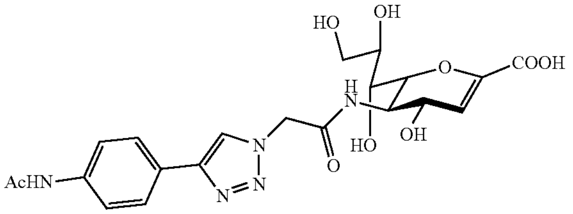

$^1$H NMR (500 MHz, $CD_3OD$) δ 8.30 (s, 1H, C═CH—N), 7.75 (d, J=8.6 Hz, 2H, Ar—H), 7.62 (d, J=8.6 Hz, 2H, Ar—H), 5.69 (d, J=2.2 Hz, 1H, H-3), 5.26 (s, 2H, N—$CH_2$—CO), 4.43 (dd, J=8.6, 2.2 Hz, 1H, H-4), 4.23 (d, J=10.8 Hz, 1H, H-6), 4.10 (dd, J=10.8, 8.6 Hz, 1H, H-5), 3.90-3.84 (m, 1H, H-8), 3.81 (dd, J=11.4, 2.9 Hz, 1H, H-9), 3.67 (dd, J=11.4, 5.3 Hz, 1H, H-9'), 3.57 (d, J=9.2 Hz, 1H, H-7), 2.13 (s, 3H, NAc). $^{13}C$ NMR (126 MHz, $CD_3OD$) δ 171.70 (C═O), 169.98 (C-1), 168.75 (C═O), 150.14 (C-1), 148.58, 123.59 (Triazole-C), 140.08, 127.37, 127.17, 121.36 (Ar—C), 108.11 (C-3), 76.80 (C-6), 71.44 (C-8), 70.17 (C-7), 68.78 (C-4), 64.92 (C-9), 53.30 ($CH_2N_3$), 52.23 (C-5), 23.90 ($CH_3$). HRMS (ESI) calcd. for $C_{21}H_{25}N_5O_9$ $[M-H]^-$, 490.1574; found 490.1584.

Example 72: General Procedure for Synthesis of C5, 9-Amido Compounds

Figure 22:
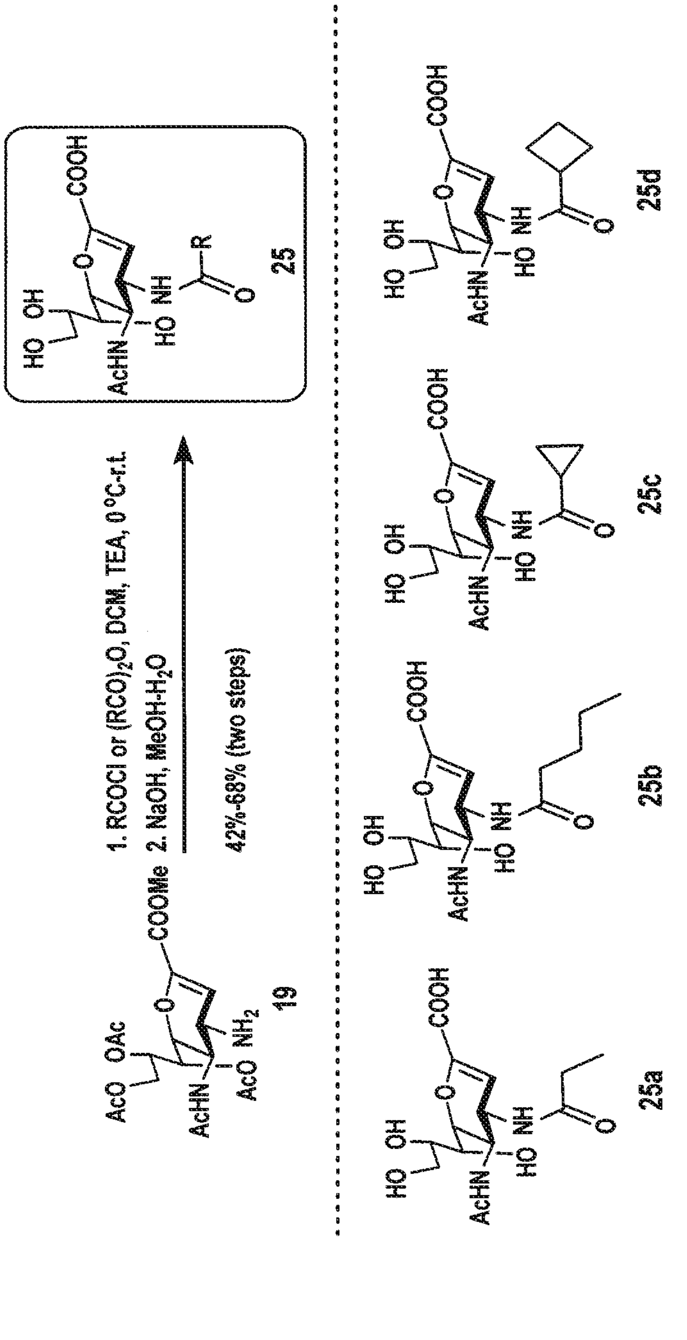
FIG. 22: Presents the synthetic routes for compounds 25a-d.
Figure 23:
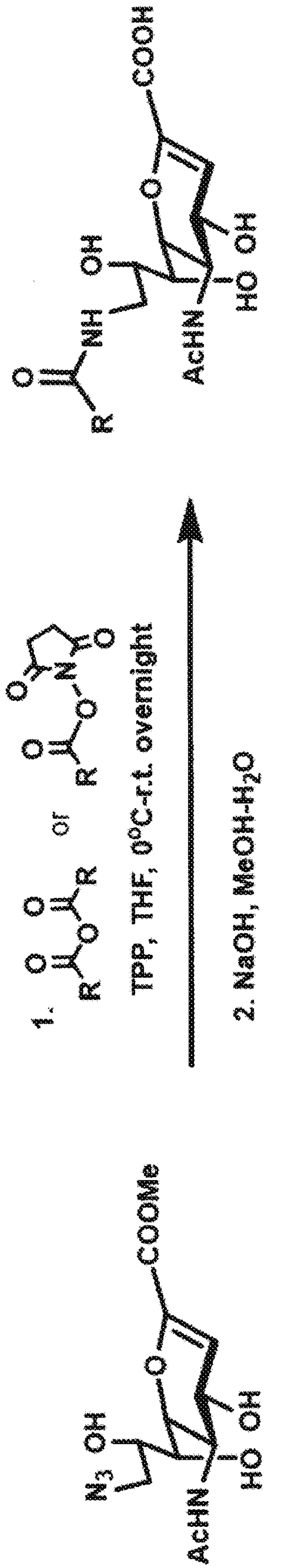
FIG. 23: Presents the synthetic routes for compounds 49, 50, 51, 52, 53, 54, 55 and 56.
Figure 24:
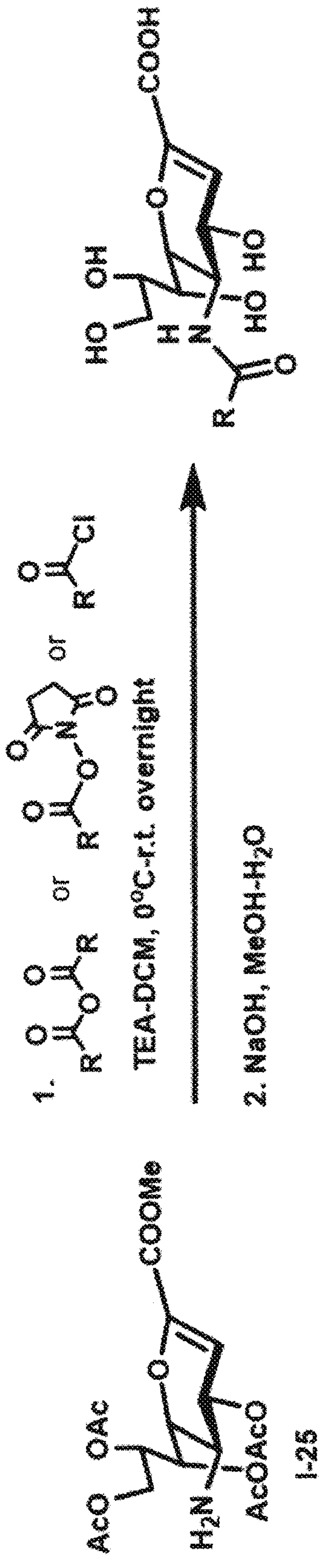
FIG. 24: Presents the synthetic routes for compounds 29, 30, 31, 32, 33, 34, 35, 36, 37, 38, 39, 40.
Figure 25:
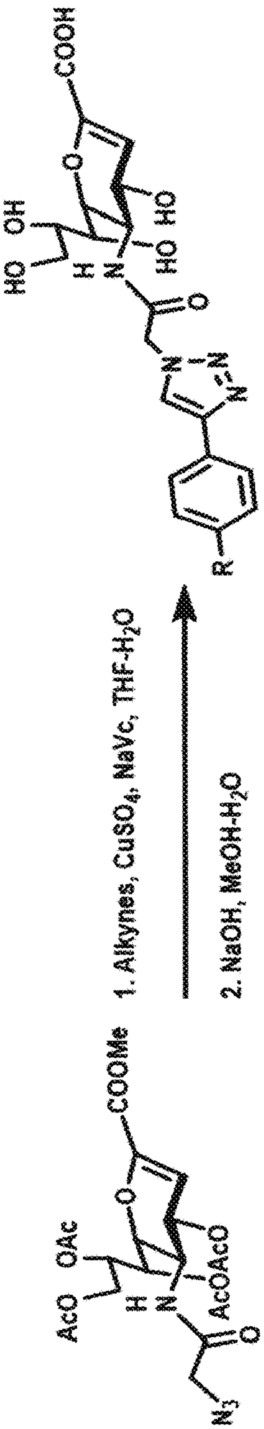
FIG. 25: Presents the synthetic routes for compounds 41, 42, 43, 44, 45, 46, 47, 48.
Figure 26:
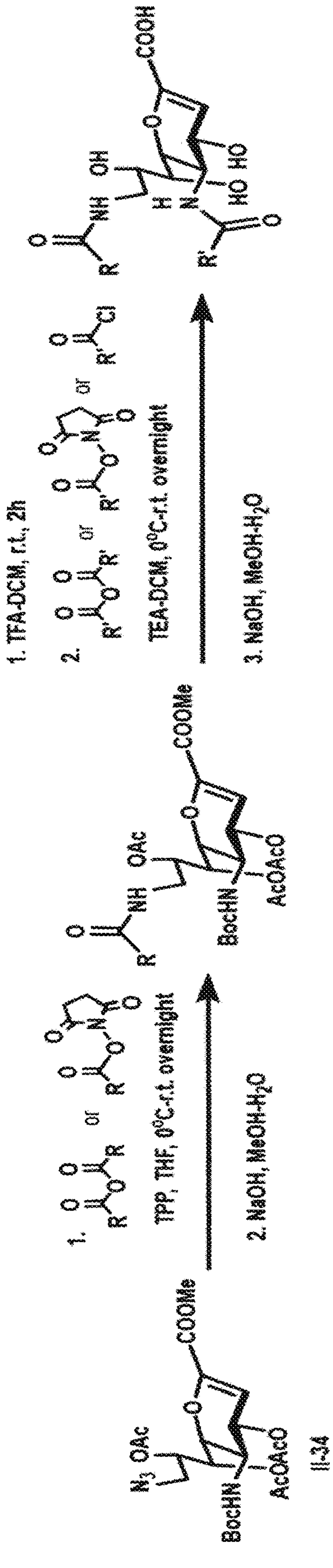
FIG. 26: Presents the synthetic routes for compound 57.

Fully protected C9-azido DANA was dissolved in THF-$H_2O$, and cooled down to 0° C. with ice water bath. Triphenyl phosphate was then added followed with activated carboxylic acids. The solution was allowed to warm to room temperature and kept stirring overnight. After completion, the reaction was quenched with water, concentrated and purified by flash chromatography to give the desired C9-modified product. The product was then dissolved in anhydrous DCM and TEA and then cooled down to 0° C. Corresponding activated carboxylic acids for $C_5$ modifications was added in dropwise. The solution was allowed to warm to room temperature and kept stirring overnight. After completion, the reaction was quenched with water, concentrated and purified by flash chromatography to give the desired C5-modified product. The product was then dissolved in MeOH, and 0.5 M NaOH was added (FIG. 22). The mixture was kept stirring at room temperature. After completion, the mixture was neutralized with Amberlite™ IR-120 ($H^+$ form), filtered and purified by flash chromatography to provide the final C5-, C9-modified compounds.

Example 73: 5-Pentanamido-9-pentanamido-2,6-anhydro-3,5-dideoxy-D-glycero-D-galacto-non-2-enonic acid (57)

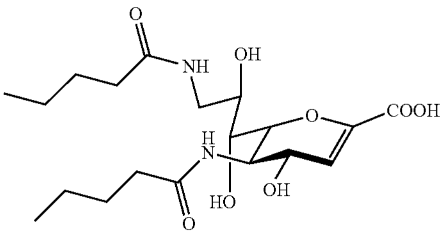

$^1H$ NMR (500 MHz, $CD_3OD$) δ 5.74 (d, J=1.9 Hz, 1H, H-3), 4.38 (dd, J=8.7, 1.9 Hz, 1H, H-4), 4.11 (d, J=10.8 Hz, 1H, H-6), 3.97 (dd, J=10.7, 8.8 Hz, 1H, H-5), 3.93-3.85 (m, 1H, H-8), 3.57 (dd, J=13.4, 3.1 Hz, 1H, H-9), 3.38 (d, J=8.7 Hz, 1H, H-7), 3.26 (dd, J=13.4, 6.0 Hz, 1H, H-9'), 2.30-2.23 (m, 2H, α-$CH_2$), 2.23-2.15 (m, 2H, α'-$CH_2$), 1.59 (tdd, J=15.3, 11.2, 7.5 Hz, 4H, β-$CH_2$, (3'-$CH_2$), 1.34 (dq, J=22.0, 7.4 Hz, 4H, γ-$CH_2$, γ'-$CH_2$), 0.92 (q, J=7.4 Hz, 6H, δ-$CH_2$, 5'-$CH_2$) $^{13}C$ NMR (126 MHz, $CD_3OD$) δ 177.78, 176.97 (N—C═O), 109.98 (C-3), 77.36 (C-6), 71.51 (C-7), 70.36 (C-4), 68.40 (C-8), 51.87 (C-5), 44.27 (C-9), 36.96, 36.89 (C-α, C-α'), 29.24, 29.11 (C-β, C-β'), 23.49, 23.45 (C-γ, C-γ'), 14.19 ($COCH_3$). HRMS (ESI) calcd. for $C_{19}H_{31}N_2O_8$ $[M-H]^-$, 415.2086; found 415.2081.

Example 74: General Procedure of Staudinger Reaction for Synthesis of Compounds 58-62

C9-azido DANA methyl ester was dissolved in THF-$H_2O$, and cooled down to 0° C. with ice water bath. Triphenyl phosphate was then added followed with anhydrides or acyl chlorides. The solution was allowed to warm to room temperature and kept stirring overnight. After completion, the reaction was quenched with water, concentrated and purified by flash chromatography to give the desired product. The product was then dissolved in MeOH, and 0.5 M NaOH was added. The mixture was kept stirring at room temperature. After completion, the mixture was neutralized with Amberlite™ IR-120 ($H^+$ form), filtered and purified by flash chromatography to provide the desired products.

Example 75: 5-Acetamido-9-(4-acetamido)benzamido-2,6-anhydro-3,5-dideoxy-d-glycero-d-galacto-non-2-enonic acid (58)

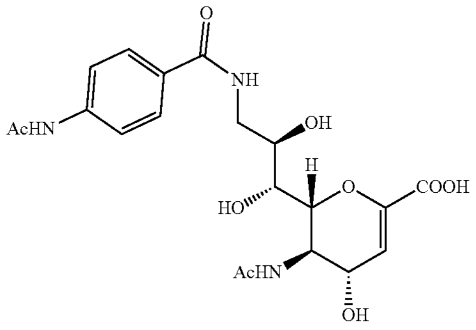 [SMILES: CC(=O)Nc1ccc(C(=O)NC[C@@H](O)[C@@H](O)[C@@H]2OC(C(=O)O)=C[C@H](O)[C@H]2NC(C)=O)cc1]

Compound 58 was synthesized from C9-azido DANA methyl ester using 4-acetamidobenzyl chloride. 45 mg (28% (36%×77%, over two steps). $^1H$ NMR (500 MHz, $D_2O$) δ 7.80 (d, J=8.2 Hz, 2H, Ar—H), 7.58 (d, J=8.2 Hz, 2H, Ar—H), 5.95 (s, 1H, H-3), 4.54 (d, J=7.8 Hz, 1H, H-4), 4.33 (d, J=10.9 Hz, 1H, H-6), 4.14 (t, J=9.5 Hz, 2H, H-5, H-8), 3.86-3.80 (m, 1H, H-9), 3.68-3.58 (m, 2H, H-7, H-9'), 2.22 (s, 3H, $COCH_3$), 2.07 (s, 3H, $COCH_3$). $^{13}C$ NMR (126 MHz, $D_2O$) δ 175.64, 173.90, 171.46 (3×N—C═O), 168.07 (C-1), 141.49, 130.56, 129.13, 121.72 (Ar—C), 111.40 (C-3), 76.57 (C-6), 70.37 (C-7), 69.56 (C-4), 68.16 (C-8), 50.72 (C-5), 44.12 (C-9), 24.04, 23.02 (2×$COCH_3$). HRMS (ESI) calcd. for $C_{18}H_{21}N_2O_8[M-H]^-$, 450.1518; found 450.1525.

Example 76: 5-Acetamido-9-(4-amino)benzamido-2,6-anhydro-3,5-dideoxy-b-glycero-D-galacto-non-2-enonic acid (59)

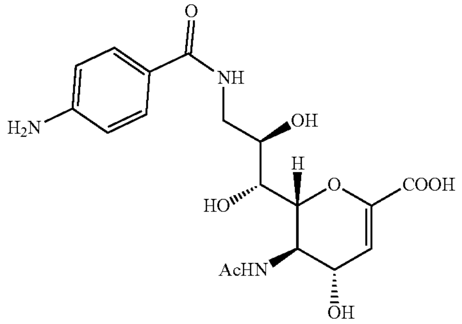 [SMILES: CC(=O)N[C@H]1[C@H]([C@H](O)[C@H](O)CNC(=O)c2ccc(N)cc2)OC(C(=O)O)=C[C@@H]1O]

Compound 59 was synthesized from C9-azido DANA methyl ester using N-hydroxysuccinimidyl-4-((tert-butoxycarbonyl) amino) benzoate. 30 mg (20%(45%×45% (yields for two steps of deprotection), over three steps).

$^1H$ NMR (500 MHz, $CD_3OD$) δ 7.91 (d, J=7.3 Hz, 2H), 7.33 (d, J=7.3 Hz, 2H), 5.94 (s, 1H, H-3), 4.46 (d, J=8.0 Hz, 1H, H-4), 4.21 (d, J=10.6 Hz, 1H, H-6), 4.08-3.96 (m, 2H, H-5, H-8), 3.77 (d, J=12.9 Hz, 1H, H-9), 3.51 (m, 2H, H-9', H-7), 1.97 (s, 3H, $COCH_3$). $^{13}C$ NMR (126 MHz, $CD_3OD$) δ 165.66 (C-1), 145.21, 130.38, 122.41 (Ar—C), 113.68 (C-3), 77.75 (C-6), 71.40 (C-7), 70.28 (C-4), 67.93 (C-8), 51.73 (C-5), 45.05 (C-9), 22.92 ($COCH_3$). HRMS (ESI) calcd. for $C_{18}{}^{1}$-121$N_2O_8$ $[M-H]^-$, 408.1412; found 408.1415.

Example 77: 5-Acetamido-9-(3-acetamido)benzamido-2,6-anhydro-3,5-dideoxy-d-glycero-d-galacto-non-2-enonic acid (60)

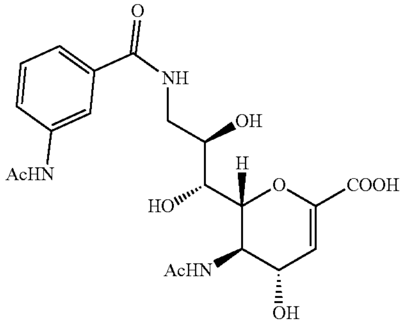 [SMILES: CC(=O)Nc1cccc(C(=O)NC[C@@H](O)[C@@H](O)[C@@H]2OC(C(=O)O)=C[C@H](O)[C@H]2NC(C)=O)c1]

Compound 60 was synthesized from C9-azido DANA methyl ester using 3-acetamidobenzyl chloride. 40 mg (30% (36%×82%, over two steps). $^{1}$H NMR (500 MHz, $CD_3OD$) δ 7.97 (t, J=1.5 Hz, 1H, Ar—H), 7.69 (dd, J=7.9, 1.5 Hz, 1H, Ar—H), 7.52 (d, J=7.9 Hz, 1H, Ar—H), 7.37 (t, J=7.9 Hz, 1H, Ar—H), 5.78 (d, J=2.0 Hz, 1H, H-3), 4.38 (dd, J=8.6, 2.0 Hz, 1H, H-4), 4.16 (d, J=10.8 Hz, 1H, H-6), 4.00 (m, 2H, H-5, H-8), 3.76 (dd, J=13.8, 3.3 Hz, 1H, H-9), 3.53 (dd, J=13.8, 6.8 Hz, 1H, H-9'), 3.47 (d, J=8.8 Hz, 1H, H-7), 2.12 (s, 3H, $COCH_3$), 1.97 (s, 3H, $COCH_3$). $^{13}$C NMR (126 MHz, $CD_3OD$) δ 174.74, 171.81, 170.56 (3×N—C═O), 140.21, 136.51, 130.03, 124.15, 123.74, 120.14 (Ar—C), 110.38 (C-3), 77.38 (C-6), 71.78 (C-7), 70.21 (C-4), 68.40 (C-8), 51.96 (C-5), 45.07 (C-9), 23.86, 22.77 (2×$COCH_3$). HRMS (ESI) calcd. for $C_{13}H_{21}N_2O_8$ $[M-H]^-$, 450.1518; found 450.1515.

Example 78: 5-Acetamido-9-(3-amino)benzamido-2,6-anhydro-3,5-dideoxy-b-glycero-D-galacto-non-2-enonic acid (61)

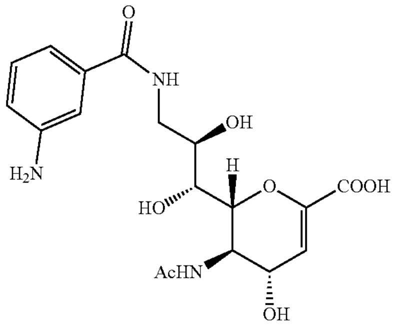 [SMILES: CC(=O)N[C@H]1[C@H]([C@H](O)[C@H](O)CNC(=O)c2cccc(N)c2)OC(C(=O)O)=C[C@@H]1O]

Compound 61 was synthesized from C9-azido DANA methyl ester using 3-aminobenzyl chloride. $^{1}$H NMR (500 MHz, $CD_3OD$) 30 mg (18%(46%×40%, over two steps). δ 7.94 (d, J=7.8 Hz, 1H, Ar—H), 7.89 (s, 1H, Ar—H), 7.63 (t, J=7.8 Hz, 1H, Ar—H), 7.60-7.56 (m, 1H, Ar—H), 5.95 (d, J=2.4 Hz, 1H, H-3), 4.45 (dd, J=8.7, 2.4 Hz, 1H, H-4), 4.21 (d, J=10.9 Hz, 1H, H-6), 4.08-3.97 (m, 2H, H-5, H-8), 3.84-3.79 (m, 1H, H-9), 3.57-3.48 (m, 2H, H-7, H-9'), 1.99 (s, 3H, $COCH_3$). $^{13}$C NMR (126 MHz, $CD_3OD$) δ 175.00, 168.86 (2×N—C═O), 165.60 (C-1), 145.27 (C-2), 137.83, 132.62, 131.55, 128.67, 127.16, 123.51 (Ar—C), 113.61 (C-3), 77.79 (C-6), 71.72 (C-7), 70.03 (C-4), 67.90 (C-8), 51.81 (C-5), 45.29 (C-9), 22.80 ($COCH_3$). HRMS (ESI) calcd. for $C_{18}H_{21}N_2O_8$ $[M-H]^-$, 408.1412; found 408.1411.

Example 79: 5-Acetamido-9-(5-(4-acetamidobenzamido))pentanamido-2,6-anhydro-3,5-dideoxy-d-glycero-d-galacto-non-2-enonic acid (62)

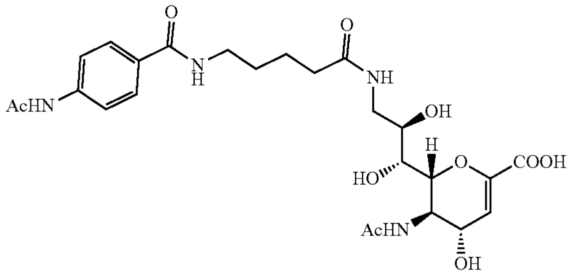 [SMILES: CC(=O)Nc1ccc(C(=O)NCCCCC(=O)NC[C@@H](O)[C@@H](O)[C@@H]2OC(C(=O)O)=C[C@H](O)[C@H]2NC(C)=O)cc1]

Compound 62 was synthesized from C9-azido DANA methyl ester using N-hydroxysuccinimidyl-5-(4-acetamidobenzamido) pentanoate. 30 mg (22%(42%×53%, over two steps). $^{1}$H NMR (500 MHz, $CD_3OD$) δ 7.77 (d, J=8.7 Hz, 2H, Ar—H), 7.64 (d, J=8.7 Hz, 2H, Ar—H), 5.90 (d, J=2.3 Hz, 1H, H-3), 4.42 (dd, J=8.7, 2.3 Hz, 1H, H-4), 4.19-4.13 (d, J=10.7, 1H, H-6), 3.98 (dd, J=10.7, 8.7 Hz, 1H, H-5), 3.93-3.86 (m, 1H, H-8), 3.59 (dd, J=13.8, 3.1 Hz, 1H, H-9), 3.42 (d, J=8.9 Hz, 1H, H-7), 3.37 (t, J=6.0 Hz, 2H, δ—$CH_2$), 2.27 (t, J=7.1 Hz, 2H, α-$CH_2$), 2.13, 2.01 (2×s, 2×3H, 2×$COCH_3$), 1.73-1.56 (m, 4H, β-$CH_2$, γ-$CH_2$). $^{13}$C NMR (126 MHz, $CD_3OD$) δ 176.77, 174.82, 171.90, 169.57 (4×N—C═O), 143.07 (C-2), 130.74, 129.15, 120.26 (Ar—C), 112.90 (C-3), 77.69 (C-6), 71.35 (C-8), 70.24 (C-7), 51.81 (C-4), 49.88 (C-5), 44.28 (C-9), 40.53 (δ—$CH_2$), 36.59 (α-$CH_2$), 30.04 (γ-$CH_2$), 24.42 (α-$CH_2$), 24.03, 22.86 (2×$COCH_3$). HRMS (ESI) calcd. for $C_{25}H_{33}N_4O_{10}$ $[M-H]^-$, 549.2202; found 549.2207.

Example 80: 5-Acetamido-9-(4-pentyl)triazolyl-2,6-anhydro-3,5-dideoxy-d-glycero-d-galacto-non-2-enonic acid (63)

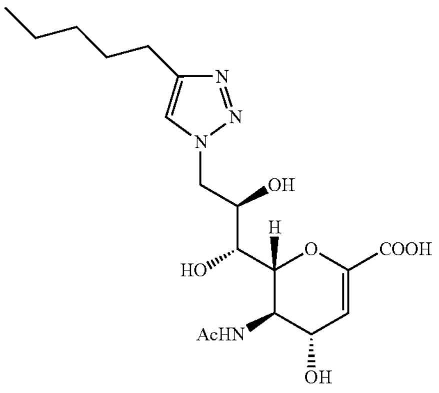 [SMILES: CCCCCc1cn(C[C@@H](O)[C@@H](O)[C@@H]2OC(C(=O)O)=C[C@H](O)[C@H]2NC(C)=O)nn1]

Compound 63: To a solution of methyl 5-acetamido-9-azido-2,6-anhydro-3,5-dideoxy-d-glycero-d-galacto-non-2-enonate (50 mg, 1 eq) and the heptyne (30 mg, 2 eq) in THF-$H_2O$ (2:1), sodium L-ascorbate (5 mg, 0.3 eq) and copper (II) sulfate (3 mg, 0.2 eq) were added sequentially. The reaction mixture was kept stirring at room temperature and monitored by TLC until no azide remained. Silica gel was then added to the reaction mixture and the solvent was removed under reduced pressure. The residue was separated by flash chromatography to provide the desired product 59 mg (92%). To hydrolyze the C1-methyl ester, the product was dissolved in MeOH, and 0.5 M NaOH was added. The mixture was kept stirring at room temperature. After completion, the pH of the solution was adjusted to 2 with Amberlite™ IR-120 (He). The solution was filtered, concentrated and purified by flash chromatography or recrystallization to provide the desired product 40 mg (70%). $^1H$ NMR (500 MHz, $CD_3OD$) δ 7.71 (s, 1H, Triazole-H), 5.91 (d, J=2.3 Hz, 1H, H-3), 4.77 (dd, J=14.0, 2.5 Hz, 1H, H-4), 4.44-4.33 (m, 2H, H-6, H-5), 4.24-4.16 (m, 1H, H-8), 4.13 (d, J=10.9 Hz, 1H, H-9), 3.98 (dd, J=10.7, 8.7 Hz, 1H, H-9'), 3.39 (d, J=9.1 Hz, 1H, H-7), 2.66 (t, J=7.7 Hz, 2H, α-$CH_2$), 2.01 (s, 3H, $COCH_3$), 1.71-1.59 (m, 2H), 1.39-1.27 (m, 4H, β-$CH_2$, γ-$CH_2$), 0.89 (dd, J=9.7, 4.3 Hz, 3H, δ—$CH_3$). $^{13}C$ NMR (126 MHz, $CD_3OD$) δ 175.10, 166.11, 145.91, 124.31, 112.97, 77.69, 71.34, 69.86, 67.93, 55.00, 51.92, 32.51, 30.36, 26.29, 23.46, 22.72, 14.35). HRMS (ESI) calcd. for $C_{18}H_{27}N_4O_7$ $[M-H]^-$, 411.1885; found 411.1889.

Example 81: General procedure for synthesis of C5, C9 double modified DANA analogue compounds 64-70, 73-74

Compound methyl 5-(tert-butoxycarbonyl)amino-9-azido-4,7,8-di-O-acetyl-2,6-anhydro-3,5-dideoxy-b-glycero-D-galacto-non-2-enonate was dissolved in THF-$H_2O$, and cooled down to 0° C. with ice water bath. Triphenyl phosphate was then added followed with activated carboxylic acids. The solution was allowed to warm to room temperature and kept stirring overnight. After completion, the reaction was quenched with water, concentrated and purified by flash chromatography to give the desired C9-modified product. The product was then dissolved in anhydrous TFA-DCM (10%) and the solution was stirred for 2-4 hours at r.t. Solvents were removed under vacuum and the residue was dissolved in anhydrous DCM and TEA was added. The solution was cooled down to 0° C. and corresponding activated carboxylic acids for C5 modifications was added in dropwise. The solution was allowed to warm to room temperature and kept stirring overnight. After completion, the reaction was quenched with water, concentrated and purified by flash chromatography to give the desired C5-modified product. The product was then dissolved in MeOH, and 0.5 N NaOH was added. The mixture was kept stirring at room temperature. After completion, the mixture was neutralized with Amberlite™ IR-120 ($H^+$ form), filtered and purified by flash chromatography to provide the final C5, C9-double modified compounds.

Example 82: 5-Hexanamido-9-hexanamido-2,6-anhydro-3,5-dideoxy-d-glycero-d-galacto-non-2-enonic acid (64)

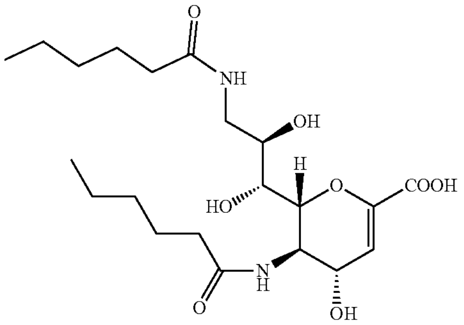 [SMILES: CCCCCC(=O)NC[C@@H](O)[C@@H](O)[C@@H]1OC(C(=O)O)=C[C@H](O)[C@H]1NC(=O)CCCCC]

Compound 64 was synthesized from compound methyl 5-(tert-butoxycarbonyl)amino-9-azido-4,7,8-di-O-acetyl-2,6-anhydro-3,5-dideoxy-D-glycero-h-galacto-non-2-enonate using hexanoic anhydride. 20 mg. (22%(77%×54%×52%), over three steps)$^1H$ NMR (500 MHz, $CD_3OD$) δ 5.78 (s, 1H, H-3), 4.38 (d, J=8.5 Hz, 1H, H-4), 4.13 (d, J=10.6 Hz, 1H, H-6), 4.02-3.86 (m, 2H, H-5, H-8), 3.56 (d, J=13.2 Hz, 1H, H-9), 3.42 (d, J=7.9 Hz, 1H, H-7), 2.31-2.12 (m, 4H, α-$CH_2$, α'-$CH_2$), 1.68-1.53 (m, 4H, β-$CH_2$, β'-$CH_2$), 1.40-1.23 (m, 8H, γ-$CH_2$, γ'-$CH_2$, δ—$CH_2$, δ—$CH_2$), 0.90 (q, J=6.9 Hz, 6H, ε—$CH_3$, ε'-$CH_3$). $^{13}C$ NMR (126 MHz, $CD_3OD$) δ 177.85, 177.06 (N—C=O), 110.69 (C-3), 77.49 (C-6), 71.39 (C-7), 70.66 (C-4), 68.30 (C-8), 51.88 (C-5), 44.25 (C-9), 37.18, 37.11 (C-α, C-α'), 32.64, 32.61 (C-β, C-β'), 26.78, 26.66 (C-γ, C-γ'), 23.46 (C-6, C-6'), 14.32, 14.30 (C-ε, C-ε'). HRMS (ESI) calcd. for $C_{21}{}^1$-$135N_2O_8$ $[M-H]^-$, 443.2399; found 443.2396.

Example 83: 5-Propionamido-9-pentanamido-2,6-anhydro-3,5-dideoxy-D-glycero-D-galacto-non-2-enonic acid (65)

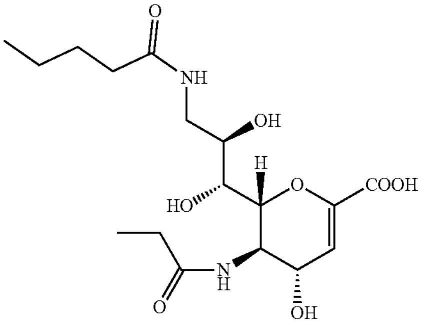 [SMILES: CCCCC(=O)NC[C@@H](O)[C@@H](O)[C@@H]1OC(C(=O)O)=C[C@H](O)[C@H]1NC(=O)CC]

Compound 65 was synthesized from compound methyl 5-(tert-butoxycarbonyl)amino-9-azido-4,7,8-di-O-acetyl-2,6-anhydro-3,5-dideoxy-D-glycero-D-galacto-non-2-enonate using valeric anhydride and propionic anhydride. 15 mg. (18%(60%×53%×58%), over three steps). $^1H$ NMR (500 MHz, $CD_3OD$) δ 5.90 (d, J=2.4 Hz, 1H, H-3), 4.41 (dd, J=8.7, 2.3 Hz, 1H, H-4), 4.16 (d, J=10.8 Hz, 1H, H-6), 4.01-3.87 (m, 2H, H-5, H-8), 3.61-3.53 (m, 1H, H-9), 3.41-3.35 (m, 1H, H-7), 2.28 (q, J=7.6 Hz, 2H, α-$CH_2$), 2.24-2.17 (m, 2H, α-$CH_2$'), 1.57 (dt, J=13.0, 7.5 Hz, 2H, (3'-$CH_2$), 1.33 (dq, J=14.7, 7.4 Hz, 2H, γ'-$CH_2$), 1.14 (t, J=7.6 Hz, 3H, β—$CH_3$), 0.91 (t, J=7.4 Hz, 3H, 6'-$CH_3$). $^{13}C$ NMR (126 MHz, $CD_3OD$) δ 178.61, 177.24 (N—C═O), 112.84 (C-3), 77.83 (C-6), 71.51 (C-7), 70.19 (C-4), 68.00 (C-8), 51.87 (C-5), 44.40 (C-9), 36.82 (C-α'), 30.20 (C-β'), 29.23 (C-γ'), 23.42 (C-α), 14.13 (C-δ'), 10.37 (C-β). HRMS (ESI) calcd. for $C_{17}H_{27}N_2O_8$ $[M-H]^-$, 387.1773; found 387.1770.

Example 84: 5-Propionamido-9-hexanamido-2,6-anhydro-3,5-dideoxy-D-glycero-D-galacto-non-2-enonic acid (66)

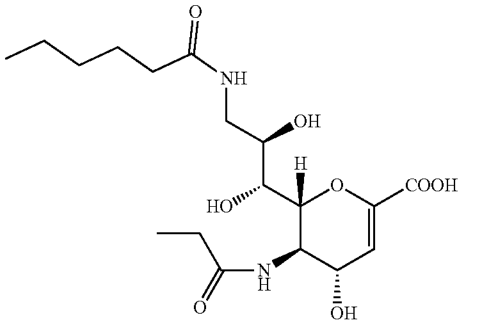 [SMILES: CCCCCC(=O)NC[C@@H](O)[C@@H](O)[C@@H]1OC(C(=O)O)=C[C@H](O)[C@H]1NC(=O)CC]

Compound 66 was synthesized from methyl 5-(tert-butoxycarbonyl)amino-9-azido-4,7,8-di-O-acetyl-2,6-anhydro-3,5-dideoxy-D-glycero-D-galacto-non-2-enonate using hexanoic anhydride and propionic anhydride. 13 mg. (17%(63%×46%×60%), over three steps). $^1H$ NMR (500 MHz, $CD_3OD$) δ 5.89 (s, 1H, H-3), 4.40 (d, J=8.7 Hz, 1H, H-4), 4.15 (d, J=10.7 Hz, 1H, H-6), 4.01-3.86 (m, 2H, H-5, H-8), 3.57 (d, J=11.9 Hz, 1H, H-9), 3.39 (d, J=8.6 Hz, 1H, H-7), 2.28 (q, J=7.5 Hz, 2H, α-$CH_2$), 2.24-2.14 (m, 2H, α'-$CH_2$), 1.59 (dt, J=14, 8, 7.5 Hz, 2H, (3'-$CH_2$), 1.38-1.25 (m, 4H, γ'-$CH_2$, 6'-$CH_3$), 1.14 (t, J=7.6 Hz, 3H, p-$CH_3$), 0.89 (t, J=7.0 Hz, 3H, ε-$CH_3$'). $^{13}C$ NMR (126 MHz, $CD_3OD$) δ 178.60, 177.22 (2×N—C═O), 112.68 (C-3), 77.89 (C-6), 71.56 (C-7), 70.25 (C-4), 68.10 (C-8), 51.87 (C-6), 44.40 (C-9), 37.07 (C-α'), 32.58 (C-β'), 30.21 (C-γ'), 26.77 (C-δ'), 23.44 (C-α), 14.27 (C-ε'), 10.37 (C-β). HRMS (ESI) calcd. for $C_{18}H_{29}N_2O_8$ $[M-H]^-$, 401.1929; found 401.1926.

Example 85: 5-Pentanamido-9-acetamido-2,6-anhydro-3,5-dideoxy-D-glycero-D-galacto-non-2-enonic acid (67)

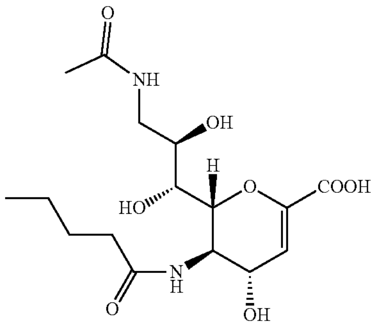 [SMILES: CCCCC(=O)N[C@H]1[C@H]([C@H](O)[C@H](O)CNC(C)=O)OC(C(=O)O)=C[C@@H]1O]

Compound 67 was synthesized from compound methyl 5-(tert-butoxycarbonyl)amino-9-azido-4,7,8-di-O-acetyl-2,6-anhydro-3,5-dideoxy-b-glycero-D-galacto-non-2-enonate using acetic anhydride and valeric anhydride. 20 mg. (24% (74%×50%×65%), over three steps) $^1H$ NMR (500 MHz, $CD_3OD$) δ 5.86 (d, J=2.4 Hz, 1H, H-3), 4.40 (dd, J=8.7, 2.4 Hz, 1H, H-4), 4.14 (d, J=10.7 Hz, 1H, H-6), 3.96 (dd, J=10.7, 8.7 Hz, 1H, H-5), 3.93-3.87 (m, 1H, H-8), 3.58 (dd, J=13.9, 3.2 Hz, 1H, H-9), 3.38 (dd, J=9.0, 0.7 Hz, 1H, H-7), 3.27-3.23 (m, 1H, H-9'), 2.27 (t, 2H, J=7.5 Hz, α-$CH_2$), 1.95 (s, 3H, $COCH_3$), 1.61 (dt, J=13.1, 7.5 Hz, 2H, β-$CH_2$), 1.37 (dt, J=15.0, 7.4 Hz, 2H, γ-$CH_2$), 0.93 (t, J=7.4 Hz, 3H, δ—$CH_3$). $^{13}C$ NMR (126 MHz, $CD_3OD$) δ 177.96, 174.02 (2×N—C═O), 166.67 (C-1), 112.19 (C-3), 77.73 (C-6), 71.69 (C-7), 70.00 (C-4), 68.08 (C-8), 51.87 (C-5), 44.58 (C-9), 36.90 (C-α), 29.13 (C-β), 23.45 (C-γ), 22.58 ($COCH_3$), 14.16 (C-6). HRMS (ESI) calcd. for $C_{16}H_{25}N_2O_8$ $[M-H]^-$, 373.1616; found 373.1615.

Example 86: 5-Hexanamido-9-acetamido-2,6-anhydro-3,5-dideoxy-D-glycero-D-galacto-non-2-enonic acid (68)

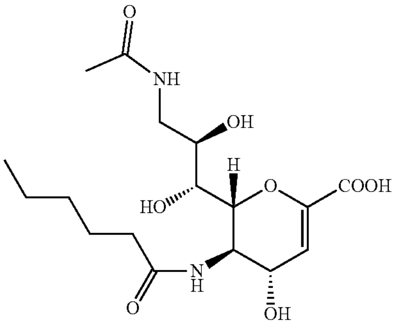 [SMILES: CCCCCC(=O)N[C@H]1[C@H]([C@H](O)[C@H](O)CNC(C)=O)OC(C(=O)O)=C[C@@H]1O]

Compound 68 was synthesized from compound methyl 5-(tert-butoxycarbonyl)amino-9-azido-4,7,8-di-O-acetyl-2,6-anhydro-3,5-dideoxy-D-glycero-D-galacto-non-2-enonate using acetic anhydride and hexanoic anhydride. 24 mg (30%(74%×55%×74%), over three steps). $^1H$ NMR (500 MHz, $CD_3OD$) δ 5.74 (d, J=2.3 Hz, 1H, H-3), 4.39 (dd, J=8.7, 2.3 Hz, 1H, H-4), 4.11 (d, J=10.8 Hz, 1H, H-6), 3.96 (dd, J=10.8, 8.7 Hz, 1H, H-5), 3.93-3.87 (m, 1H, H-8), 3.60 (dd, J=13.8, 3.2 Hz, 1H, H-9), 3.40-3.35 (m, 1H, H-7), 3.23 (dd, J=13.8, 7.2 Hz, 1H, H-9'), 2.29-2.23 (m, 2H, α-$CH_2$), 1.95 (s, 3H, $COCH_3$), 1.66-1.59 (m, 2H, β-$CH_2$), 1.37-1.28 (m, 4H, γ-$CH_2$, δ—$CH_3$), 0.90 (t, J=7.0 Hz, 3H, ε—$CH_3$). $^{13}C$ NMR (126 MHz, $CD_3OD$) δ 178.01, 174.03 (2×N—C═O), 168.67 (C-1), 110.16 (C-3), 77.34 (C-6), 71.71 (C-7), 70.06 (C-4), 68.37 (C-8), 51.82 (C-5), 44.53 (C-9), 37.25 (C-α), 32.61 (C-β), 26.70 (C-γ), 23.45 (C-6), 22.69 ($COCH_3$), 14.37 (C-ε). HRMS (ESI) calcd. for $C_{16}H_{25}N_2O_8$ $[M-H]^-$, 387.1773; found 387.1774

Example 87: 5-Hexanamido-9-propionamido-2,6-anhydro-3,5-dideoxy-d-glycero-d-galacto-non-2-enonic acid (69)

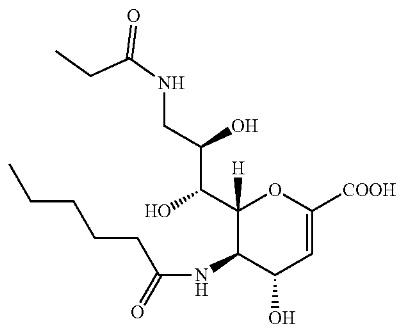 [SMILES: CCCCCC(=O)N[C@H]1[C@H]([C@H](O)[C@H](O)CNC(=O)CC)OC(C(=O)O)=C[C@@H]1O]

Compound 69 was synthesized from compound methyl 5-(tert-butoxycarbonyl)amino-9-azido-4,7,8-di-O-acetyl-2,6-anhydro-3,5-dideoxy-D-glycero-D-galacto-non-2-enonate using propionic anhydride and hexanoic anhydride. 20 mg (30%(96%×41%×75%), over three steps). $^{1}$H NMR (500 MHz, $CD_3OD$) δ 5.73 (d, J=2.3 Hz, 1H, H-3), 4.36 (dd, J=8.6, 2.3 Hz, 1H, H-4), 4.10 (dd, J=10.8, 0.8 Hz, 1H, H-6), 3.97 (dd, J=10.8, 8.7 Hz, 1H, H-5), 3.89 (ddd, J=9.2, 5.2, 2.7 Hz, 1H, H-8), 3.59 (dd, J=13.8, 3.2 Hz, 1H, H-9), 3.36 (dd, J=9.0, 0.7 Hz, 1H, H-7), 3.25 (dd, J=13.8, 7.1 Hz, 1H, H-9'), 2.29-2.15 (m, 4H, α-$CH_2$, α'-$CH_2$), 1.63 (dt, J=14.8, 7.6 Hz, 2H, (3-$CH_2$), 1.38-1.28 (m, 4H, γ- $CH_2$, δ—$CH_2$), 1.11 (t, J=7.6 Hz, 3H, β'-$CH_3$), 0.91 (t, J=7.0 Hz, 3H, ε—$CH_3$). $^{13}$C NMR (126 MHz, $CD_3OD$) δ 177.78, 177.58 (2×N—C═O), 109.74 (C-3), 77.38 (C-6), 71.81 (C-7), 70.10 (C-4), 68.43 (C-8), 51.87 (C-5), 44.43 (C-9), 37.17 (C-α), 32.63 (C-β), 30.18 (C-α'), 26.67 (C-γ), 23.45 (C-6), 14.32 (C-ε), 10.55 (C-β'). HRMS (ESI) calcd. for $C_{18}H_{29}N_2O_8$ [M−H]$^-$, 401.1929; found 401.1929.

Example 88: 5-Hexanamido-9-butanamido-2,6-anhydro-3,5-dideoxy-D-glycero-D-galacto-non-2-enonic acid (70)

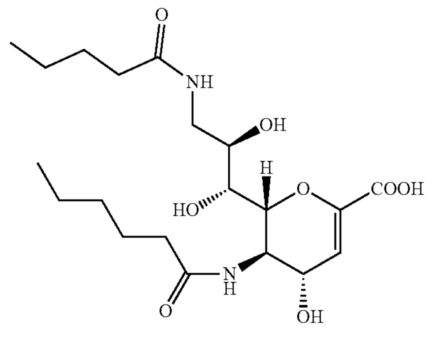 [SMILES: CCCCCC(=O)N[C@H]1[C@H]([C@H](O)[C@H](O)CNC(=O)CCCC)OC(C(=O)O)=C[C@@H]1O]

Compound 70 was synthesized from compound methyl 5-(tert-butoxycarbonyl)amino-9-azido-4,7,8-di-O-acetyl-2,6-anhydro-3,5-dideoxy-D-glycero-D-galacto-non-2-enonate using butyric anhydride and hexanoic anhydride. 22 mg (34%(96%×46%×78%), over three steps). $^{1}$H NMR (500 MHz, $CD_3OD$) δ 5.70 (d, J=2.2 Hz, 1H, H-3), 4.36 (dd, J=8.6, 2.3 Hz, 1H, H-4), 4.09 (dd, J=10.8, 0.8 Hz, 1H, H-6), 3.97 (dd, J=10.8, 8.7 Hz, 1H, H-5), 3.92-3.85 (m, 1H, H-8), 3.59 (dd, J=13.8, 3.2 Hz, 1H, H-9), 3.36 (d, J=8.9 Hz, 1H, H-7), 3.25 (dd, J=13.8, 7.0 Hz, 1H, H-9'), 2.29-2.21 (m, 2H, α-$CH_2$), 2.20-2.11 (m, 2H, α'-$CH_2$), 1.62 (ddd, J=14.9, 7.5, 2.6 Hz, 4H, β-$CH_2$, 13'-$CH_2$), 1.34-1.32 (m, 4H, γ-$CH_2$, δ—$CH_2$), 0.94-0.89 (m, 6H, ε—$CH_3$, γ'-$CH_3$). $^{13}$C NMR (126 MHz, $CD_3OD$) δ 177.75, 176.70 (2×N—C═O), 109.28 (C-3), 77.31 (C-4), 71.74 (C-7), 70.22 (C-6), 68.50 (C-8), 51.89 (C-5), 44.32 (C-9), 39.04 (C-α), 37.18 (C-α'), 32.63 (C-β), 26.66 (C-γ), 23.46 (C-β'), 20.44 (C-δ), 14.33 (C-ε), 14.08 (C-γ'). HRMS (ESI) calcd. for $C_{19}H_{32}N_2O_8$ [M−H]$^-$, 415.2086; found 415.2088.

Example 89: 5-(2-Ethyl)hexanamido(S/R)-9-acetanamido-2,6-anhydro-3,5-dideoxy-d-glycero-d-galacto-non-2-enonic acid (73)

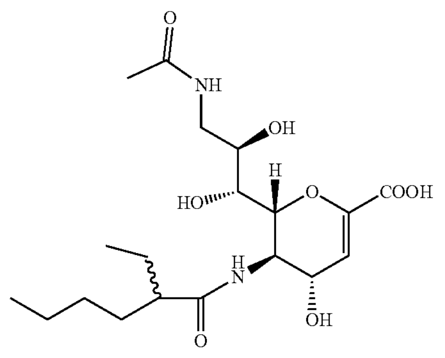 [SMILES: CCCCC(CC)C(=O)N[C@H]1[C@H]([C@H](O)[C@H](O)CNC(C)=O)OC(C(=O)O)=C[C@@H]1O]

Compound 73 was synthesized from compound methyl 5-(tert-butoxycarbonyl)amino-9-azido-4,7,8-di-O-acetyl-2,6-anhydro-3,5-dideoxy-d-glycero-d-galacto-non-2-enonate using acetic anhydride and 2-ethylhexanoyl chloride. The product was obtained as a mixture of diastereoisomers at a position of the hexanamido group. 6.0 mg (24%(96%×67%×38%), over three steps). $^{1}$H NMR (500 MHz, $CD_3OD$) δ 5.67 (2H), 4.36-4.33 (2H), 4.14-4.07 (2H), 4.01-3.97 (2H), 3.90-3.87 (2H), 3.64-3.56 (2H), 3.41-3.39 (2H), 3.26-3.14 (2H), 2.22-2.13 (4H), 1.93 (3H), 1.94 (3H) 1.63-1.26 (8H), 1.50-1.24 (m, 7H), 0.97-0.84 (6H). $^{13}$C NMR (126 MHz, $CD_3OD$) δ 180.53, 173.75, 173.65, 108.90, 79.80, 77.38, 72.33, 72.01, 70.03, 69.94, 68.58, 68.54, 51.97, 51.95, 50.21, 50.14, 44.78, 44.54, 33.69, 33.51, 31.07, 30.78, 27.27, 27.12, 23.77, 22.60, 14.31, 12.68, 12.45. HRMS (ESI) calcd. for $C_{19}H_{31}N_2O_8$ [M−H]$^-$, 415.2086; found 415.2088.

Example 90: 5-(2-Methyl)hexanamido(S/R)-9-acetanamido-2,6-anhydro-3,5-dideoxy-d-glycero-d-galacto-non-2-enonic acid (74)

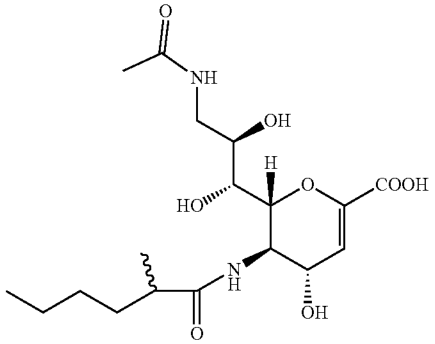 [SMILES: CCCCC(C)C(=O)N[C@H]1[C@H]([C@H](O)[C@H](O)CNC(C)=O)OC(C(=O)O)=C[C@@H]1O]

Compound 74 was synthesized from compound methyl 5-(tert-butoxycarbonyl)amino-9-azido-4,7,8-di-O-acetyl-2,6-anhydro-3,5-dideoxy-d-glycero-d-galacto-non-2-enonate using acetic anhydride and 2-methylhexanoyl chloride. The product was obtained as a mixture of diastereoisomers at a position of the hexanamido group. 10.2 mg (54%(96%×70%×60%), over three steps). $^1$H NMR (500 MHz, $CD_3OD$) δ 5.76 (d, J=2.2 Hz, 1H), 5.72 (d, J=2.3 Hz, 1H), 4.43 (dd, J=8.8, 2.3 Hz, 1H), 4.40-4.35 (m, 1H), 4.32 (dd, J=11.0, 1.0 Hz, 1H), 4.17-4.14 (m, 1H), 4.11 (dd, J=10.9, 3.0 Hz, 1H), 3.98-3.93 (m, 1H), 3.92-3.85 (m, 2H), 3.64-3.53 (m, 3H), 3.39-3.30 (m, 2H), 3.20 (dd, J=13.7, 7.5 Hz, 1H), 2.41-2.32 (m, 2H), 1.68-1.58 (m, 2H), 1.42-1.24 (m, 10H), 1.14-1.09 (m, 6H), 0.93-0.86 (m, 6H). $^{13}$C NMR (126 MHz, $CD_3OD$) δ 181.38, 174.09, 173.80, 168.70, 110.49, 110.37, 109.65, 77.58, 77.54, 76.27, 72.09, 71.74, 71.39, 70.24, 70.00, 69.96, 68.31, 68, 28, 68.21, 52.30, 51.88, 51.69, 44.75, 44.52, 44.35, 42.25, 42.21, 35.05, 34.90, 30.93, 30.74, 23.74, 22.60, 22.57, 22.45, 18.57, 18.30, 14.40, 14.33. HRMS (ESI) calcd. for $C_{18}H_{29}N_2O_8$ [M−H]$^-$, 401.1929; found 401.1926.

Example 91: General Procedure for Synthesis of Compounds 75 and 72

A solution of compound methyl 5-amino-4,7,8,9-tetra-O-acetyl-2,6-anhydro-3,5-dideoxy-d-glycero-d-galacto-non-2-enonate in anhydrous dichloromethane and triethylamine (4 eq) was cooled down to 0° C. and anhydrides or acyl chlorides (1.5 eq) was added in dropwise. The solution was allowed to warm to room temperature and kept stirring overnight. After completion, the reaction was quenched with water, concentrated and purified by flash chromatography to give the protected product. The protected product was then dissolved in methanol and 0.5 N NaOH was added. The solution was stirred under room temperature until completion. After completion, the solution was neutralized by Amberlite™ IR 120 (H). The suspension was then filtered, and the filtrate was concentrated and purified by flash chromatography or precipitated in a mixture of methanol and ethyl acetate to give the desired product.

Example 92: 5-(2-Ethyl)hexanamido(SIR)-2,6-anhydro-3,5-dideoxy-d-glycero-d-galacto-non-2-enonic acid (75)

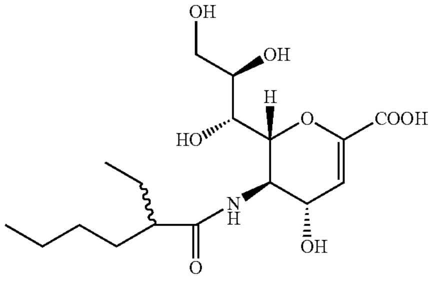 [SMILES: CCCCC(CC)C(=O)N[C@H]1[C@H]([C@H](O)[C@H](O)CO)OC(C(=O)O)=C[C@@H]1O]

Compound 75 was synthesized from compound methyl 5-amino-4,7,8,9-tetra-O-acetyl-2,6-anhydro-3,5-dideoxy-d-glycero-d-galacto-non-2-enonate using 2-ethylhexanoyl chloride, and the product was obtained as a mixture of diastereoisomers at a position of the hexanamido group. 18.6 mg (25% (45%×55%), over two steps). $^1$H NMR (500 MHz, $CD_3OD$) δ 5.64 (2H), 4.42 (dd, J=8.8, 2.2 Hz, 1H), 4.34 (dt, J=8.6, 2.6 Hz, 1H), 4.29 (dd, J=11.0, 0.8 Hz, 1H), 4.15 (dd, J=11.0, 8.8 Hz, 1H), 4.09 (ddd, J=10.9, 2.4, 1.1 Hz, 1H), 3.99 (ddd, J=10.8, 8.6, 7.0 Hz, 1H), 3.90-3.77 (m, 4H), 3.63 (dd, J=11.5, 5.5 Hz, 1H), 3.58-3.50 (m, 2H), 3.44 (dd, J=9.2, 0.9 Hz, 1H), 2.17 (dq, J=9.4, 5.0 Hz, 1H), 1.65-1.22 (m, 17H), 0.95-0.84 (m, 12H). $^{13}$C NMR (126 MHz, $CD_3OD$) δ 180.56, 180.54, 170.35, 170.19, 159.62, 159.32, 150.18, 150.08, 118.72, 108.41, 107.90, 77.41, 76.07, 71.44, 71.36, 71.30, 70.80, 70.63, 70.16, 68.63, 68.59, 68.50, 65.45, 65.24, 64.84, 52.30, 51.89, 51.83, 50.23, 50.20, 33.70, 33.56, 31.11, 30.79, 27.33, 27.11, 23.83, 23.80, 14.39, 14.32, 12.61, 12.44. HRMS (ESI) calcd. for $C_{17}H_{28}NO_8$ [M−H]$^-$, 374.1820; found 374.1811.

Example 93: 5-(2-Methyl)hexanamido(S/R)-2,6-anhydro-3,5-dideoxy-d-glycero-d-galacto-non-2-enonic acid (72)

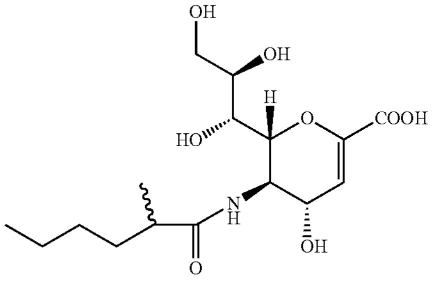 [SMILES: CCCCC(C)C(=O)N[C@H]1[C@H]([C@H](O)[C@H](O)CO)OC(C(=O)O)=C[C@@H]1O]

Compound 72 was synthesized from compound methyl 5-amino-4,7,8,9-tetra-O-acetyl-2,6-anhydro-3,5-dideoxy-d-glycero-d-galacto-non-2-enonate using 2-methylhexanoyl chloride, and the product was obtained as a mixture of diastereoisomers at a position of the hexanamido group. 8.7 mg (10% (18%×55%), over two steps). $^1$H NMR (500 MHz, $CD_3OD$) δ 5.70 (d, J=1.5 Hz, 1H), 5.68 (d, J=2.2 Hz, 1H), 4.43 (dd, J=8.8, 2.2 Hz, 1H), 4.36 (ddd, J=8.6, 4.1, 2.4 Hz, 1H), 4.31 (dd, J=11.0, 0.7 Hz, 1H), 4.18-4.15 (m, 1H), 4.12-4.08 (m, 1H), 3.96 (dd, J=10.8, 8.7 Hz, 1H), 3.90-3.78

(m, 4H), 3.65-3.53 (m, 3H), 3.52-3.47 (m, 1H), 3.45 (dd, J=9.3, 0.8 Hz, 1H), 2.40-2.32 (m, 1H), 1.69-1.57 (m, 1H), 1.40-1.21 (m, 12H), 1.15-1.05 (m, 6H), 0.89 (dt, J=7.0, 4.4 Hz, 6H). $^{13}$C NMR (126 MHz, $CD_3OD$) δ 181.39, 181.37, 169.55, 169.33, 116.42, 109.43, 109.33, 108.68, 77.57, 76.22, 71.43, 71.26, 71.20, 70.67, 70.41, 70.17, 68.51, 68.46, 68.41, 65.38, 65.11, 64.87, 52.25, 51.81, 51.69, 42.32, 42.23, 35.13, 34.98, 30.96, 30.74, 23.79, 23.76, 18.47, 18.36, 14.38, 14.33. HRMS (ESI) calcd. for $C_{16}H_{26}NO_8$ $[M-H]^-$, 360.1664; found 360.1663.

Example 94: Methyl 5-(tert-butoxycarbonyl)amino-4-azido-2,6-anhydro-3,4,5-trideoxy-dideoxy-D-glycero-D-galacto-non-2-enonate (76)

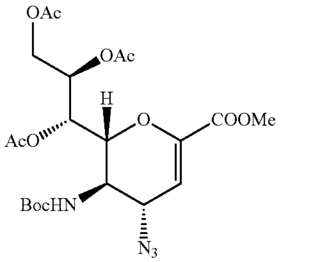 [SMILES: COC(=O)C1=C[C@H](N=[N+]=[N-])[C@@H](NC(=O)OC(C)(C)C)[C@H]([C@H](OC(C)=O)[C@@H](COC(C)=O)OC(C)=O)O1]

Compound methyl 5-acetamido-4-azido-7,8,9-tri-O-acetyl-2,6-anhydro-3,4,5-trideoxy-D-glycero-D-galacto-non-2-enonate (200 mg, 1 eq), di-tert-butyl dicarbonate (241 mg, 2.7 eq) and 4-dimethylaminopyridine (76 mg, 1.6 eq) were dissolved in 60 ml anhydrous THF. The solution was then refluxed for 2 hours. After completion, solvents were removed under reduced pressure and the residue was separated by flash chromatography, providing crude product 240 mg. The crude product was dissolved in 10 ml MeOH. After the solution was cooled down to 0° C., NaOMe (20 mg, 1 eq) was added slowly. The mixture was stirred under 0° C. for about 1 hour. After completion, Amberlite™ IR 120 ($H^+$) was added to adjust the pH of the solution to 7. After filtration, solvent was removed under reduced pressure and the residue was purified by flash chromatography, providing the desired product 140 mg (82%, over two steps) $^1$H NMR (500 MHz, $CD_3OD$) δ 5.86 (d, J=2.4 Hz, 1H, H-3), 4.31 (dd, J=9.4, 2.4 Hz, 1H, H-4), 4.21 (d, J=10.9 Hz, 1H, H-6), 3.88-3.79 (m, 3H, H-5, H-8, H-9), 3.77 (s, 3H, $COOCH_3$), 3.71-3.61 (m, 2H, H-7, H-9'), 1.45 (s, 9H, $^t$Boc). $^{13}$C NMR (126 MHz, $CD_3OD$) δ 169.53, 163.95 (C-1), 158.44 ($^t$Boc-OCO), 146.55 (C-2), 108.74 (C-3), 81.25 ($^t$Boc-$CCH_3$), 78.40 (C-6), 71.28 (C-8), 69.75 (C-7), 64.87 (C-9), 60.08 (C-4), 53.00 (C-5), 50.53 ($COOCH_3$), 28.57 ($^t$Boc-$CH_3$). HRMS (ESI) calcd. for $C_{15}H_{24}N_4NaO_8$ $[M-H]^-$, 411.1486; found 411.1487.

Example 95: Methyl 5-(4-methylpentanamido)-4-azido-7,8,9-tri-O-acetyl-2,6-anhydro-3,4,5-trideoxy-D-glycero-D-galacto-non-2-enonate (77)

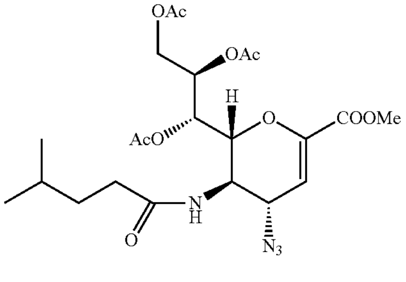 [SMILES: COC(=O)C1=C[C@H](N=[N+]=[N-])[C@@H](NC(=O)CCC(C)C)[C@H]([C@H](OC(C)=O)[C@@H](COC(C)=O)OC(C)=O)O1]

A solution of compound 76 (140 mg, 1 eq) in anhydrous pyridine was cooled down to 0° C. and acetic anhydride (400 μl, 10 eq) was added in dropwise. The mixture was then allowed to warm to temperature and kept stirring overnight. After completion, the reaction was quenched with methanol and solvents were removed under reduced pressure. The residue was dissolved in 200 ml ethyl acetate and carefully washed with 0.1 M HCl, water, brine and dried over $Na_2SO_4$. The solution was concentrated to give 160 mg yellow oil, which was dissolved in 20 ml anhydrous DCM and 2 ml TFA was added slowly. The solution was then stirred at room temperature for 2 hours. After completion, DCM and TFA were removed under reduced pressure. The residue was dissolved in 10 ml anhydrous DCM and TEA (124 μl, 3 eq) was added. The mixture was then cooled down to 0° C. and 4-methylpentanoyl chloride (75 mg, 1.2 eq) was added. The solution was allowed to warm to room temperature and kept stirring overnight. After completion, the reaction was quenched with water, concentrated and purified by flash chromatography to give the desired product. 105 mg (52%, over three steps). $^1$H NMR (500 MHz, $CDCl_3$) δ 6.05 (d, J=8.3 Hz, 1H, NH), 5.94 (d, J=2.1 Hz, 1H, H-3), 5.41 (d, J=5.2 Hz, 1H, H-7), 5.29 (td, J=6.5, 2.7 Hz, 1H, H-8), 4.59 (dd, J=12.4, 2.6 Hz, 1H, H-9), 4.54-4.50 (m, H5, H-4), 4.16 (dd, J=12.4, 6.6 Hz, 1H, H-9'), 3.78 (s, 3H, $COOCH_3$), 2.17 (t, J=7.8 Hz, 2H, α-$CH_2$), 2.11, 2.03, 2.02 (3×s, 9H, 3×$COCH_3$), 1.62-1.43 (m, 3H, β-$CH_2$, γ-CH), 0.88 (d, J=6.3 Hz, 6H, 2×δ—$CH_3$). $^{13}$C NMR (126 MHz, $CDCl_3$) δ 174.00, 170.69, 170.27, 170.08 (4×C═O), 161.55 (C-1), 145.05 (C-2), 107.66 (C-3), 75.58 (C-6), 70.66 (C-8), 67.74 (C-7), 62.00 (C-9), 57.51 (C-4), 52.56 ($COOCH_3$), 48.74 (C-5), 34.71 (C-β), 34.00 (C-γ), 27.72, 22.24, 22.20 (3×$COCH_3$), 20.82, 20.72 (2×C-6). HRMS (ESI) calcd. for $C_{22}H_{32}N_4NaO_8$ $[M-H]^-$, 535.2011; found 535.2003.

Example 96: Methyl 5-(4-methylpentanamido)-7,8,9-tri-O-acetyl-2,6-anhydro-4-[2,3-bis(tert-butoxycarbonyl)guanidino]-3,4,5-trideoxy-D-glycero-D-galacto-non-2-enonate (78)

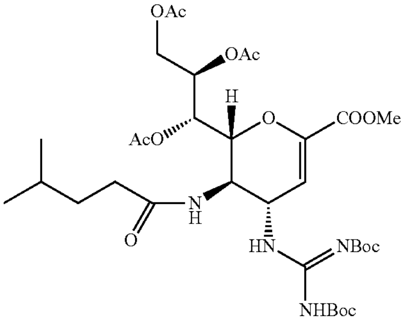

To a solution of compound 77 (50 mg, 1 eq) in THF (2 ml), 1 N HCl (200 μl, 2.2 eq) was added, followed by triphenylphosphine (29 mg, 1.2 eq). The resulting mixture was stirred at room temperature overnight. After completion, solvents were removed under reduced pressure and the residue was purified by flash chromatography, providing crude product 50 mg. The residue was dissolved in 5 ml anhydrous DCM, and TEA (50 μl, 4 eq) was added. The solution was cooled down to 0° C. and N, N'-Di-Boc-1H-pyrazole-1-carboxamidine (600 mg, 2 eq) added. The reaction mixture was allowed to warm up to room temperature and kept stirring overnight. After completion, the reaction was quenched with water, extracted with ethyl acetate. The organic phase was washed with brine, dried over $Na_2SO_4$, concentrated and purified by flash chromatography to give the desired product. 60 mg (87%, over two steps). $^1$H NMR (500 MHz, $CDCl_3$) δ 8.46 (d, J=8.9 Hz, 1H, NH), 7.76 (brs, 1H, NH), 6.16 (d, J=9.2 Hz, 1H, NH), 5.88 (d, J=2.4 Hz, 1H, H-3), 5.42 (dd, J=4.9, 1.7 Hz, 1H, H-7), 5.28 (ddd, J=7.4, 4.9, 2.7 Hz, 1H, H-8), 5.19 (td, J=9.7, 2.4 Hz, 1H, H-4), 4.67 (dd, J=12.4, 2.7 Hz, 1H, H-9), 4.31 (dd, J=10.5, 9.7 Hz, 1H, H-5), 4.26 (dd, J=10.5, 1.7 Hz, 1H, H-6), 4.15 (dd, J=12.4, 7.4 Hz, 1H, H-9'), 3.79 (s, 3H, $COOCH_3$), 2.17-1.96 (m, 11H, $3\times COCH_3$, α-$CH_2$), 1.56-1.33 (m, 21H, $2\times^t$Boc, β-$CH_2$, γ-CH), 0.85 (dd, J=6.5, 2.7 Hz, 6H, 2×δ—$CH_3$). $^{13}$C NMR (126 MHz, $CDCl_3$) δ 174.01, 170.56, 170.24, 170.07 (4×C═O), 161.70 ($^t$Boc-OCO), 157.23 (C-1), 152.62 (C═N), 145.07 (C-2), 109.71 (C-3), 83.87, 79.77 ($^t$Boc-C $(CH_3)_3$), 78.11 (C-6), 71.57 (C-8), 67.76 (C-7), 62.29 (C-9), 52.45 ($COOCH_3$), 48.88 (C-4), 47.60 (C-5), ($COCH_3$), 34.67 (C-α), 34.12 (C-β), 28.27, 28.03 ($^t$Boc-$C(CH_3)_3$), 27.70 (C-γ), 22.32, 22.13 (C-δ), 20.91, 20.87, 20.79 ($COCH_3$). HRMS (ESI) calcd. for $C_{33}H_{52}N_4NaO_{14}$ $[M+Na]^+$, 751.3372; found 751.3378.

Example 97: 5-(4-methylpentanamido)-2,6-anhydro-4-guanidino-3, 4, 5-trideoxy-D-glycero-D-galacto-non-2-enonic acid (71)

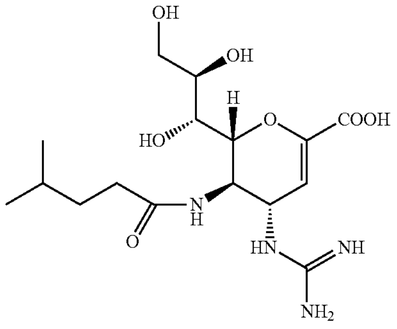 [SMILES: CC(C)CCC(=O)N[C@H]1[C@H]([C@H](O)[C@H](O)CO)OC(C(=O)O)=C[C@@H]1NC(=N)N]

To a solution of compound 78 (60 mg) in 5 ml DCM, 500 μl TFA was added. The solution was then stirred at room temperature for 2 hours. After completion, DCM and TFA were removed under reduced pressure. The residue was dissolved in methanol and 2 ml 1 N NaOH was added. The solution was stirred at room temperature for 1 hour. After completion, the reaction mixture was added with Amberlite™ IR 120 (H) to make the pH of the solution as 7. The suspension was then filtered, and the filtrate was concentrated to give a light-yellow oil. The residue was dissolved in minimum methanol and the product was precipitated by ethyl acetate. The product was obtained by filtering as a white solid. 15 mg (48%, over two steps). $^1$H NMR (700 MHz, $CD_3OD$) δ 5.50 (s, 1H, H-3), 4.37 (d, J=8.5 Hz, 1H, H-4), 4.33 (d, J=10.0 Hz, 1H, H-6), 4.19 (t, J=9.4 Hz, 1H, H-5), 3.89-3.79 (m, 2H, H-8, H-9), 3.65 (dd, J=11.3, 5.4 Hz, 1H, H-9'), 3.58 (d, J=9.2 Hz, 1H, H-7), 2.26 (t, J=7.5 Hz, 2H, α-$CH_2$), 1.61-1.49 (m, 3H, β-$CH_2$, γ-CH), 0.92 (d, J=6.4 Hz, 6H, 2×δ—$CH_3$). $^{13}$C NMR (176 MHz, $CD_3OD$) δ 177.19 ($COCH_3$), 169.63 (C-1), 158.78 (C═N), 151.58 (C-2), 103.33 (C-3), 77.04 (C-6), 71.33 (C-8), 70.31 (C-7), 64.88 (C-9), 52.26 (C-4), 35.85 (C-α), 35.21 (C-β), 28.86 (C-γ), 22.72, 22.63 (2×C-6). HRMS (ESI) calcd. for $C_{33}H_{52}N_4NaO_{14}$ $[M+Na]^+$, 387.1885; found 387.1879.

Example 98: Material and Methods for Example 99

Inhibition Assay

Inhibition assays against 4MU-NANA (2'-(4-methylumbelliferyl)-α-D-N-acetylneuraminic acid) cleavage and GM3 cleavage was performed using protocols reported previously (Zhang, 2013). NEU3 and NEU2 were expressed as N-terminal MBP fusion protein in *E. coli* and purified as previously reported (Albohy, 2010). NEU4 was expressed as a GST fusion protein in *E. coli* and purified as previously reported (Albohy, 2011). NEU1 was expressed as His fusion protein in HEK293 cells and cell lysate was used without further purification (Pshezhetsky, 1996). All assays were conducted in 0.1 M sodium acetate buffer at optimum pH for each enzyme (4.5 for NEU1, NEU3 and NEU4; 5.5 for NEU2) (Zhang, 2013). To get comparable $IC_{50}$ among the four isoenzymes, similar activity units of each enzyme were used in the assay.

For assays using 4MU-NANA as the substrate, inhibitors with of a 3-fold serial dilution of concentrations were incubated with enzyme at 0° C. for 15 min. 4MU-NANA was then added to the mixture, making the final concentration of 4MU-NANA as 50 μM and the total volume of the reaction mixture as 20 μL. After incubation at 37° C. for 30 min, the reaction was quenched with 100 μL of 0.2 M sodium glycine buffer (pH 10.2). The reaction mixture was transferred to 386-well plate and the enzyme activity was determined by measuring fluorescence ($\lambda_{ex}$=365 nm; $\lambda_{em}$=445 nm) using a plate reader (Molecular Devices, Sunnyvale CA). Assays were performed with duplicates for each point and $IC_{50}$ was obtained by plotting the data with Graphpad™ Prism 5.0. For curves that showed less than a 50% decrease in signal, fits were conducted using maximum inhibition values found for DANA.

For inhibition assays against GM3 cleavage, a method developed by Markely and coworkers was adopted (Markely, 2010). The assay was conducted in 0.1 M sodium acetate buffer (pH 4.5). After serial concentrations of inhibitors were incubated with enzyme at 0° C. for 15 min, GM3 was added, making the final concentration of GM3 as 500 μM and the total volume of the reaction mixture as 20 μL. The reaction mixture was incubated at 37° C. for 30 min and quenched with 100 μL of freshly made 0.2 M sodium borate buffer (pH 10.2). 0.8% malononitrile solution (40 μL) was added to form a fluorescent adduct with the free sialic acids. Fluorescence was obtained ($\lambda_{ex}$=357 nm; $\lambda_{em}$=434 nm) and the data was processed using Graphpad™ Prism 5.0. For curves that showed less than a 50% decrease in signal, fits were conducted using maximum inhibition values found for DANA.

$K_i$ Determinations

Enzymes were incubated with serial concentrations of inhibitors at 0° C. for 15 min and serial concentrations of 4MU-NANA were added. The reaction mixture was transferred to 386-well plate immediately and the rate of product formation was obtained by measuring fluorescence ($\lambda_{ex}$=315 nm; $\lambda_{em}$=450 nm) every 30 s for 30 min. The obtained data was processed with Graphpad™ Prism 5.0 for $K_i$ determination.

Example 99: Inhibition Assays

To evaluate the inhibitory effects of the compounds against individual isoenzymes, each enzyme was produced recombinantly or purification (Albohy, 2013; Zhang, 2013; Albohy, 2010) and the $IC_{50}$ tested using an artificial substrate, 2'-(4-methylumbelliferyl)-α-D-N-acetylneuraminic acid (4MU-NANA) (Potier, 1979; Warner, 1979). The inhibitory effects are reported in Table III below.

TABLE III

IC$_{50}$ data using 4MU-NANA as the substrate

Formula II

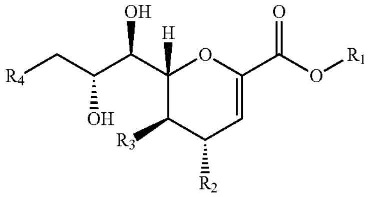

| Compound of formula II | Structure: R$_2$ (at position C4) | Structure: R$_4$ (at position C9) | IC$_{50}$ [μM] NEU1 | NEU2 | NEU3 | NEU4 | Target | Selectivity |
|---|---|---|---|---|---|---|---|---|
| R$_3$ (at position C5) is $CH_3C(O)NH$— — | | | | | | | | |
| 1 (DANA) | HO— — | HO— — | 49 ± 8 | 37 ± 6 | 7.7 ± 0.8 | 8.3 ± 1.0 | NA | NA |
| 6 (Zanamivir) | 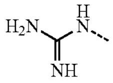 | HO— — | >500 | 7.8 ± 2.0 | 4.0 ± 0.6 | 47 ± 6 | NEU2/ NEU3 | 6 |
| 7a | HO— — | 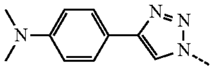 | 190 ± 40 | 250 ± 40 | 9.3 ± 0.8 | 28 ± 3 | NEU3/ NEU4 | 7 |
| 7b | HO— — | 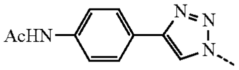 | 59 ± 5 | 78 ± 20 | 5.5 ± 0.5 | 11 ± 1 | NEU3/ NEU4 | 5 |
| 7c | HO— — | 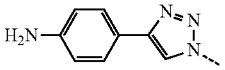 | 76 ± 16 | 350 ± 90 | 8.7 ± 0.9 | 12 ± 1 | NEU3/ NEU4 | 6 |
| 7d | HO— — | 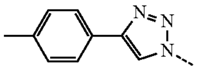 | 51 ± 7 | 290 ± 50 | 8.2 ± 1.3 | 3.9 ± 0.4 | NEU3/ NEU4 | 6 |
| 7e | HO— — | 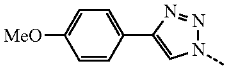 | 47 ± 6 | 430 ± 200 | 5.9 ± 0.4 | 2.6 ± 0.3 | NEU3/ NEU4 | 8 |
| 7f | HO— — | 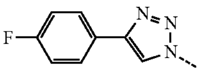 | 100 ± 40 | >500 | 17 ± 2 | 1.3 ± 0.2 | NEU4 | 10 |
| 7g | HO— — | 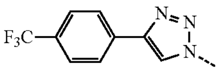 | 140 ± 30 | 360 ± 50 | 3.3 ± 0.5 | 5.0 ± 0.9 | NEU3/ NEU4 | 28 |
| 7h | HO— — | 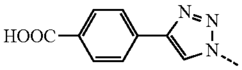 | 240 ± 90 | 110 ± 10 | 1.1 ± 0.1 | 3.0 ± 0.3 | NEU3/ NEU4 | 37 |
| 7i | HO— — | 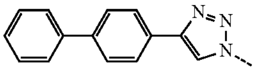 | >500 | 32 ± 5 | 0.70 ± 0.10 | 0.52 ± 0.10 | NEU3/ NEU4 | 45 |
| 7j | HO— — | 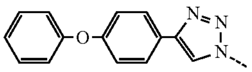 | >500 | 84 ± 24 | 1.0 ± 0.1 | 0.97 ± 0.24 | NEU3/ NEU4 | 84 |
| 8a | 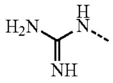 | 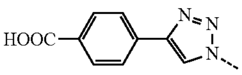 | >500 | 45 ± 5 | 0.61 ± 0.10 | 24 ± 2 | NEU3 | 40 |

TABLE III-continued
IC$_{50}$ data using 4MU-NANA as the substrate
Formula II
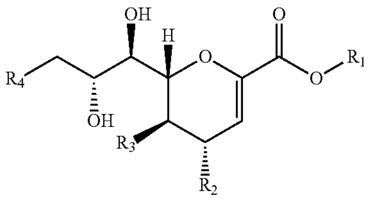
| | | | | | | | | |
|---|---|---|---|---|---|---|---|---|
| 8b | 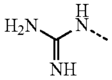 | 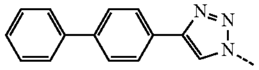 | >500 | 5.9 ± 1.1 | 0.58 ± 0.14 | 5.9 ± 1.4 | NEU3 | 10 |
| 13 | $N_3$— — | 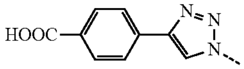 | >500 | >500 | 20 ± 6 | 400 ± 70 | NEU3 | 20 |
| 15 | $H_2N$— — | 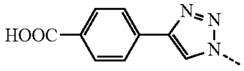 | >500 | >500 | >500 | >500 | NA | NA |
| 18 | 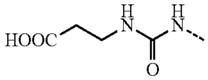 | 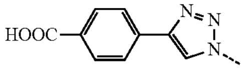 | >500 | 430 ± 300 | >500 | 66 ± 16 | NEU4 | 6 |
| 25a | 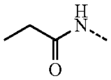 | HO— — | >500 | >500 | >500 | >500 | NA | NA |
| 25b | 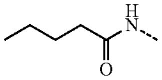 | HO— — | >500 | >500 | >500 | >500 | NA | NA |
| 25c | 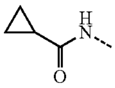 | HO— — | >500 | >500 | >500 | >500 | NA | NA |
| 25d | 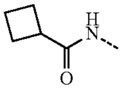 | HO— — | >500 | >500 | >500 | >500 | NA | NA |
| 26 | HO— — | 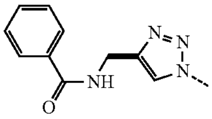 | >500 | 240 ± 50 | 15 ± 1 | 1.1 ± 0.2 | NEU4 | 15 |
| 27 | HO— — | 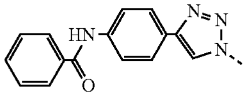 | 190 ± 70 | 110 ± 40 | 2.9 ± 0.2 | 3.7 ± 0.4 | NEU3/ NEU4 | 30 |
| (C9-4HMT-DANA) 28 | HO— — | 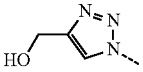 | >500 | >500 | 80 ± 10 | 0.16 ± 0.01 | NEU4 | 500 |
| 58 | HO— — | 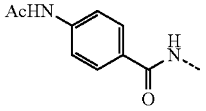 | 1.9 ± 0.4 | 90 ± 20 | 7.2 ± 1.2 | 24 ± 6 | NEU1 | 4 |
| 59 | HO— — | 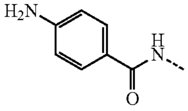 | 29 ± 5 | 190 ± 70 | 31 ± 6 | 210 ± 80 | NEU1/ NEU3 | 6 |

TABLE III-continued
$IC_{50}$ data using 4MU-NANA as the substrate
Formula II
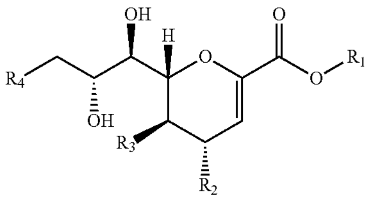
| | | | | | | | | |
|---|---|---|---|---|---|---|---|---|
| 60 | HO— — | 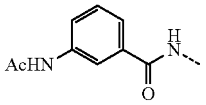 | 6.5 ± 1.1 | 130 ± 10 | 7.1 ± 0.7 | 52 ± 9 | NEU1/ NEU3 | 7 |
| 61 | HO— — | 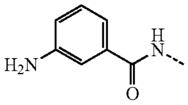 | 6.5 ± 0.7 | 180 ± 40 | 35 ± 6 | 150 ± 40 | NEU1 | 5 |
| 62 | HO— — | 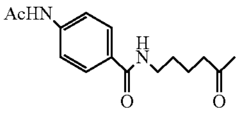 [SMILES: CC(=O)CCCCNC(=O)c1ccc(NC(C)=O)cc1] | 240 ± 70 | 390 ± 80 | 31 ± 5 | 46 ± 13 | NEU3/ NEU4 | 5 |
| 63 | HO— — | 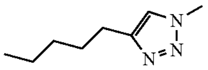 | 77 ± 30 | 450 ± 170 | 6.7 ± 1.2 | 2.6 ± 0.6 | NEU3/ NEU4 | 11 |
$R_2$ (at position C4) is HO— —
| Compound of formula II | Structure: $R_3$ (at position C5) | Structure: $R_4$ (at position C9) | $IC_{50}$ [μM] NEU1 | NEU2 | NEU3 | NEU4 | Target | Selectivity |
|---|---|---|---|---|---|---|---|---|
| 29 | 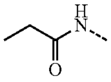 | HO— — | 18 ± 1 | 86 ± 4 | 60 ± 7 | 87 ± 18 | NEU1 | 3 |
| 30 | 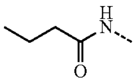 | HO— — | 8.4 ± 0.5 | 40 ± 5 | 15 ± 2 | 8.4 ± 0.4 | NEU1/ NEU4 | 2 |
| 31 | 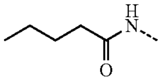 | HO— — | 0.99 ± 0.07 | 33 ± 2 | 140 ± 10 | 110 ± 20 | NEU1 | 33 |
| 32 | 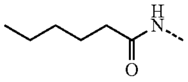 | HO— — | 0.42 ± 0.06 | 15 ± 2 | 210 ± 60 | 440 ± 150 | NEU1 | 36 |
| 33 | 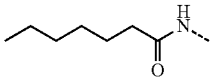 | HO— — | 2.1 ± 0.2 | 37 ± 6 | 210 ± 70 | 470 ± 200 | NEU1 | 18 |
| 34 | 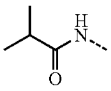 | HO— — | 5.3 ± 0.8 | 170 ± 50 | >500 | 71 ± 17 | NEU1 | 13 |
| 35 | 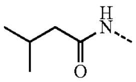 | HO— — | 32 ± 5 | 39 ± 10 | >500 | >500 | NEU1/ NEU2 | 13 |

TABLE III-continued
$IC_{50}$ data using 4MU-NANA as the substrate
Formula II
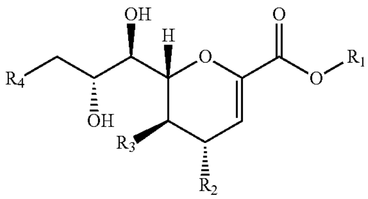
| | | | | | | | | |
|---|---|---|---|---|---|---|---|---|
| 36 | 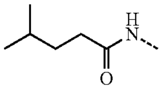 | HO— — | 1.7 ± 0.1 | 7 ± 1 | 150 ± 20 | 370 ± 160 | NEU1 | 4 |
| 37 | 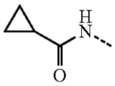 | HO— — | 6.9 ± 0.4 | 220 ± 10 | 170 ± 40 | 150 ± 40 | NEU1 | 32 |
| 38 | 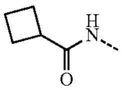 | HO— — | 12 ± 2 | 60 ± 3 | 100 ± 20 | 81 ± 15 | NEU1 | 5 |
| 39 | 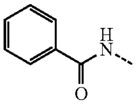 | HO— — | 11 ± 1 | 41 ± 12 | 480 ± 100 | >500 | NEU1 | 3 |
| 40 | 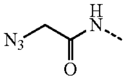 | HO— — | 24 ± 2 | 21 ± 3 | 4.4 ± 0.9 | 5.6 ± 0.8 | NEU3/ NEU4 | 5 |
| 41 | 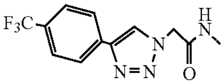 | HO— — | >500 | 50 ± 7 | >500 | 300 ± 60 | NEU2 | 6 |
| 42 | 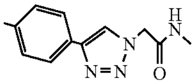 | HO— — | >500 | 3.3 ± 0.3 | >500 | 110 ± 20 | NEU2 | 30 |
| 43 | 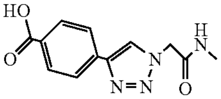 | HO— — | >500 | 180 ± 30 | >500 | 400 ± 160 | NEU2 | NA |
| 44 | 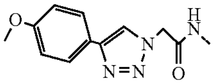 | HO— — | >500 | 13 ± 1 | >500 | 87 ± 14 | NEU2 | 6 |
| 45 | 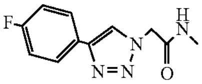 | HO— — | >500 | 4.6 ± 0.3 | 240 ± 40 | 100 ± 20 | NEU2 | 21 |
| 46 | 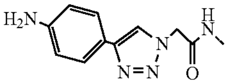 | HO— — | >500 | 4.4 ± 0.3 | 430 ± 100 | 130 ± 20 | NEU2 | 29 |
| 47 | 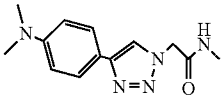 | HO— — | 110 ± 10 | 76 ± 6 | 46 ± 7 | 36 ± 5 | NEU1/ NEU2/ NEU3/ NEU4 | NA |
| 48 | 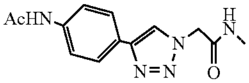 | HO— — | >500 | 20 ± 3 | >500 | >500 | NEU2 | 25 |

TABLE III-continued
$IC_{50}$ data using 4MU-NANA as the substrate
Formula II
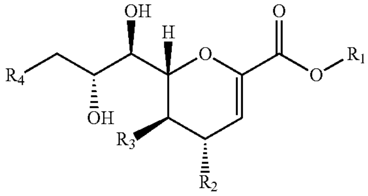
| | | | | | | | | |
|---|---|---|---|---|---|---|---|---|
| 49 | 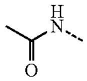 | 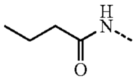 | 4.0 ± 0.5 | >500 | 250 ± 90 | 73 ± 14 | NEU1 | 18 |
| 50 | 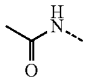 | 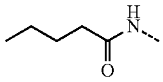 | 3.4 ± 0.2 | >500 | 110 ± 40 | 220 ± 50 | NEU1 | 32 |
| 51 | 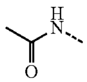 | 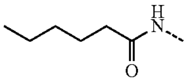 | 2.9 ± 0.2 | >500 | 83 ± 9 | 290 ± 30 | NEU1 | 28 |
| 52 | 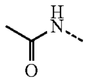 | 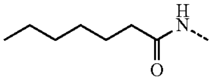 | 9.9 ± 1.3 | 410 ± 110 | 39 ± 8 | 310 ± 30 | NEU1 | 4 |
| 53 | 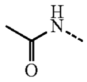 | 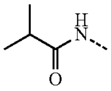 | 250 ± 60 | 220 ± 30 | 96 ± 28 | 230 ± 60 | NA | NA |
| 54 | 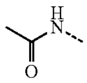 | 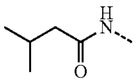 | 2.5 ± 0.3 | 120 ± 20 | 72 ± 20 | 130 ± 40 | NEU1 | 28 |
| 55 | 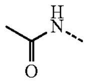 | 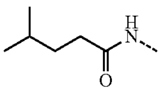 | 3.2 ± 0.3 | 160 ± 40 | 54 ± 6 | 150 ± 50 | NEU1 | 16 |
| 56 | 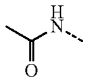 | 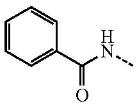 | 2.5 ± 0.3 | >500 | 34 ± 5 | 150 ± 10 | NEU1 | 13 |
| 57 | 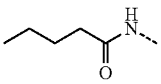 | 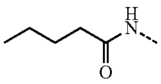 | 1.5 ± 0.2 | 59 ± 26 | >500 | >500 | NEU1 | 39 |
| 64 | 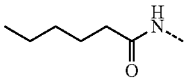 | 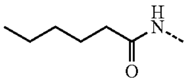 | 4.3 ± 0.8 | 26 ± 6 | >500 | >500 | NEU1 | 6 |
| 65 | 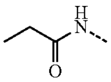 | 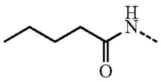 | 1.6 ± 0.2 | 140 ± 30 | >500 | 190 ± 70 | NEU1 | 88 |
| 66 | 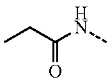 | 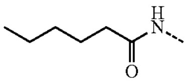 | 1.4 ± 0.2 | 31 ± 8 | 260 ± 70 | 210 ± 90 | NEU1 | 22 |
| 67 | 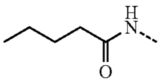 | 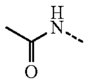 | 0.35 ± 0.03 | 170 ± 70 | >500 | >500 | NEU1 | 486 |

TABLE III-continued $IC_{50}$ data using 4MU-NANA as the substrate

Formula II

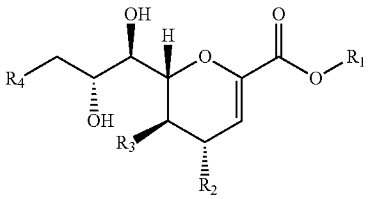

| | | | | | | | | |
|---|---|---|---|---|---|---|---|---|
| 68 | 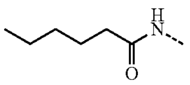 | 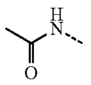 | 0.14 ± 0.01 | 47 ± 14 | >500 | 170 ± 100 | NEU1 | 336 |
| 69 | 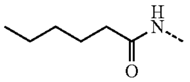 | 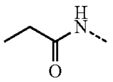 | 0.40 ± 0.10 | 90 ± 10 | >500 | 270 ± 70 | NEU1 | 225 |
| 70 | 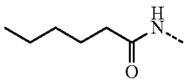 | 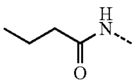 | 1.2 ± 0.1 | 32 ± 4 | >500 | >500 | NEU1 | 27 |
| 72 | 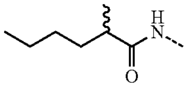 | HO— — | 0.55 ± 0.07 | | | | | |
| 73 | 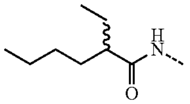 | 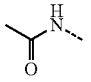 | 1.8 ± 0.2 | | | | | |
| 74 | 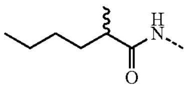 | 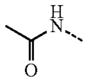 | 0.42 ± 0.07 | | | | | |
| 75 | 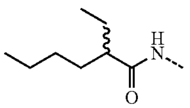 | HO— — | 0.58 ± 0.03 | | | | | |

$R_2$ (at position C4) is $NH_2C(=NH)NH$— —

| Compound of formula II | Structure: $R_3$ (at position C5) | Structure: $R_4$ (at position C9) | $IC_{50}$ [μM] NEU1 | NEU2 | NEU3 | NEU4 | Target | Selectivity |
|---|---|---|---|---|---|---|---|---|
| 71 | 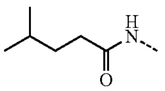 | HO— — | 14 ± 2 | 2.1 ± 0.1 | 150 ± 20 | 47 ± 7 | NEU2 | 7 |

In Table III, the specificity of a compound it designated as dual (bispecific) e.g., Neu3/Neu4, when the ratio of IC50 of this compound against an enzyme over the IC50 of this compound against another enzyme is of about 3 or less. Compounds 72-75 were tested as a mixture of diasteroisomers. All the others are pure compounds of a single stereochemistry.

In Table III, the specificity of a compound it designated as dual (bispecific) e.g., Neu3/Neu4, when the ratio of IC50 of this compound against an enzyme over the IC50 of this compound against another enzyme is of about 3 or less. Compounds 72-75 were tested as a mixture of diastereoisomers. All the others are pure compounds of a single stereochemistry.

The compounds with phenyltriazole groups (7a-j) were significantly more potent against NEU3 and NEU4 than NEU1 and NEU2. Tested compounds with C9-phenyltriazole groups showed single digit IC50 towards NEU3, and compounds with an acidic group (7h) or larger aromatic groups (7i and 7j) were slightly better than compounds with basic groups (7a and 7c) or neutral electron-withdrawing groups (7f). Among all the C9-modified compounds, C9-biphenyltriazole-DANA (7i) was the most potent with $IC_{50}$ of 0.70±0.10 μM and 0.52±0.10 μM towards NEU3 and NEU4, respectively. These activities are at least 40-fold more potent than towards NEU1 and NEU2. The tested library of C4 modifications revealed the importance of the guanidino group. Comparing DANA to Zanamivir (6) finds improved potency for NEU2 (37±6 μM vs 7.8±2.0 μM) and NEU3 (7.7±0.8 μM vs 4.0±0.6 μM), but decreased potency for NEU1 (49±8 μM vs >500 μM) and NEU4 (8.3±1.0 μM vs 47±6 μM). Other compounds with nitrogen-containing functional groups at C4 (13, 15, 18, 25) decreased potency, indicating the necessity of a positively-charged group with reasonable size at C4 for NEU3. Thus, a guanidino group at C4 combined with C9 modification conferred selectivity between NEU3 and NEU4, and gave selective and potent inhibitors for NEU3 like compound 8a and 8b. Compound 8a showed $IC_{50}$ against NEU3 of 0.6±0.1 μM with 40-fold selectivity and compound 8b showed $IC_{50}$ of 0.58±0.14 μM with 10-fold selectivity separately.

The inhibition constants ($K_i$) of selected compounds was then determined (Table IV). The trend of the $K_i$ values is similar to that for the $I_C$H values. Compound 6 (Zanamivir) showed K values as 5.7±1.5 μM, 0.62±0.09 μM, 26±4 μM against NEU2, NEU3 and NEU4 separately, which is more potent than DANA for NEU2 and NEU3, but less potent for NEU4. Compound 7i showed similar $K_i$ values towards NEU3 and NEU4 (0.28±0.04 μM and 0.26±0.04 μM separately) while $K_i$ values of its 4-guanidino derivative (8b) showed more than 13-fold selectivity between NEU3 and NEU4 with 0.28±0.04 μM against NEU3 and 5±1 μM against NEU4.

TABLE IV

| Ki determinations | | | | | | |
|---|---|---|---|---|---|---|
| Compound | $IC_{50}$ [μM] | Selectivity | NEU1[b] | NEU2 | NEU3 $K_i$ [μM] | NEU4 |
| DANA (1) | 8 | NEU3/4; 4× | ND | 25 ± 4 | 1.6 ± 0.3 | 5.8 ± 0.6 |
| Zanamivir (6) | 8 | NEU3/2; 6× | ND | 5.7 ± 1.5 | 0.62 ± 0.09 | 26 ± 4 |

TABLE IV-continued

| Ki determinations | | | | | | |
|---|---|---|---|---|---|---|
| Compound | $IC_{50}$ [μM] | Selectivity | NEU1[b] | NEU2 | NEU3 $K_i$ [μM] | NEU4 |
| 7i | 0.7/ 0.5 | NEU3/4; 45× | ND | 48 ± 9 | 0.28 ± 0.04 | 0.26 ± 0.04 |
| 8b | 0.6 | NEU3; 10× | ND | 17 ± 4 | 0.36 ± 0.04 | 5 ± 1 |
| [a] C9-4HMT-DANA (28) | 0.2 | NEU4; 500× | ND | ND | ND | 0.030 ± 0.02 |
| 31 | 0.99 | NEU1; 33× | Ip | ND | ND | ND |
| 32 | 0.4 | NEU1; 36× | Ip | ND | ND | ND |
| 50 | 3 | NEU1; 32× | Ip | ND | ND | ND |

[a] 9-[4-hydroxymethyl-[1,2,3]triazol-1-yl]-2,3-didehydro-N-acetyl-neuraminic acid (C9-4HMT-DANA (28)), previously reported data from Albohy, 2013.

[b]NEU1 $IC_{50}$ were determined, while $K_i$ measurements were made for compounds with IC50 lower than 2 μM for the given isoenzyme, unless the experiments are in progress. (IP)

[c] Selectivity was calculated from $IC_{50}$ data and compares the activity of the compound for its target isoenzyme relative to its next most active isoenzyme. For samples that target more than one isoenzyme, the largest $IC_{50}$ value was used for the calculation.

The inhibitory effects of selected NEU3 inhibitors were also tested against GM3 cleavage, and the results are shown in Table V. In comparison with DANA, 7i was more potent in inhibiting GM3 cleavage catalyzed by NEU3 (12 ± 2 μM vs 54 ± 10 μM) and NEU4 (3.7 ± 0.7 μM vs 26 ± 8 μM), and 8b was 13-fold more potent than DANA (3.8 ± 0.5 μM vs 54 ± 10 μM).

TABLE V

| Inhibition of GM3 cleavage | | | | | | |
|---|---|---|---|---|---|---|
| Structure | | | $IC_{50}$ [μM] | | | |
| Compound | R at C4 | R at C9 | NEU3 | NEU4 | Rel/NEU3[b] | Rel/NEU4[b] |
| DANA | HO— — | HO— — | 54 ± 10 | 26 ± 8 | | |
| 7i | HO— — | 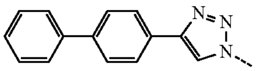 | 12 ± 2 | 3.7 ± 0.7 | 4.1 | 7.0 |
| 8b | 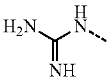 | 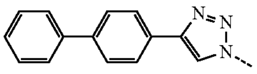 | 3.8 ± 0.5 | | 13 | |
| C9-4HMT-DANA[a] (28) | HO— — | 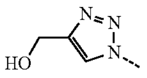 | | 0.74 ± 0.7 | | 351 |

[a]Previously reported in 19.

[b]Relative activity in comparing with DANA

Example 100: Specific Inhibitors Neu1 and Neu3 Reduce Activities of these Enzymes in Mouse Tissues Mouse treatment: Wild-type two months old C57B16 mice received two intraperitoneal injections of the methyl ester form of the Neu1 specific inhibitor compound 50 in saline (30 mg/kg BW, n=3) (solubility ≥1 mg/ml ($H_2O$)), or the methyl ester form of the Neu3 bispecific inhibitor compound 7i in saline containing 2% DMSO (v/v) (1 mg/kg BW, n=3) (solubility 100 μg/ml (2% DMSO)). The two injections were performed 24 hours apart. 17 hours after the second injection, the kidney and spleen were collected. Untreated C57B16 mice (n=2), Neu1 KO (n=2) and Neu3/4 DKO mice (n=2) were used as positive and negative controls for these compounds.

Histochemical Staining of Sialidase Activity in Tissues: Sialidase activity in was analysed in situ using the histochemical substrate X-Neu5Ac: 5-bromo-4-chloroindol-3-yl-alpha-D-N-acetylneuraminic acid and Fast Red Violet B. X-Neu5Ac is hydrolyzed by neuraminidases to release a halogenated product undergoing rapid aerobic oxidation to form the dark blue dye. Conjugate with Fast Red Violet B was used for fluorescence detection.

Figure 10:
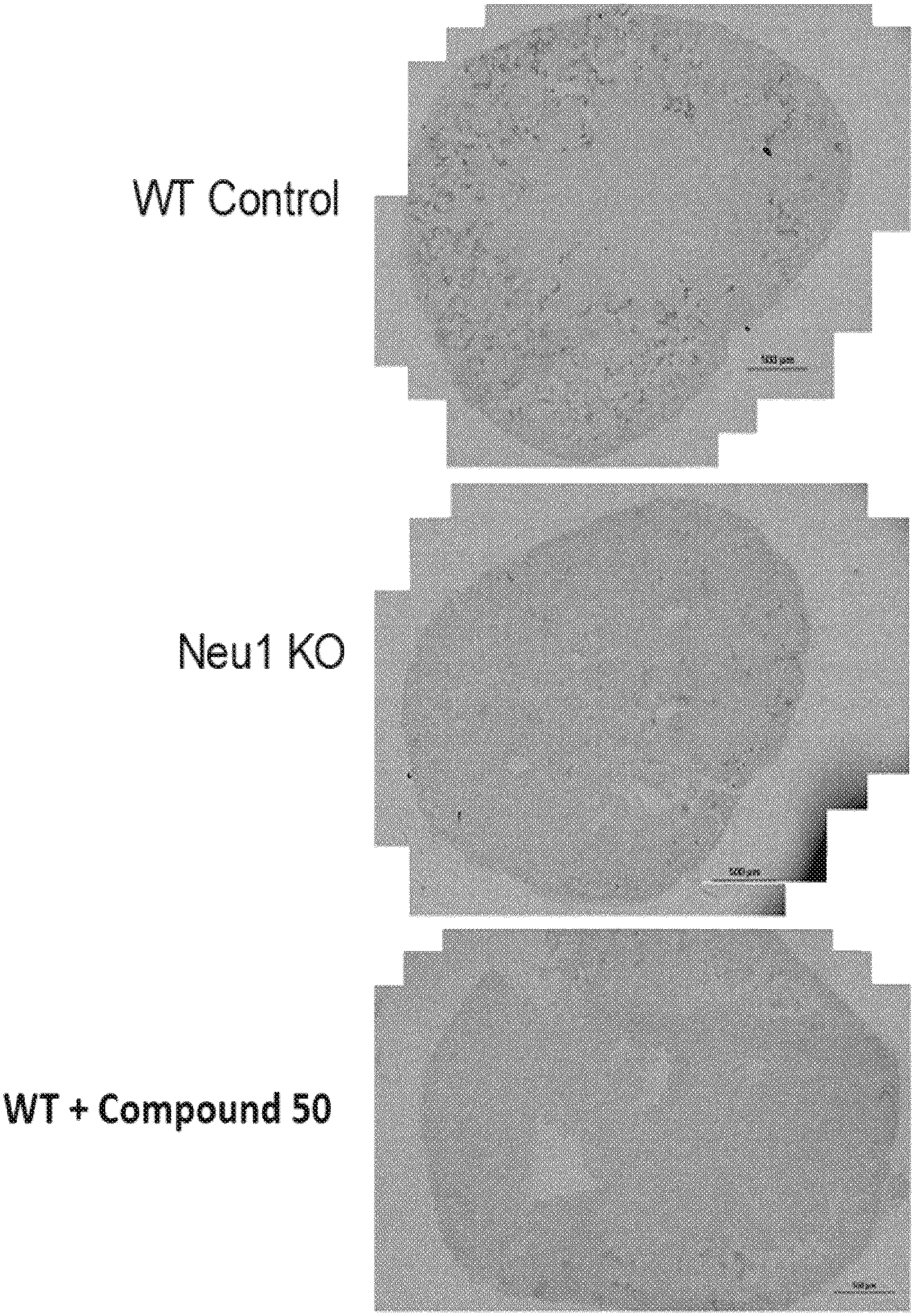
FIG. 10: In vivo treatment of mice with a specific Neu1-inhibitor (compound 50) blocks Neu1 activity in kidney tissues. Four-week-old WT or Neu1 KO mice were injected intraperitoneally with compound 50 (30 mg/kg) or saline for 2 consecutive days. Twenty hours after the last injection mice were sacrificed and their kidney removed and frozen in OCT. Five μm-thick sections were stained with histochemical neuraminidase substrate, X-Neu5Ac.

According to the results of the histochemical assay of neuraminidase activity in the mouse kidney tissues (almost exclusively expressing the Neu1 isoform) the treatment with the methyl ester form of compound 50 resulted in ~90% inhibition of the Neu1 (FIG. 10 showing results with compound 50). According to the results of the histochemical assay of neuraminidase activity in the mouse spleen tissues (almost exclusively expressing the Neu3 and Neu4 isoforms) the treatment with methyl ester form of compound 7i resulted in ~70-80% inhibition of the Neu3 and Neu4.

Example 101: Pharmacological Modulation of Neu1 and Neu3 Reduces Atherosclerosis in ApoE KO Mice The inventors further tested if pharmacological inhibition of Neu1 or Neu3 had a preventive effect on atherogenesis in ApoE mouse model, comparable to genetic inactivation of these enzymes.

In the first experiment, 14-week-old ApoE female mice (n=6 for each group) received intraperitoneal injections of the methyl ester form of compound 50 (30 mg/kg BW) (solubility 1 mg/ml ($H_2O$)) dissolved in saline, or saline only. The methyl ester form of compound 50 was dissolved in saline. The injections were given for 2 weeks: once every 2 days for the first weeks, and then every day for the second week. According to the results of the histochemical assay of neuraminidase activity in the mouse kidney tissues (almost exclusively expressing the Neu1 isoform) such treatment resulted in −70-80% inhibition of the Neu1 (FIG. 10).

At the end of the second week mice were sacrificed and their hearts were removed and embedded in optimal cutting temperature compound (OCT). Aortic root serial sections of 10 μm were collected using a cryostat and stained with Red Oil O to visualize atherosclerotic lesions.

The quantification of the images (FIG. 11B, 2 weeks) showed that the compound 50 2-week treatments significantly reduced the size of atherosclerotic lesions in 16-week-old ApoE KO mice. The lesions were on average reduced to 25% of those in untreated ApoE mice. Importantly treatment did not result in any changes in the mice weight or behaviour. Specific changes known to be associated with toxicity such as bleeding, leukocyte infiltration, or cytoplasmic vacuolation were not observed in the treated mice as compared to untreated animals.

In the second round of testing the Applicants treated 12-week-old $ApoE^{-/-}$ female mice with intraperitoneal injections of the methyl ester form of Compound 50 (C9-BA-DANA) (30 mg/kg BW) as well as the methyl ester form of compound 7i (the inhibitor of NEU3 and NEU4, 1 mg/kg BW saline containing 2% DMSO (solubility 100 μg/ml (2% DMSO)), compound 31 (NEU1 inhibitor, 10 mg/kg BW in saline), of the methyl ester form of compound 31 (NEU3 inhibitor, 1 mg/kg BW in saline solubility 10 mg/ml ($H_2O$). Control mice were injected with saline or 2% DMSO (compound 7i control group). Because the previous study did not identify obvious side effects of systematic 2-week treatment injections were given for 1 month, once every 2 days for the first 2 weeks and then every day for the third and the fourth weeks. At 16 weeks, mice were sacrificed and their hearts were removed and embedded in OCT. Aortic root serial sections of 10 μm were collected and stained with Red Oil O to visualize atherosclerotic lesions.

Figure 11A:
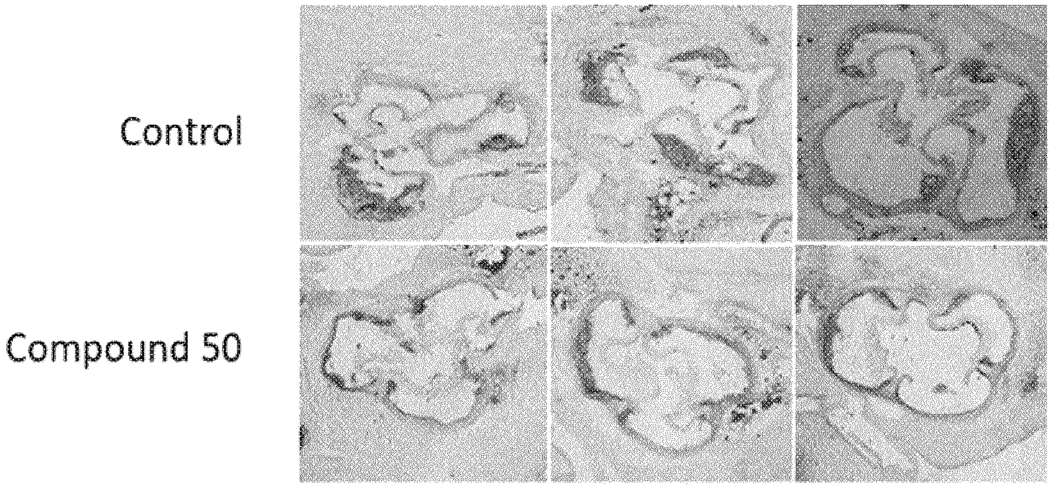
FIGS. 11A-B: Reduced size of fatty streaks in the aortic root of 16-week-old ApoE$^{-/-}$ mice treated for 2 or 4 weeks with a specific neu1 inhibitor (compound 50).
Figure 11B:
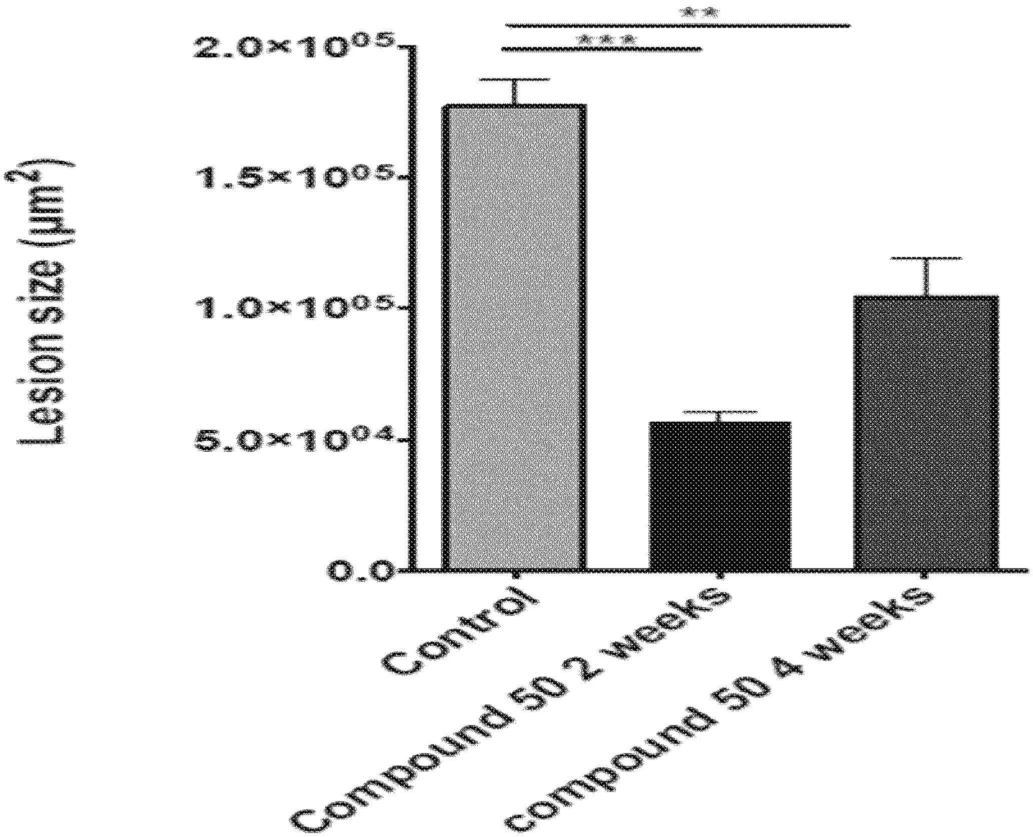
Figure 12A:
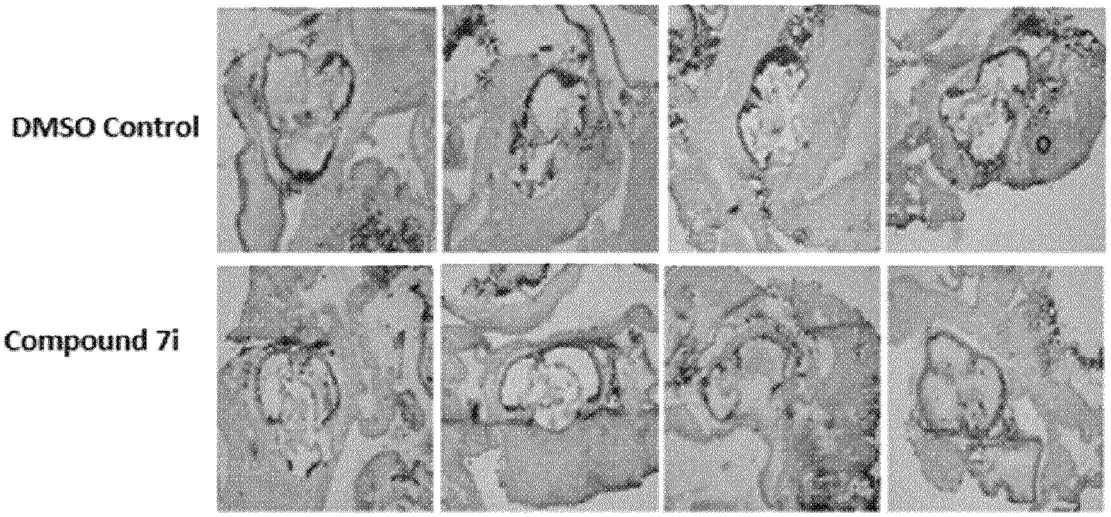
FIGS. 12A-C: Reduced size of fatty streaks in the aortic root of 16-week-old ApoE$^{-/-}$ mice treated for 4 weeks with NEU3/NEU4-bispecific inhibitor compound 7i, NEU1-specific inhibitor compound 31 and NEU3-specific inhibitor compound 8b. Twelve-week-old ApoE KO female mice (r=6) fed normal diet were treated intraperitoneally with compound 7i (1 mg/kg), in 2% DMSO for 4 weeks as described and sacrificed at 16 weeks and with compounds 8b and 31 in saline. Saline-treated and 2% DMSO treated mice were used as controls. Ten-μm serial sections of aortic root were collected using a cryostat and stained with Red Oil O to visualize atherosclerotic lesions.
Figure 12B:
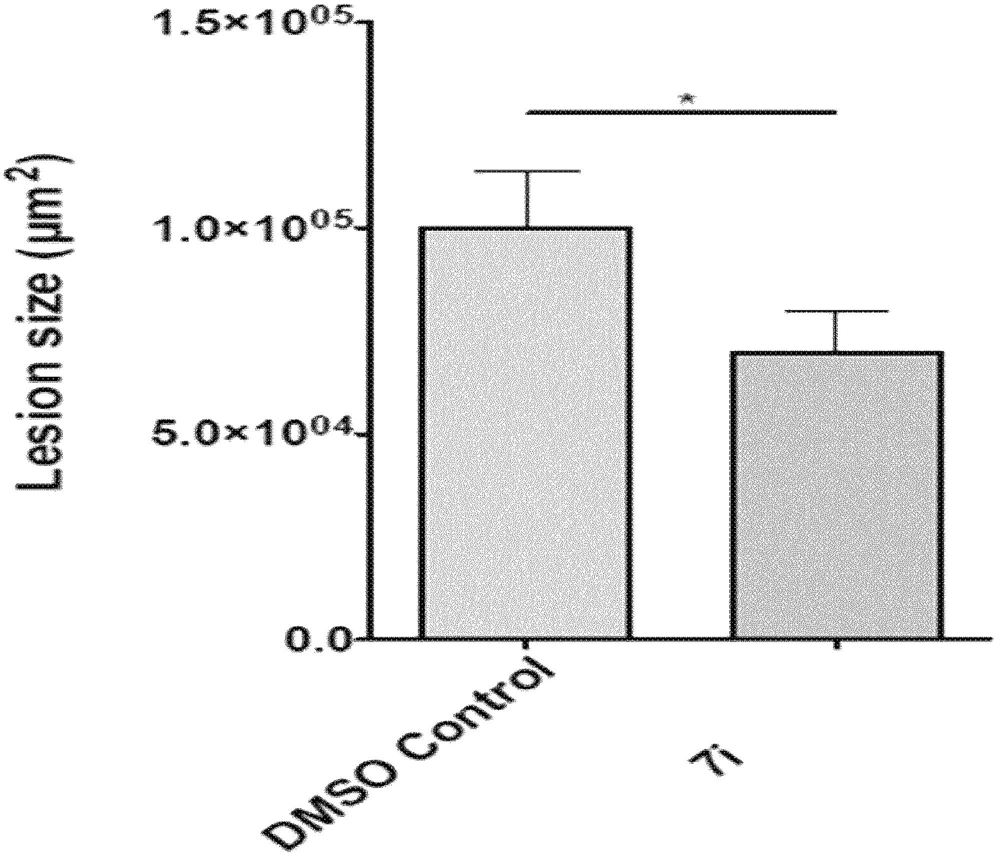
Figure 12C:
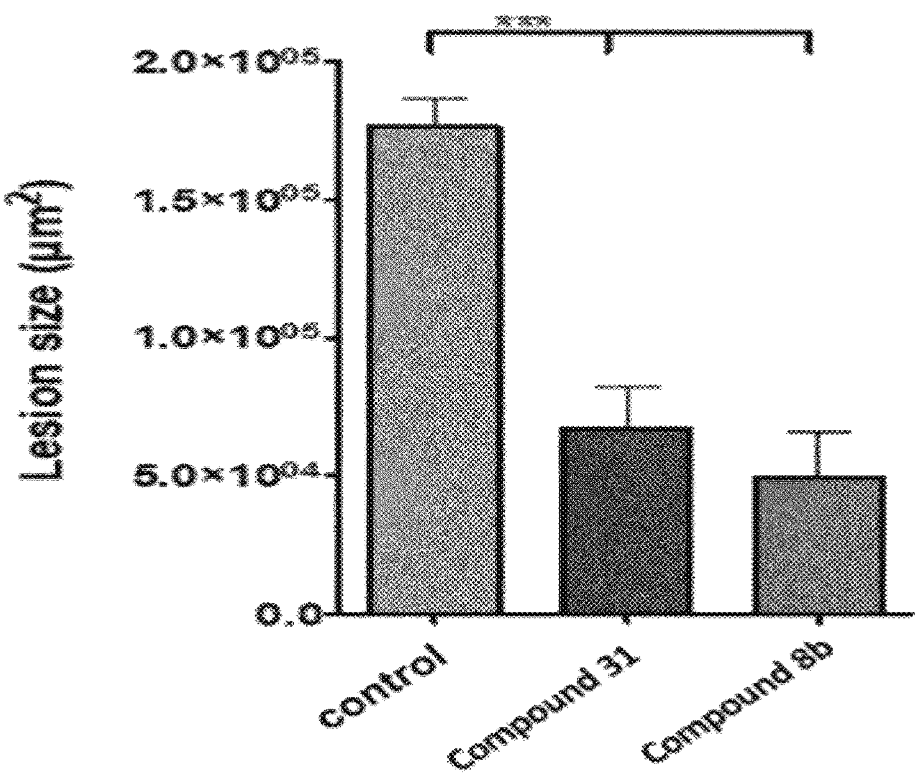
Figure 13A:
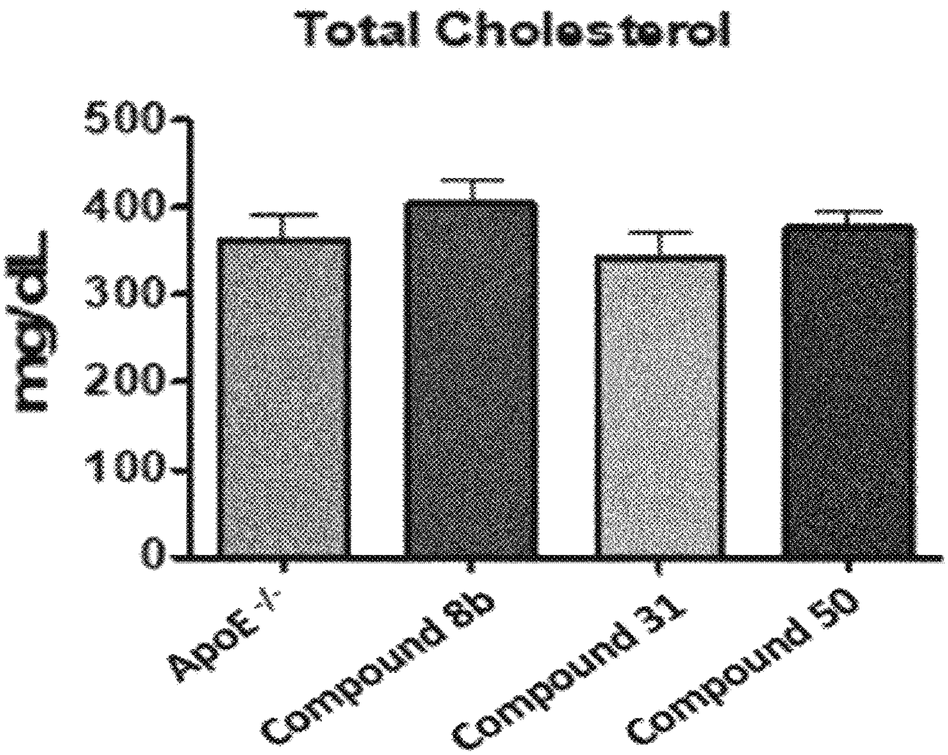
FIGS. 13A-D. Lipid plasma composition of 16-week-old ApoE$^{-/-}$ mice treated for 4 weeks with NEU3-specific inhibitor compound 8b and specific NEU1-specific inhibitors compounds 50 and 31. Total cholesterol (FIG. 13A), triglyceride (FIG. 13B), HDL cholesterol (FIG. 13C) and LDL cholesterol (FIG. 13D) levels were measured in mouse plasma samples. Data represent means±SEM (* significantly different, P<0.05) as compared with ApoE$^{-/-}$ mice.
Figure 13B:
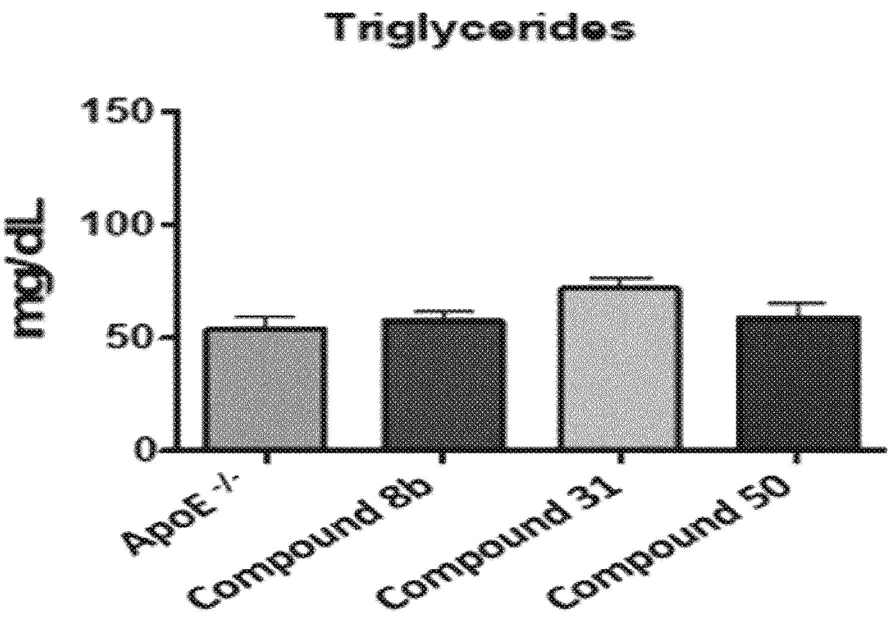
Figure 13C:
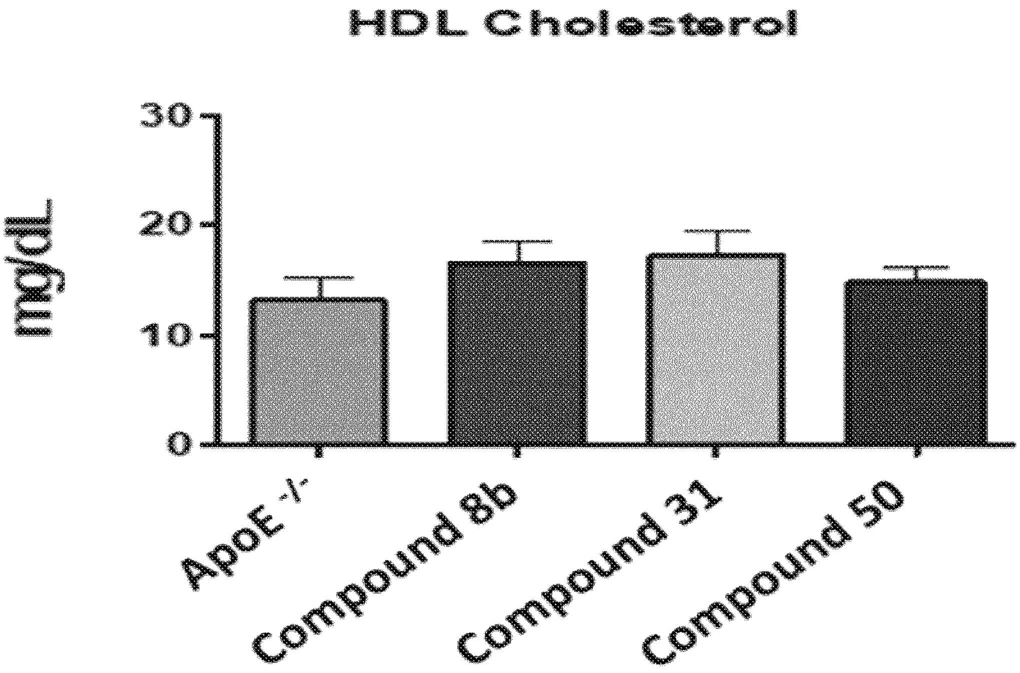
Figure 13D:
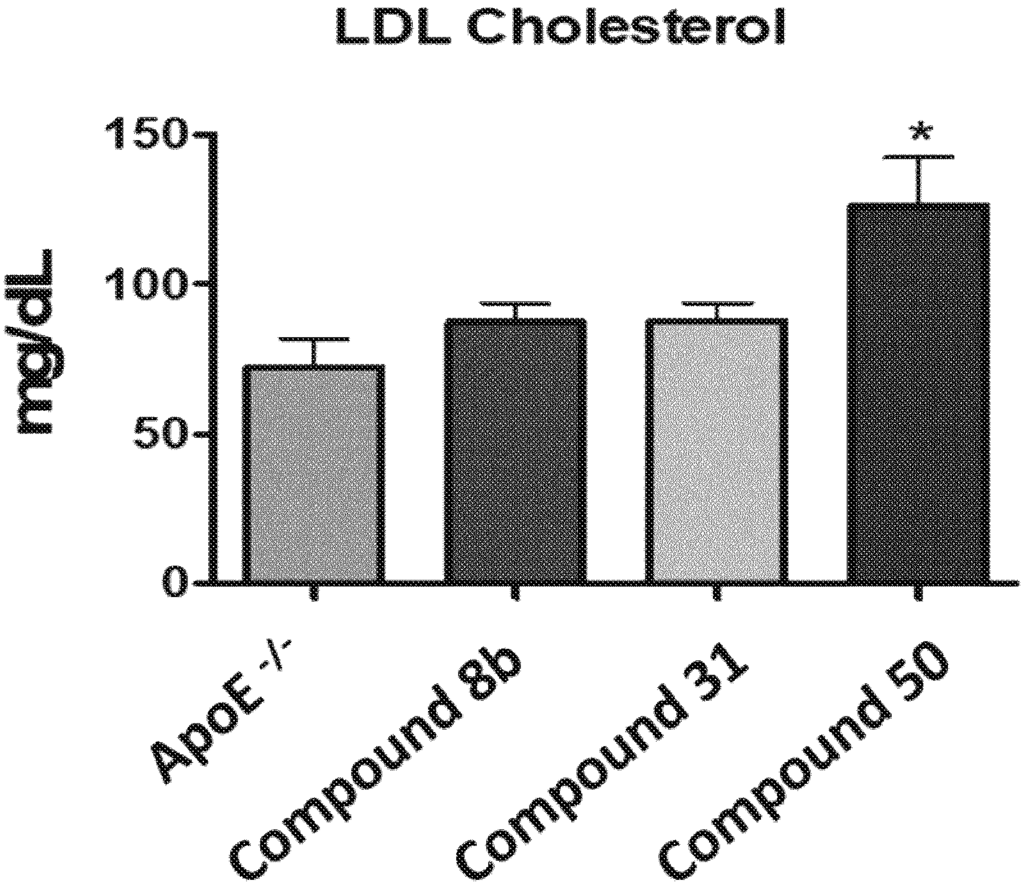

The quantification of the images (FIG. 11B (4 weeks results); 12B and 12C) also showed that all tested inhibitors (i.e. compounds 50, 7i 8b and 31) significantly reduced the size of atherosclerotic lesions in 16-week-old ApoE KO mice as compared with 2%-DMSO treated group. In all cases the lesions were on average reduced to 25-50% of those in untreated ApoE mice. Although 2% DMSO injections also reduced the lesion size the average lesion size in mice injected with 7i was significantly lower even when compared with this group. Importantly, treatment did not result in any changes in the mice weight or behaviour. We also did not see specific changes known to be associated with toxicity such as bleeding, leukocyte infiltration, or cytoplasmic vacuolisation in the treated mice as compared to untreated animals. No specific changes known to be associated with toxicity such as bleeding, leukocyte infiltration, or cytoplasmic vacuolisation were detected in the treated mice as compared to untreated animals. Again, treatment did not either result in any detectable changes in the mice weight or behaviour. Additional testing of NEU1 and NEU3 specific inhibitors in LDLR KO mouse model of atherosclerosis is currently underway.

Example 102: In Vivo Effect of NEU1 Specific Inhibitor on Lipid Composition of $ApoE^{-/-}$ Mice It was then determined whether treatment with the inhibitors changes the lipid composition in the $ApoE^{-/-}$ mice. Similar levels of total cholesterol, LDL cholesterol, HDL-cholesterol or triglycerides were found in treated and untreated mice with the exception of LDL cholesterol which was significantly increased by about 50% only in compound 50 treated group (FIGS. 13A-D). Considering that concentrations and regimens of compound 50 were used that resulted in almost complete inhibition of NEU1 in the tissues, the increase of plasma cholesterol was consistent with the suggestion that the inhibitor blocks desialylation of LDL and its uptake by macrophages thus augmenting its levels in circulation.

To verify this directly LDL cholesterol was measured in the blood plasma of C57BI6 mice and in 3 strains of NEU1-deficient mice: the previously described $CathA^{S190A\text{-}Neo}$ mice with 90% NEU1 deficiency and in two constitutive NEU1 KO strains. The previously described $Neu1^{ENSMUSE141558}$ mouse strain was generated by microinjection in C57BL6J blastocytes of the ES cells with targeted disruption of the Neu1 gene generated by the EUCOMM consortia. The targeted neu1 allele contains LacZ/BactPNeo cassette inserted into the intron 2 of the mouse neu1 gene, resulting in the expression of a fusion protein containing the mouse NEU1 amino acid sequence encoded by the exons 1-2 followed by the bacterial 8-galactosidase encoded by the LacZ gene under the control of the endogenous Neu1 promoter Pan (Pan., 2017). The second strain, Neu1$^{\Delta Ex3}$ was obtained by crossing the Neu1$^{ENSMUSE141558}$ mouse with C57BI6J mice constitutively expressing Cre recombinase resulting in removal of the entire exon 3 from the Neu1 gene. In both strains we detected a complete absence of full-size Neu1 mRNA and NEU1 activity in tissues (not shown).

In the WT C57BI6J mice as expected the LDL levels were at or below detection level (3 mg/dL) (FIG. 14). The CathA$^{S190A\text{-}Neo}$ mice also showed similar levels, but in both Neu1 KO strain were detected significantly increased LDL levels of ~10 mg/dL (FIG. 14). This not only independently confirmed the NEU1-driven uptake of LDL but also established that the safe threshold for inhibition of NEU1 in circulation at 80-90%, since similarly reduced levels in the CathA$^{S190A\text{-}Neo}$ mice significantly delayed the atherogenesis but did not interfere with the LDL level or caused lysosomal storage in tissues.

Example 103: Further In Vivo Testing and Biochemical Characterization

Further in vivo testing in atherosclerosis model animal are underway to determine their cytokine levels, activation markers in macrophages, and immunohistochemistry when they are administered inhibitors of the present invention.

A study of glycosylation changes of ApoB after NEU1 treatment will be performed. A glycolipid analysis will be used to quantify changes to glycolipid content in LDL after NEU treatment. Sialoglycoprotein and ganglioside profiling will be performed in the tissues of mice treated with NEU inhibitors to determine if NEU1 and NEU3 isoenzyme-selective inhibitors lead to significant changes in tissue glycans. Uptake of desLDL treated with beta-galactosidase will be studied. The reaction will be monitored by lectin blot with Gal-specific lectin (PNA).

The scope of the claims should not be limited by the preferred embodiments set forth in the examples, but should be given the broadest interpretation consistent with the description as a whole.

REFERENCES

A. L. Bingham et al, Chem. Commun., 603-604 (2001).

Ahotupa, M., et al., *Lipoprotein-specific transport of circulating lipid peroxides*. Ann Med, 2010. 42 (7): p. 521-9.

Albohy, A.; Zhang, Y.; Smutova, V.; Pshezhetsky, A. V.; Cairo, C. W. *Identification of Selective Nanomolar Inhibitors of the Human Neuraminidase*, NEU4. ACS Med Chem Lett, 2013. 4 (6): p. 532-7.

Albohy, A.; Mohan, S.; Zheng, R. B.; Pinto, B. M.; Cairo, C. W. *Inhibitor selectivity of a new class of oseltamivir analogs against viral neuraminidase over human neuraminidase enzymes*. Bioorg. Med. Chem. Lett., 2011. 19 (9): p. 2817-2822.

Albohy, A., et al., *Insight into substrate recognition and catalysis by the human neuraminidase* 3 (*NEU*3) *through molecular modeling and site-directed mutagenesis*. Glycobiology, 2010. 20 (9): p. 1127-1138.

Albohy, A.; Richards, M. R.; Cairo, C. W. Mapping substrate interactions of the human membrane-associated neuraminidase, NEU3, using STD NMR. *Glycobiology* 2015, 25, 284-293.

Allain et al. (Clin. Chem. 20, 470 (1974))

Arnold, K.; Bordoli, L.; Kopp, J.; Schwede, T. The SWISS-MODEL workspace: a web-based environment for protein structure homology modelling. *Bioinformatics* 2006, 22, 195-201.

Avogadro: an open-source molecular builder and visualization tool., Version 1.1.1, http://avogadro.openmolecules.net/; 2012.

Bartlett A L, Grewal T, De Angelis E, Myers S, Stanley K K. Role of the macrophage galactose lectin in the uptake of desialylated LDL. Atherosclerosis 2000; 153:219-30.

Bentzon, J. F., et al., *Mechanisms of plaque formation and rupture*. Circ Res, 2014. 114 (12): p. 1852-66.

Berendsen, H. J. C.; Postma, J. P. M.; Gunsteren, W. F. v.; DiNola, A.; Haak, J. R. Molecular dynamics with coupling to an external bath. *J. Chem. Phys.* 1984, 81, 3684-3690.

Biasini, M.; Bienert, S.; Waterhouse, A.; Arnold, K.; Studer, G.; Schmidt, T.; Kiefer, F.; Cassarino, T. G.; Bertoni, M.; Bordoli, L.; Schwede, T. SWISS-MODEL: modelling protein tertiary and quaternary structure using evolutionary information. *Nucleic Acids Res.* 2014, 42, W252-W258.

Bordoli, L.; Kiefer, F.; Arnold, K.; Benkert, P.; Battey, J.; Schwede, T. Protein structure homology modeling using SWISS-MODEL workspace. *Nat. Protocols* 2008, 4, 1-13.

Caira M. et al, J. Pharmaceutical Sci., 93(3), 601-611 (2004).

Case, D. A.; Berryman, J. T.; Betz, R. M.; Cerutti, D. S.; T. E. Cheatham III; Darden, T. A.; Duke, R. E.; Giese, T. J.; Gohlke, H.; Goetz, A. W.; Homeyer, N.; Izadi, S.; Janowski, P.; Kaus, J.; Kovalenko, A.; Lee, T. S.; LeGrand, S.; Li, P.; Luchko, T.; Luo, R.; Madej, B.; Merz, K. M.; Monard, G.; Needham, P.; Nguyen, H.; Nguyen, H. T.; Omelyan, I.; Onufriev, A.; Roe, D. R.; Roitberg, A.; Salomon-Ferrer, R.; Simmerling, C. L.; Smith, W.; Swails, J.; Walker, R. C.; Wang, J.; Wolf, R. M.; Wu, X.; York, D. M.; Kollman, P. A. *AMBER* 15, University of California: San Francisco, C A, 2015.

Chavas, L. M. G., Kato, R., McKimm-Breschkin, J., Colman, P. M., Fusi, P., Tringali, C., Venerando, B., Tettamanti, G., Monti, E., Wakatsuki, S. Crystal Structure of the Human Sialidase Neu2 in Complex with Zanamivir Inhibitor (PDB ID: 2FOZ). 2006.

Chavas, L. M. G.; Tringali, C.; Fusi, P.; Venerando, B.; Tettamanti, G.; Kato, R.; Monti, E.; Wakatsuki, S. Crystal structure of the human cytosolic sialidase Neu2—Evidence for the dynamic nature of substrate recognition. *J. Biol. Chem.* 2005, 280, 469-475.

de Geest, N., et al., *Systemic and neurologic abnormalities distinguish the lysosomal disorders sialidosis and galactosialidosis in mice*. Hum Mol Genet, 2002. 11 (12): p. 1455-64.

E. C. van Tonder et al, AAPS Pharm Sci Tech., 5(1), article 12 (2004).

Gayral, S., et al., *Elastin-derived peptides potentiate atherosclerosis through the immune Neu*1*-PI3Kgamma pathway*. Cardiovasc Res, 2014. 102 (1): p. 118-27.

Grewal T, Bartlett A, Burgess J W, Packer N H, Stanley K K. Desialylated LDL uptake in human and mouse macrophages can be mediated by a lectin receptor. Atherosclerosis 1996; 121:151-63.

Guo, T.; Datwyler, P.; Demina, E.; Richards, M. R.; Ge, P.; Zou, C.; Zheng, R.; Fougerat, A.; Pshezhetsky, A. V.; Ernst, B.; Cairo, C. W. *Selective Inhibitors of Human Neuraminidase* 3. *J. Med. Chem.* 2018, 61, 1990-2008.

Hanwell, M. D.; Curtis, D. E.; Lonie, D. C.; Vandermeersch, T.; Zurek, E.; Hutchison, G. R. Avogadro: an advanced semantic chemical editor, visualization, and analysis platform. *J. Cheminform.* 2012, 4, 17.

Hornak, V.; Abel, R.; Okur, A.; Strockbine, B.; Roitberg, A.; Simmerling, C. Comparison of multiple Amber force fields and development of improved protein backbone parameters. *Proteins* 2006, 65, 712-725.

Hsu D K, Yang R Y, Pan Z, et al. *Targeted disruption of the galectin*-3 *gene results in attenuated peritoneal inflammatory responses*. Am J Pathol 2000; 156:1073-83.

Jakalian, A.; Bush, B. L.; Jack, D. B.; Bayly, C. I. Fast, efficient generation of high-quality atomic charges. AM1-BCC model: I. Method. *J. Comput. Chem.* 2000, 21, 132-146.

Jawien, J., P. Nastalek, and R. Korbut, *Mouse models of experimental atherosclerosis*. J Physiol Pharmacol, 2004. 55 (3): p. 503-17.

Jorgensen, W. L.; Chandrasekhar, J.; Madura, J. D.; Impey, R. W.; Klein, M. L. Comparison of simple potential functions for simulating liquid water. *J. Chem. Phys.* 1983, 79, 926-935.

Kalanuria, A. A., P. Nyquist, and G. Ling, *The prevention and regression of atherosclerotic plaques: emerging treatments*. Vasc Health Risk Manag, 2012. 8: p. 549-61.

Keys, A., *Coronary heart disease in seven countries*. 1970. Nutrition, 1997. 13 (3): p. 250-2; discussion 249, 253.

Kiefer, F.; Arnold, K.; Künzli, M.; Bordoli, L.; Schwede, T. The SWISS-MODEL Repository and associated resources. *Nucleic Acids Res.* 2009, 37, D387-D392.

Knibbs, R. N., et al., *Characterization of the carbohydrate binding specificity of the leukoagglutinating lectin from Maackia amurensis. Comparison with other sialic acid-specific lectins*. J Biol Chem, 1991. 266 (1): p. 83-8.

Levy, E., et al., *Mechanisms of hypercholesterolaemia in glycogen storage disease type I: defective metabolism of low density lipoprotein in cultured skin fibroblasts*. Eur J Clin Invest, 1990. 20 (3): p. 253-60.

Lozano, R., et al., *Global and regional mortality from* 235 *causes of death for* 20 *age groups in* 1990 *and* 2010*: a systematic analysis for the Global Burden of Disease Study* 2010. Lancet, 2012. 380 (9859): p. 2095-128.

Lusis, A. J., *Atherosclerosis*. Nature, 2000. 407 (6801): p. 233-41.

Magesh, S., et al., *Design, synthesis, and biological evaluation of human sialidase inhibitors. Part* 1*: Selective inhibitors of lysosomal sialidase* (*NEU*1). Bioorganic & Medicinal Chemistry Letters, 2008. 18 (2): p. 532-537.

Markely, L. R. A.; Ong, B. T.; Hoi, K. M.; Teo, G.; Lu, M. Y.; Wang, D. I. C. A high-throughput method for quantification of glycoprotein sialylation. Anal. Biochem. 2010, 407, 128-133.

Martin, M. J., et al., *Serum cholesterol, blood pressure, and mortality: implications from a cohort of* 361,662 *men*. Lancet, 1986. 2 (8513): p. 933-6.

Meager, A., *Cytokine regulation of cellular adhesion molecule expression in inflammation*. Cytokine Growth Factor Rev, 1999. 10 (1): p. 27-39.

Meir, K. S. and E. Leitersdorf, *Atherosclerosis in the apolipoprotein-E-deficient mouse: a decade of progress*. Arterioscler Thromb Vasc Biol, 2004. 24 (6): p. 1006-14.

Packard, R. R. and P. Libby, *Inflammation in atherosclerosis: from vascular biology to biomarker discovery and risk prediction*. Clin Chem, 2008. 54 (1): p. 24-38.

Pan X, De Aragao C B P, Velasco-Martin J P, et al. *Neuraminidases* 3 *and* 4 *regulate neuronal function by catabolizing brain gangliosides*. FASEB J 2017; 31:3467-83.

Pettersen, E. F.; Goddard, T. D.; Huang, C. C.; Couch, G. S.; Greenblatt, D. M.; Meng, E. C.; Ferrin, T. E. UCSF Chimera—A visualization system for exploratory research and analysis. *J. Comput. Chem.* 2004, 25, 1605-1612.

Pilatte, Y., J. Bignon, and C. R. Lambre, *Sialic acids as important molecules in the regulation of the immune system: pathophysiological implications of sialidases in immunity*. Glycobiology, 1993. 3 (3): p. 201-18.

Pitas, R. E., et al., *Acetoacetylated lipoproteins used to distinguish fibroblasts from macrophages in vitro by fluorescence microscopy*. Arteriosclerosis, 1981. 1 (3): p. 177-85.

Potier, M.-C.; Mameli, L.; Belisle, M.; Dallaire, L.; Melancon, S. B. Fluorometric assays of neuraminidase with a sodium (4-methylumbellifery-α-D-N-Acetylneuraminate) substrate. *Anal. Biochem.* 1979, 94, 287-296.

Pshezhetsky, A. V.; Potier, M. Association of N-acetylgalactosamine-6-sulfate sulfatase with the multienzyme lysosomal complex of 8-galactosidase, cathepsin A, and neuraminidase: possible implication for intralysosomal catabolism of keratan sulfate. *J. Biol. Chem.* 1996, 271 (45), 28359-28365.

Pshezhetsky, A. V. and L. I. Ashmarina, *Desialylation of surface receptors as a new dimension in cell signaling*. Biochemistry (Mosc), 2013. 78 (7): p. 736-45.

Resource for Biocomputing, Visualization, and Informatics, *UCSF Chimera*, candidate version 1.11; University of California, San Francisco (supported by NIGMS P41-GM103311), 2016.

Roe, D. R.; Cheatham, T. E. PTRAJ and CPPTRAJ: Software for Processing and Analysis of Molecular Dynamics Trajectory Data. *J. Chem. Theory Comput.* 2013, 9, 3084-3095.

Roeschlau et al. (J. Clin. Chem. Clin. Biochem, 12, 226 (1974))

Ryckaert, J.-P.; Ciccotti, G.; Berendsen, H. J. C. Numerical integration of the cartesian equations of motion of a system with constraints: molecular dynamics of n-alkanes. *J. Comput. Phys.* 1977, 23, 327-341.

Šali, A.; Blundell, T. L. Comparative Protein Modelling by Satisfaction of Spatial Restraints. *J. Mol. Biol.* 1993, 234, 779-815.

Seyrantepe, V., et al., *Enzymatic activity of lysosomal carboxypeptidase* (*cathepsin*) *A is required for proper elastic fiber formation and inactivation of endothelin*-1. Circulation, 2008b. 117(15): p. 1973-81.

Seyrantepe, V., et al., *Mice deficient in Neu*4 *sialidase exhibit abnormal ganglioside catabolism and lysosomal storage*. Hum Mol Genet, 2008a. 17(11): p. 1556-68.

Shibuya, N., et al., *The elderberry* (*Sambucus nigra L.*) *bark lectin recognizes the Neu5Ac*(*alpha* 2-6)*Gal/GalNAc sequence*. J Biol Chem, 1987. 262 (4): p. 1596-601.

Shidmoossavee, F. S.; Watson, J. N.; Bennet, A. J. Chemical insight into the emergence of influenza virus strains that are resistant to Relenza. *J. Am. Chem. Soc.* 2013, 135, 13254-13257.

Sin, Y. M.; Sedgwick, A. D.; Chea, E. P.; Willoughby, D. A Mast cells in newly formed lining tissue during acute inflammation: A six day air pouch model in the mouse.

Annals of the Rheumatic Diseases 1986, 45, 873.Smutova, V., et al., *Structural basis for substrate specificity of mammalian neuraminidases*. PLoS One, 2014. 9 (9): p. e106320.

Spitz, C., et al., *Regulatory T cells in atherosclerosis: critical immune regulatory function and therapeutic potential*. Cell Mol Life Sci, 2016. 73 (5): p. 901-22.

Staudinger, H.; Meyer, J. Über neue organische Phosphorverbindungen III. Phosphinmethylenderivate and Phosphinimine. *Helvetica Chimica Acta* 1919, 2, 635-646.

Steinbrecher, U. P., et al., *Decrease in reactive amino groups during oxidation or endothelial cell modification of LDL. Correlation with changes in receptor-mediated catabolism*. Arteriosclerosis, 1987. 7 (2): p. 135-43.

Swiss Institute of Bioinformatics. SWISS-MODEL. https://swissmodel.expasy.org/interactive (7/8/2016).

von Itzstein, M.; Wu, W.-Y.; Jin, B. The synthesis of 2,3-didehydro-2,4-dideoxy-4-guanidinyl-N-acetyl-neuraminic acid: a potent influenza virus sialidase inhibitor. *Carbohydr. Res.* 1994, 259, 301-305.

von Itzstein, M.; Wu, W.-Y.; Kok, G. B.; Pegg, M. S.; Dyason, J. C.; Jin, B.; Phan, T. V.; Smythe, M. L.; White, H. F.; Oliver, S. W.; Colman, P. M.; Varghese, J. N.; Ryan, D. M.; Woods, J. M.; Bethell, R. C.; Hotham, V. J.; Cameron, J. M.; Penn, C. R. Rational design of potent sialidase-based inhibitors of influenza virus replication. *Nature* 1993, 363, 418-423.

Wang, J.; Wolf, R. M.; Caldwell, J. W.; Kollman, P. A.; Case, D. A. Development and testing of a general amber force field. *J. Comput. Chem.* 2004, 25, 1157-1174.

Warner, T. G.; O'Brien, J. S. Synthesis of 2'-(4-methylumbelliferyl)-.alpha.-D-N-acetylneuraminic acid and detection of skin fibroblast neuraminidase in normal humans and in sialidosis. *Biochemistry* 1979, 18, 2783-2787.

Weber, C., A. Zernecke, and P. Libby, *The multifaceted contributions of leukocyte subsets to atherosclerosis: lessons from mouse models*. Nat Rev Immunol, 2008. 8 (10): p. 802-15.

Yamaguchi, K., et al., *Reduced susceptibility to colitis-associated colon carcinogenesis in mice lacking plasma membrane-associated sialidase*. PLoS One, 2012. 7 (7): p. e41132.

Yang, Z.; Lasker, K.; Schneidman-Duhovny, D.; Webb, B.; Huang, C. C.; Pettersen, E. F.; Goddard, T. D.; Meng, E. C.; Šali, A.; Ferrin, T. E. UCSF Chimera, MODELLER, and IMP: An integrated modeling system. *J. Struct. Biol.* 2012, 179, 269-278.

Yang W H, Aziz P V, Heithoff D M, Mahan M J, Smith J W, Marth J D. *An intrinsic mechanism of secreted protein aging and turnover*. Proc Natl Acad Sci USA 2015; 112:13657-62.

Yu, X. H., et al., *Foam cells in atherosclerosis*. Clin Chim Acta, 2013.424: p. 245-52.

Zhang, Y.; Albohy, A.; Zou, Y.; Smutova, V.; Pshezhetsky, A. V.; Cairo, C. W. Identification of selective inhibitors for human neuraminidase isoenzymes using C4,C7-modified 2-deoxy-2,3-didehydro-N-acetylneuraminic acid (DANA) analogues. *J. Med. Chem.,* 2013. 56 (7): p. 2948-2958.

Zou, Y.; Albohy, A.; Sandbhor, M.; Cairo, C. W. Inhibition of human neuraminidase 3 (NEU3) by C9-triazole derivatives of 2,3-didehydro-N-acetyl-neuraminic acid. *Bioorg. Med. Chem. Lett.* 2010, 20, 7529-7533.

The invention claimed is:

1. A compound of formula I (I)

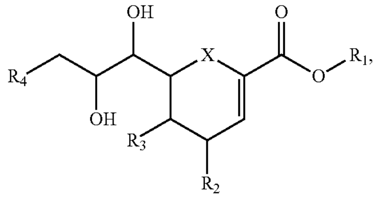

wherein $R_1$ is H, a C1-C10 alkyl, C2-C10 heteroalkyl; C3-C7 cycloalkyl; C3-C7 heterocycloalkyl; C6-C8 aryl; or C3-C8 heteroaryl; wherein the alkyl, heteroalkyl, cycloalkyl, heterocycloalkyl, aryl and heteroaryl are optionally substituted by at least one substituent, each substituent being independently a C1-C10 alkyl, a C3-C8 cycloalkyl, C6-C7 aryl, a halogen, an amide or a hydroxyl;

$R_2$ is H; —OH; —NHC(═NH)$NH_2$; azide; or —NHC(O)R;

wherein R is —$NH(CH_2)_m$COOH, wherein m is 1, 2 or 3;

$R_3$ is —NHC(O)$(CH_2)$n$R_5$, wherein $R_5$ is H; —OH; C1-C10 alkyl; C2-C10 heteroalkyl; C3-C7 cycloalkyl; C3-C7 heterocycloalkyl; C6-C8 aryl; C3-C8 heteroaryl; or

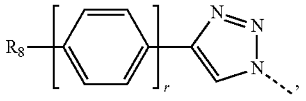

wherein the alkyl, heteroalkyl, cycloalkyl, heterocycloalkyl, aryl and heteroaryl are optionally substituted by at least one substituent, each substituent being independently a C1-C10 alkyl; a C3-C8 cycloalkyl; C6-C7 aryl; a halogen; a —C(O)OH; an amide; or a hydroxyl;

$R_a$ is a trifluoromethyl, a C1-C10 alkyl, a —C(O)OH, a —O—C1-C10 alkyl, a halogen, an amine, or —NH-acetamido; and r is 0, 1, 2 or 3; and n is 0 to 7;

$R_4$ is H; —OH; —O-alkyl; —C(O)-alkyl-NHC(O)-aryl; —NHC(O)$R_6$; or

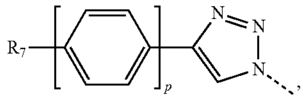

wherein the alkyl and aryl are optionally substituted by at least one substituent, each substituent being independently a C1-C10 alkyl, a C3-C8 cycloalkyl, C6-C7 aryl, a halogen, an amine, an amide or a hydroxyl, and wherein:

$R_6$ is H, C1-C10 alkyl; or C6-C7 aryl, wherein the C1-C10 alkyl and C6-C7 aryl are optionally substituted by at least one substituent, each substituent being independently a C1-C10 alkyl, a C3-C8 cycloalkyl, a C6-C7 aryl, a halogen, an amide, an amine or a hydroxyl;

$R_7$ is H; halogen; —O-alkyl; —C(O)OH; amine; amide; —C1-C10 alkyl; O—C6-C7 aryl; or —$(CH_2)$qNH(CO)aryl, wherein q is 0 or 1; and p is 0, 1, 2 or 3; and X is O or $CH_2$, or an ester, solvate, hydrate or pharmaceutical salt thereof, with the proviso that:

when $R_2$ and $R_4$ are —OH, $R_3$ is not —NHC(═O)$CH_3$, —NHC(═O)$CH_2CH_3$, —NHC(═O)$(CH_2)_2CH_3$, —NHC(═O)$CH(CH_3)_2$, —NHC(═O)$CH_2CH(CH_3)_2$, —NHC(═O)cyclopropyl, —NHC(═O)cyclobutyl, or —NHC(═O)phenyl;

when $R_2$ is —OH and $R_3$ is —NHC(═O)$CH_3$, $R_4$ is not -1,2,3-triazolyl-$CH_2OH$, —NHC(═O)$(CH_2)_2CH_3$, —NHC(═O)$(CH_2)_3CH_3$, —NHC(═O)$CH(CH_3)_2$, —NHC(═O)$CH_2CH(CH_3)_2$, or —NHC(═O)phenyl;

when $R_3$ is —NHC(═O)$CH_3$ and $R_4$ is OH, $R_2$ is not —NHC(═NH)$NH_2$ or azide;

when $R_2$ is —NHC(═NH)$NH_2$ and $R_3$ is —NHC(O)$(CH_2)_nR_5$, where n=1 and $R_5$═C1-C10 alkyl or n=0 and $R_5$═C6-C8 aryl, $R_4$ is not OH;

and when $R_3$ is —NHC(═O)$CF_3$ and $R_4$ is OH, $R_2$ is not —NHC(═NH)$NH_2$.

2. The compound or ester, solvate, hydrate or pharmaceutical salt thereof of claim 1, with the further proviso that:

when $R_3$ is —NHC(═O)$CH_3$, $R_2$ is —OH, and $R_4$ is

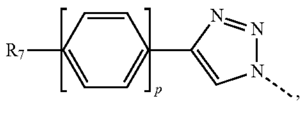

$R_7$ is not —N$(CH_3)_2$, —NHC(═O)$CH_3$, —$NH_2$, —$CH_3$, —$OCH_3$, F, —$CF_3$, or —C(═O)OH.

3. The compound or ester, solvate, hydrate or pharmaceutical salt thereof of claim 1, wherein $R_3$ is —NHC(O)$(CH_2)$n$R_5$.

4. The compound or ester, solvate, hydrate or pharmaceutical salt thereof of claim 3, wherein $R_5$ is cycloalkyl, aryl, C1-C10 alkyl, or C1-C10 alkyl substituted with a C1-C10 alkyl.

5. The compound or ester, solvate, hydrate or pharmaceutical salt thereof of claim 1, wherein n is 1 and wherein $R_5$ is H, straight or branched C1-C5 alkyl, heteroaryl, or

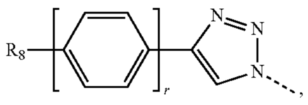

wherein $R_8$ is —$CF_3$, —$CH_3$, —C(═O)OH, —$OCH_3$, F, —$NH_2$, —N$(CH_3)_2$, or —NHC(═O)$CH_3$.

6. The compound or ester, solvate, hydrate or pharmaceutical salt thereof of claim 5, wherein r is 1.

7. The compound or ester, solvate, hydrate or pharmaceutical salt thereof of claim 1, wherein $R_2$ is OH, —NHC(═NH)$NH_2$, azido, —NHC(O)R or —NH$(CH_2)_m$C(O)OH, wherein m is 1, 2 or 3.

8. The compound or ester, solvate, hydrate or pharmaceutical salt thereof of claim 1, wherein $R_4$ is —OH or —NHC(O)$R_6$.

9. The compound or ester, solvate, hydrate or pharmaceutical salt thereof of claim 8, wherein $R_6$ is straight or branched C1-C10 alkyl or, C6-C7 aryl, wherein the C6-C7 aryl is optionally substituted with an amine or an amide.

10. The compound or ester, solvate, hydrate or pharmaceutical salt thereof of claim 1, wherein $R_4$ is

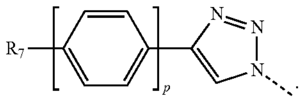

11. The compound or ester, solvate, hydrate or pharmaceutical salt thereof of claim 10, wherein p is 0 and $R_7$ is —$(CH_2)$qNH(CO)aryl or C1-C10 alkyl.

12. The compound or ester, solvate, hydrate or pharmaceutical salt thereof of claim 10, wherein p is 1 and $R_7$ is halogen, O-alkyl, —C(O)OH, amine, acetamide, C1-C10 alkyl, $CH_2$NH(CO)aryl, or —O—C6-C7 aryl.

13. The compound or ester, solvate, hydrate or pharmaceutical salt thereof of claim 10, wherein p is 2 and $R_7$ is H.

14. The compound or ester, solvate, hydrate or pharmaceutical salt thereof of claim 1, wherein $R_4$ is —C(O)-alkyl-NHC(O)-aryl.

15. The compound or ester, solvate, hydrate or pharmaceutical salt thereof of claim 14, wherein the alkyl is C1-C10 alkyl and the aryl is C6-C7 aryl, which is optionally substituted with an amide.

16. The compound of claim 1, wherein:

(i) $R_3$ is —NHC(O)$(CH_2)_nR_5$, wherein n is 0 to 7 and wherein $R_5$ is C1-C10 alkyl, C3-C7 cycloalkyl, C6-C8 aryl, wherein the alkyl, cycloalkyl, and aryl are optionally substituted by at least one substituent, each substituent being independently a C1-C10 alkyl, a C3-C8 cycloalkyl, C6-C7 aryl, a halogen, an amide or a hydroxyl;

(ii) $R_2$ is —OH, —NHC(═NH)$NH_2$ or azide; and (iii) $R_4$ is —OH; —NHC(O)$R_6$, wherein $R_6$ is C1-C10 alkyl; —$(CH_2)$qNH(CO)aryl, wherein q is 0 or 1; or

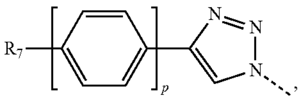

wherein p is 0, 1, 2 or 3, and $R_7$ is H, —C(═O)OH, phenyl, or phenyloxy, with the proviso that:

when $R_2$ and $R_4$ is —OH, $R_3$ is not —NHC(═O)$CH_3$, —NHC(═O)$CH_2CH_3$, —NHC(═O)$(CH_2)_2CH_3$, —NHC(═O)CH$(CH_3)_2$, —NHC(═O)$CH_2$CH$(CH_3)_2$, —NHC(═O)cyclopropyl, —NHC(═O)cyclobutyl, or —NHC(═O)phenyl;

when $R_2$ is —OH and $R_3$ is —NHC(═O)$CH_3$, $R_4$ is not —NHC(═O)$(CH_2)_2CH_3$, —NHC(═O)$(CH_2)_3CH_3$, —NHC(═O)CH$(CH_3)_2$, —NHC(═O)$CH_2$CH$(CH_3)_2$, or —NHC(═O)phenyl; and when $R_3$ is —NHC(═O)$CH_3$ and $R_4$ is OH, $R_2$ is not —NHC(═NH)$NH_2$, or wherein:

(i) $R_3$ is —NHC(O)$(CH_2)$n$CH_3$, wherein n is 0 to 7;

(ii) $R_2$ is —OH or —NHC(═NH)$NH_2$; and (iii) $R_4$ is —OH; —NHC(O)$R_6$, wherein $R_6$ is C6-C7 aryl or C1-C10 alkyl; or

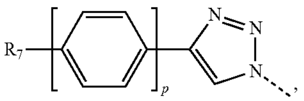

wherein p is 1, 2 or 3, and $R_7$ is H, —C(═O)OH, phenyl, or phenyloxy.

17. The compound or ester, solvate, hydrate or pharmaceutical salt thereof of claim 1, wherein X is O.

18. The compound or ester, solvate, hydrate or pharmaceutical salt thereof of claim 1, wherein $R_1$ is H or alkyl.

19. The compound of claim 1, wherein the compound is of formula I, wherein X is O, $R_1$ is H, and $R_3$, $R_2$ and $R_4$ are as set forth below:

| R₃ (at position C5) is $CH_3C(O)NH$— — | | |
|---|---|---|
| compound | $R_2$ (at position C4) | $R_4$ (at position C9) |
| 7a | HO— — | 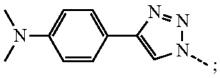 |
| 7b | HO— — | 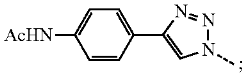 |
| 7c | HO— — | 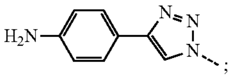 |
| 7d | HO— — | 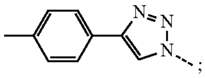 |
| 7e | HO— — | 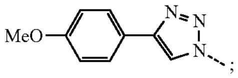 |
| 7f | HO— — | 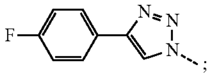 |
| 7g | HO— — | 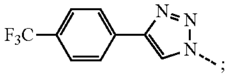 |
| 7h | HO— — | 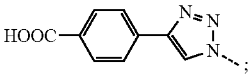 |
| 7i | HO— — | 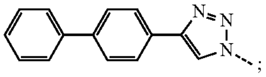 |
| 7j | HO— — | 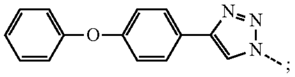 |
| 8a | 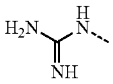 | 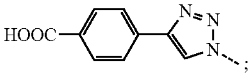 |
| 8b | 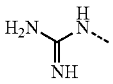 | 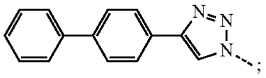 |
| 13 | $N_3$— — | 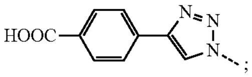 |
| 18 | 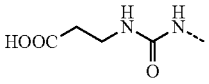 | 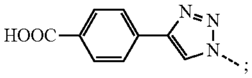 |
| 26 | HO— — | 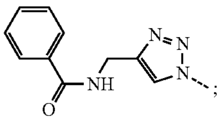 |
| 27 | HO— — | 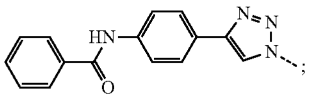 |

-continued
| | | |
|---|---|---|
| 58 | HO— — | 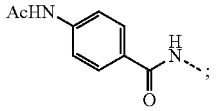 |
| 59 | HO— — | 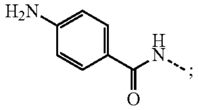 |
| 60 | HO— — | 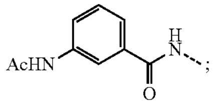 |
| 61 | HO— — | 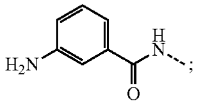 |
| 62 | HO— — | 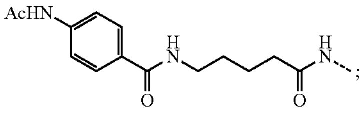 |
| 63 | HO— — | 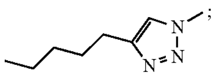 |
$R_2$ (at position C4) is HO— —
| compound | $R_3$ (at position C5) | $R_4$ (at position C9) |
|---|---|---|
| 31 | 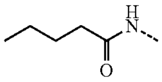 | HO— —; |
| 32 | 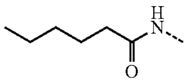 | HO— —; |
| 33 | 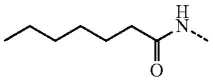 | HO— —; |
| 36 | 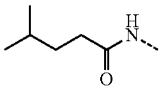 | HO— —; |
| 40 | 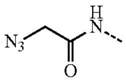 | HO— —; |
| 41 | 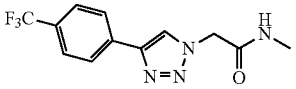 [SMILES: CNC(=O)Cn1cc(-c2ccc(C(F)(F)F)cc2)nn1] | HO— —; |
| 42 | 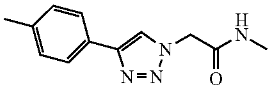 | HO— —; |
| 43 | 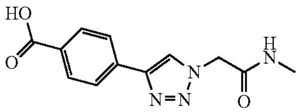 [SMILES: CNC(=O)Cn1cc(-c2ccc(C(=O)O)cc2)nn1] | HO— —; |

-continued
| | | |
|---|---|---|
| 44 | 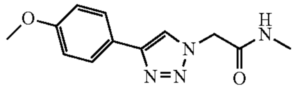 | HO— —; |
| 45 | 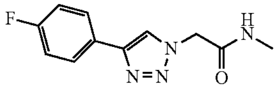 [SMILES: CNC(=O)Cn1cc(-c2ccc(F)cc2)nn1] | HO— —; |
| 46 | 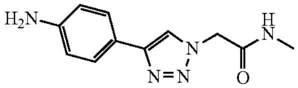 [SMILES: CNC(=O)Cn1cc(-c2ccc(N)cc2)nn1] | HO— —; |
| 47 | 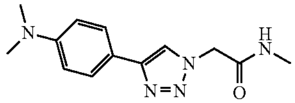 | HO— —; |
| 48 | 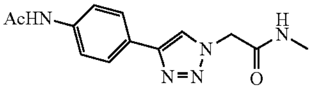 [SMILES: CNC(=O)Cn1cc(-c2ccc(NC(C)=O)cc2)nn1] | HO— —; |
| 51 | 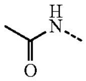 | 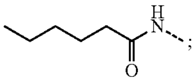 |
| 52 | 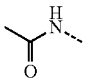 | 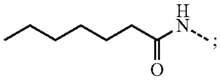 |
| 55 | 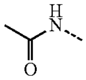 | 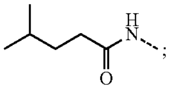 |
| 57 | 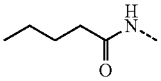 | 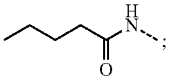 |
| 64 | 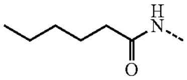 | 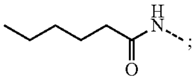 |
| 65 | 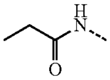 | 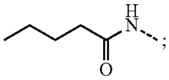 |
| 66 | 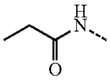 | 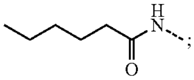 |
| 67 | 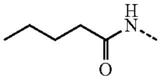 | 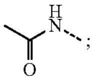 |
| 68 | 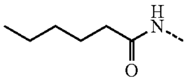 | 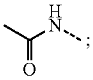 |
| 69 | 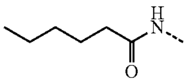 | 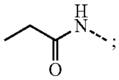 |
| 70 | 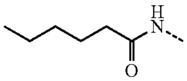 | 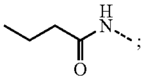 |

-continued
| | | |
|---|---|---|
| 72 | 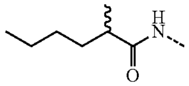 | HO— —; |
| 73 | 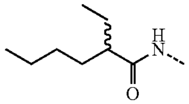 | 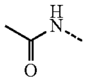 ; |
| 74 | 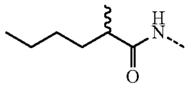 | 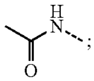 ; or |
| 75 | 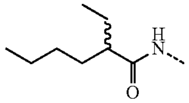 | HO— —; |
or an ester, solvate, hydrate or pharmaceutical salt thereof.
20. The compound of claim 1, wherein $R_3$, $R_2$ and $R_4$ are as set forth below:
| $R_3$ (at position C5) is $CH_3C(O)NH$— — | | |
|---|---|---|
| compound | $R_2$ (at position C4) | $R_4$ (at position C9) |
| 7i | HO— — | 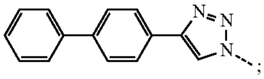 ; |
| 7j | HO— — | 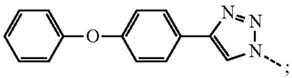 ; |
| 8a | 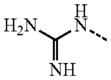 | 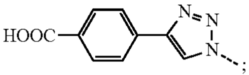 ; |
| 8b | 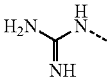 | 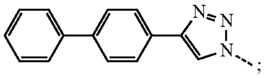 ; |
| 13 | $N_3$— — | 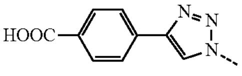 ; |
| 15 | $H_2N$— — | 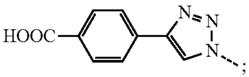 ; |
| 18 | 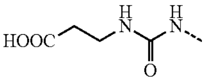 | 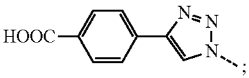 ; |
| 26 | HO— — | 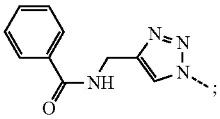 ; |
| 27 | HO— — | 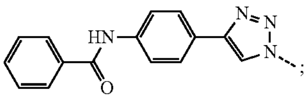 ; |

-continued
| | | |
|---|---|---|
| 58 | HO— — | 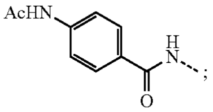 |
| 59 | HO— — | 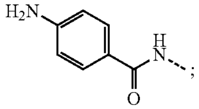 |
| 60 | HO— — | 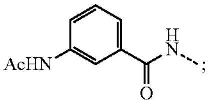 |
| 61 | HO— — | 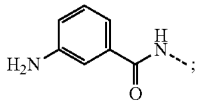 |
| 62 | HO— — | 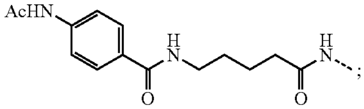 |
| 63 | HO— — | 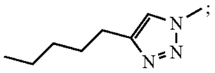 |
$R_2$ (at position C4) is HO— —
| compound | $R_3$ (at position C5) | $R_4$ (at position C9) |
|---|---|---|
| 31 | 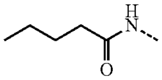 | HO— —; |
| 32 | 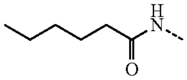 | HO— —; |
| 33 | 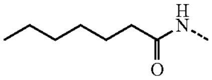 | HO— —; |
| 36 | 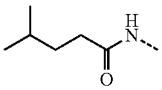 | HO— —; |
| 40 | 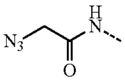 | HO— —; |
| 41 | 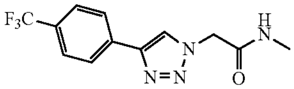 [SMILES: CNC(=O)Cn1cc(-c2ccc(C(F)(F)F)cc2)nn1] | HO— —; |
| 42 | 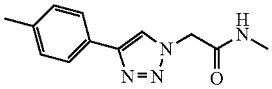 | HO— —; |
| 43 | 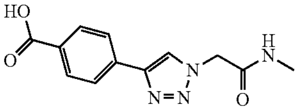 [SMILES: CNC(=O)Cn1cc(-c2ccc(C(=O)O)cc2)nn1] | HO— —; |

-continued
| | | |
|---|---|---|
| 44 | 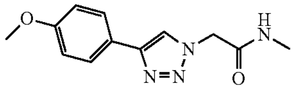 | HO— —; |
| 45 | 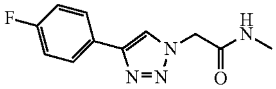 [SMILES: CNC(=O)Cn1cc(-c2ccc(F)cc2)nn1] | HO— —; |
| 46 | 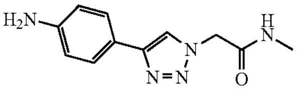 [SMILES: CNC(=O)Cn1cc(-c2ccc(N)cc2)nn1] | HO— —; |
| 47 | 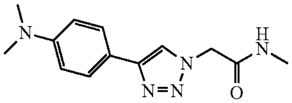 | HO— —; |
| 48 | 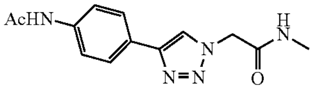 [SMILES: CNC(=O)Cn1cc(-c2ccc(NC(C)=O)cc2)nn1] | HO— —; |
| 51 | 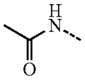 | 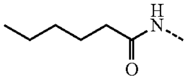; |
| 52 | 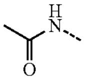 | 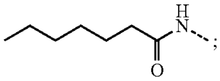; |
| 55 | 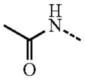 | 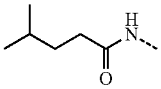; |
| 57 | 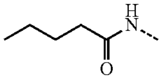 | 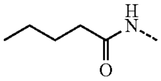, |
| 64 | 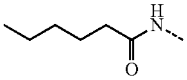 | 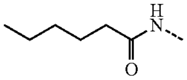; |
| 65 | 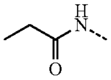 | 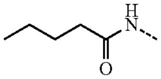; |
| 66 | 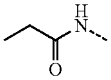 | 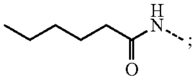; |
| 67 | 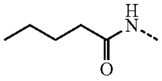 | 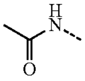; |
| 68 | 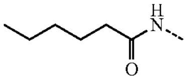 | 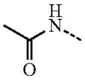; |
| 69 | 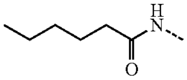 | 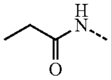; |
| 70 | 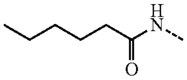 | 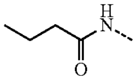; |

-continued

| | | |
|---|---|---|
| 72 | 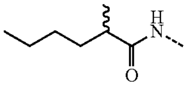 | HO— —; |
| 73 | 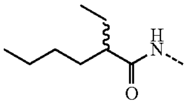 | 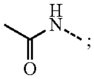 |
| 74 | 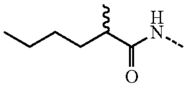 | 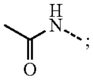 or |
| 75 | 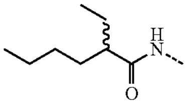 | HO— —; |

or an ester, solvate, hydrate or pharmaceutical salt thereof.

21. The compound of claim 1, wherein the compound is of formula I, wherein X is O, $R_1$ is H, and $R_3$, $R_2$ and $R_4$ are as set forth below:

| $R_3$ (at position C5) is $CH_3C(O)NH$— — | | |
|---|---|---|
| compound | $R_2$ (at position C4) | $R_4$ (at position C9) |
| 7h | HO— — | 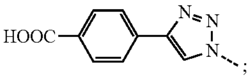 |
| 7i | HO— — | 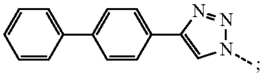 |
| 7j | HO— — | 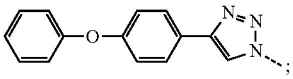 |
| 8a | 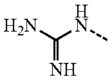 | 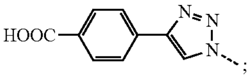 |
| 8b | 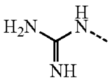 | 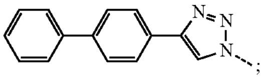 |
| 58 | HO— — | 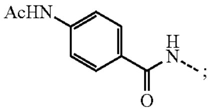 |

| $R_2$ (at position C4) is HO— — | | |
|---|---|---|
| compound | $R_3$ (at position C5) | $R_4$ (at position C9) |
| 31 | 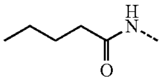 | HO— —; |
| 32 | 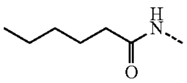 | HO— —; |

-continued

| | | |
|---|---|---|
| 33 | 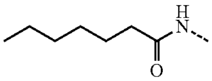 | HO— —; |
| 36 | 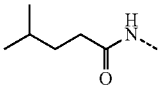 | HO— —; |
| 51 | 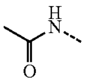 | 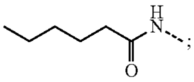 |
| 57 | 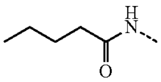 | 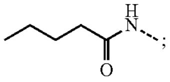 |
| 65 | 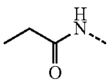 | 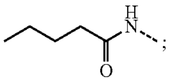 |
| 66 | 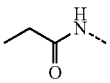 | 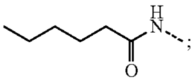 |
| 67 | 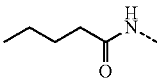 | 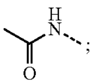 |
| 68 | 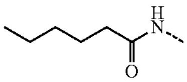 | 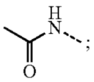 |
| 69 | 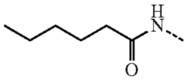 | 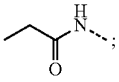 |
| 70 | 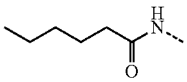 | 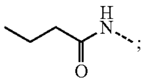 |

-continued

| | | |
|---|---|---|
| 72 | 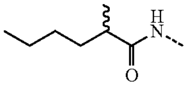 | HO— —; |
| 73 | 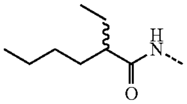 | 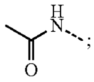 |
| 74 | 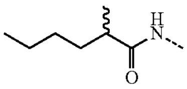 | 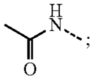 or |
| 75 | 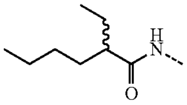 | HO— —, |

or an ester, solvate, hydrate or pharmaceutical salt thereof.

22. The compound of claim 1, wherein the compound is of formula I, wherein X is O, $R_1$ is H, and $R_3$, $R_2$ and $R_4$ are as set forth below:

| $R_3$ (at position C5) is $CH_3C(O)NH$— — | | |
|---|---|---|
| compound | $R_2$ (at position C4) | $R_4$ (at position C9) |
| 7i | HO— — | 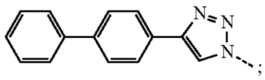 |
| 7j | HO— — | 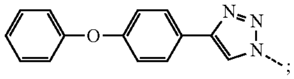 |
| 8a | 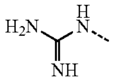 | 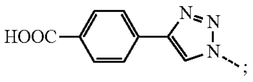 |
| 8b | 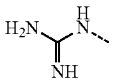 | 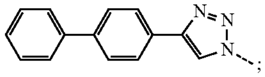 |
| 58 | HO— — | 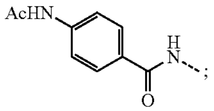 |

| $R_2$ (at position C4) is HO— — | | |
|---|---|---|
| compound | $R_3$ (at position C5) | $R_4$ (at position C9) |
| 31 | 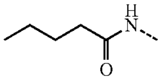 | HO— —; |
| 32 | 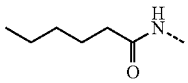 | HO— —; |
| 33 | 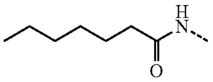 | HO— —; |
| 36 | 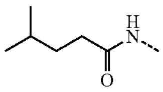 | HO— —; |
| 51 | 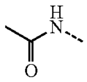 | 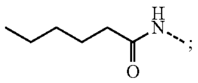 |
| 57 | 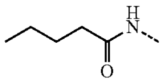 | 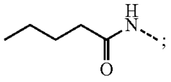 |
| 65 | 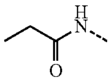 | 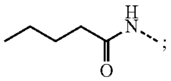 |
| 66 | 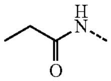 | 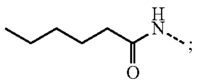 |
| 67 | 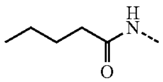 | 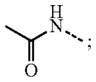 |
| 68 | 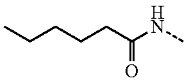 | 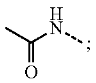 |
| 69 | 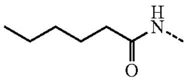 | 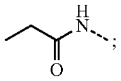 |
| 70 | 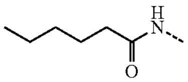 | 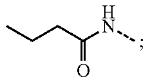 |
| 72 | 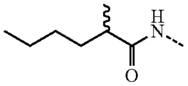 | HO— —; |
| 73 | 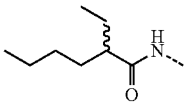 | 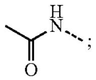 |
| 74 | 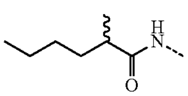 | 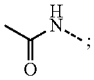 or |
| 75 | 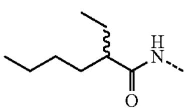 | HO— —, |

or an ester, solvate, hydrate or pharmaceutical salt thereof.

23. The compound of claim 1, wherein the compound is of formula Ia or Ib:
(Ia)
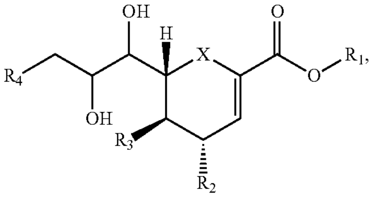
(Ib)
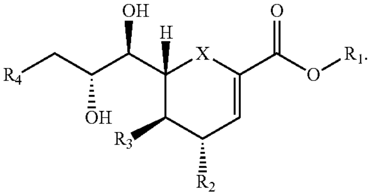
24. A pharmaceutical composition comprising the compound, ester, solvate, hydrate or pharmaceutical salt thereof defined in claim 1 and a pharmaceutically acceptable carrier.
* * * * *

SEQUENCE LISTING

```
<160> NUMBER OF SEQ ID NOS: 8

<210> SEQ ID NO 1
<211> LENGTH: 415
<212> TYPE: PRT
<213> ORGANISM: Homo sapiens

<400> SEQUENCE: 1

Met Thr Gly Glu Arg Pro Ser Thr Ala Leu Pro Asp Arg Arg Trp Gly
1               5                   10                  15

Pro Arg Ile Leu Gly Phe Trp Gly Gly Cys Arg Val Trp Val Phe Ala
            20                  25                  30

Ala Ile Phe Leu Leu Leu Ser Leu Ala Ala Ser Trp Ser Lys Ala Glu
        35                  40                  45

Asn Asp Phe Gly Leu Val Gln Pro Leu Val Thr Met Glu Gln Leu Leu
    50                  55                  60

Trp Val Ser Gly Arg Gln Ile Gly Ser Val Asp Thr Phe Arg Ile Pro
65                  70                  75                  80

Leu Ile Thr Ala Thr Pro Arg Gly Thr Leu Leu Ala Phe Ala Glu Ala
                85                  90                  95

Arg Lys Met Ser Ser Ser Asp Glu Gly Ala Lys Phe Ile Ala Leu Arg
            100                 105                 110

Arg Ser Met Asp Gln Gly Ser Thr Trp Ser Pro Thr Ala Phe Ile Val
        115                 120                 125

Asn Asp Gly Asp Val Pro Asp Gly Leu Asn Leu Gly Ala Val Val Ser
    130                 135                 140

Asp Val Glu Thr Gly Val Val Phe Leu Phe Tyr Ser Leu Cys Ala His
```

-continued

```
145                 150                 155                 160

Lys Ala Gly Cys Gln Val Ala Ser Thr Met Leu Val Trp Ser Lys Asp
                165                 170                 175

Asp Gly Val Ser Trp Ser Thr Pro Arg Asn Leu Ser Leu Asp Ile Gly
            180                 185                 190

Thr Glu Val Phe Ala Pro Gly Pro Gly Ser Gly Ile Gln Lys Gln Arg
        195                 200                 205

Glu Pro Arg Lys Gly Arg Leu Ile Val Cys Gly His Gly Thr Leu Glu
    210                 215                 220

Arg Asp Gly Val Phe Cys Leu Leu Ser Asp Asp His Gly Ala Ser Trp
225                 230                 235                 240

Arg Tyr Gly Ser Gly Val Ser Gly Ile Pro Tyr Gly Gln Pro Lys Gln
                245                 250                 255

Glu Asn Asp Phe Asn Pro Asp Glu Cys Gln Pro Tyr Glu Leu Pro Asp
            260                 265                 270

Gly Ser Val Val Ile Asn Ala Arg Asn Gln Asn Asn Tyr His Cys His
        275                 280                 285

Cys Arg Ile Val Leu Arg Ser Tyr Asp Ala Cys Asp Thr Leu Arg Pro
    290                 295                 300

Arg Asp Val Thr Phe Asp Pro Glu Leu Val Asp Pro Val Val Ala Ala
305                 310                 315                 320

Gly Ala Val Val Thr Ser Ser Gly Ile Val Phe Phe Ser Asn Pro Ala
                325                 330                 335

His Pro Glu Phe Arg Val Asn Leu Thr Leu Arg Trp Ser Phe Ser Asn
            340                 345                 350

Gly Thr Ser Trp Arg Lys Glu Thr Val Gln Leu Trp Pro Gly Pro Ser
        355                 360                 365

Gly Tyr Ser Ser Leu Ala Thr Leu Glu Gly Ser Met Asp Gly Glu Glu
    370                 375                 380

Gln Ala Pro Gln Leu Tyr Val Leu Tyr Glu Lys Gly Arg Asn His Tyr
385                 390                 395                 400

Thr Glu Ser Ile Ser Val Ala Lys Ile Ser Val Tyr Gly Thr Leu
                405                 410                 415


<210> SEQ ID NO 2
<211> LENGTH: 380
<212> TYPE: PRT
<213> ORGANISM: Homo sapiens

<400> SEQUENCE: 2

Met Ala Ser Leu Pro Val Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110
```

-continued

```
Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Ile Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Cys Ala Tyr Ser Asp
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln
    370                 375                 380


<210> SEQ ID NO 3
<211> LENGTH: 428
<212> TYPE: PRT
<213> ORGANISM: Homo sapiens

<400> SEQUENCE: 3

Met Glu Glu Val Thr Thr Cys Ser Phe Asn Ser Pro Leu Phe Arg Gln
1               5                   10                  15

Glu Asp Asp Arg Gly Ile Thr Tyr Arg Ile Pro Ala Leu Leu Tyr Ile
            20                  25                  30

Pro Pro Thr His Thr Phe Leu Ala Phe Ala Glu Lys Arg Ser Thr Arg
        35                  40                  45

Arg Asp Glu Asp Ala Leu His Leu Val Leu Arg Arg Gly Leu Arg Ile
    50                  55                  60

Gly Gln Leu Val Gln Trp Gly Pro Leu Lys Pro Leu Met Glu Ala Thr
65                  70                  75                  80

Leu Pro Gly His Arg Thr Met Asn Pro Cys Pro Val Trp Glu Gln Lys
                85                  90                  95

Ser Gly Cys Val Phe Leu Phe Phe Ile Cys Val Arg Gly His Val Thr
            100                 105                 110
```

```
Glu Arg Gln Gln Ile Val Ser Gly Arg Asn Ala Ala Arg Leu Cys Phe
        115                 120                 125

Ile Tyr Ser Gln Asp Ala Gly Cys Ser Trp Ser Glu Val Arg Asp Leu
    130                 135                 140

Thr Glu Glu Val Ile Gly Ser Glu Leu Lys His Trp Ala Thr Phe Ala
145                 150                 155                 160

Val Gly Pro Gly His Gly Ile Gln Leu Gln Ser Gly Arg Leu Val Ile
                165                 170                 175

Pro Ala Tyr Thr Tyr Tyr Ile Pro Ser Trp Phe Phe Cys Phe Gln Leu
            180                 185                 190

Pro Cys Lys Thr Arg Pro His Ser Leu Met Ile Tyr Ser Asp Asp Leu
        195                 200                 205

Gly Val Thr Trp His His Gly Arg Leu Ile Arg Pro Met Val Thr Val
    210                 215                 220

Glu Cys Glu Val Ala Glu Val Thr Gly Arg Ala Gly His Pro Val Leu
225                 230                 235                 240

Tyr Cys Ser Ala Arg Thr Pro Asn Arg Cys Arg Ala Glu Ala Leu Ser
                245                 250                 255

Thr Asp His Gly Glu Gly Phe Gln Arg Leu Ala Leu Ser Arg Gln Leu
            260                 265                 270

Cys Glu Pro Pro His Gly Cys Gln Gly Ser Val Val Ser Phe Arg Pro
        275                 280                 285

Leu Glu Ile Pro His Arg Cys Gln Asp Ser Ser Ser Lys Asp Ala Pro
    290                 295                 300

Thr Ile Gln Gln Ser Ser Pro Gly Ser Ser Leu Arg Leu Glu Glu Glu
305                 310                 315                 320

Ala Gly Thr Pro Ser Glu Ser Trp Leu Leu Tyr Ser His Pro Thr Ser
                325                 330                 335

Arg Lys Gln Arg Val Asp Leu Gly Ile Tyr Leu Asn Gln Thr Pro Leu
            340                 345                 350

Glu Ala Ala Cys Trp Ser Arg Pro Trp Ile Leu His Cys Gly Pro Cys
        355                 360                 365

Gly Tyr Ser Asp Leu Ala Ala Leu Glu Glu Glu Gly Leu Phe Gly Cys
    370                 375                 380

Leu Phe Glu Cys Gly Thr Lys Gln Glu Cys Glu Gln Ile Ala Phe Arg
385                 390                 395                 400

Leu Phe Thr His Arg Glu Ile Leu Ser His Leu Gln Gly Asp Cys Thr
                405                 410                 415

Ser Pro Gly Arg Asn Pro Ser Gln Phe Lys Ser Asn
            420                 425


<210> SEQ ID NO 4
<211> LENGTH: 461
<212> TYPE: PRT
<213> ORGANISM: Homo sapiens

<400> SEQUENCE: 4

Met Arg Pro Ala Asp Leu Pro Pro Arg Pro Met Glu Glu Ser Pro Ala
1               5                   10                  15

Ser Ser Ser Ala Pro Thr Glu Thr Glu Glu Pro Gly Ser Ser Ala Glu
            20                  25                  30

Val Met Glu Glu Val Thr Thr Cys Ser Phe Asn Ser Pro Leu Phe Arg
        35                  40                  45

Gln Glu Asp Asp Arg Gly Ile Thr Tyr Arg Ile Pro Ala Leu Leu Tyr
```

```
    50                  55                  60

Ile Pro Pro Thr His Thr Phe Leu Ala Phe Ala Glu Lys Arg Ser Thr
65                  70                  75                  80

Arg Arg Asp Glu Asp Ala Leu His Leu Val Leu Arg Arg Gly Leu Arg
                85                  90                  95

Ile Gly Gln Leu Val Gln Trp Gly Pro Leu Lys Pro Leu Met Glu Ala
            100                 105                 110

Thr Leu Pro Gly His Arg Thr Met Asn Pro Cys Pro Val Trp Glu Gln
        115                 120                 125

Lys Ser Gly Cys Val Phe Leu Phe Phe Ile Cys Val Arg Gly His Val
    130                 135                 140

Thr Glu Arg Gln Gln Ile Val Ser Gly Arg Asn Ala Ala Arg Leu Cys
145                 150                 155                 160

Phe Ile Tyr Ser Gln Asp Ala Gly Cys Ser Trp Ser Glu Val Arg Asp
                165                 170                 175

Leu Thr Glu Glu Val Ile Gly Ser Glu Leu Lys His Trp Ala Thr Phe
            180                 185                 190

Ala Val Gly Pro Gly His Gly Ile Gln Leu Gln Ser Gly Arg Leu Val
        195                 200                 205

Ile Pro Ala Tyr Thr Tyr Tyr Ile Pro Ser Trp Phe Phe Cys Phe Gln
    210                 215                 220

Leu Pro Cys Lys Thr Arg Pro His Ser Leu Met Ile Tyr Ser Asp Asp
225                 230                 235                 240

Leu Gly Val Thr Trp His His Gly Arg Leu Ile Arg Pro Met Val Thr
                245                 250                 255

Val Glu Cys Glu Val Ala Glu Val Thr Gly Arg Ala Gly His Pro Val
            260                 265                 270

Leu Tyr Cys Ser Ala Arg Thr Pro Asn Arg Cys Arg Ala Glu Ala Leu
        275                 280                 285

Ser Thr Asp His Gly Glu Gly Phe Gln Arg Leu Ala Leu Ser Arg Gln
    290                 295                 300

Leu Cys Glu Pro Pro His Gly Cys Gln Gly Ser Val Val Ser Phe Arg
305                 310                 315                 320

Pro Leu Glu Ile Pro His Arg Cys Gln Asp Ser Ser Ser Lys Asp Ala
                325                 330                 335

Pro Thr Ile Gln Gln Ser Ser Pro Gly Ser Ser Leu Arg Leu Glu Glu
            340                 345                 350

Glu Ala Gly Thr Pro Ser Glu Ser Trp Leu Leu Tyr Ser His Pro Thr
        355                 360                 365

Ser Arg Lys Gln Arg Val Asp Leu Gly Ile Tyr Leu Asn Gln Thr Pro
    370                 375                 380

Leu Glu Ala Ala Cys Trp Ser Arg Pro Trp Ile Leu His Cys Gly Pro
385                 390                 395                 400

Cys Gly Tyr Ser Asp Leu Ala Ala Leu Glu Glu Glu Gly Leu Phe Gly
                405                 410                 415

Cys Leu Phe Glu Cys Gly Thr Lys Gln Glu Cys Glu Gln Ile Ala Phe
            420                 425                 430

Arg Leu Phe Thr His Arg Glu Ile Leu Ser His Leu Gln Gly Asp Cys
        435                 440                 445

Thr Ser Pro Gly Arg Asn Pro Ser Gln Phe Lys Ser Asn
    450                 455                 460
```

<210> SEQ ID NO 5

<211> LENGTH: 496
<212> TYPE: PRT
<213> ORGANISM: Homo sapiens

<400> SEQUENCE: 5

```
Met Met Ser Ser Ala Ala Phe Pro Arg Trp Leu Ser Met Gly Val Pro
1               5                   10                  15

Arg Thr Pro Ser Arg Thr Val Leu Phe Glu Arg Glu Arg Thr Gly Leu
            20                  25                  30

Thr Tyr Arg Val Pro Ser Leu Leu Pro Val Pro Pro Gly Pro Thr Leu
        35                  40                  45

Leu Ala Phe Val Glu Gln Arg Leu Ser Pro Asp Asp Ser His Ala His
    50                  55                  60

Arg Leu Val Leu Arg Arg Gly Thr Leu Ala Gly Gly Ser Val Arg Trp
65                  70                  75                  80

Gly Ala Leu His Val Leu Gly Thr Ala Ala Leu Ala Glu His Arg Ser
                85                  90                  95

Met Asn Pro Cys Pro Val His Asp Ala Gly Thr Gly Thr Val Phe Leu
            100                 105                 110

Phe Phe Ile Ala Val Leu Gly His Thr Pro Glu Ala Val Gln Ile Ala
        115                 120                 125

Thr Gly Arg Asn Ala Ala Arg Leu Cys Cys Val Ala Ser Arg Asp Ala
    130                 135                 140

Gly Leu Ser Trp Gly Ser Ala Arg Asp Leu Thr Glu Glu Ala Ile Gly
145                 150                 155                 160

Gly Ala Val Gln Asp Trp Ala Thr Phe Ala Val Gly Pro Gly His Gly
                165                 170                 175

Val Gln Leu Pro Ser Gly Arg Leu Leu Val Pro Ala Tyr Thr Tyr Arg
            180                 185                 190

Val Asp Arg Arg Glu Cys Phe Gly Lys Ile Cys Arg Thr Ser Pro His
        195                 200                 205

Ser Phe Ala Phe Tyr Ser Asp Asp His Gly Arg Thr Trp Arg Cys Gly
    210                 215                 220

Gly Leu Val Pro Asn Leu Arg Ser Gly Glu Cys Gln Leu Ala Ala Val
225                 230                 235                 240

Asp Gly Gly Gln Ala Gly Ser Phe Leu Tyr Cys Asn Ala Arg Ser Pro
                245                 250                 255

Leu Gly Ser Arg Val Gln Ala Leu Ser Thr Asp Glu Gly Thr Ser Phe
            260                 265                 270

Leu Pro Ala Glu Arg Val Ala Ser Leu Pro Glu Thr Ala Trp Gly Cys
        275                 280                 285

Gln Gly Ser Ile Val Gly Phe Pro Ala Pro Ala Pro Asn Arg Pro Arg
    290                 295                 300

Asp Asp Ser Trp Ser Val Gly Pro Gly Ser Pro Leu Gln Pro Pro Leu
305                 310                 315                 320

Leu Gly Pro Gly Val His Glu Pro Pro Glu Glu Ala Ala Val Asp Pro
                325                 330                 335

Arg Gly Gly Gln Val Pro Gly Gly Pro Phe Ser Arg Leu Gln Pro Arg
            340                 345                 350

Gly Asp Gly Pro Arg Gln Pro Gly Pro Arg Pro Gly Val Ser Gly Asp
        355                 360                 365

Val Gly Ser Trp Thr Leu Ala Leu Pro Met Pro Phe Ala Ala Pro Pro
    370                 375                 380

Gln Ser Pro Thr Trp Leu Leu Tyr Ser His Pro Val Gly Arg Arg Ala
```

```
385                 390                 395                 400

Arg Leu His Met Gly Ile Arg Leu Ser Gln Ser Pro Leu Asp Pro Arg
                405                 410                 415

Ser Trp Thr Glu Pro Trp Val Ile Tyr Glu Gly Pro Ser Gly Tyr Ser
            420                 425                 430

Asp Leu Ala Ser Ile Gly Pro Ala Pro Glu Gly Gly Leu Val Phe Ala
        435                 440                 445

Cys Leu Tyr Glu Ser Gly Ala Arg Thr Ser Tyr Asp Glu Ile Ser Phe
    450                 455                 460

Cys Thr Phe Ser Leu Arg Glu Val Leu Glu Asn Val Pro Ala Ser Pro
465                 470                 475                 480

Lys Pro Pro Asn Leu Gly Asp Lys Pro Arg Gly Cys Cys Trp Pro Ser
                485                 490                 495


<210> SEQ ID NO 6
<211> LENGTH: 497
<212> TYPE: PRT
<213> ORGANISM: Homo sapiens

<400> SEQUENCE: 6

Met Met Ser Ser Ala Ala Phe Pro Arg Trp Leu Gln Ser Met Gly Val
1               5                   10                  15

Pro Arg Thr Pro Ser Arg Thr Val Leu Phe Glu Arg Glu Arg Thr Gly
            20                  25                  30

Leu Thr Tyr Arg Val Pro Ser Leu Leu Pro Val Pro Pro Gly Pro Thr
        35                  40                  45

Leu Leu Ala Phe Val Glu Gln Arg Leu Ser Pro Asp Asp Ser His Ala
    50                  55                  60

His Arg Leu Val Leu Arg Arg Gly Thr Leu Ala Gly Gly Ser Val Arg
65                  70                  75                  80

Trp Gly Ala Leu His Val Leu Gly Thr Ala Ala Leu Ala Glu His Arg
                85                  90                  95

Ser Met Asn Pro Cys Pro Val His Asp Ala Gly Thr Gly Thr Val Phe
            100                 105                 110

Leu Phe Phe Ile Ala Val Leu Gly His Thr Pro Glu Ala Val Gln Ile
        115                 120                 125

Ala Thr Gly Arg Asn Ala Ala Arg Leu Cys Cys Val Ala Ser Arg Asp
    130                 135                 140

Ala Gly Leu Ser Trp Gly Ser Ala Arg Asp Leu Thr Glu Glu Ala Ile
145                 150                 155                 160

Gly Gly Ala Val Gln Asp Trp Ala Thr Phe Ala Val Gly Pro Gly His
                165                 170                 175

Gly Val Gln Leu Pro Ser Gly Arg Leu Leu Val Pro Ala Tyr Thr Tyr
            180                 185                 190

Arg Val Asp Arg Arg Glu Cys Phe Gly Lys Ile Cys Arg Thr Ser Pro
        195                 200                 205

His Ser Phe Ala Phe Tyr Ser Asp Asp His Gly Arg Thr Trp Arg Cys
    210                 215                 220

Gly Gly Leu Val Pro Asn Leu Arg Ser Gly Glu Cys Gln Leu Ala Ala
225                 230                 235                 240

Val Asp Gly Gly Gln Ala Gly Ser Phe Leu Tyr Cys Asn Ala Arg Ser
                245                 250                 255

Pro Leu Gly Ser Arg Val Gln Ala Leu Ser Thr Asp Glu Gly Thr Ser
            260                 265                 270
```

```
Phe Leu Pro Ala Glu Arg Val Ala Ser Leu Pro Glu Thr Ala Trp Gly
        275                 280                 285

Cys Gln Gly Ser Ile Val Gly Phe Pro Ala Pro Ala Pro Asn Arg Pro
    290                 295                 300

Arg Asp Asp Ser Trp Ser Val Gly Pro Gly Ser Pro Leu Gln Pro Pro
305                 310                 315                 320

Leu Leu Gly Pro Gly Val His Glu Pro Pro Glu Glu Ala Ala Val Asp
                325                 330                 335

Pro Arg Gly Gly Gln Val Pro Gly Gly Pro Phe Ser Arg Leu Gln Pro
            340                 345                 350

Arg Gly Asp Gly Pro Arg Gln Pro Gly Pro Arg Pro Gly Val Ser Gly
        355                 360                 365

Asp Val Gly Ser Trp Thr Leu Ala Leu Pro Met Pro Phe Ala Ala Pro
    370                 375                 380

Pro Gln Ser Pro Thr Trp Leu Leu Tyr Ser His Pro Val Gly Arg Arg
385                 390                 395                 400

Ala Arg Leu His Met Gly Ile Arg Leu Ser Gln Ser Pro Leu Asp Pro
                405                 410                 415

Arg Ser Trp Thr Glu Pro Trp Val Ile Tyr Glu Gly Pro Ser Gly Tyr
            420                 425                 430

Ser Asp Leu Ala Ser Ile Gly Pro Ala Pro Glu Gly Gly Leu Val Phe
        435                 440                 445

Ala Cys Leu Tyr Glu Ser Gly Ala Arg Thr Ser Tyr Asp Glu Ile Ser
    450                 455                 460

Phe Cys Thr Phe Ser Leu Arg Glu Val Leu Glu Asn Val Pro Ala Ser
465                 470                 475                 480

Pro Lys Pro Pro Asn Leu Gly Asp Lys Pro Arg Gly Cys Cys Trp Pro
                485                 490                 495

Ser


<210> SEQ ID NO 7
<211> LENGTH: 484
<212> TYPE: PRT
<213> ORGANISM: Homo sapiens

<400> SEQUENCE: 7

Met Gly Val Pro Arg Thr Pro Ser Arg Thr Val Leu Phe Glu Arg Glu
1               5                   10                  15

Arg Thr Gly Leu Thr Tyr Arg Val Pro Ser Leu Leu Pro Val Pro Pro
            20                  25                  30

Gly Pro Thr Leu Leu Ala Phe Val Glu Gln Arg Leu Ser Pro Asp Asp
        35                  40                  45

Ser His Ala His Arg Leu Val Leu Arg Arg Gly Thr Leu Ala Gly Gly
    50                  55                  60

Ser Val Arg Trp Gly Ala Leu His Val Leu Gly Thr Ala Ala Leu Ala
65                  70                  75                  80

Glu His Arg Ser Met Asn Pro Cys Pro Val His Asp Ala Gly Thr Gly
                85                  90                  95

Thr Val Phe Leu Phe Phe Ile Ala Val Leu Gly His Thr Pro Glu Ala
            100                 105                 110

Val Gln Ile Ala Thr Gly Arg Asn Ala Ala Arg Leu Cys Cys Val Ala
        115                 120                 125

Ser Arg Asp Ala Gly Leu Ser Trp Gly Ser Ala Arg Asp Leu Thr Glu
    130                 135                 140
```

```
Glu Ala Ile Gly Gly Ala Val Gln Asp Trp Ala Thr Phe Ala Val Gly
145                 150                 155                 160

Pro Gly His Gly Val Gln Leu Pro Ser Gly Arg Leu Leu Val Pro Ala
                165                 170                 175

Tyr Thr Tyr Arg Val Asp Arg Arg Glu Cys Phe Gly Lys Ile Cys Arg
            180                 185                 190

Thr Ser Pro His Ser Phe Ala Phe Tyr Ser Asp Asp His Gly Arg Thr
        195                 200                 205

Trp Arg Cys Gly Gly Leu Val Pro Asn Leu Arg Ser Gly Glu Cys Gln
    210                 215                 220

Leu Ala Ala Val Asp Gly Gly Gln Ala Gly Ser Phe Leu Tyr Cys Asn
225                 230                 235                 240

Ala Arg Ser Pro Leu Gly Ser Arg Val Gln Ala Leu Ser Thr Asp Glu
                245                 250                 255

Gly Thr Ser Phe Leu Pro Ala Glu Arg Val Ala Ser Leu Pro Glu Thr
            260                 265                 270

Ala Trp Gly Cys Gln Gly Ser Ile Val Gly Phe Pro Ala Pro Ala Pro
        275                 280                 285

Asn Arg Pro Arg Asp Asp Ser Trp Ser Val Gly Pro Gly Ser Pro Leu
    290                 295                 300

Gln Pro Pro Leu Leu Gly Pro Gly Val His Glu Pro Pro Glu Glu Ala
305                 310                 315                 320

Ala Val Asp Pro Arg Gly Gly Gln Val Pro Gly Gly Pro Phe Ser Arg
                325                 330                 335

Leu Gln Pro Arg Gly Asp Gly Pro Arg Gln Pro Gly Pro Arg Pro Gly
            340                 345                 350

Val Ser Gly Asp Val Gly Ser Trp Thr Leu Ala Leu Pro Met Pro Phe
        355                 360                 365

Ala Ala Pro Pro Gln Ser Pro Thr Trp Leu Leu Tyr Ser His Pro Val
    370                 375                 380

Gly Arg Arg Ala Arg Leu His Met Gly Ile Arg Leu Ser Gln Ser Pro
385                 390                 395                 400

Leu Asp Pro Arg Ser Trp Thr Glu Pro Trp Val Ile Tyr Glu Gly Pro
                405                 410                 415

Ser Gly Tyr Ser Asp Leu Ala Ser Ile Gly Pro Ala Pro Glu Gly Gly
            420                 425                 430

Leu Val Phe Ala Cys Leu Tyr Glu Ser Gly Ala Arg Thr Ser Tyr Asp
        435                 440                 445

Glu Ile Ser Phe Cys Thr Phe Ser Leu Arg Glu Val Leu Glu Asn Val
    450                 455                 460

Pro Ala Ser Pro Lys Pro Pro Asn Leu Gly Asp Lys Pro Arg Gly Cys
465                 470                 475                 480

Cys Trp Pro Ser
```

<210> SEQ ID NO 8
<211> LENGTH: 569
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(80)
<223> OTHER INFORMATION: Xaa can be any naturally occurring amino acid
<220> FEATURE:
<221> NAME/KEY: misc_feature
<222> LOCATION: (82)..(82)

<223> OTHER INFORMATION: Xaa can be any naturally occurring amino acid
<220> FEATURE:
<221> NAME/KEY: misc_feature
<222> LOCATION: (84)..(94)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (102)..(106)
<223> OTHER INFORMATION: Xaa can be any naturally occurring amino acid
<220> FEATURE:
<221> NAME/KEY: misc_feature
<222> LOCATION: (108)..(109)
<223> OTHER INFORMATION: Xaa can be any naturally occurring amino acid
<220> FEATURE:
<221> NAME/KEY: misc_feature
<222> LOCATION: (111)..(114)
<223> OTHER INFORMATION: Xaa can be any naturally occurring amino acid
<220> FEATURE:
<221> NAME/KEY: misc_feature
<222> LOCATION: (118)..(128)
<223> OTHER INFORMATION: Xaa can be any naturally occurring amino acid
<220> FEATURE:
<221> NAME/KEY: misc_feature
<222> LOCATION: (130)..(156)
<223> OTHER INFORMATION: Xaa can be any naturally occurring amino acid
<220> FEATURE:
<221> NAME/KEY: misc_feature
<222> LOCATION: (158)..(159)
<223> OTHER INFORMATION: Xaa can be any naturally occurring amino acid
<220> FEATURE:
<221> NAME/KEY: misc_feature
<222> LOCATION: (163)..(189)
<223> OTHER INFORMATION: Xaa can be any naturally occurring amino acid
<220> FEATURE:
<221> NAME/KEY: misc_feature
<222> LOCATION: (191)..(191)
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid
<220> FEATURE:
<221> NAME/KEY: misc_feature
<222> LOCATION: (195)..(196)
<223> OTHER INFORMATION: Xaa can be any naturally occurring amino acid
<220> FEATURE:
<221> NAME/KEY: misc_feature
<222> LOCATION: (198)..(200)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (204)..(208)
<223> OTHER INFORMATION: Xaa can be any naturally occurring amino acid
<220> FEATURE:
<221> NAME/KEY: misc_feature
<222> LOCATION: (210)..(217)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
<220> FEATURE:
<221> NAME/KEY: misc_feature
<222> LOCATION: (224)..(226)
<223> OTHER INFORMATION: Xaa can be any naturally occurring amino acid
<220> FEATURE:
<221> NAME/KEY: misc_feature
<222> LOCATION: (228)..(236)
<223> OTHER INFORMATION: Xaa can be any naturally occurring amino acid
<220> FEATURE:
<221> NAME/KEY: misc_feature
<222> LOCATION: (238)..(267)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (273)..(274)
<223> OTHER INFORMATION: Xaa can be any naturally occurring amino acid
<220> FEATURE:
<221> NAME/KEY: misc_feature
<222> LOCATION: (276)..(277)
<223> OTHER INFORMATION: Xaa can be any naturally occurring amino acid
<220> FEATURE:
<221> NAME/KEY: misc_feature
<222> LOCATION: (279)..(298)
<223> OTHER INFORMATION: Xaa can be any naturally occurring amino acid
<220> FEATURE:
<221> NAME/KEY: misc_feature
<222> LOCATION: (301)..(317)
<223> OTHER INFORMATION: Xaa can be any naturally occurring amino acid
<220> FEATURE:
<221> NAME/KEY: misc_feature
<222> LOCATION: (320)..(353)
<223> OTHER INFORMATION: Xaa can be any naturally occurring amino acid
<220> FEATURE:
<221> NAME/KEY: misc_feature
<222> LOCATION: (355)..(463)
<223> OTHER INFORMATION: Xaa can be any naturally occurring amino acid
<220> FEATURE:
<221> NAME/KEY: misc_feature
<222> LOCATION: (465)..(469)
<223> OTHER INFORMATION: Xaa can be any naturally occurring amino acid
<220> FEATURE:
<221> NAME/KEY: misc_feature
<222> LOCATION: (471)..(486)
<223> OTHER INFORMATION: Xaa can be any naturally occurring amino acid
<220> FEATURE:
<221> NAME/KEY: misc_feature
<222> LOCATION: (488)..(496)
<223> OTHER INFORMATION: Xaa can be any naturally occurring amino acid
<220> FEATURE:
<221> NAME/KEY: misc_feature
<222> LOCATION: (498)..(500)
<223> OTHER INFORMATION: Xaa can be any naturally occurring amino acid
<220> FEATURE:
<221> NAME/KEY: misc_feature
<222> LOCATION: (503)..(503)
<223> OTHER INFORMATION: Xaa can be any naturally occurring amino acid
<220> FEATURE:
<221> NAME/KEY: misc_feature
<222> LOCATION: (505)..(522)
<223> OTHER INFORMATION: Xaa can be any naturally occurring amino acid
<220> FEATURE:
<221> NAME/KEY: misc_feature
<222> LOCATION: (524)..(524)
<223> OTHER INFORMATION: Xaa can be any naturally occurring amino acid
<220> FEATURE:
<221> NAME/KEY: misc_feature
<222> LOCATION: (526)..(534)
<223> OTHER INFORMATION: Xaa can be any naturally occurring amino acid
<220> FEATURE:
<221> NAME/KEY: misc_feature
<222> LOCATION: (536)..(569)
<223> OTHER INFORMATION: Xaa can be any naturally occurring amino acid

<400> SEQUENCE: 8

Xaa Xaa Xaa Xaa Xaa Xaa Xaa Xaa Xaa Xaa Xaa Xaa Xaa Xaa Xaa Xaa
1               5                   10                  15

-continued

```
Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Arg Xaa Pro Xaa Xaa Xaa Xaa Xaa Xaa Xaa Xaa Xaa Xaa Xaa Leu Ala
                85                  90                  95

Phe Xaa Glu Xaa Arg Xaa Xaa Xaa Xaa Xaa Asp Xaa Xaa Ala Xaa Xaa
            100                 105                 110

Xaa Xaa Leu Arg Arg Xaa Xaa Xaa Xaa Xaa Xaa Xaa Xaa Xaa Xaa Xaa
        115                 120                 125

Trp Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Gly Xaa Xaa Phe
145                 150                 155                 160

Leu Phe Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Ser Xaa Asp
            180                 185                 190

Xaa Gly Xaa Xaa Trp Xaa Xaa Xaa Arg Xaa Leu Xaa Xaa Xaa Xaa Xaa
        195                 200                 205

Gly Xaa Xaa Xaa Xaa Xaa Xaa Xaa Xaa Phe Ala Xaa Gly Pro Gly Xaa
    210                 215                 220

Xaa Xaa Gln Xaa Xaa Xaa Xaa Xaa Xaa Xaa Xaa Xaa Leu Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Ser Xaa Asp Xaa Gly
            260                 265                 270

Xaa Xaa Trp Xaa Xaa Gly Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Glu Cys Xaa Xaa Xaa Xaa
    290                 295                 300

Xaa Xaa Xaa Xaa Xaa Xaa Xaa Xaa Xaa Xaa Xaa Xaa Xaa Ala Arg Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Cys Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa Xaa
            420                 425                 430
```

-continued

```
Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Pro
    450                 455                 460

Xaa Xaa Xaa Xaa Xaa Arg Xaa Xaa Xaa Xaa Xaa Xaa Xaa Xaa Xaa Xaa
465                 470                 475                 480

Xaa Xaa Xaa Xaa Xaa Xaa Trp Xaa Xaa Xaa Xaa Xaa Xaa Xaa Xaa Xaa
                485                 490                 495

Gly Xaa Xaa Xaa Tyr Ser Xaa Leu Xaa Xaa Xaa Xaa Xaa Xaa Xaa Xaa
            500                 505                 510

Xaa Xaa Xaa Xaa Xaa Xaa Xaa Xaa Xaa Xaa Leu Xaa Glu Xaa Xaa Xaa
        515                 520                 525

Xaa Xaa Xaa Xaa Xaa Xaa Ile Xaa Xaa Xaa Xaa Xaa Xaa Xaa Xaa Xaa
    530                 535                 540

Xaa Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa
                565
```